(12) United States Patent
Kovalsky et al.

(10) Patent No.: US 11,123,190 B2
(45) Date of Patent: Sep. 21, 2021

(54) HEART VALVE PROSTHESIS

(71) Applicant: MEDTRONIC, INC., Minneapolis, MN (US)

(72) Inventors: Igor Kovalsky, Mounds View, MN (US); Jason Quill, Forest Lake, CA (US)

(73) Assignee: MEDTRONIC, INC., Minneapolis, MN (US)

( * ) Notice: Subject to any disclaimer, the term of this patent is extended or adjusted under 35 U.S.C. 154(b) by 81 days.

(21) Appl. No.: 16/259,400

(22) Filed: Jan. 28, 2019

(65) Prior Publication Data

US 2019/0240013 A1 Aug. 8, 2019

Related U.S. Application Data

(63) Continuation of application No. 14/175,100, filed on Feb. 7, 2014, now Pat. No. 10,206,775, which is a
(Continued)

(51) Int. Cl.
*A61F 2/24* (2006.01)

(52) U.S. Cl.
CPC .......... *A61F 2/2436* (2013.01); *A61F 2/2418* (2013.01); *A61F 2/2409* (2013.01); *A61F 2/2457* (2013.01); *A61F 2210/0004* (2013.01); *A61F 2220/005* (2013.01); *A61F 2220/0008* (2013.01); *A61F 2220/0016* (2013.01); *A61F 2220/0058* (2013.01); *A61F 2220/0075* (2013.01); *A61F 2230/005* (2013.01); *A61F 2230/008* (2013.01); *A61F 2230/0054* (2013.01); *A61F 2230/0067* (2013.01);
(Continued)

(58) Field of Classification Search
CPC ........ A61F 2/2418; A61F 2/24; A61F 2/2436; A61F 2/2476; A61F 2220/0008; A61F 2220/0016
See application file for complete search history.

(56) References Cited

U.S. PATENT DOCUMENTS

| 5,545,215 A | 8/1996 | Duran |
| 5,957,949 A | 9/1999 | Leonhardt et al. |

(Continued)

FOREIGN PATENT DOCUMENTS

| CA | 2827556 A1 | 7/2012 |
| CN | 101172055 A | 5/2008 |

(Continued)

OTHER PUBLICATIONS

The International Search Report and Written Opinion issued in International Application No. PCT/US2014/020876, dated Jul. 2, 2014.

(Continued)

*Primary Examiner* — Dinah Baria
(74) *Attorney, Agent, or Firm* — Medler Ferro Woodhouse & Mills PLLC

(57) ABSTRACT

Heart valve prosthesis are disclosed that include a frame or support structure having an inflow portion, a valve-retaining tubular or central portion and a pair of support arms. The inflow portion radially extends from a first end of the valve-retaining tubular portion and the pair of support arms are circumferentially spaced apart and radially extend from an opposing second end of the valve-retaining tubular portion.

8 Claims, 69 Drawing Sheets

Related U.S. Application Data continuation-in-part of application No. 13/736,460, filed on Jan. 8, 2013, now Pat. No. 9,232,995, and a continuation-in-part of application No. 13/572,842, filed on Aug. 13, 2012, now Pat. No. 9,468,525.

(60) Provisional application No. 61/895,106, filed on Oct. 24, 2013, provisional application No. 61/822,616, filed on May 13, 2013.

(52) U.S. Cl.
CPC ............... *A61F 2250/0036* (2013.01); *A61F 2250/0071* (2013.01)

(56) References Cited

U.S. PATENT DOCUMENTS

| | | |
|---|---|---|
| 6,458,153 B1 | 10/2002 | Bailey et al. |
| 7,101,396 B2 | 9/2006 | Artof et al. |
| 7,399,315 B2 | 7/2008 | Iobbi |
| 7,748,389 B2 | 7/2010 | Salaheih et al. |
| 7,780,725 B2 | 8/2010 | Haug et al. |
| 7,837,727 B2 | 11/2010 | Goetz et al. |
| 7,947,075 B2 | 5/2011 | Goetz et al. |
| 8,167,934 B2 | 5/2012 | Styrc et al. |
| 8,449,599 B2 | 5/2013 | Chau et al. |
| 9,398,951 B2 | 7/2016 | Alkhatib et al. |
| 2003/0036791 A1 | 2/2003 | Philipp et al. |
| 2003/0199963 A1 | 10/2003 | Tower et al. |
| 2003/0199971 A1 | 10/2003 | Tower et al. |
| 2004/0111111 A1 | 6/2004 | Lin |
| 2004/0210304 A1 | 10/2004 | Seguin et al. |
| 2006/0020333 A1 | 1/2006 | Lashinski et al. |
| 2008/0071361 A1 | 3/2008 | Tuval et al. |
| 2009/0216313 A1 | 8/2009 | Straubinger et al. |
| 2009/0240320 A1 | 9/2009 | Tuval et al. |
| 2009/0276027 A1 | 11/2009 | Glynn |
| 2010/0036479 A1 | 2/2010 | Hill et al. |
| 2010/0094411 A1 | 4/2010 | Tuval et al. |
| 2010/0191320 A1 | 7/2010 | Straubinger et al. |
| 2010/0262231 A1 | 10/2010 | Tuval et al. |
| 2010/0268332 A1 | 10/2010 | Tuval et al. |
| 2011/0137397 A1 | 6/2011 | Chau et al. |
| 2011/0208297 A1 | 8/2011 | Tuval et al. |
| 2011/0208298 A1 | 8/2011 | Tuval et al. |
| 2011/0224785 A1 | 9/2011 | Hgacohen |
| 2011/0238168 A1 | 9/2011 | Pellegrini et al. |
| 2011/0264206 A1 | 10/2011 | Tabor |
| 2011/0313515 A1 | 12/2011 | Quadri et al. |
| 2011/0319989 A1 | 12/2011 | Lane et al. |
| 2012/0022640 A1 | 1/2012 | Gross et al. |
| 2012/0041550 A1 | 2/2012 | Salahieh et al. |
| 2012/0053685 A1 | 3/2012 | Cerf et al. |
| 2012/0078360 A1 | 3/2012 | Rafiee |
| 2012/0101572 A1 | 4/2012 | Kovalsky et al. |
| 2012/0303116 A1 | 11/2012 | Gorman, III et al. |
| 2013/0035759 A1 | 2/2013 | Gross et al. |
| 2013/0261738 A1 | 10/2013 | Clague et al. |
| 2014/0067054 A1 | 3/2014 | Chau et al. |
| 2014/0222136 A1 | 8/2014 | Geist et al. |
| 2014/0277390 A1 | 9/2014 | Ratz et al. |
| 2014/0277563 A1 | 9/2014 | White |
| 2015/0173897 A1 | 6/2015 | Raanani et al. |

FOREIGN PATENT DOCUMENTS

| | | |
|---|---|---|
| CN | 102639179 A | 8/2012 |
| CN | 102958469 A | 3/2013 |
| CN | 103079498 A | 5/2013 |
| CN | 103153232 A | 6/2013 |
| DE | 10 2006 052 564 B3 | 12/2007 |
| EP | 2520249 A1 | 11/2012 |
| WO | 2004/019825 A1 | 3/2004 |
| WO | 2005/062980 A2 | 7/2005 |
| WO | 2009/108615 A1 | 9/2009 |
| WO | 2011/051043 A1 | 5/2011 |
| WO | 2011/057087 A1 | 5/2011 |
| WO | 2011/137531 A1 | 11/2011 |
| WO | 2012/061809 A2 | 5/2012 |
| WO | 2012/085913 A2 | 6/2012 |
| WO | 2012/095159 A2 | 7/2012 |
| WO | 2012/177942 A2 | 12/2012 |
| WO | 2013/021374 A2 | 2/2013 |
| WO | 2013/028387 A2 | 2/2013 |
| WO | 2013/059747 A1 | 4/2013 |
| WO | 2013/072496 A1 | 5/2013 |
| WO | 2013/086413 A1 | 6/2013 |
| WO | 2013/114214 A2 | 8/2013 |
| WO | 2013/155970 A1 | 10/2013 |
| WO | 2013/175468 A2 | 11/2013 |
| WO | 2013/177684 A1 | 12/2013 |
| WO | 2014/028112 A1 | 2/2014 |

OTHER PUBLICATIONS

Boudjemline et al. "Steps Toward Percutaneous Aortic Valve Replacement" Circulation 2002; 105; 775-558.

Lauten et al., "Experimental Evaluation of the JenaClip Transcatheter Aortic Valve" Catheterization and Cardiovascular Interventions 74:514-519 (2009).

Chau, Mark, U.S. Appl. No. 61/287,099, "Prosthetic Mitral Valve With Subvalvular Anchoring" filed Dec. 16, 2009.

Chau et al. U.S. Appl. No. 61/266,774, "Prosthetic Mitral Valve with Subvalvular Anchoring" filed Dec. 4, 2009.

International Search Report and Written Opinion, Int'l Appl. No. PCT/US2013/045789, dated Dec. 6, 2013.

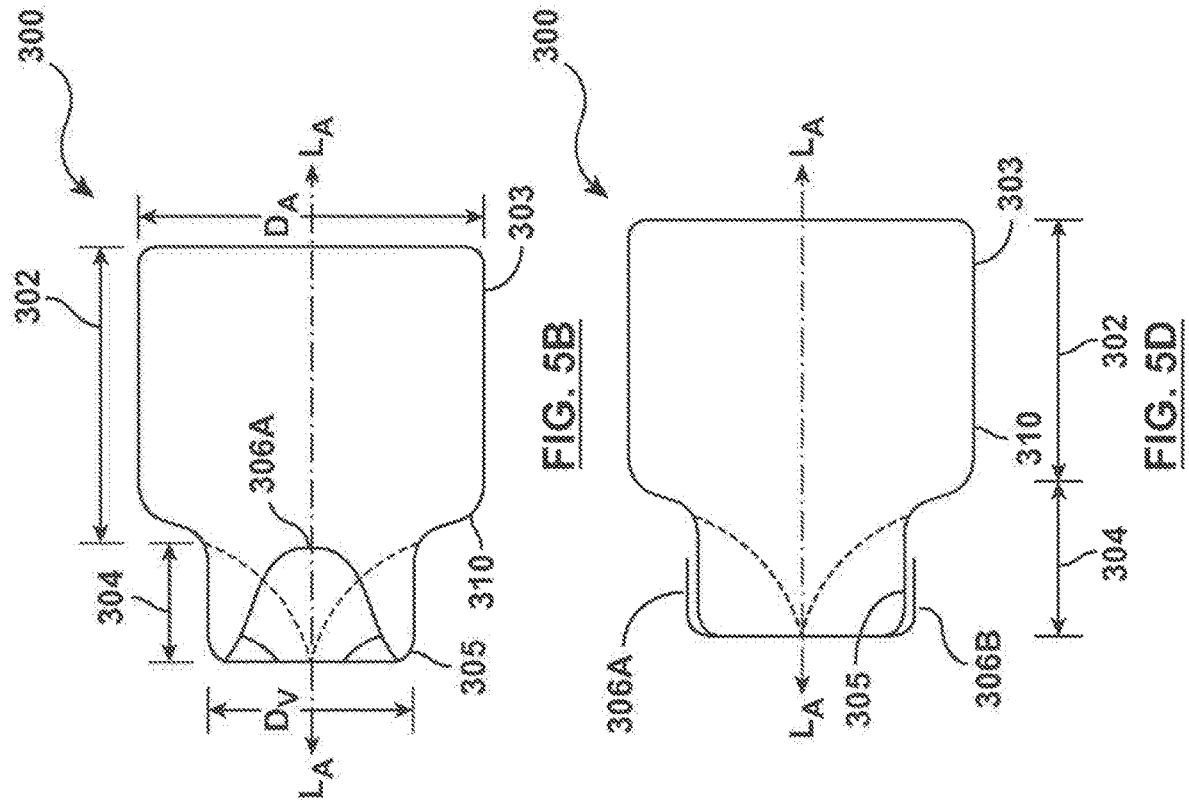
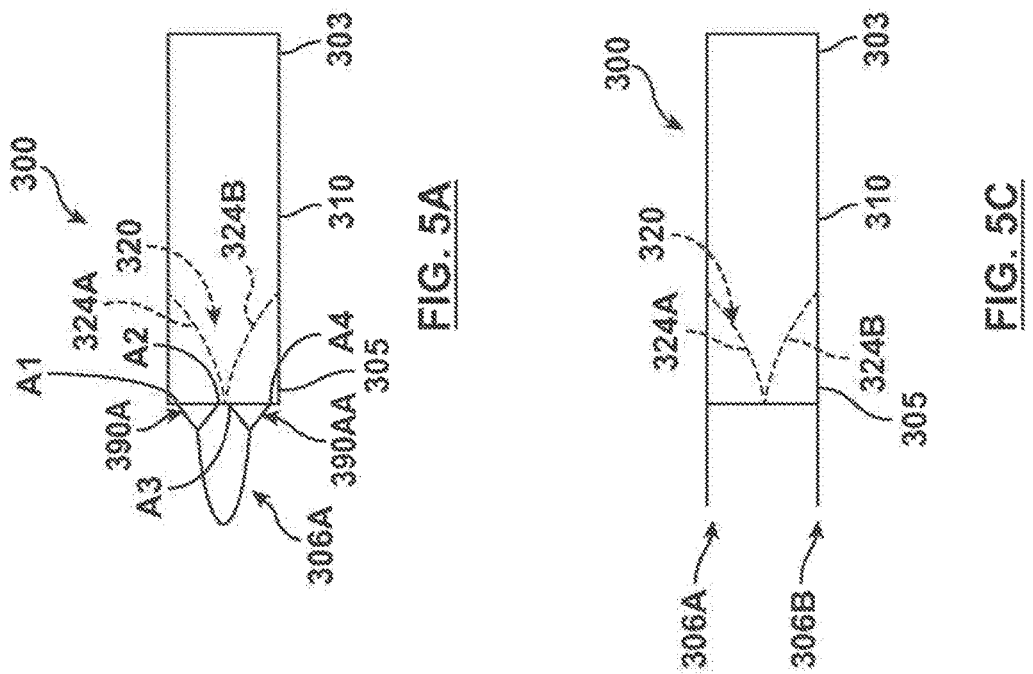

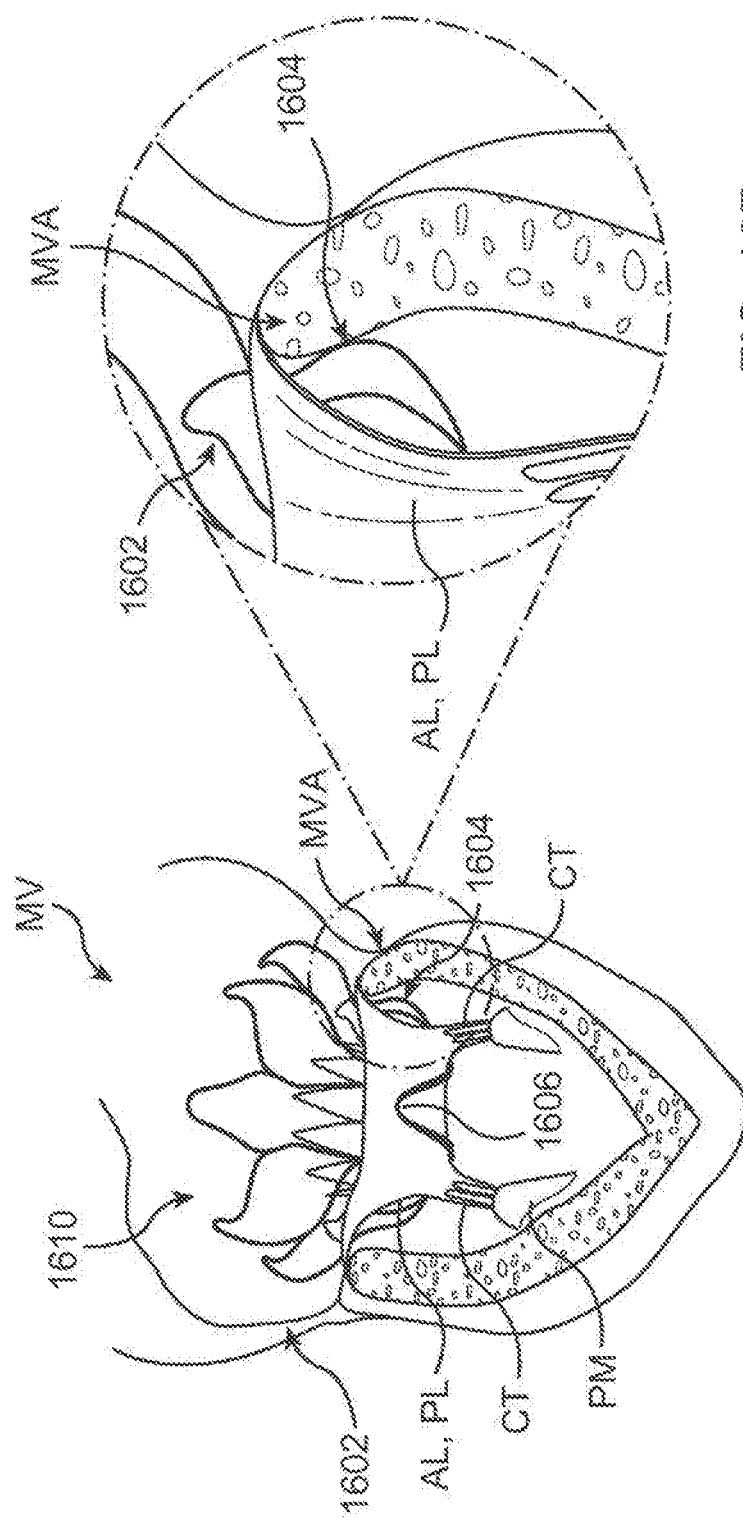

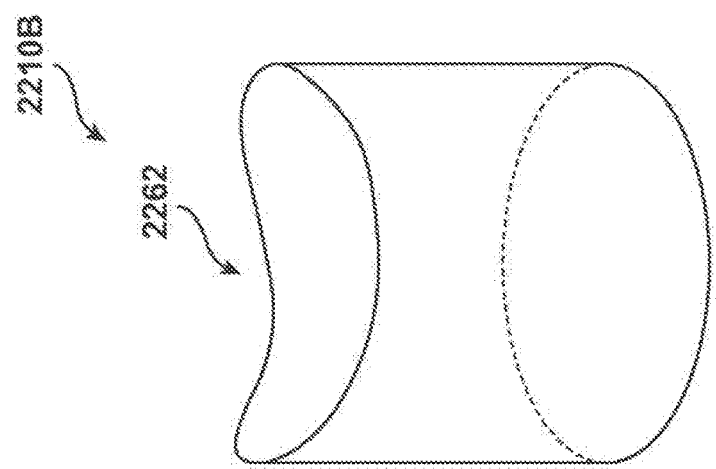
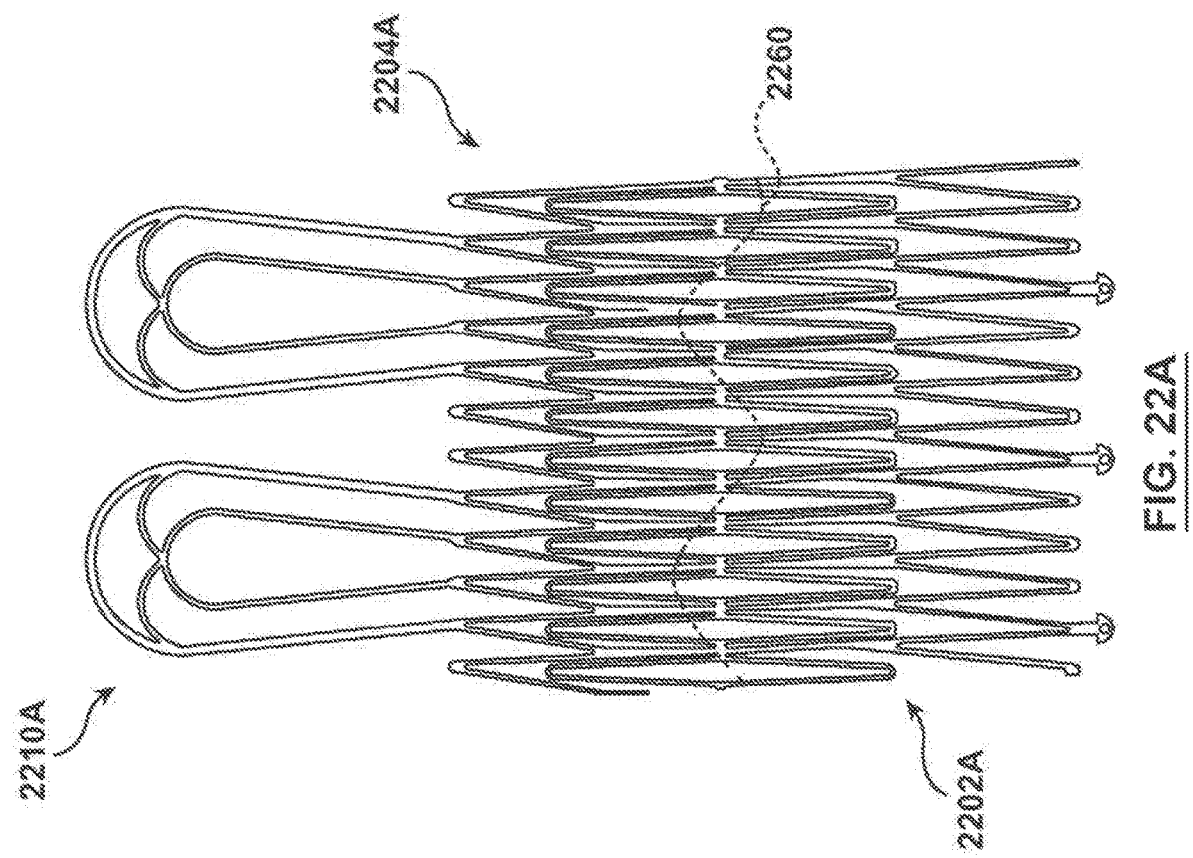

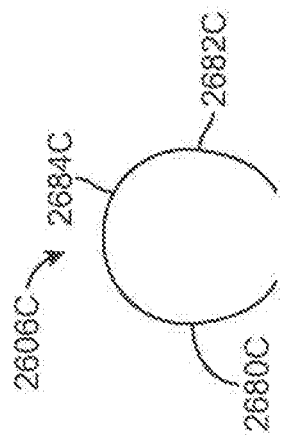
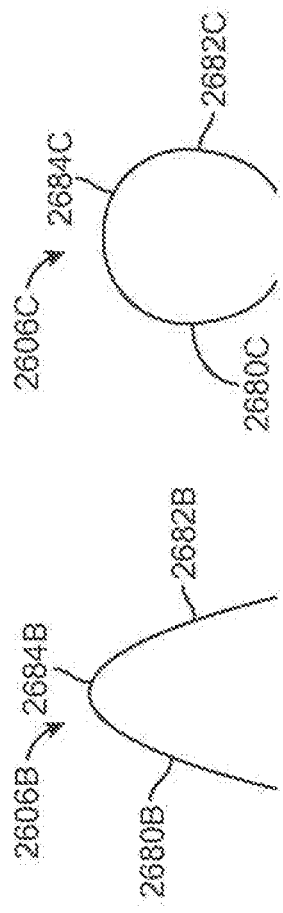
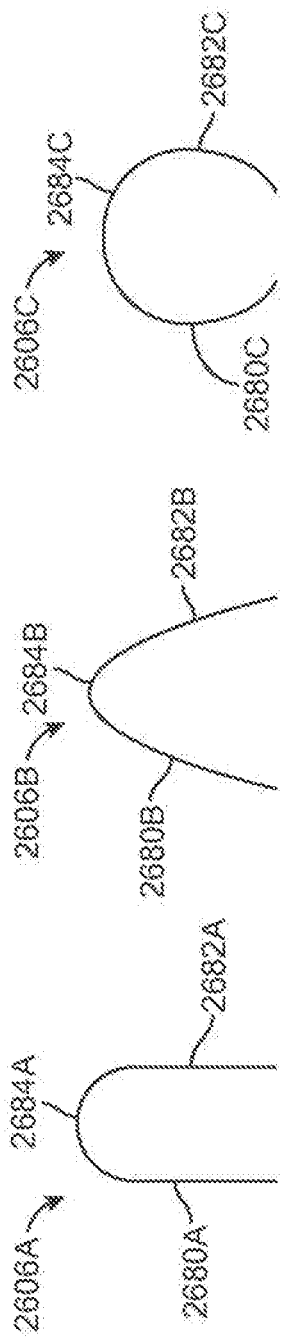
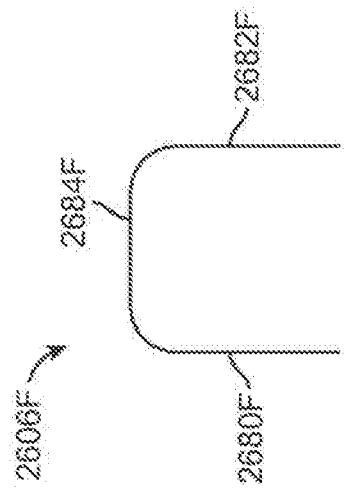
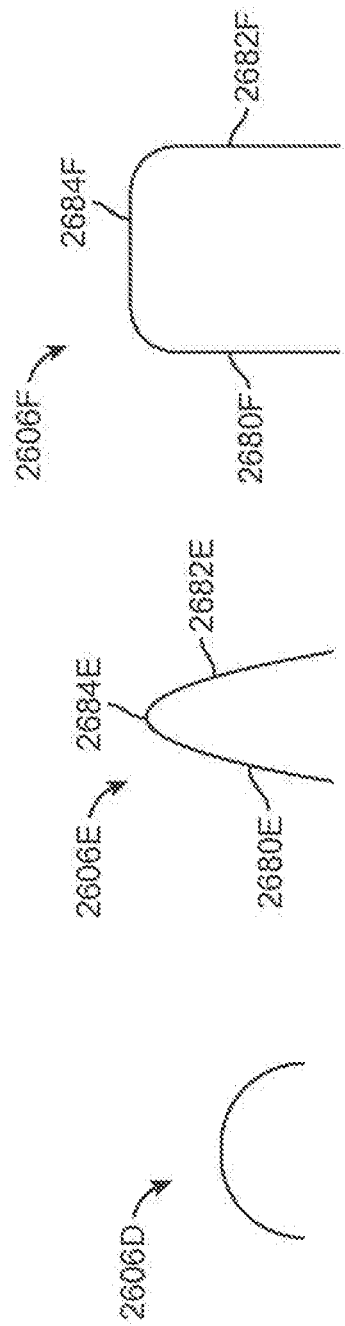

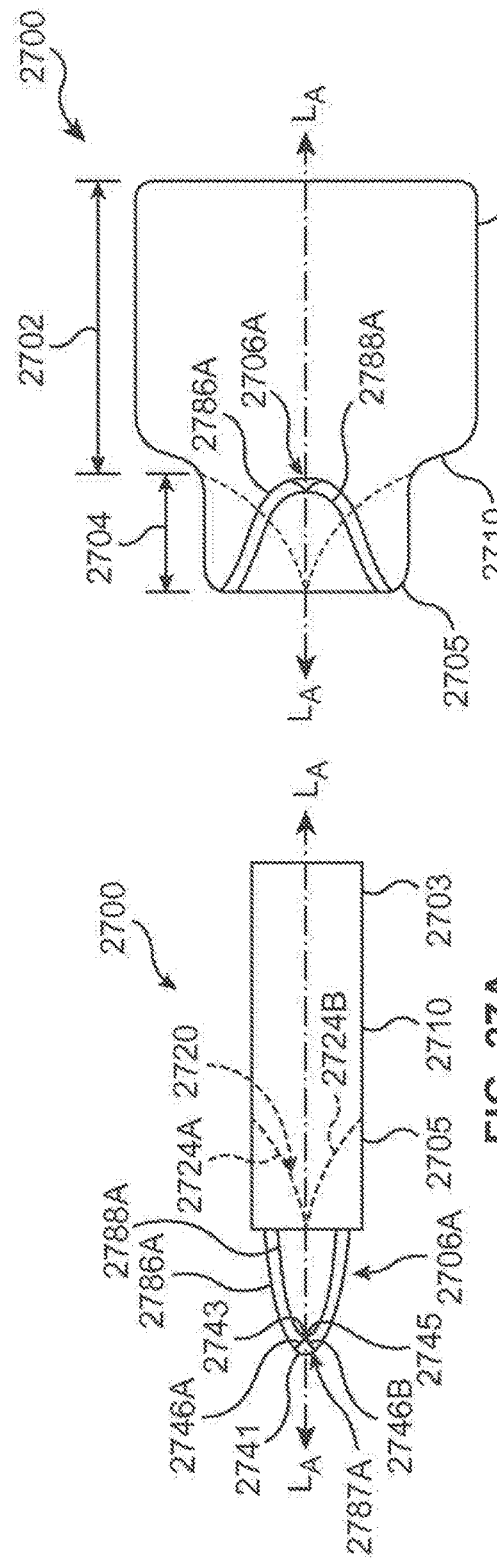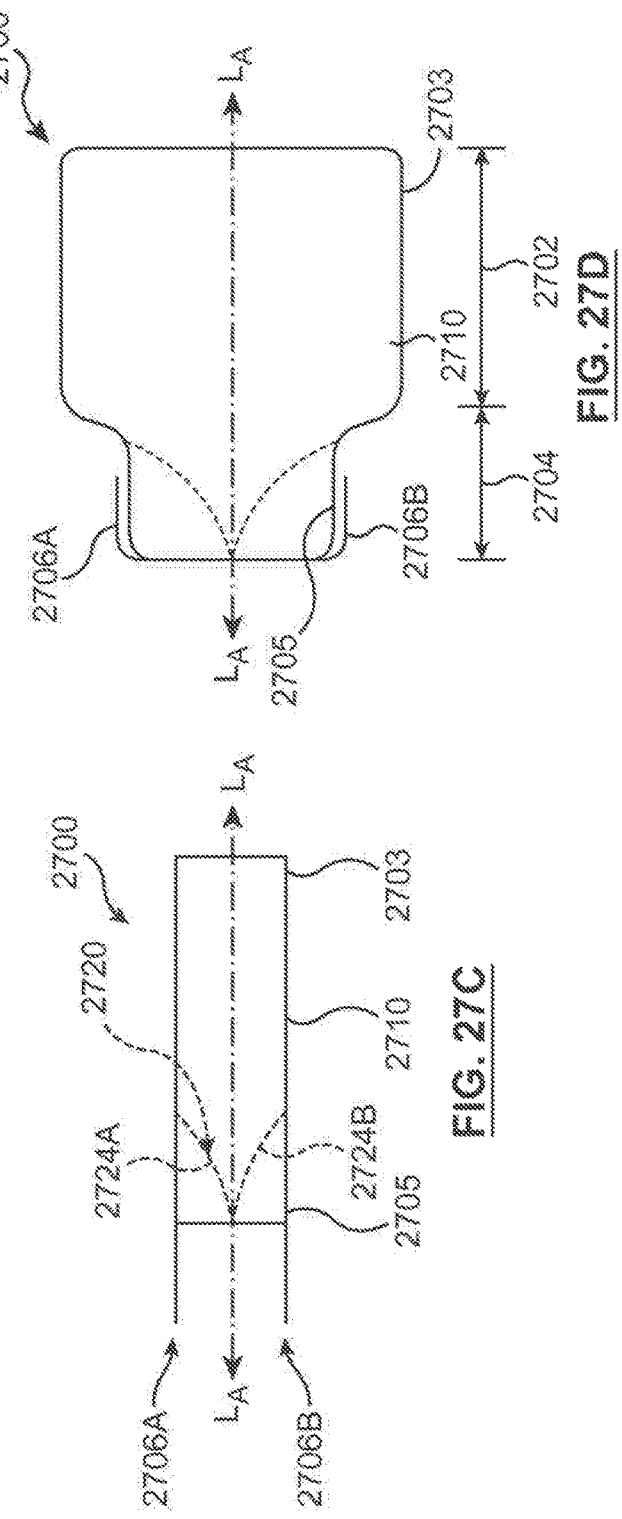

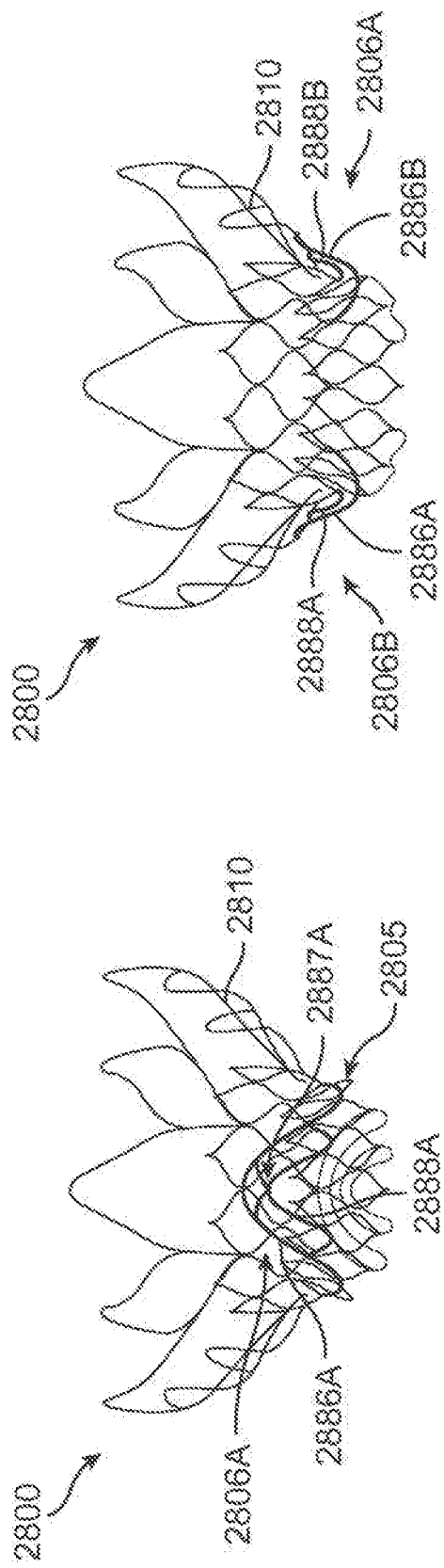
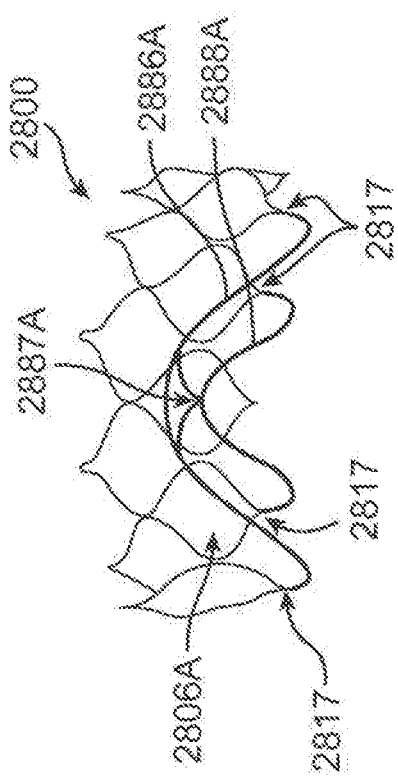
FIG. 28A
FIG. 28B
FIG. 28C

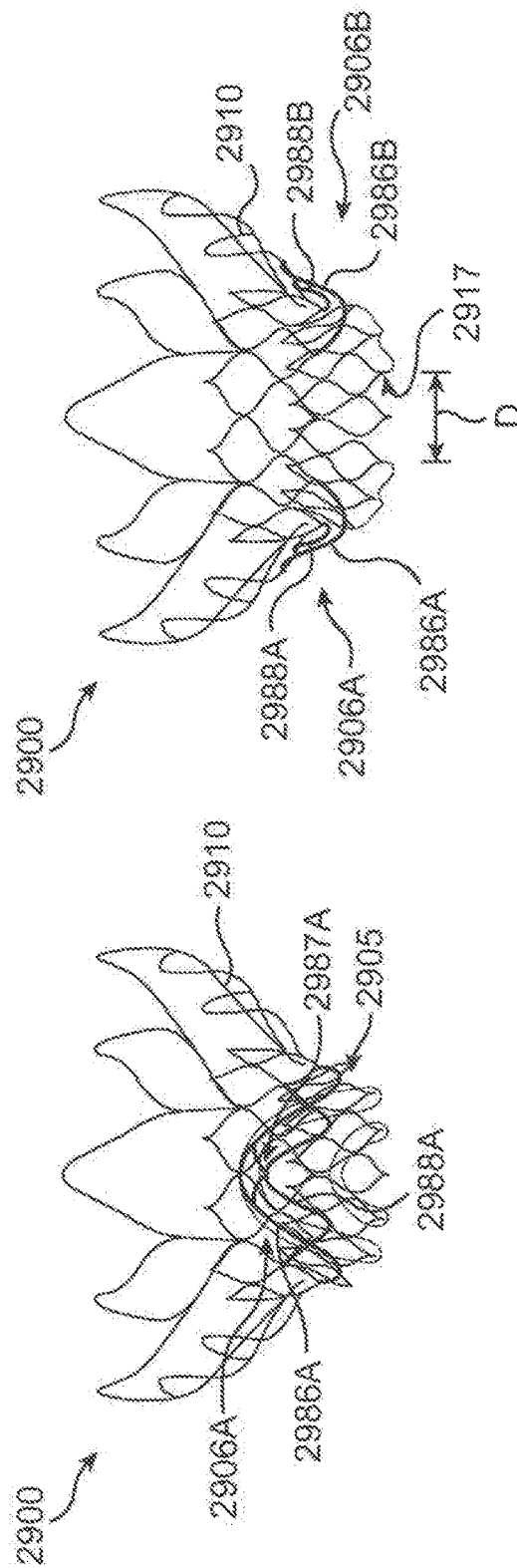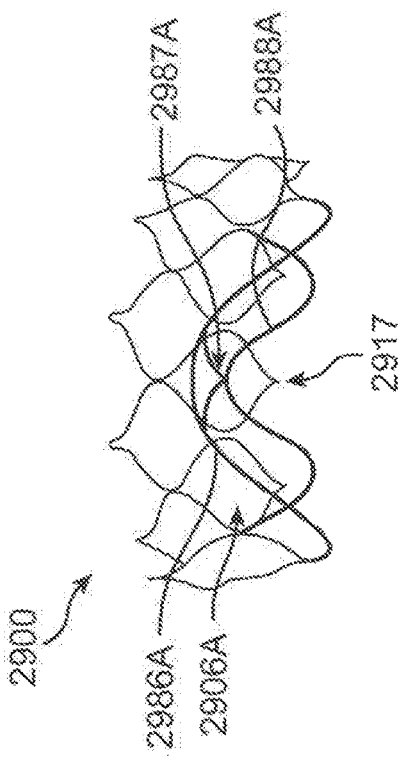

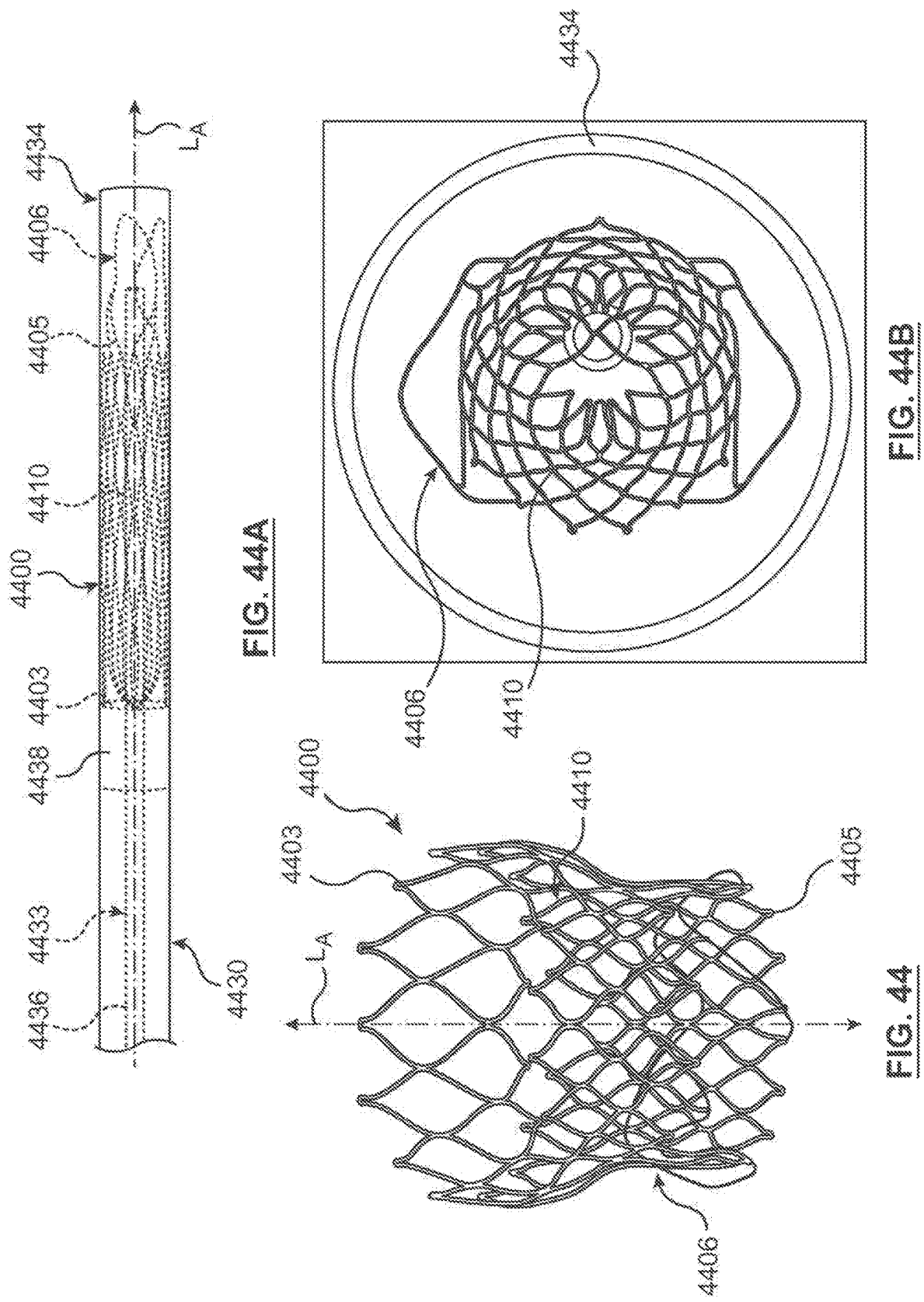

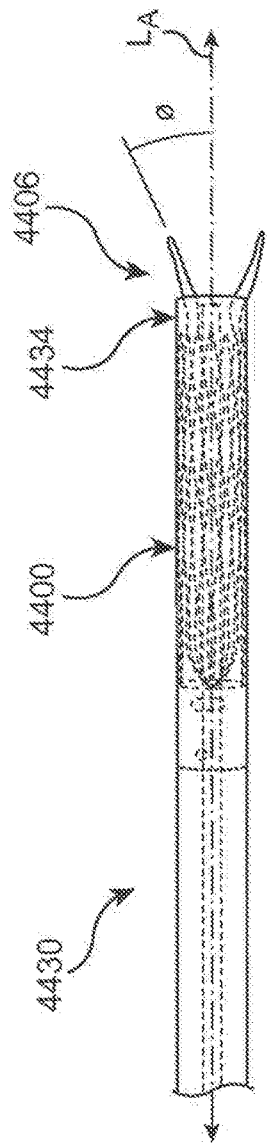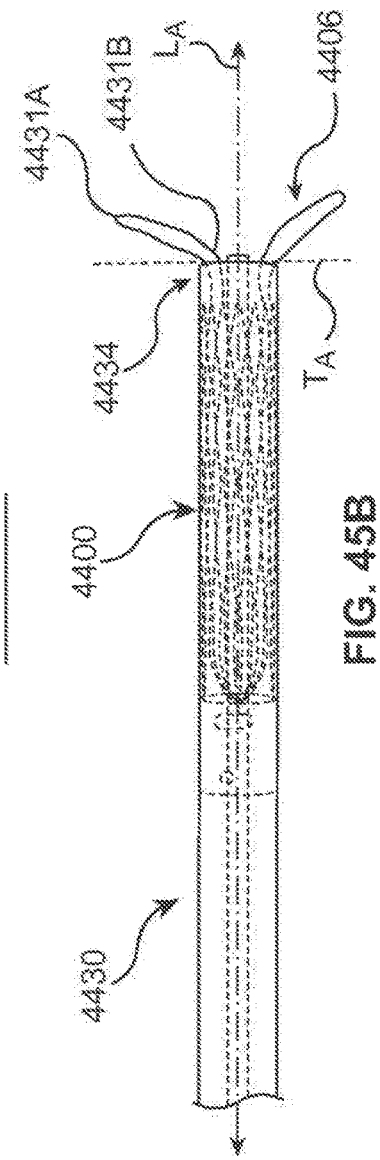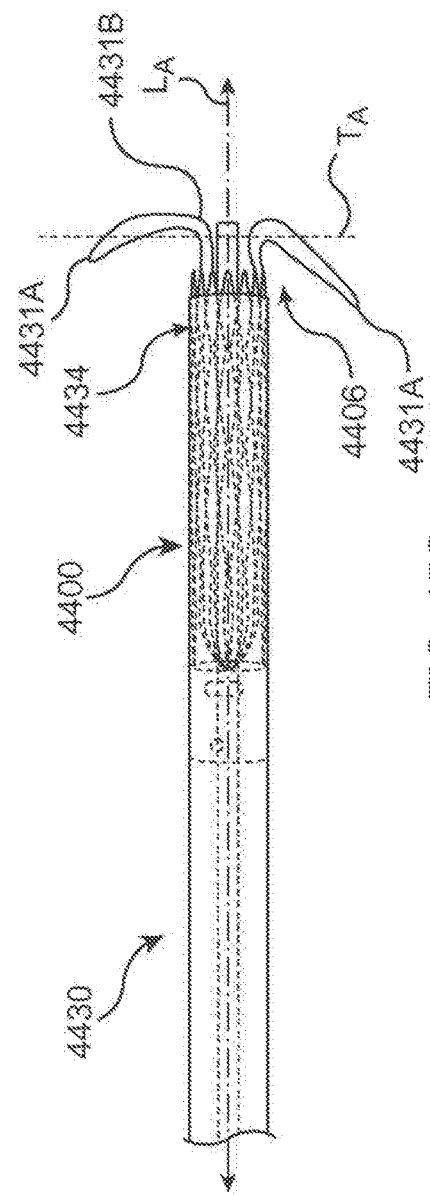

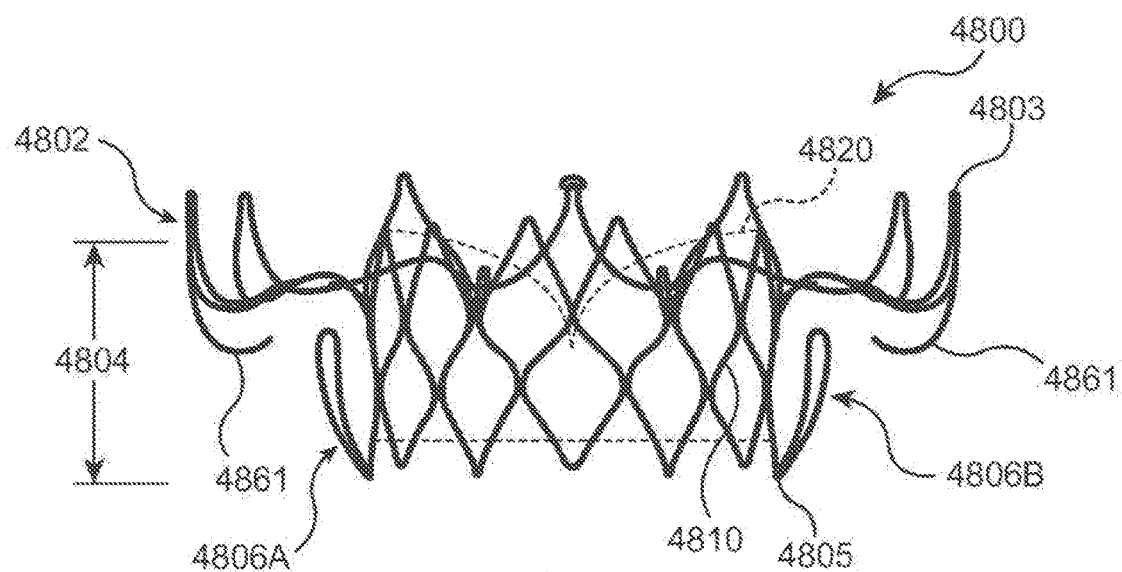
FIG. 48
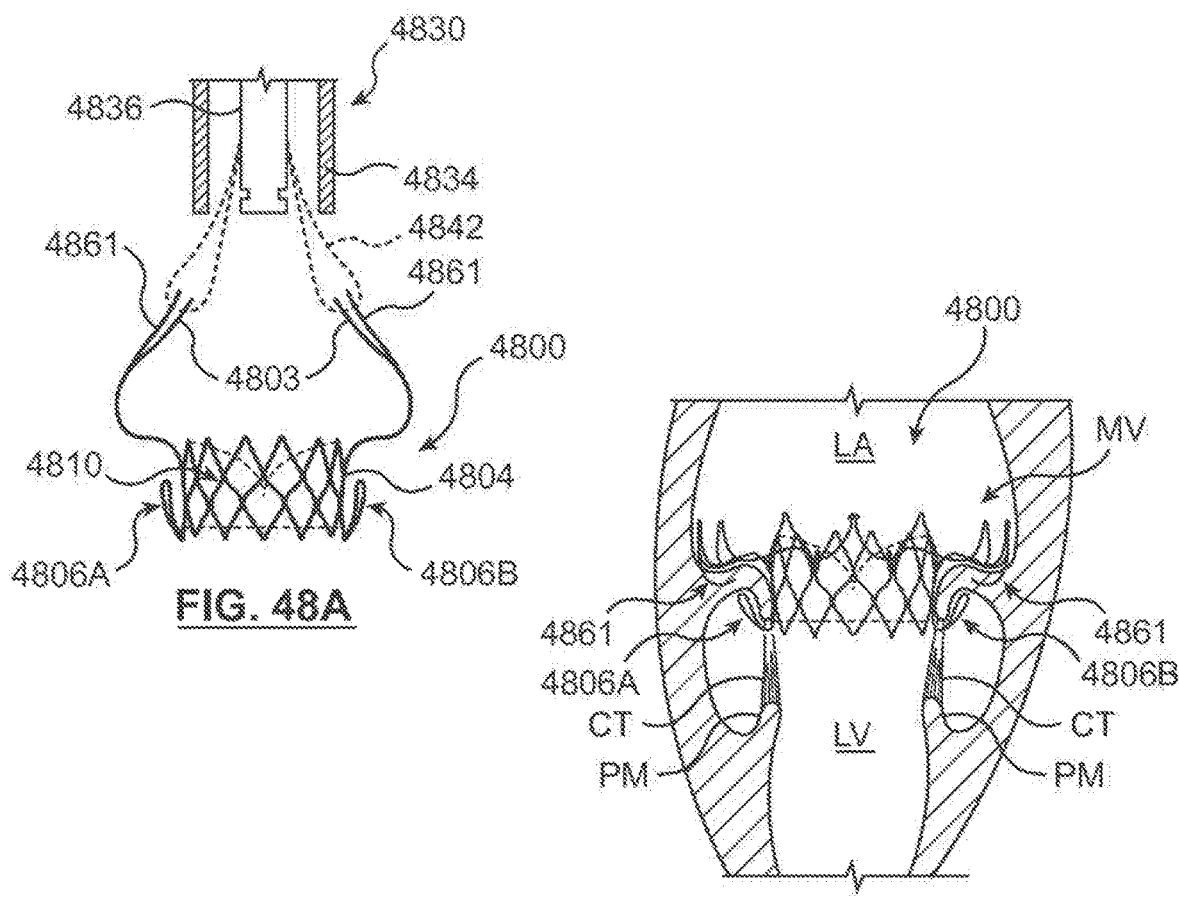
FIG. 48A
FIG. 48B

HEART VALVE PROSTHESIS

CROSS-REFERENCE TO RELATED APPLICATIONS

This application is a continuation of U.S. application Ser. No. 14/175,100, filed Feb. 7, 2014, which is a continuation-in-part of U.S. application Ser. No. 13/572,842 filed Aug. 13, 2012, now U.S. Pat. No. 9,468,525. U.S. application Ser. No. 14/175,100 is also a continuation-in-part of U.S. application Ser. No. 13/736,460 filed Jan. 8, 2013, now U.S. Pat. No. 9,232,995. U.S. application Ser. No. 14/175,100 also claimed the benefit of U.S. Provisional Appl. No. 61/822,616 filed May 13, 2013, and U.S. Provisional Appl. No. 61/895,106 filed Oct. 24, 2013, each of which is incorporated by reference herein in its entirety.

FIELD OF THE INVENTION

The present invention is directed to heart valve prosthesis and methods of percutaneously delivering heart valve prosthesis to a target location.

BACKGROUND OF THE INVENTION

A human heart includes four heart valves that determine the pathway of blood flow through the heart: the mitral valve, the tricuspid valve, the aortic valve, and the pulmonary valve. The mitral and tricuspid valves are atrioventricular valves, which are between the atria and the ventricles, while the aortic and pulmonary valves are semilunar valves, which are in the arteries leaving the heart. Ideally, native leaflets of a heart valve move apart from each other when the valve is in an open position, and meet or "coapt" when the valve is in a closed position. Problems that may develop with valves include stenosis in which a valve does not open properly, and/or insufficiency or regurgitation in which a valve does not close properly. Stenosis and insufficiency may occur concomitantly in the same valve. The effects of valvular dysfunction vary, with regurgitation or backflow typically having relatively severe physiological consequences to the patient.

Recently, prosthetic valves supported by stent structures that can be delivered percutaneously using a catheter-based delivery system have been developed for heart and venous valve replacement. These prosthetic valves may include either self-expanding or balloon-expandable stent structures with valve leaflets attached to the interior of the stent structure. The prosthetic valve can be reduced in diameter, by crimping onto a balloon catheter or by being contained within a sheath component of a delivery catheter, and advanced through the venous or arterial vasculature. Once the prosthetic valve is positioned at the treatment site, for instance within an incompetent native valve, the stent structure may be expanded to hold the prosthetic valve firmly in place. One example of a stented prosthetic valve is disclosed in U.S. Pat. No. 5,957,949 to Leonhardt et al., which is incorporated by reference herein in its entirety.

Due to the different physical characteristics of the mitral valve and its location within the heart, percutaneous implantation of a prosthetic heart valve in the mitral position has its own unique requirements for prosthetic valve structure and replacement methods. Accordingly, there is a continued need to provide improved mitral valve replacement devices and methods for replacing the mitral valve percutaneously.

BRIEF SUMMARY OF THE INVENTION

Certain embodiments in accordance herewith are directed to valve prosthesis for implantation into a native valve site of an individual, such as a native cardiac or heart valve site, that may include a valve body or component and a frame supporting the valve body. The frame may include an inlet portion configured to engage the floor of the outflow tract of the native heart atrium and restrict movement of the valve prosthesis in a downstream direction of blood flow at the valve site. In some embodiments in accordance herewith, the inlet portion can be substantially s-shaped.

Certain embodiments in accordance herewith are directed to valve prosthesis that include a valve body or component and a frame supporting the valve body, wherein the frame may include a central portion configured to fit securely within an annulus of the native valve site. The central portion may have an hourglass shape configured to pinch the annulus in order to provide axial fixation of the valve prosthesis within the valve site.

Certain embodiments in accordance herewith are directed to valve prosthesis that may include a valve body or component and a frame supporting the valve body, wherein the frame may include a central portion configured to fit securely within an annulus of the valve site, a support arm extending from the central portion and configured to extend over and secure a native valve leaflet, and/or a chordae engagement element extending from the support arm and configured to engage chordae of the valve site. The chordae engagement element may be configured to angle the chordae so that the chordae are stretched to restrict movement of the valve prosthesis in an upstream direction of blood flow at the valve site. The chordae engagement element may be configured to reduce bending of the chordae to reduce stress on the chordae during the cardiac cycle.

Certain embodiments in accordance herewith are directed to valve prosthesis that may include a valve body or component including prosthetic leaflets and a frame secured to the valve body, wherein the frame may include an inlet portion configured to engage the floor of an outflow tract of a native heart chamber and restrict movement of the frame in a downstream direction of blood flow at a valve site and may include a central portion connected to the inlet portion and configured to fit securely within a native valve annulus. Portions of the outflow end of the frame may be flared to provide a gap between an outflow end of the frame and an outflow end of the prosthetic leaflets when the prosthetic leaflets are fully opened.

Certain embodiments in accordance herewith relate to a heart valve prosthesis that may include a tubular stent or frame and a prosthetic valve component disposed within and secured to the frame. The frame may have a compressed configuration for delivery within a vasculature and a deployed configuration for deployment within or adjacent a native heart valve. In addition, at least two positioning elements or support arms may be coupled to a distal end of the frame to position and anchor the prosthesis within the native heart valve. Each support arm may include an outer U-shaped or V-shaped support arm and/or an inner U-shaped or V-shaped support arm that both distally extend from a distal end portion of the frame when the frame is in a compressed configuration. During deployment of the prosthesis, each support arm may bend radially outward and then towards an outer surface of the frame such that it translates more than ninety degrees from a compressed configuration to proximally extend from the distal end portion of the frame when the frame is in a deployed configuration.

According to another embodiment hereof, a heart valve prosthesis may include a tubular stent or frame and a prosthetic valve component disposed within and secured to the frame. The frame may have a compressed configuration for delivery within a vasculature and a deployed configuration for deployment within a native heart valve. In addition, at least two positioning elements or support arms may be coupled to a distal end portion of the frame to position and anchor the prosthesis within the native heart valve. Each support arm may be attached to the frame by two V-shaped connectors such that there are four connection points between each support arm and the frame. Each support arm may include a U-shaped or V-shaped support and may be approximately parallel with a longitudinal axis of the frame and may distally extend from a distal end portion of the frame when the frame is in a compressed configuration. During deployment of the prosthesis, each support arm may bend radially outward and then towards an outer surface of the frame such that the support arm translates between 135 degrees and 180 degrees from a compressed configuration to proximally extend from the distal end portion of the frame when the frame is in a deployed configuration.

Certain embodiments in accordance herewith relate to a method of percutaneously delivering and deploying a prosthetic valve within a native mitral valve. A prosthetic valve delivery system may be tracked through the vasculature to a native heart valve. The prosthetic valve delivery system may include a valve prosthesis having a tubular stent or frame, a prosthetic valve component disposed within and secured to the frame, and/or at least two positioning elements or support arms coupled to a distal end portion of the frame, the two support arms may each have an outer U-shaped or V-shaped support arm and/or an inner U-shaped or V-shaped support arm that may both distally extend from the distal end portion of the frame when the frame is in a compressed configuration for delivery. An outer sheath of the prosthetic valve delivery system may be retracted to expose the support arms, wherein each support arm may bend radially outward and then towards an outer surface of the frame such that it translates more than ninety degrees from the compressed configuration to proximally extend from a distal end portion of the frame and press against and/or trap a native heart valve portion and/or a heart structure in order to position the valve prosthesis. The outer sheath may be further retracted to expose the frame, thereby allowing a self-expandable frame portion to self-expand into a deployed configuration.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIGS. 5A and 5C are schematic side views, respectively, of a valve prosthesis having support arms or positioning elements according to an embodiment hereof, wherein the valve prosthesis is in a delivery or compressed configuration with the support arms or positioning elements distally extending from a distal end of the prosthesis.

FIGS. 5B and 5D are schematic side views, respectively, of the valve prosthesis as shown in FIGS. 5A and 5C, wherein the valve prosthesis is in an expanded or deployed configuration with the support arms or positioning elements proximally extending from a distal end of the prosthesis.

FIGS. 16A and 16B depict front or side views of the frame of FIG. 16 implanted in a native mitral valve site.

FIG. 22A depicts a patterned tube for forming a frame in accordance with an embodiment hereof laid flat for illustrative purposes.

FIG. 22B depicts a saddle shape formed when the frame of FIG. 22A is expanded.

FIGS. 26A-26F illustrates various configurations of generally U-shaped or V-shaped support arms according to embodiments hereof.

FIG. 27A and FIG. 27C are schematic side and top views, respectively, of a valve prosthesis having support arms with outer and inner U-shaped support arms according to an embodiment hereof, wherein the valve prosthesis is in a delivery or compressed configuration with positioning elements distally extending from a distal end of the prosthesis.

FIG. 27B and FIG. 27D are schematic side and top views, respectively, of the valve prosthesis of FIG. 27A and FIG. 27C, wherein the valve prosthesis is in an expanded or deployed configuration with positioning elements proximally extending from a distal end of the prosthesis.

FIGS. 28A and 28B illustrate two side views of a valve prosthesis having outer and inner U-shaped support arms according to an embodiment hereof, wherein the support arms extend from distalmost crowns of the valve prosthesis and the valve prosthesis is in an expanded or deployed configuration.

FIG. 28C is an enlarged view of a portion of the valve prosthesis of FIG. 28A.

FIGS. 29A and 29B illustrate two side views of a valve prosthesis having outer and inner U-shaped support arms according to an embodiment hereof, wherein the support arms extend from between the distalmost crowns of the valve prosthesis and the valve prosthesis is in an expanded or deployed configuration.

FIG. 29C is an enlarged view of a portion of the valve prosthesis of FIG. 29A.

FIG. 44 is a side view of a valve prosthesis in accordance with an embodiment hereof in an expanded or deployed configuration, before being loaded into and after release from its compressed configuration within a delivery system as shown in FIGS. 44A and 44B.

FIGS. 44A and 44B are side and end views, respectively, of the valve prosthesis of FIG. 44 in an unexpanded or delivery or compressed configuration, loaded into a delivery system in accordance with an embodiment hereof.

FIGS. 45A-45E illustrate side views of the valve prosthesis of FIG. 44 loaded within the delivery system of FIGS. 44A and 44B, wherein a sheath of the delivery system is progressively retracted to release the valve prosthesis therefrom.

FIG. 48 is a side view of a valve prosthesis having commissural anchors in accordance with an embodiment hereof in an expanded or deployed configuration.

FIG. 48A is a side sectional view of a distal portion of a delivery system with the valve prosthesis of FIG. 48 in a partially deployed configuration, in accordance with an embodiment hereof.

FIG. 48B illustrates the valve prosthesis of FIG. 48 implanted at a mitral valve target location within a heart in accordance with an embodiment hereof.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. As used herein with reference to an implanted valve prosthesis, the terms "distal", "outlet", and "outflow" are understood to mean downstream to the direction of blood flow, and the terms "proximal", "inlet", or "inflow" are understood to mean upstream to the direction of blood flow. In addition, as used herein, the terms "outward" or "outwardly" refer to a position radially away from a longitudinal axis of a frame of the valve prosthesis and the terms "inward" or "inwardly" refer to a position radially toward a longitudinal axis of the frame of the valve prosthesis. As well the terms "backward" or "backwardly" refer to the relative transition from a downstream position to an upstream position and the terms "forward" or "forwardly" refer to the relative transition from an upstream position to a downstream position.

The following detailed description is merely exemplary in nature and is not intended to limit the invention or the application and uses of the invention. Although the description of embodiments hereof are in the context of treatment of heart valves and particularly a mitral valve, the invention may also be adapted for use in other valve replacement procedures where it is deemed useful. Furthermore, there is no intention to be bound by any expressed or implied theory presented in the preceding technical field, background, brief summary or the following detailed description.

Figure 1:
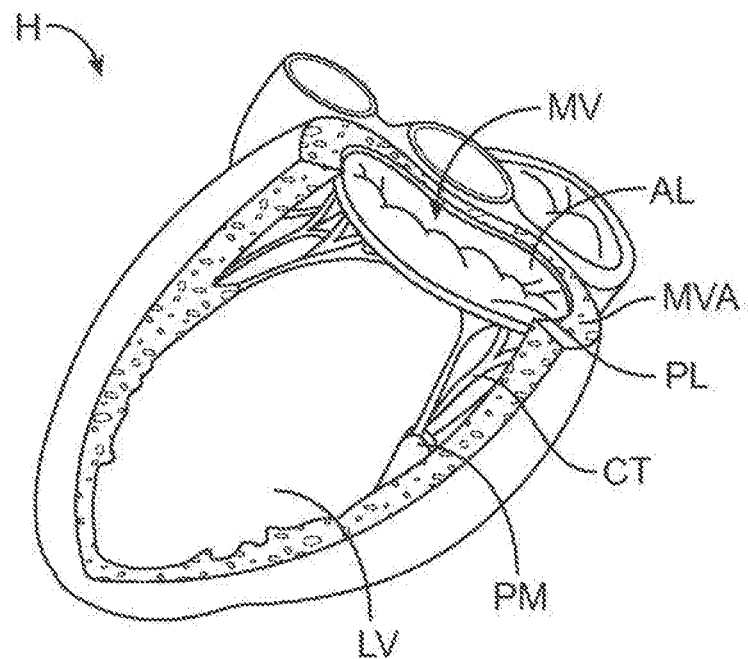
FIG. 1 is a perspective sectional view of a heart that depicts a mitral valve and various structural features related thereto.
Figure 1A:
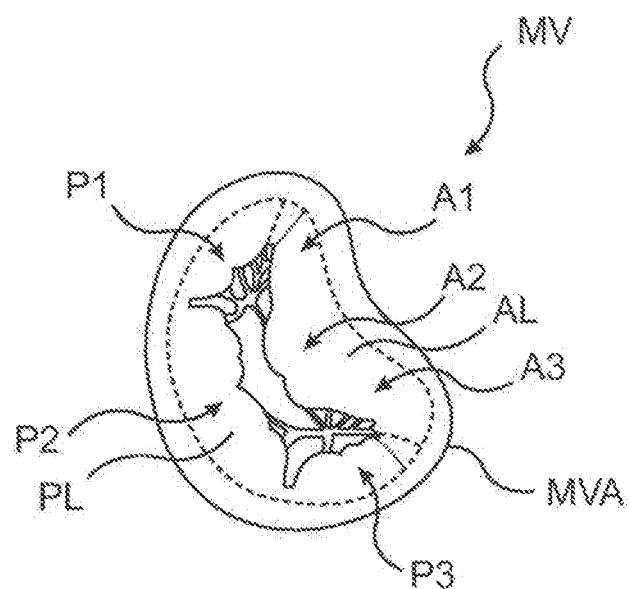
FIG. 1A is a superior view of the mitral valve shown in FIG. 1 isolated from the surrounding heart structure.

FIG. 1 is a perspective sectional view of a heart (H) that depicts a mitral valve (MV) and various structural features related thereto, with FIG. 1A being a superior view of the mitral valve isolated from surrounding heart structure. The mitral valve is found between the left atrium (not shown) and the left ventricle (LV) and is surrounded by and attached to a fibrous atrioventricular ring of the heart that may be more commonly referred to as the mitral valve annulus (MVA). As best shown in FIG. 1A, the mitral valve annulus may be considered to have a D-shape rather than being circular or elliptical. The mitral valve includes anterior and posterior leaflets (AL, PL) that open during diastole to allow blood flow from the left atrium to the left ventricle. During ventricular systole, the anterior and posterior leaflets close to prevent backflow to the left atrium while the mitral valve annulus contracts and reduces its surface area to help provide complete closure of the leaflets. The anterior and posterior leaflets are attached to papillary muscles (PM) within the left ventricle by way of the chordae tendinae (CT), which are strong, fibrous strings attached to the leaflets of the heart on the ventricular side. When the anterior and posterior leaflets of the mitral valve close, the chordae tendinae are tensioned to prevent the leaflets from swinging back into the atrium cavity.

Due to the unique shape of a native mitral valve and the functionality of the structure associated therewith that can cause axial movement of a prosthetic mitral valve during the cardiac cycle, i.e., axial movement that may be caused by the cyclic tensioning of the chordae tendinae and/or contraction of the D-shaped mitral valve annulus during ventricular systole, a mitral valve prosthesis according to embodiments hereof includes a frame having a flexible, anatomically conforming inflow portion that is designed to maintain sealing with the atrial surface surrounding the mitral valve during the cardiac cycle. In order to ensure circumferential sealing of a mitral valve prosthesis to the heart, the inflow portion of the prosthesis may comprise a larger diameter than the largest diameter of the native mitral valve annulus.

Figure 2:
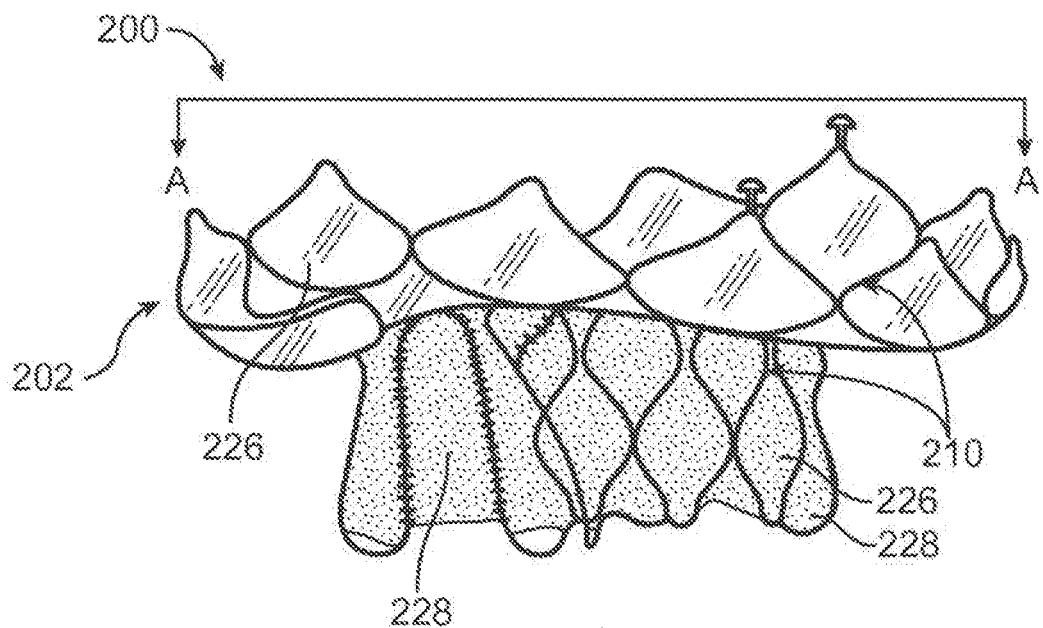
FIG. 2 is a side view of a mitral valve prosthesis in accordance with an embodiment hereof shown in a deployed configuration.
Figure 2A:
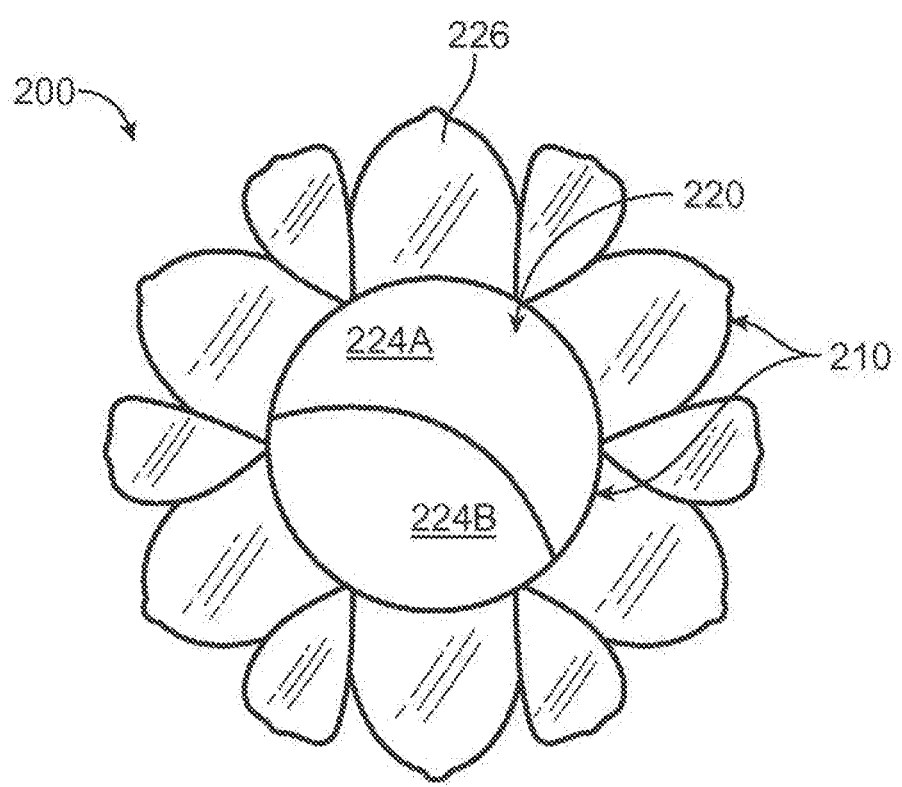
FIG. 2A is a top view of an inflow area of the mitral valve prosthesis of FIG. 2 taken in the direction of line A-A therein.

FIG. 2 is a side view of a heart or mitral valve prosthesis 200 in accordance with an embodiment hereof shown in a deployed configuration, with FIG. 2A being a top view of an inflow area of heart valve prosthesis 200 taken in the direction of line A-A in FIG. 2. Heart valve prosthesis 200 includes a valve body or component 220 attached within an interior of a frame or support structure 210, which also may be considered a stent or stent-like framework or structure. Frame 210 has an inflow portion 202 that may be described as having a hyperparabolic or saddle shape or profile such that the inflow end of frame 210 is non-planar. Stated another way, diametrically-opposed lateral portions of a peripheral or radial edge of inflow portion 202 curve downward from raised diametrically-opposed central portions of the peripheral or radial edge of inflow portion 202. A normal, non-diseased native mitral valve annulus has a hyperparabolic or saddle shape. In an embodiment, inflow portion 202 may comprise a hyperparabolic or saddle shape that matches, corresponds to or is similar to the saddle shape of a native mitral valve annulus. In an embodiment, valve component 220 is a one-way bicuspid replacement valve having first and second prosthetic valve leaflets 224A, 224B, which is capable of blocking flow in one direction to regulate flow therethrough. In embodiments hereof, prosthetic valve components may include valve leaflets to form a bicuspid, tricuspid, or tubular replacement valve, each of which is capable of blocking flow in one direction to regulate flow therethrough. Valve component 220 and/or valve leaflets 224A, 224B thereof are sutured or otherwise securely and sealingly attached to an interior surface of frame 210 and/or to graft material 226, which encloses or lines various portions of frame 210 as would be known to one of ordinary skill in the art of prosthetic tissue valve construction. In embodiments in accordance herewith and as described in more detail herein, graft material 226 secured to frame 210 within an inflow area of prosthesis 200 aids in sealing. Graft material 226 may comprise one or more pieces of material, such as a single skirt of material, attached or coupled, such as sewn, to an inner portion of the frame, one or more pieces of material, such as a single skirt of material, attached or coupled, such as sewn, to an outer portion of the frame, one or more pieces of material, such as a two-layer skirt of material, attached or coupled, such as sewn, to both an inner portion of the frame and/or an outer portion of the frame and/or any combination thereof. The graft material and/or skirts may be designed for different applications or uses. For example, an inner skirt material may be chosen so as to be impermeable to blood flow or other factors while an outer skirt material may be chosen so as to interact with heart tissue in a manner that may encourage cellular or tissue growth within and/or on the material and/or may prevent the passage of blood between the valve prosthesis and heart tissue. Graft material 226 secured to frame 210 proximate an outflow area of prosthesis 200 may provide a chordae engagement member, which may comprise a tent-like or hammock-like structure 228. The chordae engagement member may function to reduce or eliminate relative motion between frame 210 and the chordae tendinae when prosthesis 200 is implanted within a native mitral valve.

Figure 3:
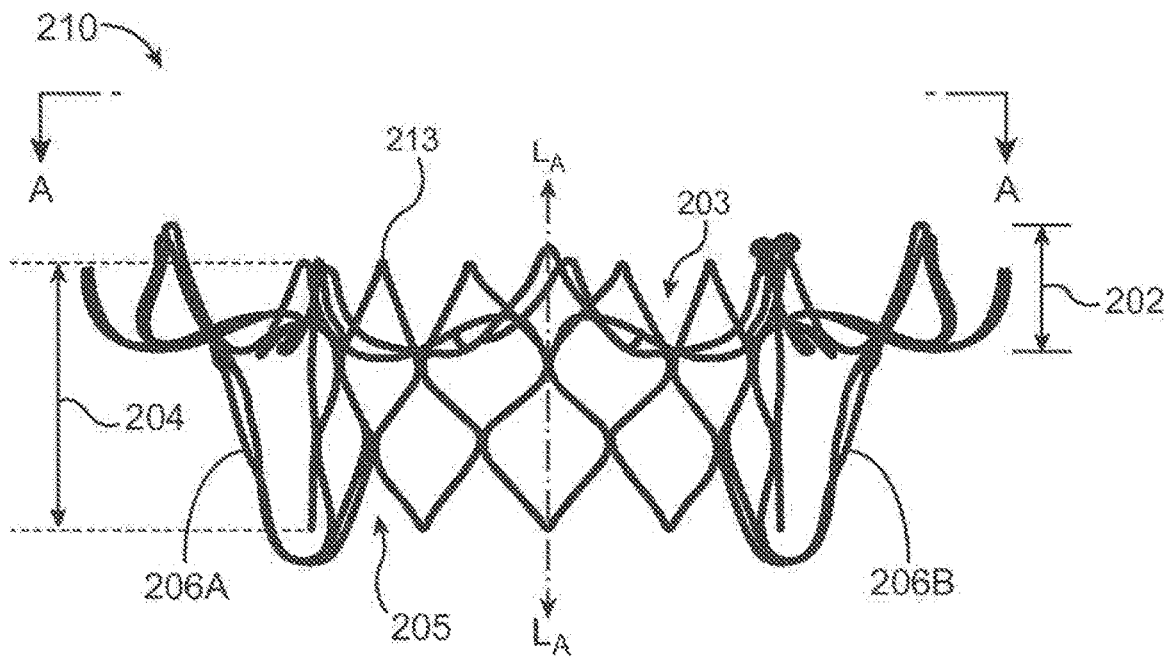
FIG. 3 is a side view of a frame of the mitral valve prosthesis of FIG. 2.
Figures 3A, 3B:
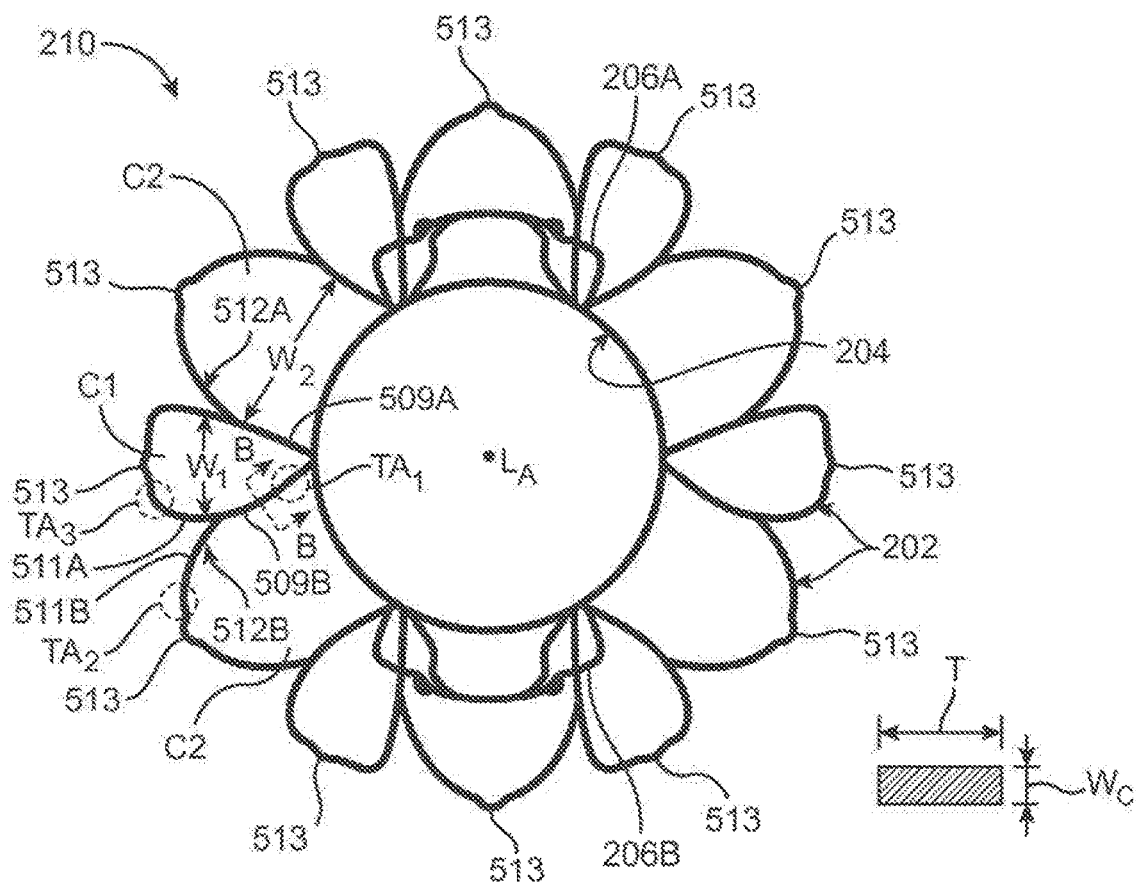
FIG. 3A is a top or inflow view of the frame of FIG. 3 taken in the direction of line A-A therein.
FIG. 3B is a cross-sectional view of a strut of the frame of FIG. 3 taken in the direction of line B-B in FIG. 3A.
Figure 4:
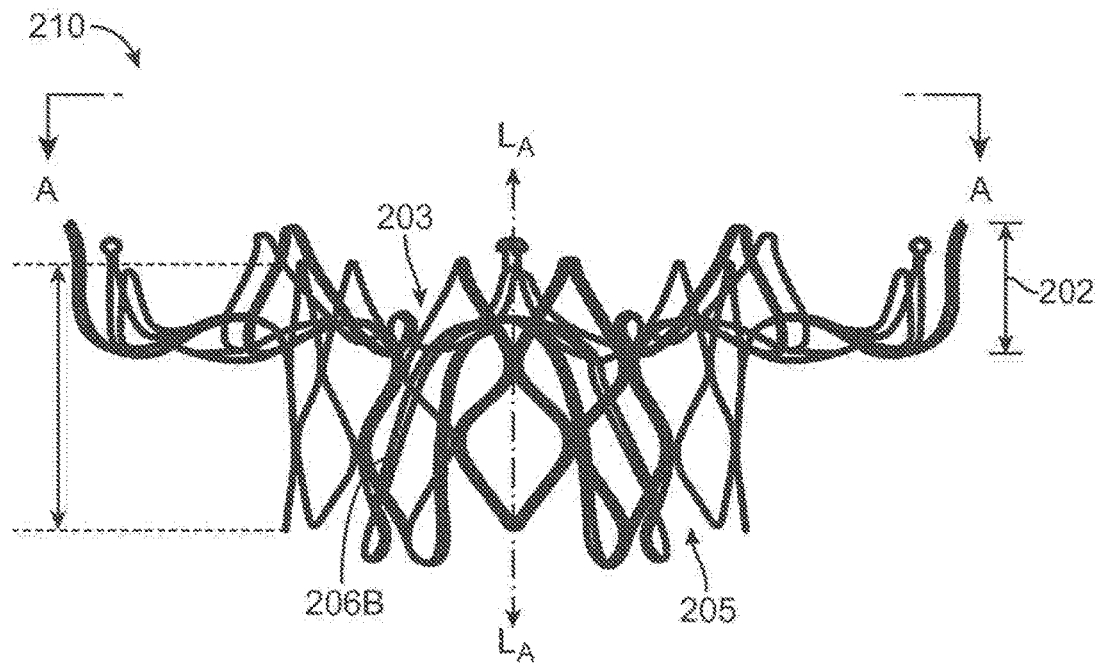
FIG. 4 is a side view of the frame of FIG. 3 rotated 90° about a longitudinal axis $L_A$ thereof from the orientation shown in FIG. 3.
Figure 4A:
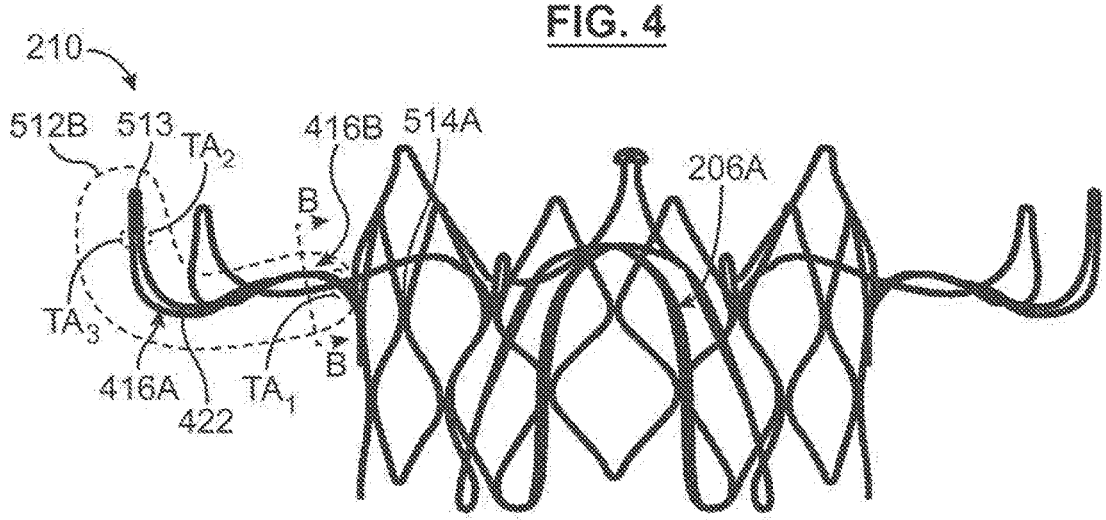
FIG. 4A is a sectional view of the frame of FIG. 4 taken along line A-A therein.
Figure 4B:
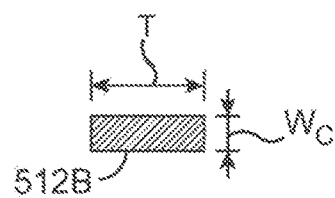
FIG. 4B is a cross-sectional view of a strut of the frame of FIG. 4A taken along line B-B therein.

FIGS. 3, 3A, 4 and 4A illustrate frame 210 in a deployed configuration removed from a remainder of prosthesis 200. FIGS. 3 and 4 are side views of frame 210, with FIG. 4 showing frame 210 rotated 90° about a longitudinal axis $L_A$ thereof from the orientation shown in FIG. 3. FIG. 3A is a top or inflow view of frame 210 taken in the direction of line A-A in FIG. 3 and FIG. 3B is a cross-sectional view of a strut 512B of frame 210 taken along line B-B in FIG. 3A. FIG. 4A is a sectional view of frame 210 taken along line A-A in FIG. 4 and FIG. 4B is a cross-sectional view of strut 512B of frame 210 taken along line B-B in FIG. 4A.

Frame 210 may be a unitary structure that defines a proximal or inflow portion 202, a central or valve-retaining tubular portion 204 and a pair of support arms or positioning elements 206A, 206B. In some embodiments hereof, proximal or inflow portion 202 may be considered an atrial segment of valve prosthesis 200 and central or valve-retaining tubular portion 204 may be considered a ventricular or annulus segment of valve prosthesis 200 without departing from the scope hereof. In the deployed configuration of frame 210, inflow portion 202 outwardly extends from a first, proximal or inflow end 203 of valve-retaining tubular portion 204 and support arms 206A, 206B backwardly extend from circumferentially spaced apart locations of an opposing second, distal or outflow end 205 of valve-retaining tubular portion 204. When prosthesis 200 is implanted within a native mitral valve, inflow portion 202 of frame 210 is configured to engage an area of the left atrium that surrounds the native mitral valve, valve-retaining tubular portion 204 of frame 210 is configured to axially extend through the native mitral valve and thusly situates valve component 220 within the mitral valve annulus, and support arms 206A, 206B are configured to capture respective valve leaflets of the mitral valve and to secure them within the left ventricle without obstructing the outflow area of prosthesis 200 or the left ventricular outflow tract. Leaflets of a valve component (not shown) may attach to upstream crowns 213 of valve-retaining tubular portion 204 to extend into atrial or inflow portion 202 (and into the left atrium when in situ) such that the valve component is not solely located on or within the outflow or ventricular portion 204 (and into the left ventricle in situ). By locating a portion of the valve leaflets in the left atrium, the required length of central or valve-retaining tubular portion 204 is minimized and the length of frame 210 that protrudes into the left ventricle may be reduced. The operation of, and various alternate embodiments for, support arms 206A, 206B will be described in more detail herein.

In accordance with some embodiments hereof, the frames or support structures for valve prosthesis in accordance herewith have a generally tubular expandable body with a stepped profile. FIGS. 5A, 5B, 5C, and 5D show simplified views of a frame or stent structure 310 in accordance with an embodiment hereof having a stepped-down profile as it extends between a proximal or inflow end 303 and a distal or outflow end 305, with FIGS. 5A and 5C showing alternate side views respectively of frame 310 in a compressed or delivery configuration and with FIGS. 5B and 5D showing alternate side views respectively of frame 310 in an expanded or deployed configuration. More particularly, FIGS. 5C and 5D are a side view of the frame as shown in FIGS. 5A and 5B rotated 90° about a longitudinal axis $L_A$ thereof from the orientation shown in FIGS. 5A and 5B. Frame 310 includes a central or ventricular segment 304 having an expanded diameter $D_V$ and a proximal, inflow or atrial segment 302 having an expanded diameter $D_A$ which is greater than diameter $D_V$. When placed at a native mitral valve target site, central or ventricular segment 304 extends into the left ventricle and inflow or atrial segment 302 extends into the left atrium. Each segment of frame or stent 310, i.e., central segment 304 and/or inflow segment 302, may be designed with a number of different configurations and sizes to meet the different requirements of the locations in which it may be implanted. As well each segment of frame or stent 310, i.e., central segment 304 and/or inflow segment 302, may have the same or different cross-section which may be for example circular, ellipsoidal, rectangular, hexagonal, square, or other polygonal shape.

Frames or support structures in accordance with some embodiments hereof may be a unitary integral structure formed from a single tubular component and, although not shown in detail in the embodiment of FIGS. 5A-5D, include a lattice or stent-like configuration that may be produced by machining or laser cutting the design from a metal tube, as is commonly employed in the manufacturing of stents. Any frame for valve prosthesis in accordance with embodiments hereof may be laser cut from a solid tubular component of a self-expanding material such that the stent is an integral, one-piece structure that does not include separate components that are joined together. A single integral structure allows the frame to be crimped or compressed to a low delivery profile. Alternatively, rather than being laser cut, frames in accordance with embodiments hereof may be formed using any of a number of different methods that would be apparent to one of ordinary skill in the art such as connecting individual elements together, such as annular stent struts, chemical etching, or another method of forming a desired shape from a solid component.

Figure 6:
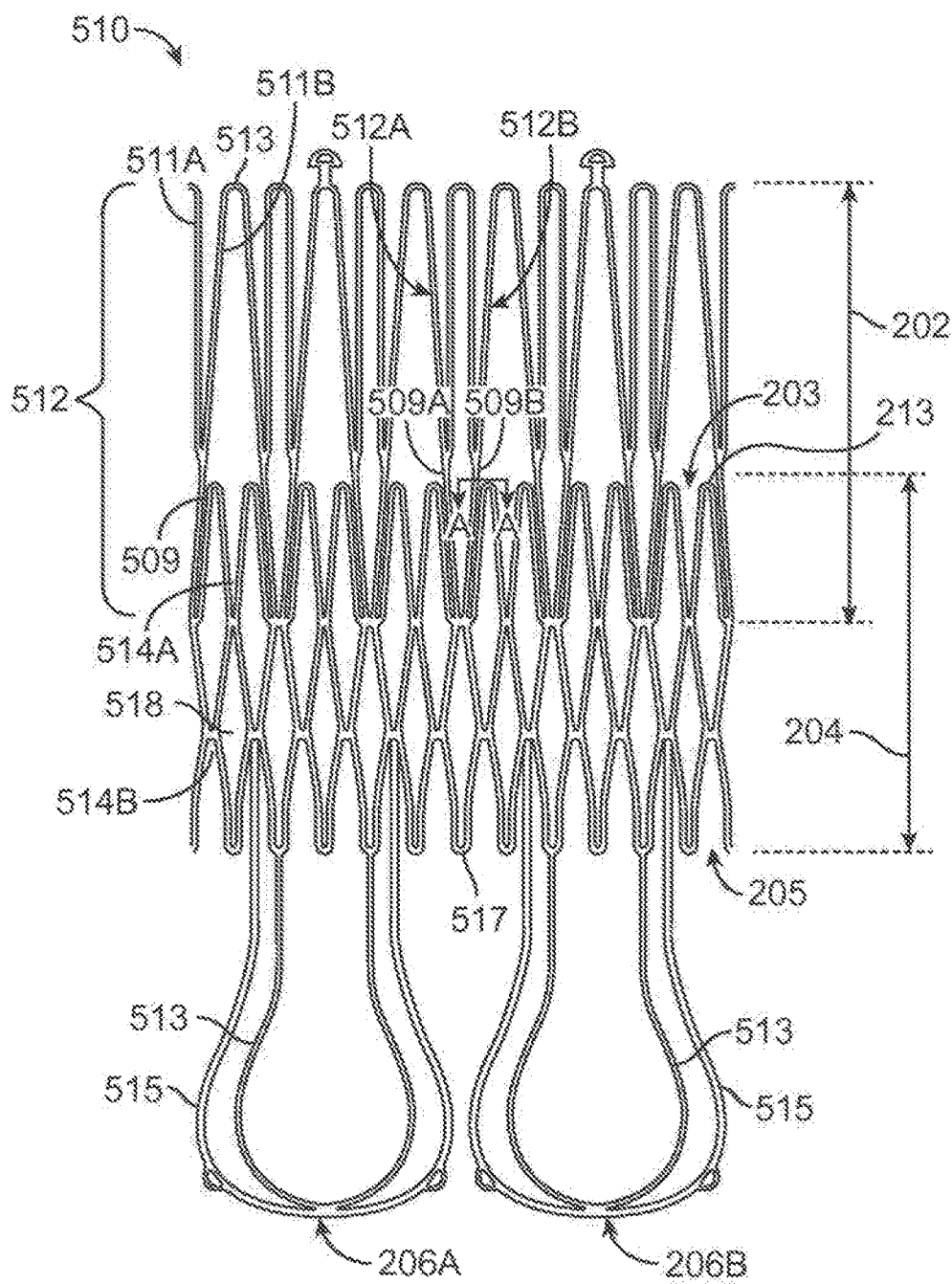
FIG. 6 depicts a patterned tube for forming the frame of FIGS. 3, 3A, 4 and 4A laid flat for illustrative purposes.

In one method of forming a frame in accordance herewith, and more particularly in an initial step in manufacturing frame 210, a tube 510 of a suitable material is etched, cut or otherwise machined to have the pattern depicted in FIG. 6. FIG. 6 depicts for illustrative purposes only patterned tube 510 laid flat so that the cut structures of inflow portion 202, valve-retaining tubular portion 204 and support arms 206A, 206B may be more readily identified and described. Valve-retaining tubular portion 204 has a stent-like framework that defines diamond-shaped openings 518 and a series of upstream valleys 514A and downstream valleys 514B. Support arms 206A, 206B are formed from inner and outer looped struts 513, 515 with the outer looped struts 515 forming outer support arms extending from spaced apart valleys 514B of valve-retaining tubular portion 204 and with the inner looped struts 513 forming inner support arms extending from spaced apart downstream peaks, crowns or apexes 517 of valve-retaining tubular portion 204. In another embodiment in accordance herewith, tube 510 may be cut into a pattern such that frame 210 is formed to have one or more support arms as described with reference to any of the other embodiments herein.

Figure 6A:
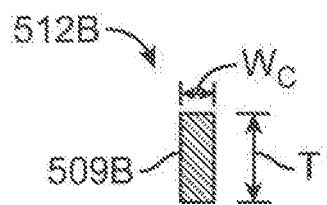
FIG. 6A is a cross-sectional view of the patterned tube of FIG. 6 taken along line A-A therein.

In one embodiment, inflow portion 202 is formed from a plurality of struts 512 having a cut width We that may be less than a thickness T thereof, as shown in FIG. 6A which is a cross-sectional view of strut 512B taken along line A-A in FIG. 6. Each strut 512 defines a base segment 509 and divergent first and second branch segments 511A, 511B. Accordingly, strut 512 may be considered to have a Y-shaped cut pattern. Base segments 509 of a respective pair of struts 512, for instance base segments 509A, 509B of struts 512A, 512B, extend from every other valley 514 at inflow end 203 of valve-retaining tubular portion 204. A plurality of crowns 513 are formed between first and second branch segments 511A, 511B of adjacent struts 512. Crowns 513 form radially outward ends of inflow portion 202 of frame 210, as shown in FIG. 3A. Circumferentially adjacent crowns 513 are not directly connected to each other and thereby provide inflow portion 202 with flexibility. In embodiments hereof, the geometry of the cut pattern, material properties, and/or the shaping processes may be selected to provide increased or decreased flexibility and/or to improve the structural integrity of the prosthesis.

Figure 7:
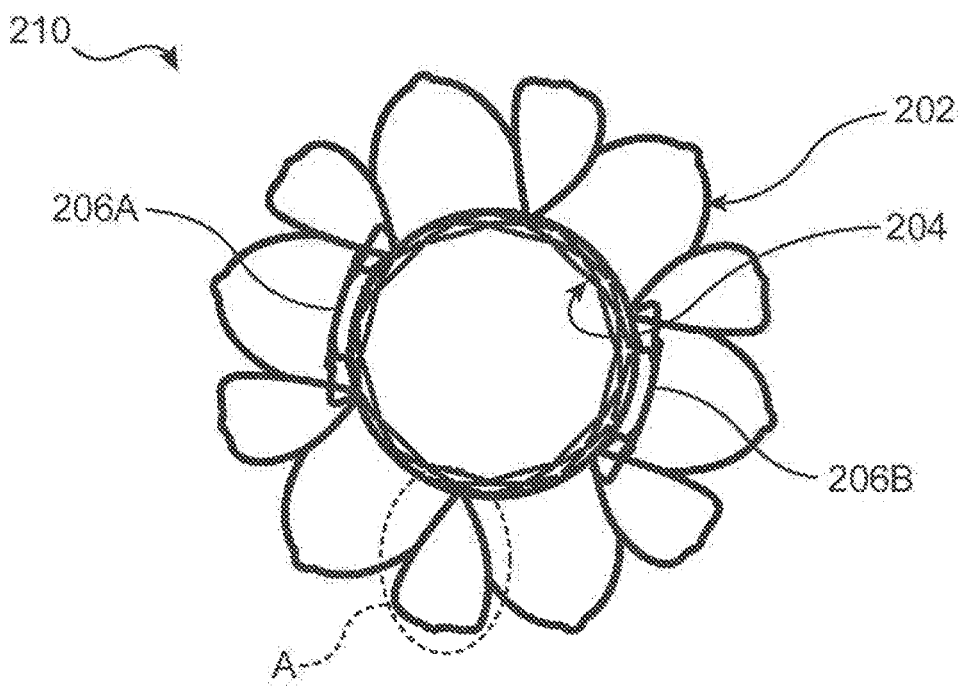
FIG. 7 is a top view of an inflow area of a frame in accordance with the embodiment of FIGS. 3, 3A, 4 and 4A.
Figure 7A:
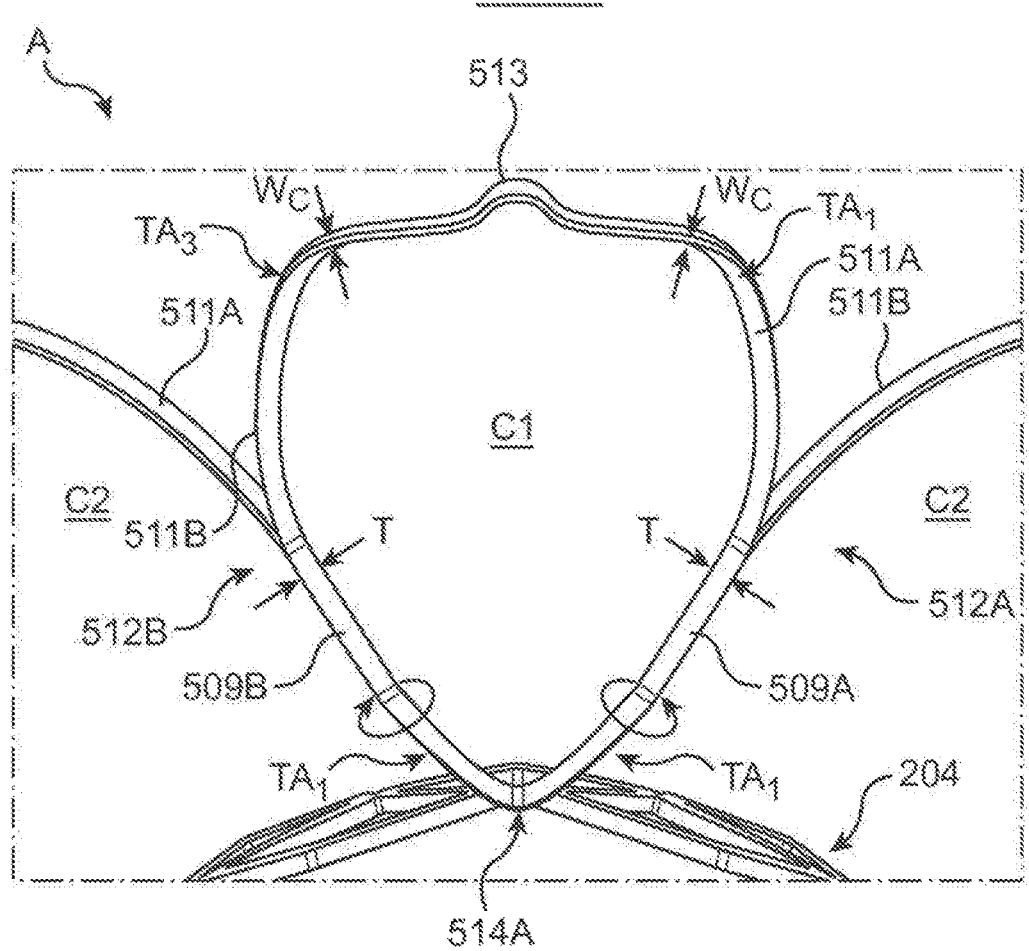
FIG. 7A is an enlarged view of an encircled area A of FIG. 7.
Figure 8:
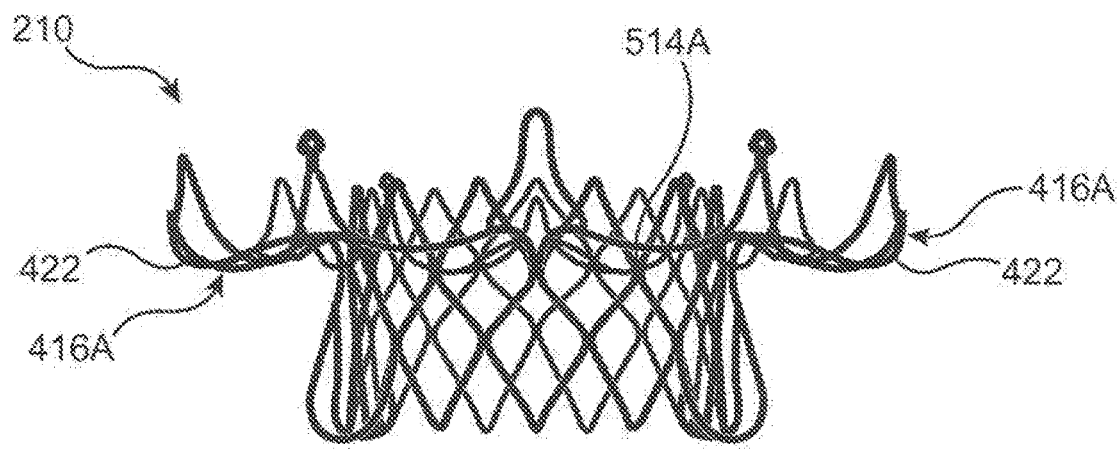
FIG. 8 is a side view of a frame in accordance with the embodiment of FIGS. 3, 3A, 4 and 4A.

In one embodiment, subsequent processing steps are performed on patterned tube 510 in order to form frame 210 in its expanded state as shown in FIGS. 3, 3A, 4 and 4A, with FIGS. 7, 7A and 8 being various views of a frame 210 in accordance with the embodiment of FIGS. 3, 3A, 4 and 4A. In one or more processing steps, patterned tube 510 may be radially expanded to set a tubular shape and expanded diameter of valve-retaining tubular portion 204 that is suitable for receiving valve component 220 therein. In one or more additional processing steps, support arms 206A, 206B may be rotated outward and backward relative to outflow end 205 of valve-retaining tubular portion 204 and heat treated to set a shape thereof. In one or more additional processing steps, struts 512 of inflow portion 202 of patterned tube 510 may be made to outwardly extend from inflow end 203 of valve-retaining tubular portion 204 and subjected to a forming process to have a substantially s-shaped profile, as best seen in FIG. 4A. Somewhat counter-intuitively, a first bend 416A and an opposing second bend 416B that form the substantially s-shaped profile of strut 512 may be bent or curved over the cut width $W_C$ of the strut, as shown in FIGS. 3B and 4B, rather than being bent or curved over thickness T of the strut. First and second bends 416A, 416B of s-shaped strut 512 may be able to be formed in this manner due to one or more twisted areas $TA_1$, $TA_2$, $TA_3$ of strut 512 that occur during formation of inflow portion 202. More particularly with reference to FIGS. 3A and 4A, base segment 509 of each strut 512 may have a twisted area $TA_1$ near or adjacent to where the respective base segment 509 outwardly extends from inflow end 203 of valve-retaining tubular portion 204. Although not intending to be bound by theory, twisted area $TA_1$ turns cut width $W_C$ of the respective strut 512 approximately 90 degrees from the cut pattern shown in FIG. 6 such that the narrower portion $W_C$ of the respective strut 512 is subjected to the forming process that creates first and second bends 416A, 416B. As well with reference to FIG. 3A, first and second branch segments 511A, 511B of each strut 512 may have twisted areas $TA_2$, $TA_3$, respectively, near or adjacent to their respective crowns 513. Although not intending to be bound by theory, twisted areas $TA_2$, $TA_3$ turn cut width $W_C$ of the respective strut 512 in a direction opposite of twisted area $TA_1$ to return cut width $W_C$ to a similar orientation as shown in the cut pattern in FIG. 6, which results in cut width We facing inward and outward along at least a portion of first and second branch segments 511A, 511B of struts 512 and through crowns 513 of inflow portion 202.

In the embodiment of frame 210 shown in FIGS. 3, 3A, 4 and 4A, inflow portion 202 may be described as having a ring of alternating openings or cells C1, C2 that are formed between respective portions of struts 512 and crowns 513. Cells C1, C2 have widths $W_1$, $W_2$, respectively, with width $W_1$ of cell C1 being less than width $W_2$ of cell C2, as best shown in FIG. 3A. Although not intending to be bound by theory, the alternating size of cells C1, C2 contributes to base segments 509 that emanate from a common valley 514 of tubular portion 204 having twisted areas $TA_1$ that twist or turn away from each other, or in other words twist in opposite directions from each other. For example with reference the pair of base segments 509A, 509B shown in FIGS. 3A, 7 and 7A, twisted area $TA_1$ of base segment 509A will turn strut 512A counterclockwise toward its adjacent cell C2, such that twisted area $TA_1$ of base segment 509A may be considered to have a left-hand twist, and twisted area $TA_1$ of base segment 509B will turn strut 512B clockwise toward its adjacent cell C2, such that twisted area $TA_1$ of base segment 509B may be considered to have a right-hand twist.

In one embodiment, the s-shaped struts 512 that form inflow portion 202 of frame 210 act similarly to cantilever beams when interacting with the anatomy of the heart as a supporting and sealing structure of prosthesis 200. During the pressure changes and cyclical contractions of the heart, the s-shaped struts 512 are able to deflect while maintaining an axial force against the atrial surface of the heart that is sufficient for sealing and the prevention of paravalvular leakage between the frame and tissue surface. As well the combination of twisted areas $TA_1$, $TA_2$, $TA_3$ and s-shape of struts 512 of inflow portion 202 permit the inflow area of prosthesis 200 to readily deflect, flex and/or move during the cardiac cycle while also maintaining sufficient axial stiffness to provide sealing contact with the atrial surface that surrounds the implanted prosthesis. In addition, the twisted areas $TA_1$, $TA_2$, $TA_3$ of s-shaped struts 512 reduce strain and improve the structural integrity of frame 210, and more particularly the structural integrity of inflow portion 202 thereof.

Figure 9:
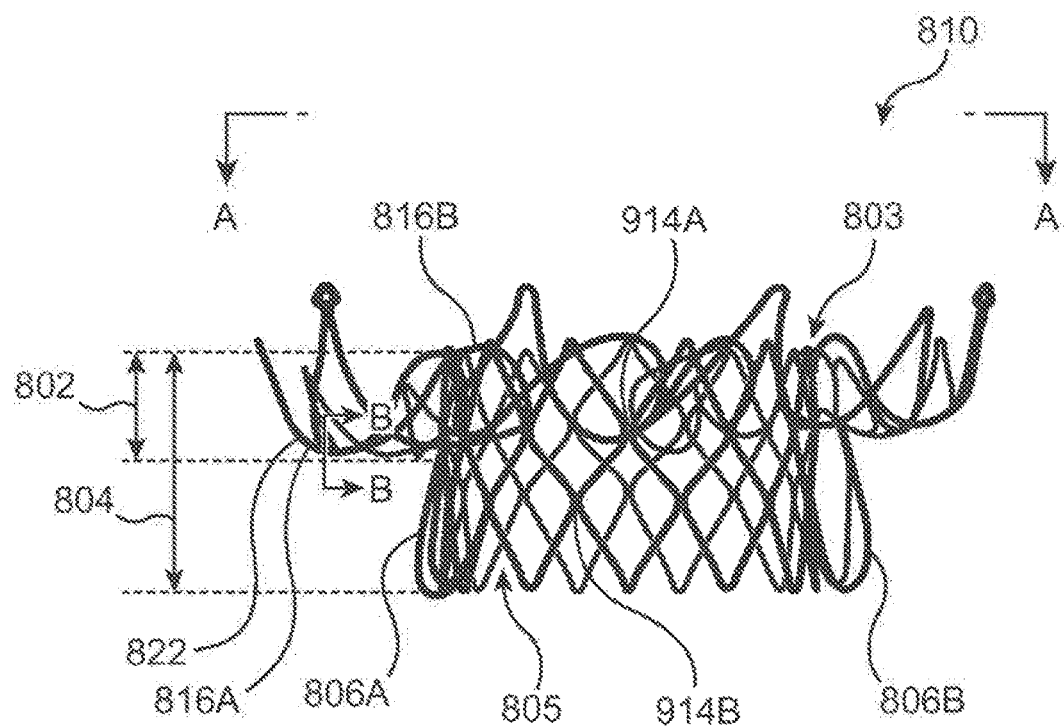
FIG. 9 is a side view of a frame in accordance with another embodiment hereof.
Figure 9A:
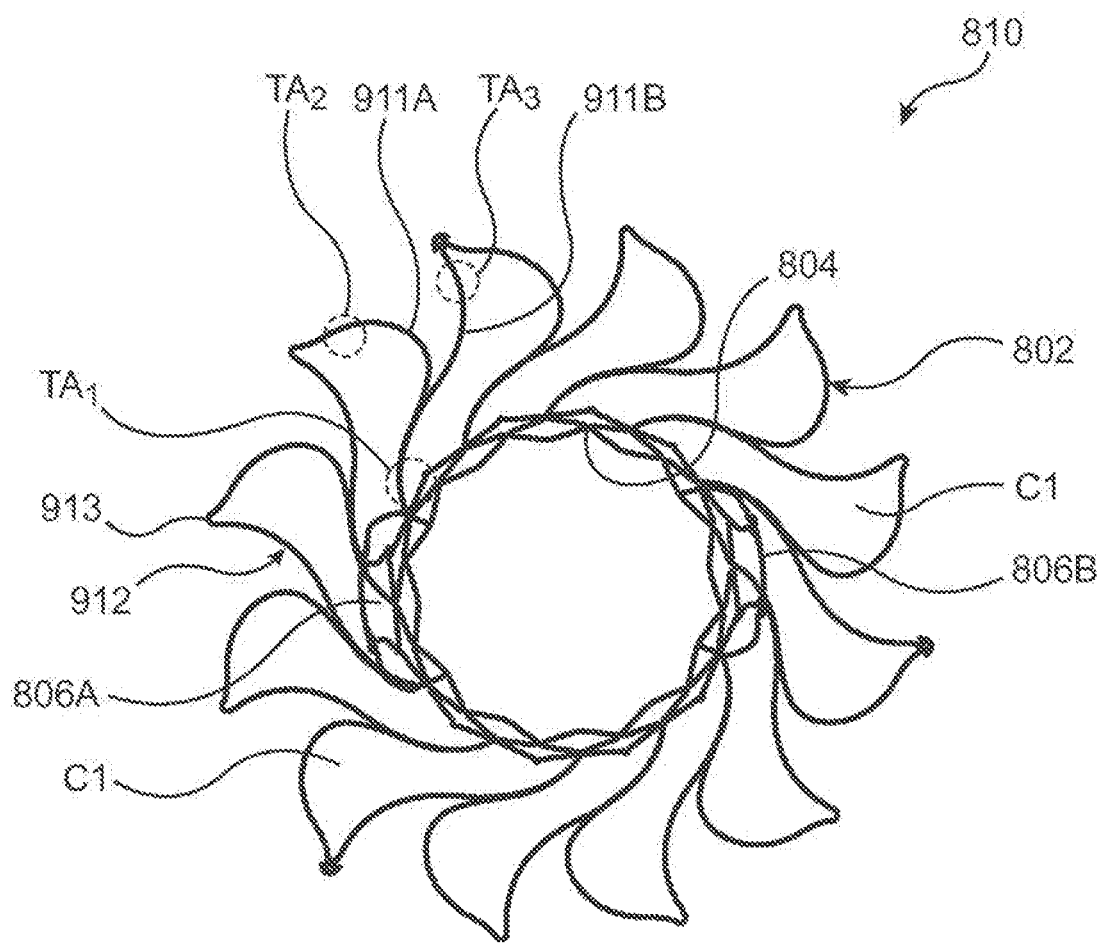
FIG. 9A is a top view of an inflow area of the frame of FIG. 9 taken in the direction of line A-A therein.

FIGS. 9 and 9A are various views of a frame 810 in a deployed configuration in accordance with another embodiment hereof that is suitable for use in forming a valve prosthesis similar to prosthesis 200 described above. FIG. 9 is a side view of frame 810, with FIG. 9A being a top or inflow view of frame 810 taken in the direction of line A-A in FIG. 9. Frame 810 may be a unitary structure that defines an inflow portion 802, a valve-retaining tubular portion 804 and a pair of support arms 806A, 806B. In a deployed configuration of frame 810, inflow portion 802 outwardly extends from a first or inflow end 803 of valve-retaining tubular portion 804 and support arms 806A, 806B backwardly extend from circumferentially spaced apart locations of an opposing second or outflow end 805 of valve-retaining tubular portion 804. When implanted within a native mitral valve as a support structure of a mitral valve prosthesis, inflow portion 802 is configured to engage an area of the left atrium that surrounds the native mitral valve, valve-retaining tubular portion 804 is configured to axially extend through the native mitral valve and thusly situates a prosthetic valve component within the mitral valve annulus, and support arms 806A, 806B are configured to capture respective valve leaflets of the mitral valve and to secure them within the left ventricle without obstructing the outflow area of the prosthetic valve or the left ventricular outflow tract.

Figure 10:
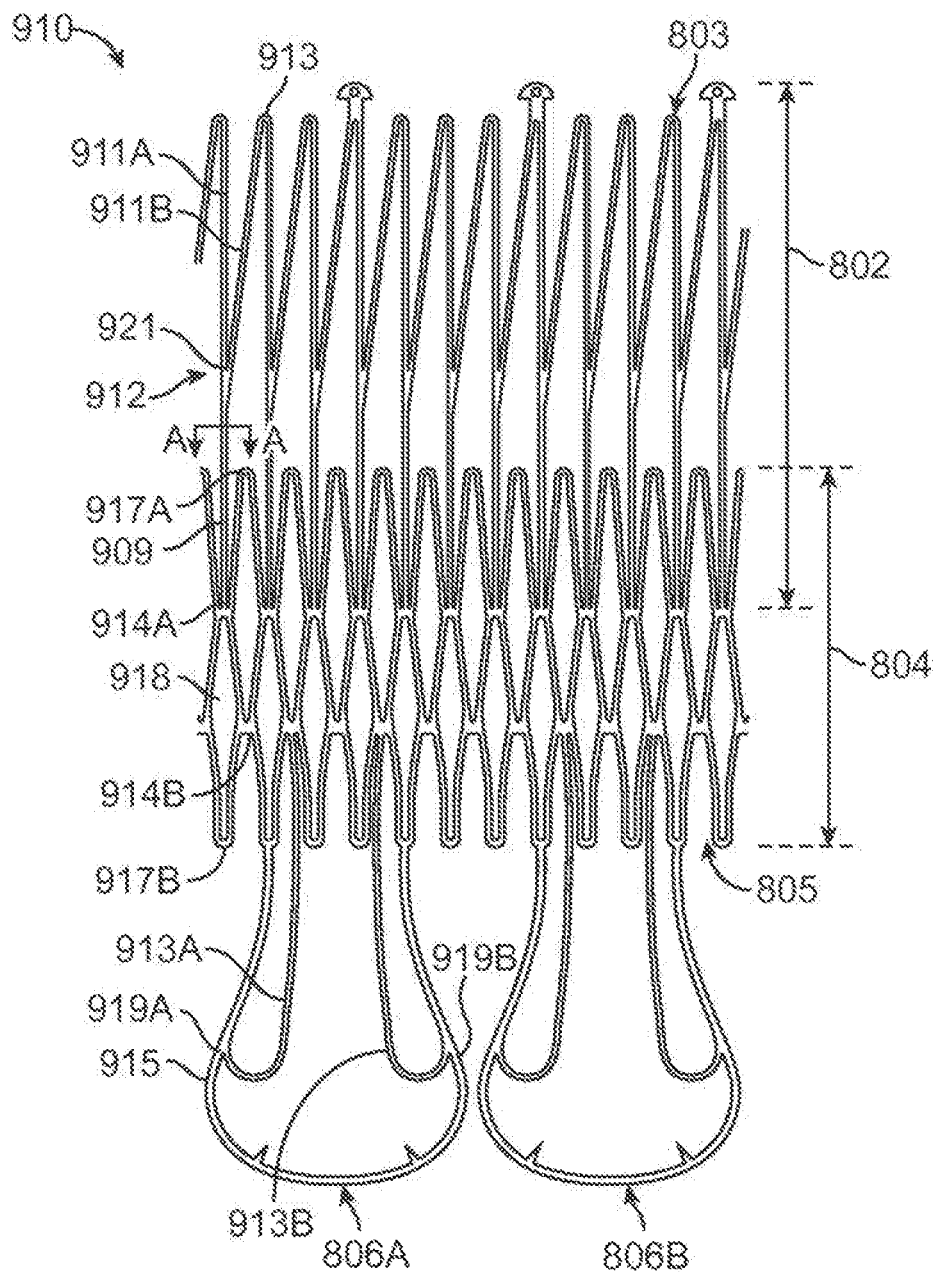
FIG. 10 depicts a patterned tube for forming the frame of FIGS. 9 and 9A laid flat for illustrative purposes.

In one embodiment, in an initial step in manufacturing frame 810, a tube 910 of a suitable material is etched, cut or otherwise machined to have the pattern depicted in FIG. 10. FIG. 10 depicts for illustrative purposes only patterned tube 910 laid flat so that the cut structures of inflow portion 802, valve-retaining tubular portion 804 and support arms 806A, 806B may be more readily identified and described. Valve-retaining tubular portion 804 may have a stent-like framework that defines diamond-shaped openings 918 and a series of upstream nodes or valleys 914A and downstream nodes or valleys 914B. Each support arm 806A, 806B may be formed to have inner side struts 913A, 913B and an outer looped strut 915. Outer looped struts 915 may form outer support arms that extend from spaced apart downstream crown or peaks 917B of valve-retaining tubular portion 804 and inner side struts 913A, 913B may form chordae engagement, guiding and/or tensioning elements, as described in more detail below, that extend from respective downstream valleys 914B within their respective outer looped strut 915 and connect therewith at opposing interior locations 919A, 919B. In another embodiment in accordance herewith, tube 910 may be cut into a pattern such that frame 810 is formed to have support arms as described with reference to any of the other embodiments herein. In one or more embodiments, support arms may comprise one or more outer loops and/or one or more inner loops. The inner loops may or may not be attached or coupled to one or more of the outer loops. In one or more embodiments, support arms may be attached or coupled at one or more frame locations. For example, the support arms may be attached or coupled to the frame at one or more points at either an outflow crown 917B, a node 914B, and/or along a strut connecting an outflow crown and a node. The support arms may be attached or coupled at one or more points located around the circumference of an outflow or distal portion of the frame.

Figure 10A:
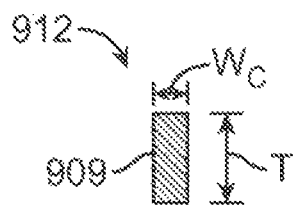
FIG. 10A is a cross-sectional view of the patterned tube of FIG. 10 taken along line A-A therein.

In one embodiment, inflow portion 802 may be formed from a plurality of struts 912 having a cut width $W_C$ that is less than a thickness T thereof, as shown in FIG. 10A which is a cross-sectional view of a strut 912 taken along line A-A in FIG. 10. Each strut 912 may define a base segment 909 and first and second branch segments 911A, 911B, which diverge from base segment 909 at a respective node 921. Accordingly, strut 912 may be considered to have a Y-shaped cut pattern. A base segment 909 of a respective strut 912 extends from every upstream valley 914A at inflow end 803 of valve-retaining tubular portion 804. Each base segment 909 has a length that disposes a respective node 921 of strut 912 upstream of upstream peaks 917A. In an embodiment, base segment 909 has a length such that node 921 of strut 912 is disposed upstream of upstream peaks 917A by at least half a length of the base segment. Crowns 913 are formed between first and second branch segments 911A, 911B of adjacent struts 912. Crowns 913 may form radially outward ends of inflow portion 902 of frame 910, as shown in FIG. 9A. Circumferentially adjacent crowns 913 may not be directly connected to each other and thereby provide inflow portion 802 with improved flexibility.

Figure 9B:
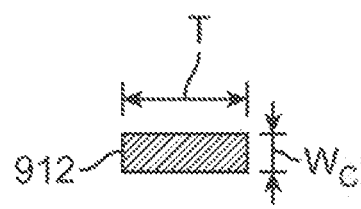
FIG. 9B is a cross-sectional view of a strut of the frame of FIG. 9 taken along line B-B therein.

In one embodiment, subsequent processing steps are performed on patterned tube 910 in order to form expanded frame 810 as shown in FIGS. 9 and 9A. In one or more processing steps, patterned tube 910 may be radially expanded to set a tubular shape and diameter of valve-retaining tubular portion 804 that is suitable for receiving a prosthetic valve component therein. In one or more additional processing steps, support arms 806A, 806B may be rotated outward and backward relative to outflow end 805 of valve-retaining tubular portion 804 and heat treated to set a shape thereof. In one or more additional processing steps, struts 912 of inflow portion 802 of patterned tube 910 may be made to outwardly extend from inflow end 803 of valve-retaining tubular portion 804 and subjected to a forming process to have a substantially s-shaped profile, as best seen in FIG. 9. Somewhat counter-intuitively, a first bend 816A and an opposing second bend 816B that form the substantially s-shaped profile of strut 912 may be bent or curved over the cut width $W_C$ of the strut, as shown in FIG. 9B, rather than being bent or curved over thickness T of the strut. First and second bends 816A, 816B of s-shaped strut 912 are able to be formed in this manner due to one or more twisted areas $TA_1$, $TA_2$, $TA_3$ of strut 912 that occur during formation of inflow portion 802. More particularly with reference to FIG. 9A, base segment 909 of each strut 912 may have a twisted area $TA_1$ near or adjacent to where the respective base segment 909 outwardly extends from inflow end 803 of valve-retaining tubular portion 804. Although not intending to be bound by theory, twisted area $TA_1$ turns cut width $W_C$ of the respective strut 912 approximately 90 degrees from the cut pattern shown in FIG. 10 such that the wider thickness T of the respective strut 912 is subjected to the forming process that creates first and second bends 816A, 816B. As well with reference to FIG. 9A, first and second branch segments 911A, 911B of each strut 912 have twisted areas $TA_2$, $TA_3$, respectively, near or adjacent to their respective crowns 913. Although not intending to be bound by theory, twisted areas $TA_2$, $TA_3$ turn cut width $W_C$ of the respective strut 912 in a direction opposite of twisted area $TA_1$ to return cut width $W_C$ to a similar orientation as shown in the cut pattern in FIG. 10, which results in cut width $W_C$ facing inward and outward along at least a portion of first and second branch segments 911A, 911B of struts 912 and through crowns 913 of inflow portion 802.

In the embodiment of frame 810 shown in FIGS. 9 and 9A, inflow portion 802 may be described as having a ring of equal or like sized and shaped cells C1 that are formed between respective portions of struts 912 and crowns 913. In contrast to the radial symmetric appearance of cells C1, C2 of inflow portion 202 of frame 210 shown in FIG. 3A, cells C1 of inflow portion 802 of frame 810 shown in FIG. 9A appear to spiral clockwise, exhibiting cyclic symmetry. Although not intending to be bound by theory, the spiral design of the inflow portion 802 results in the struts 912 having twisted areas $TA_1$ that twist or turn in a common or same direction from valve-retaining tubular section 804. In the embodiment shown in FIGS. 9 and 9A, the twisted area $TA_1$ of each base segment 909 turns the respective strut 912 clockwise relative to inflow end 803 of valve-retaining portion 804 such that twisted area $TA_1$ may be considered to have a right-hand twist. In another embodiment (not shown), the twisted area $TA_1$ of each base segment 909 turns the respective strut 912 counterclockwise relative to inflow end 803 of valve-retaining portion 804 such that twisted area $TA_1$ may be considered to have a left-hand twist.

With reference to FIG. 9, first bend 816A of each s-shaped strut 912 has an apex 822 that is longitudinally disposed at or near downstream valleys 914B of valve-retaining tubular portion 804. The increased depth of first bend 816A and the corresponding increased height of second bend 816B, as compared to first and second bends 816A, 816B, respectively, are made possible by the longer length of inflow struts 912 relative to an axial length of valve-retaining tubular portion 804 as compared to a length of inflow struts 512 relative to an axial length of valve-retaining tubular portion 204. In another embodiment, apex 822 of first bend 816A may be positioned at or near upstream valleys 914A of valve-retaining tubular portion 804, similar to the location of apex 422 of first bend 416A as shown in FIGS. 4 and 8. In other embodiments in accordance herewith, apex 822 of s-shaped struts 912 and apex 422 of s-shaped struts 512 may be suitably disposed anywhere along the axial length of valve-retaining tubular portions 204, 804, respectively, in order to tailor the flexibility of the respective inlet portion 202, 802 for a particular application.

Figure 11:
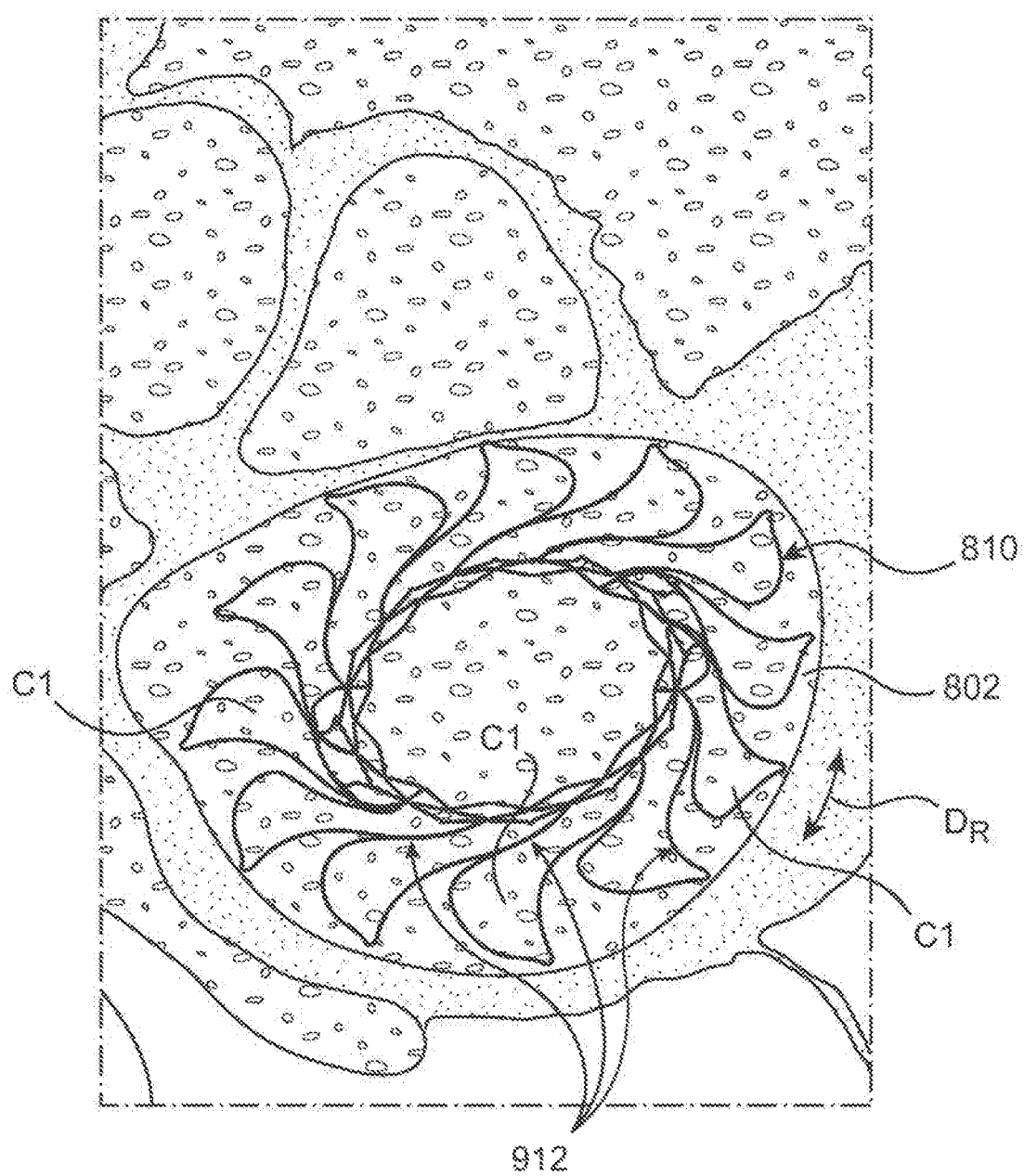
FIG. 11 depicts an implanted mitral valve prosthesis in accordance with an embodiment hereof.
Figure 12:
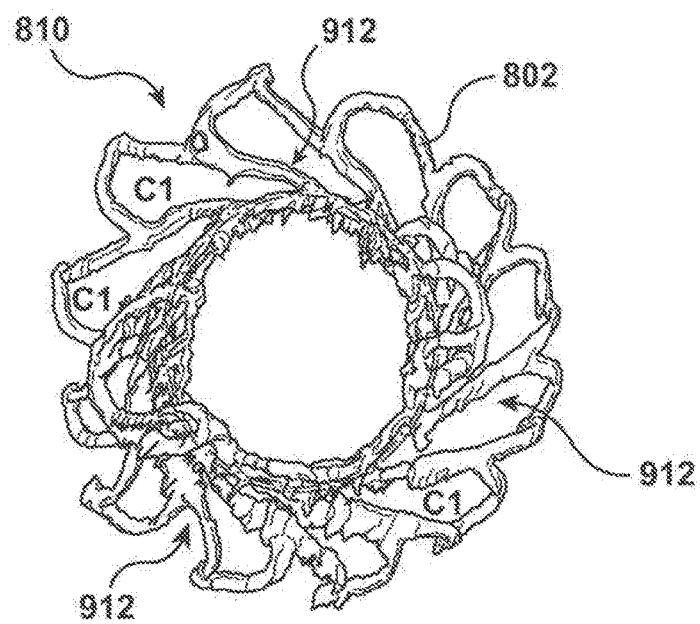
FIG. 12 shows an inflow portion of the frame of FIGS. 9 and 9A after implantation.
Figure 13:
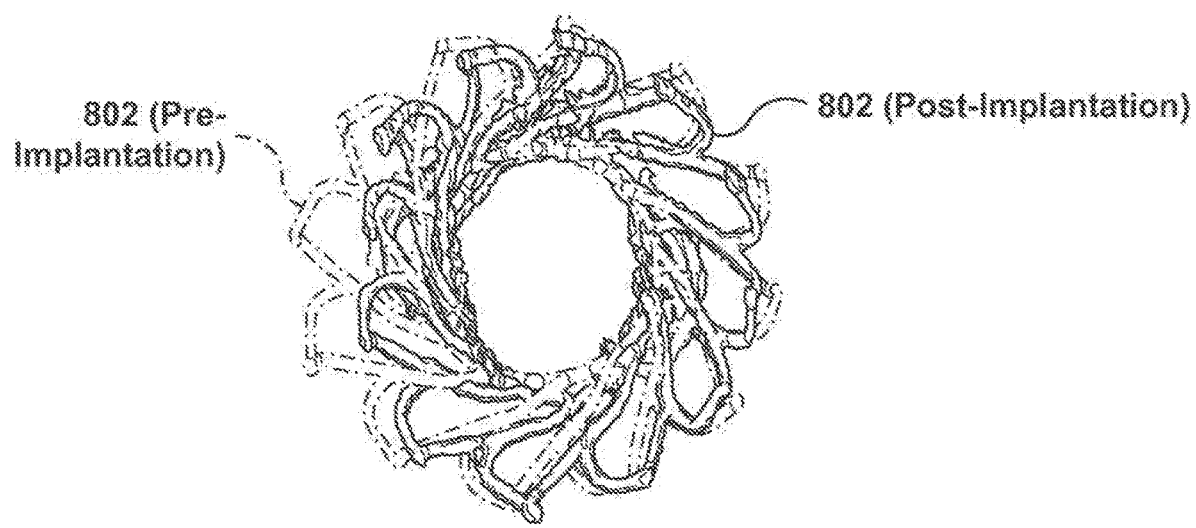
FIG. 13 shows the post-implantation inflow portion of the frame shown in FIG. 12 transposed on a pre-implantation inflow portion of the frame as shown in FIG. 9A.
Figure 14:
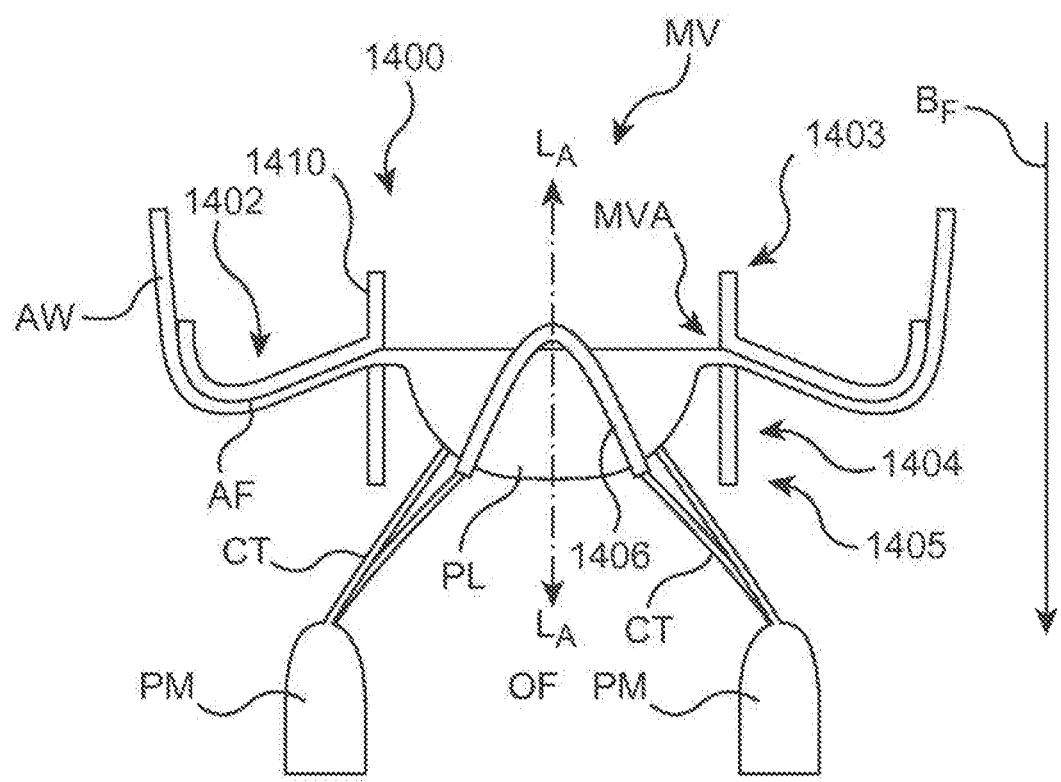
FIG. 14 is a side view of a simplified drawing of a heart valve prosthesis in accordance with an embodiment hereof implanted within a mitral valve annulus.

In some embodiments, the s-shaped struts 912 that form inflow portion 802 of frame 810 act similarly to cantilever beams when interacting with the anatomy of the heart as a supporting and sealing structure of a valve prosthesis in accordance with embodiments hereof. During the pressure changes and cyclical contractions of the heart, the s-shaped struts 912 are able to deflect while maintaining an axial force against a surface of the heart such as an atrial surface that is sufficient for sealing and the prevention of paravalvular leakage between the frame and tissue surface. As well the combination of twisted areas $TA_1$, $TA_2$, $TA_3$ and the s-shape of struts 912 of inflow portion 802 may permit the inflow area of the valve prosthesis in accordance with embodiments hereof to readily deflect, flex and/or move during the cardiac cycle while also maintaining sufficient axial stiffness to provide sealing contact with the tissue surface that surrounds the implanted prosthesis. In addition, the twisted areas $TA_1$, $TA_2$, $TA_3$ of s-shaped struts 912 reduce strain and improve the structural integrity of frame 810, and more particularly the structural integrity of inflow portion 802 thereof. Another benefit of the design of inflow portion 802 of frame 810 is that it may readily conform to the D-shape of the mitral valve annulus by allowing deflection or movement in a radial direction DR of struts 912 and the cells C1 defined thereby, as shown in FIGS. 11-13. FIG. 11 shows an implanted mitral valve prosthesis having a frame 810 that shows how individual struts 912 have radially deflected or moved after implantation to "lay down" a bit flatter and conform to the D-shape of the native mitral valve annulus. This anatomically conforming feature of frame 810 is more clearly depicted in FIGS. 12 and 13, with FIG. 12 showing the deformation of inflow portion 802 of frame 810 after implantation and with FIG. 13 showing the post-implantation deformed inflow portion 802 of FIG. 12 transposed on a pre-implantation inflow portion 802 of FIG. 9A FIG. 14 is a side view of a simplified drawing of a heart valve prosthesis 1400 in accordance with an embodiment hereof implanted within a mitral valve annulus (MVA) of a mitral valve (MV). Valve prosthesis 1400 is configured to be implanted in mitral valve annulus (MVA) to replace the function of the native mitral valve (MV). In other embodiments, valve prosthesis 1400, as well as other valve prosthesis disclosed herein, may be adapted for placement within another of the native heart valves, such as the aortic, pulmonary, or tricuspid heart valve, and the actual shape and configuration of the valve prosthesis can depend upon the native heart valve being replaced.

Heart valve prosthesis 1400 may include a frame 1410 that supports a prosthetic valve body or component (not shown). An outflow or distal portion of frame 1410 corresponds to a distal or outflow end 1405 of valve prosthesis 1400 and an opposite end of frame 1410 defines an inflow or proximal portion corresponding to a proximal or inflow end 1403 of valve prosthesis 1400. As noted above the terms "distal" or "outflow" are understood to mean downstream to the direction of blood flow $B_F$ and the terms "proximal" or "inflow" are understood to mean upstream to the direction of blood flow.

Frame 1410 may include a pair of support arms 1406 extending from a central or valve-retaining tubular portion 1404 of frame 1410 and configured to extend over and secure the native leaflet (AL, PL). In one embodiment, upon implantation, each support arm 1406 is configured to engage, capture, clamp and/or immobilize a corresponding leaflet (AL, PL) of the mitral valve (MV), and hold the leaflet close to central portion 1404. In some embodiments, one or more support arms may engage, capture, clamp, and/or immobilize one or more chordae tendinae either directly or indirectly. In other embodiments, frame 1410 may include multiple support arms 1406 with each support arm 1406 corresponding to a separate native leaflet of the heart valve within which the heart valve prosthesis is to be implanted. In embodiments hereof, proper seating of the valve prosthesis within the annulus of a native heart valve can be achieved by capturing one or more native leaflets with the support arms of the frame. For instance, a radial and/or axial force generated by the valve prosthesis 1410 in the atrium (AF, AW) against support arms 1406 can create a "sandwich effect," which in some embodiments can seat valve prosthesis 1410 by capturing or pinching leaflets (AL, PL) and atrial tissue against central portion 1404.

In embodiments hereof, support arms 1406 may be sized or shaped to tension the chordae tendinae (CT). As noted above, the chordae tendinae connect to the native valve leaflets (AL, PL) and can act like "tie rods" in an engineering sense. In some patients, not only do the chordae tendinae (CT) help prevent prolapse of the native valve leaflets during systole, they also help support the left ventricular muscle mass throughout the cardiac cycle. In embodiments in accordance herewith, the tension between the chordae tendinae (CT) and the native valve leaflets (AL, PL) can serve to prevent frame 1410 from moving or migrating, for example lifting into the patient's atrium. In some embodiments, the chordae tension can serve to substantially prevent paravalvular leakage. For example, one or more support arms that interact with chordae may create adequate tension in the chordae to deform the inflow portion of the valve prosthesis against the floor of the atrium but at forces low enough to prevent tensile failure of the chordae. To preserve this effect over time, the support arms that engage or interact with the chordae must prevent abrasion of the chordae. One method to prevent abrasion of the chordae is by eliminating or diminishing any relative motion between the chordae and the support arm, either by promoting tissue ingrowth, converting the relative motion to tension, and/or actively clamping the chordae. In one embodiment, a support arm could avoid or minimize the number of chordae it interacts with through geometric design. In one embodiment, a support arm may be designed to move with the chordae, either by absorbing the relative motion in the form of deformation or by transferring the relative motion to a different part of the valve prosthesis. In one embodiment, the relative motion between a support arm and the chordae may be allowed, but the friction between the support arm and chordae could be minimized to the point where abrasion is insignificant or not a concern. In some embodiments, paravalvular leakage can be substantially prevented by positioning a sealing member or surface of the valve prosthesis 1400 between inflow end 1403 and outflow end 1405.

In embodiments hereof, support arms 1406 may be sized or shaped to increase valve stability. Support arms 1406 may, for example, serve to substantially prevent the native valve leaflets (AL, PL) from obstructing flow through outflow tract (OF). In embodiments hereof, support arms 1406 may serve to prevent the native valve leaflets (AL, PL) from interacting with prosthetic leaflets of valve prosthesis 1410. In embodiments hereof, support arms 1406 may position the native valve leaflets (AL, PL) to minimizing paravalvular leaks and/or maintain proper alignment of the valve prosthesis. In embodiments hereof, support arms 1406 may serve to avoid systolic anterior mobility and/or maintain valve stability by preventing migration of the valve prosthesis into the atrium or ventricle. In embodiments hereof, support arms 1406 may be configured to enhance overall frame strength.

In embodiments hereof, frame 1410 may include an inlet portion 1402 configured to engage the atrial floor (AF) of the outflow tract of the native heart atrium. In embodiments hereof, inlet portion 1402 may restrict movement of valve prosthesis 1400 in a downstream direction of blood flow $B_F$ at the valve site. In embodiments hereof, inlet portion 1402 of frame 1410 may be configured to deform the atrial floor (AF) of the outflow tract in an upstream direction of blood flow $B_F$ at the valve site. For example, a "sandwich force" may be created between the inflow or inlet portion of the frame 1402 and the outflow or outlet portion 1404 of the frame 1405. This force can either deflect the inflow portion of the frame 1402 against the atrial floor AF or deform the atrial floor AF to match the contour of inflow 1402, depending upon the stiffness of the frame. In some embodiments, inlet portion 1402 may be sized to contact the entirety of the atrial floor (AF) and a portion of the atrial wall (AW), with an example of such a configuration being shown in FIG. 14. In embodiments hereof, inlet portion 1402 is sized to contact a substantial majority of the atrial floor (AF). Other suitable configurations can be used. In embodiments hereof, frame 1410 may have a transverse cross-section or diameter that is smaller than annulus (MVA). In some embodiments, such a configuration can serve to prevent radial force on frame 1410 from annulus (MVA), which can serve to maintain a desired shape of a prosthetic valve body or component supported within frame 1410.

Because valve prosthesis 1400 may be used in a portion of the body that undergoes substantial movement, it may be desirable for one or more portions of valve prosthesis 1400, such as frame 1410 to be flexible. For example, in some embodiments, at least a portion of inlet portion 1402 may have a flexibility from about 0.8 N/m to about 2 N/m. In embodiments hereof, at least a portion of inlet portion 1402 may have a flexibility of about 1.25 N/m. In some embodiments hereof, inlet portion 1402 may include one or more diamond-shaped cells. In some embodiments hereof, inlet portion 1402 may be formed of twisted strands of nitinol as previously discussed above.

Central portion 1404 of frame 1410 may be configured to conform to a heart valve annulus. In embodiments hereof, such a configuration can help anchor valve prosthesis 1400 within an annulus to prevent lateral movement or migration of valve prosthesis 1400 due to the normal movement during the cardiac cycle of the heart. In embodiments hereof, central portion 1404 may be shaped to adapt to the specific anatomy of an individual. For example, in some embodiments, central portion 1404 is configured to flex and deform so as to mimic a natural cardiac movement of the heart through the cardiac cycle. In other embodiments, central portion 1404 may be substantially rigid to avoid flexing or deformation during the cardiac cycle. In further embodiments, central portion 1404 may be sized to be smaller than the native annulus, avoiding deformation of the central portion due to the interaction with the native annulus.

The shape of central portion 1404 may be configured to reduce the risk of valve prosthesis migration and paravalvular leakage. In embodiments hereof, a transverse cross-section of central portion 1404 may define a substantially circular, oval, elliptical or another geometric or non-geometric shape, such as D-shaped, while a longitudinal profile of central portion 1404 may define any desirable geometric or non-geometric shape. In other embodiments hereof, central portion 1404 may be formed to have a substantially straight profile, for example, being substantially cylindrical and parallel to a longitudinal axis $L_A$ of frame 1410. Central portion 1404 may have one or more flared portions, for example, diverging away from a longitudinal axis $L_A$ of frame 1410.

In some embodiments, central portion 1404 may have a transverse cross-section or diameter that is greater or wider than the native valve annulus, such as the mitral valve annulus (MVA). In embodiments hereof, such a configuration can reduce the likelihood of migration of valve prosthesis 1400, for example into the ventricle. In embodiments hereof, such a configuration may improve sealing of valve prosthesis 1400 against the heart, such as the atrial wall (AW). In some embodiments hereof, frame 1410 is designed to provide axial fixation by creating tension in the chordae tendinae (CT), which can hold inlet portion 1402 of frame 1410 against a native valve annulus (MVA). A transition or sealing zone between an inflow portion and an outflow portion of frame 1410 can provide sealing with the patient's anatomy to prevent paravalvular leakage of frame 1410. In embodiments hereof, frame 1410 is shaped and sized so as to anchor frame 1410 within a valve annulus by itself or in combination with the chordae tendinae (CT).

Figure 15:
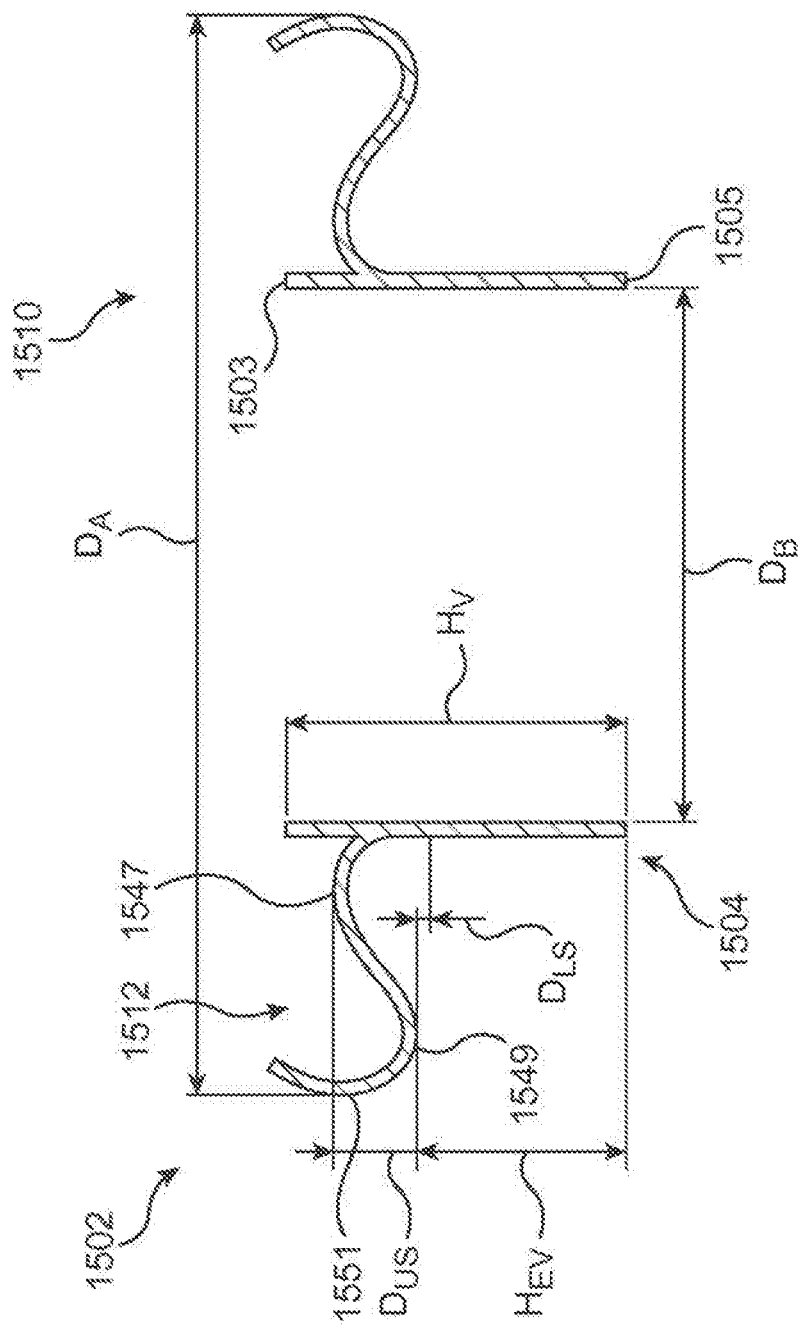
FIG. 15 is a cross-sectional view of a frame in accordance with an embodiment hereof.

FIG. 15 is a cross-sectional view of a frame 1510 in accordance with an embodiment hereof. Frame 1510 can include a central or valve-retaining tubular portion 1504 attached to an inlet portion 1502. In embodiments hereof, inlet portion 1502 may be substantially S-shaped, or may be described as having an S-shaped radial profile. For example, inlet portion 1502 can include one or more curves as it radially extends from proximal or inflow end 1503 of central portion 1504, such as curves 1547, 1549, and 1551, which together can approximate an S-shape. For example, in some embodiments, inlet portion 1502 includes extension or strut 1512 that protrudes in a radially outward direction from central portion 1504 of frame 1510. The substantial "S" shape of inlet portion 1502 can be formed by strut 1512 bending in a first curve 1547 from inflow end 1503 towards outflow end 1505, and then bending in a second curve 1549 back towards inflow end 1503. In one embodiment of such an S-shape is shown for example in FIG. 15. In embodiments hereof, extension or strut 1512 can additionally bend in a third curve 1551 towards a radially inward direction as shown in FIG. 15. Curve 1551 can prevent damage to the atrial tissue by directing the inflow crowns radially inward and away from atrial tissue. Additionally, the inflow crowns may be rounded or wrapped by an appropriate graft material to minimize damage of the atrial wall.

In one embodiment, frame 1510 may include an outer diameter $D_A$ in the range of about 60.37 mm, a valve diameter $D_V$ in the range of about 30.42 mm, a valve height $H_V$ between an outflow end 1505 of frame 1510 and inflow end 1503 of frame 1510 in the range of about 16.97 mm, an effective valve height HEN between outflow end 1505 of frame 1510 and curve 1549 in the range of about 10.56 mm, an upper s-shape dimension $D_{US}$ between curve 1547 and 1549 in the range of about 3.14 mm, and a lower s-shape dimension $D_{LS}$ between curve 1549 and the first full node of the central or valve-retaining tubular portion 1504 from inflow end 1503 in the range of about 2.51 mm.

In embodiments hereof, inlet portion 1502 can be configured to contact a patient's atrial anatomy at a lower point on frame 1510 compared to conventional frame designs. In some embodiments, such a configuration can serve to increase chordae tension. In embodiments hereof, the shape and size of inlet portion 1502 can be configured to conform to the shape of the native mitral annulus and left atrium. In embodiments hereof, such a configuration can result in varying degrees of deformation, for e.g., a flattening, of inlet portion 1502, which can serve to create an excellent seal between inlet portion 1502 and the native anatomy. In some embodiments, one or more of the above configurations can serve to reduce paravalvular leakage compared to other frame designs. Inlet portion 1502 can be configured to maintain contact throughout a patient's cardiac cycle. In embodiments hereof, changes in chordae tension may be accommodated by partially flattening inlet portion 1502. In embodiments hereof, the flattening of inlet portion 1502 can hold a spring load. In embodiments hereof as changes in the chordae tension occur throughout the cardiac cycle, the spring load may serve to maintain contact and sealing of inlet portion 1502 against the tissue despite the changing tension.

Figure 16:
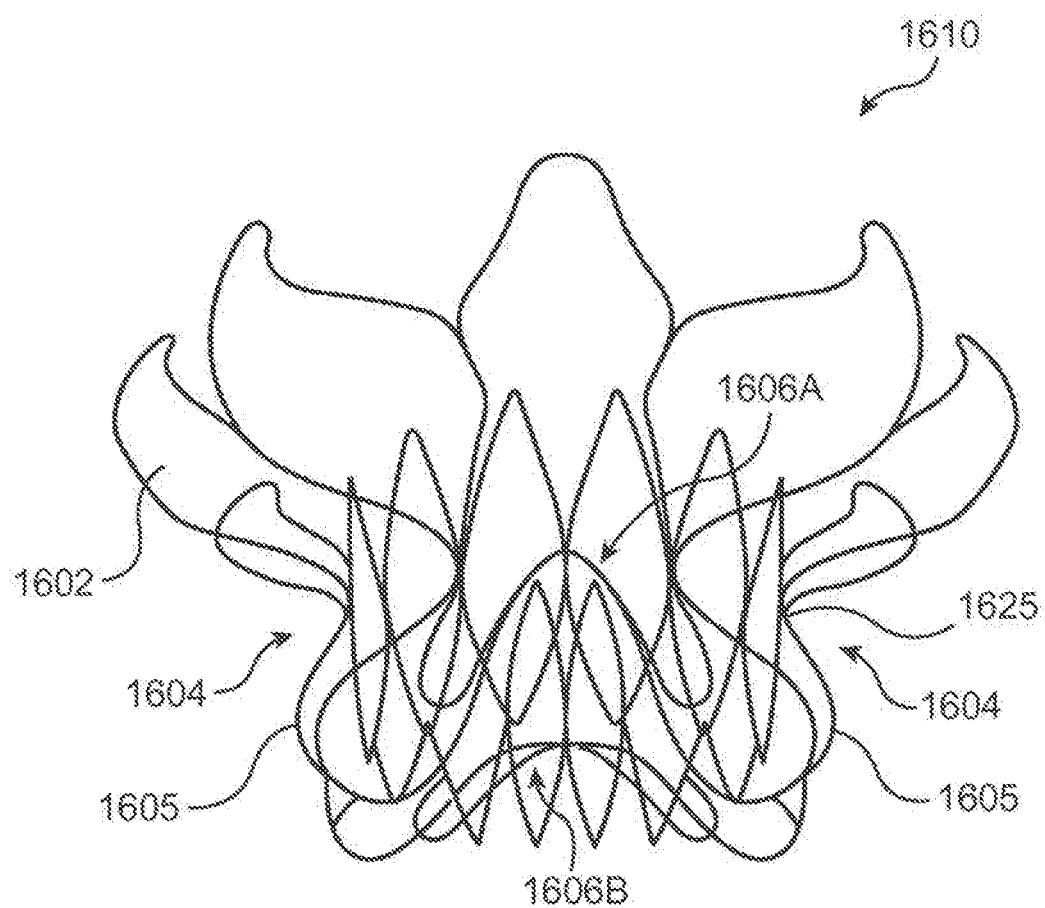
FIG. 16 is a front or side view of a frame in accordance with an embodiment hereof.

FIGS. 16, 16A and 16B illustrate a frame 1610 in accordance with another embodiment hereof. FIG. 16 illustrates a front or side view of frame 1610. FIG. 16A illustrates a view of frame 1610 implanted in a native mitral valve site (MV) and FIG. 16B illustrates an enlarged view of a portion of FIG. 16A. Valve site (MV) includes an annulus (MVA), native leaflets (AL, PL), chordae tendinae (CT), and papillary muscles (PM). Frame 1610 may include support arms 1606A, 1606B, inflow portion 1602, and a central or valve-retaining tubular portion 1604. A partially hourglass-shape of frame 1610 along central portion 1604 includes a reduced-waist region 1625 and may be configured to capture or pinch a muscular ridge of annulus (MVA) to provide axial fixation of frame 1610 within valve site (MV). The hourglass shape portion of frame 1610 may be formed by the atrial portion of the frame, i.e., inflow portion 1602, and the ventricular portion of the frame, i.e., outflow portions 1605 that outwardly extend from the reduced-waist region 1625, such that frame 1610 axially engages, fixates, or pinches the annulus from both the atrial and ventricular sides of the annulus. An example of such a configuration is shown in FIGS. 16, 16A and 16B. Other suitable configurations may be used. In embodiments hereof, the outwardly-extending outflow portions 1605 along central portion 1604 are positioned along a circumference of the central portion 1604 about 90 degrees from each support arm 1606A, 1606B, or stated another way is positioned along the circumference of central portion 1604 approximately half way between the support arms 1606A, 1606B. In another embodiment, outwardly-extending outflow portions 1605 and inflow portion 1602 that form the hourglass shape portion of frame 1610 may specifically target the annulus and/or commissures of the native valve. Frame 1610 may also provide axial fixation by creating tensioning of the chordae tendinae (CT). In some embodiments, the valve prosthesis may comprise one or more s-shaped portions or components. In some embodiments, the valve prosthesis may comprise an s-shaped inflow portion 1602. The s-shape inflow portion may comprise various dimensions relative to the central or valve-retaining tubular portion of the frame as previously described. In some embodiments, the valve prosthesis may comprise s-shaped outflow portions 1605. The s-shape outflow portions may comprise various dimensions relative to the central or valve-retaining tubular portion of the frame as previously described. In some embodiments, one or more support arms 1606A, 1606B may comprise an s-shaped portion.

Figure 17:
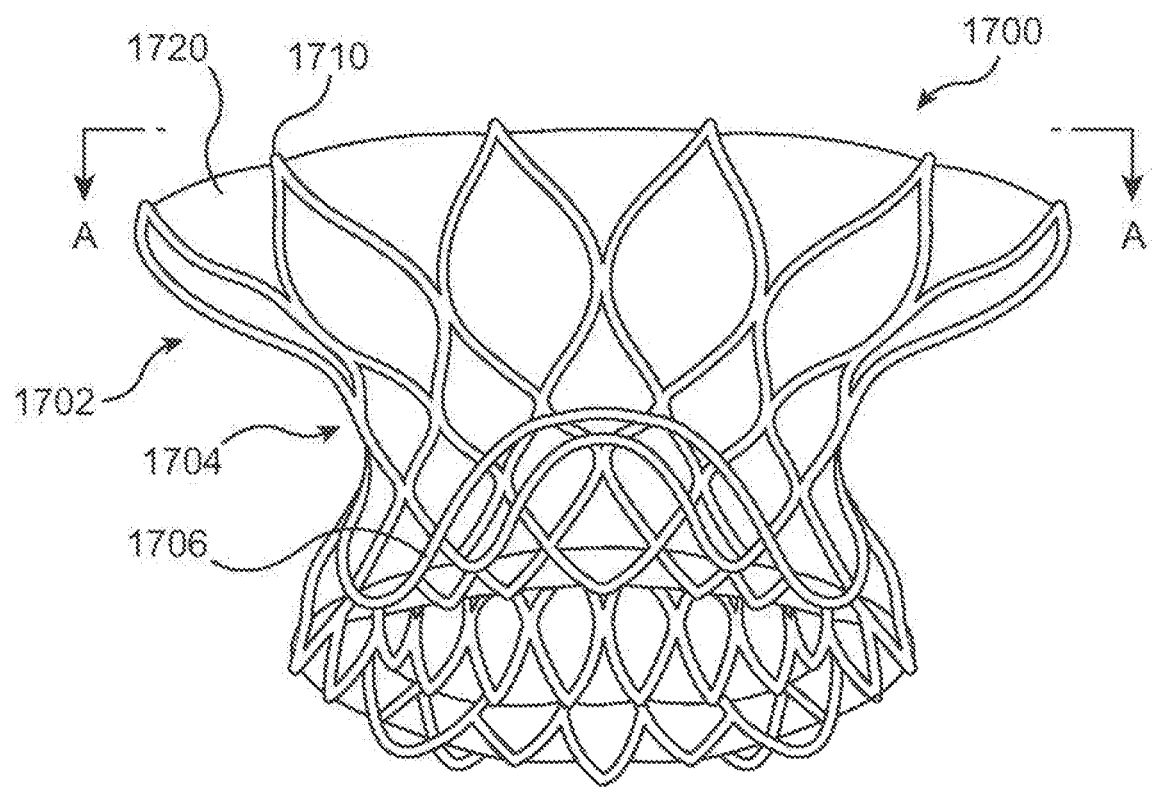
FIG. 17 is a front or side view of a valve prosthesis in accordance with an embodiment hereof.
Figure 17A:
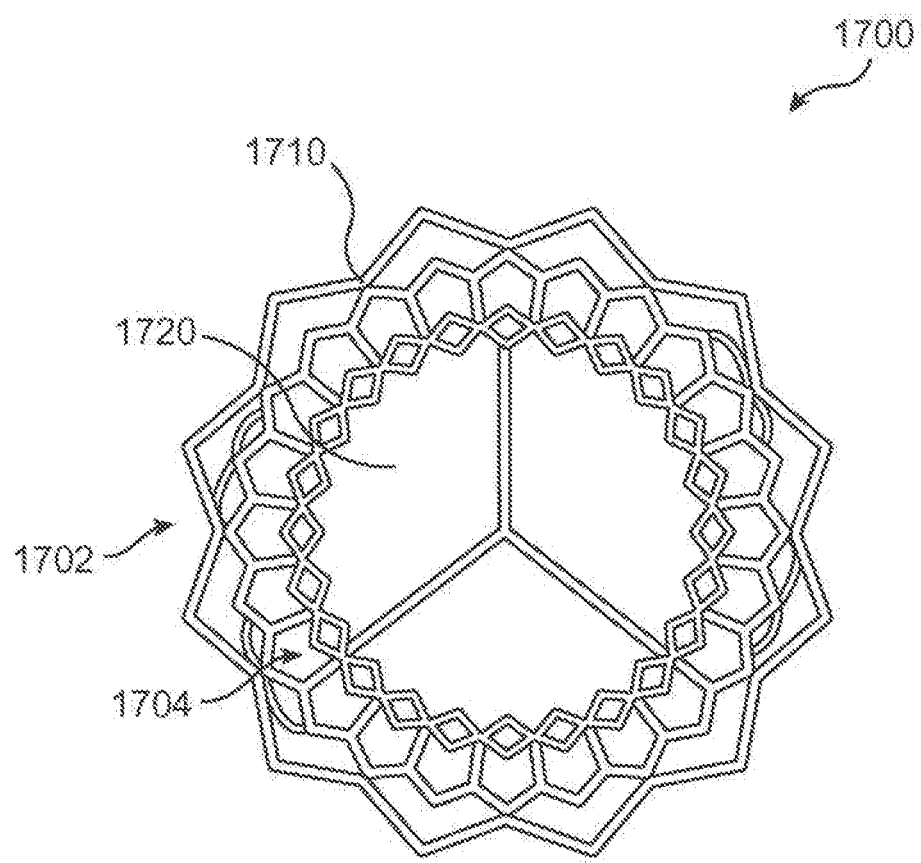
FIG. 17A is a top or inflow view of the valve prosthesis of FIG. 17 taken in the direction of line A-A therein.

FIG. 17 is a front or side view of a valve prosthesis 1700 in accordance with an embodiment hereof. FIG. 17A is a top or inflow view of valve prosthesis 1700 of FIG. 17 taken in the direction of line A-A therein. Valve prosthesis 1700 includes a valve body or component 1720 supported within a frame or support structure 1710. Frame 1710 includes an inlet portion 1702, an hourglass-shaped central or valve-retaining tubular portion 1704 and support arms 1706. Support arms 1706 may be configured to capture leaflets during delivery of valve prosthesis 1700. Central portion 1704 may be configured to pinch a muscular ridge of the native annulus when implanted therein. The reduced-waist region of the hourglass shape or profile of frame 1710 may be located on or defined within central portion 1704 around the entire circumference of frame 1710, such as the configuration is shown in FIGS. 17 and 17A. Frame 1710 may also provide axial fixation by creating tensioning of the chordae tendinae (CT).

Figure 18:
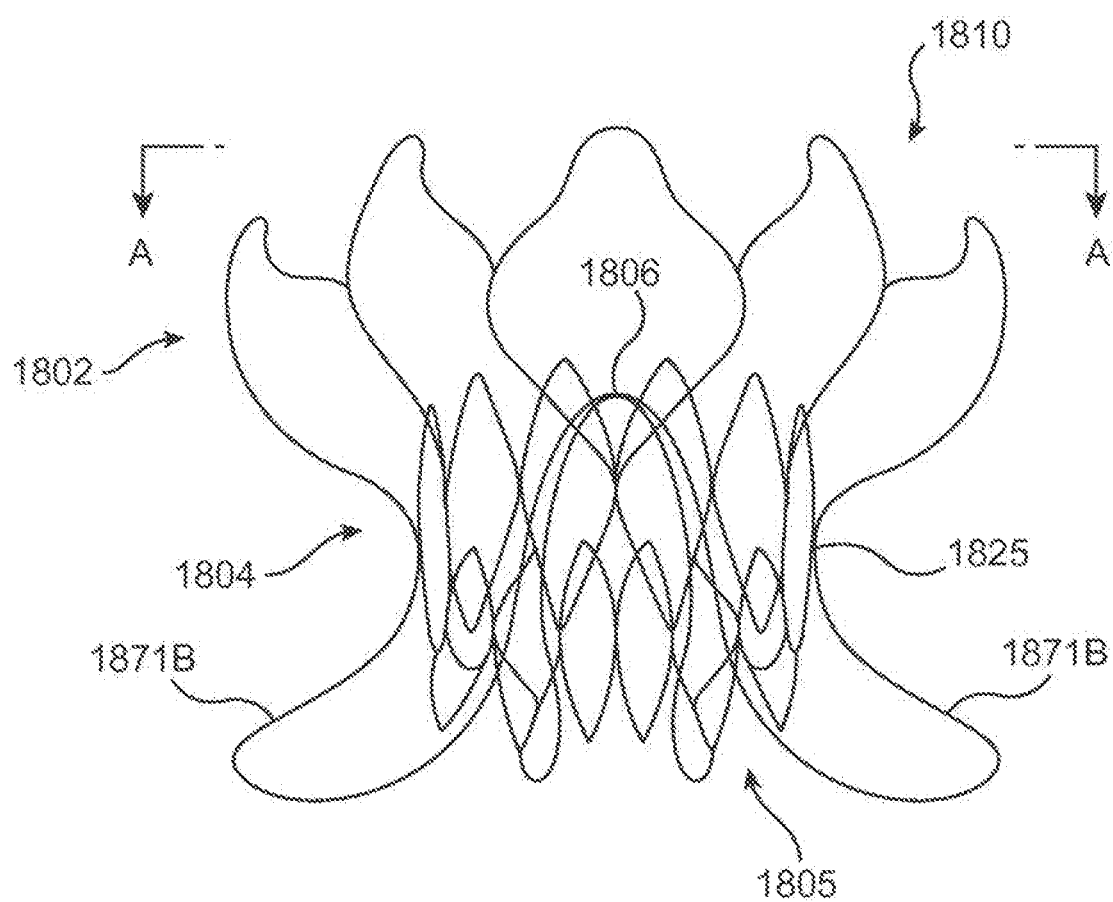
FIG. 18 is a front or side view of a frame for a valve prosthesis in accordance with an embodiment hereof.
Figure 18A:
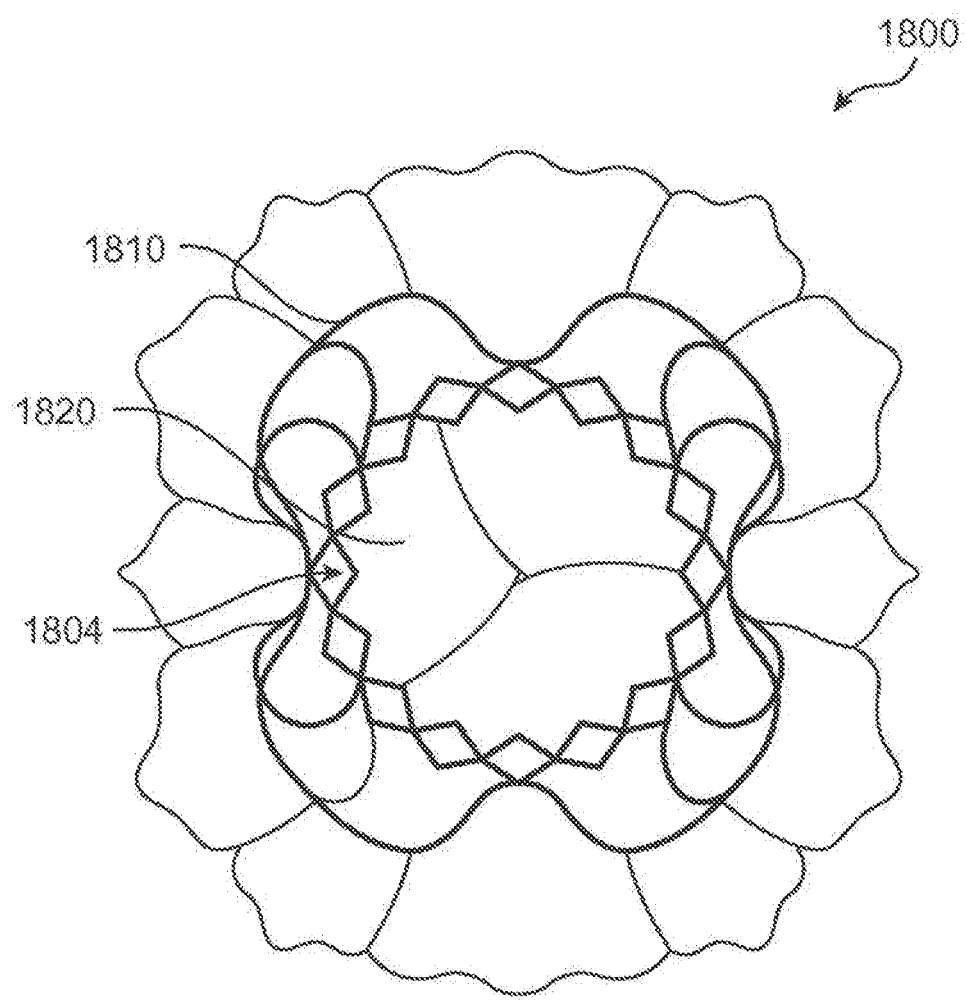
FIG. 18A is a top or inflow view of a valve prosthesis utilizing the frame of FIG. 18 taken in the direction of line A-A therein.
Figure 18C:
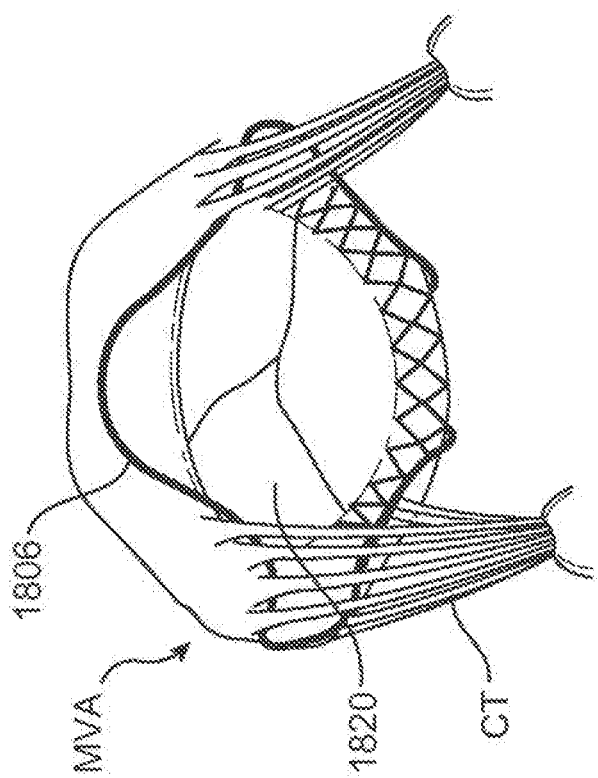
FIGS. 18B and 18C depict front or side views of the valve prosthesis of FIG. 18A implanted in a native valve site.
Figure 18B:
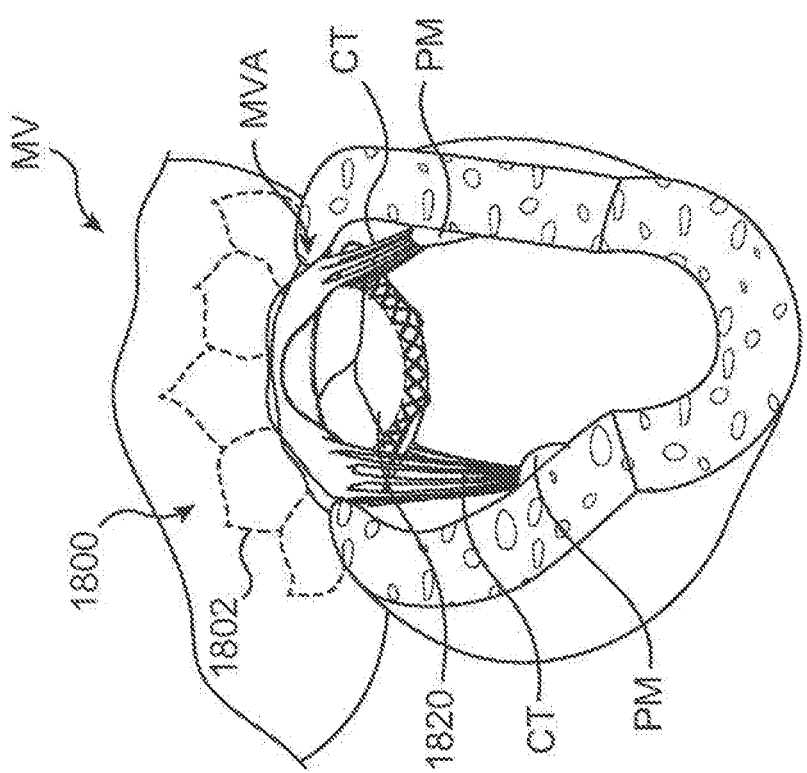

FIG. 18 is a front or side view of a frame 1810 for a valve prosthesis 1800 in accordance with an embodiment hereof. FIG. 18A is a top or inflow view of valve prosthesis 1800 utilizing the frame 1810 of FIG. 18 taken in the direction of line A-A therein. FIG. 18B shows valve prosthesis 1800 implanted in a native valve site (MV) with FIG. 18C being an enlarged view of a portion of FIG. 18B. The valve site (MV) depicted in FIGS. 18B and 18C includes annulus (MVA), chordae tendinae (CT), and papillary muscles (PM).

Figure 18D:
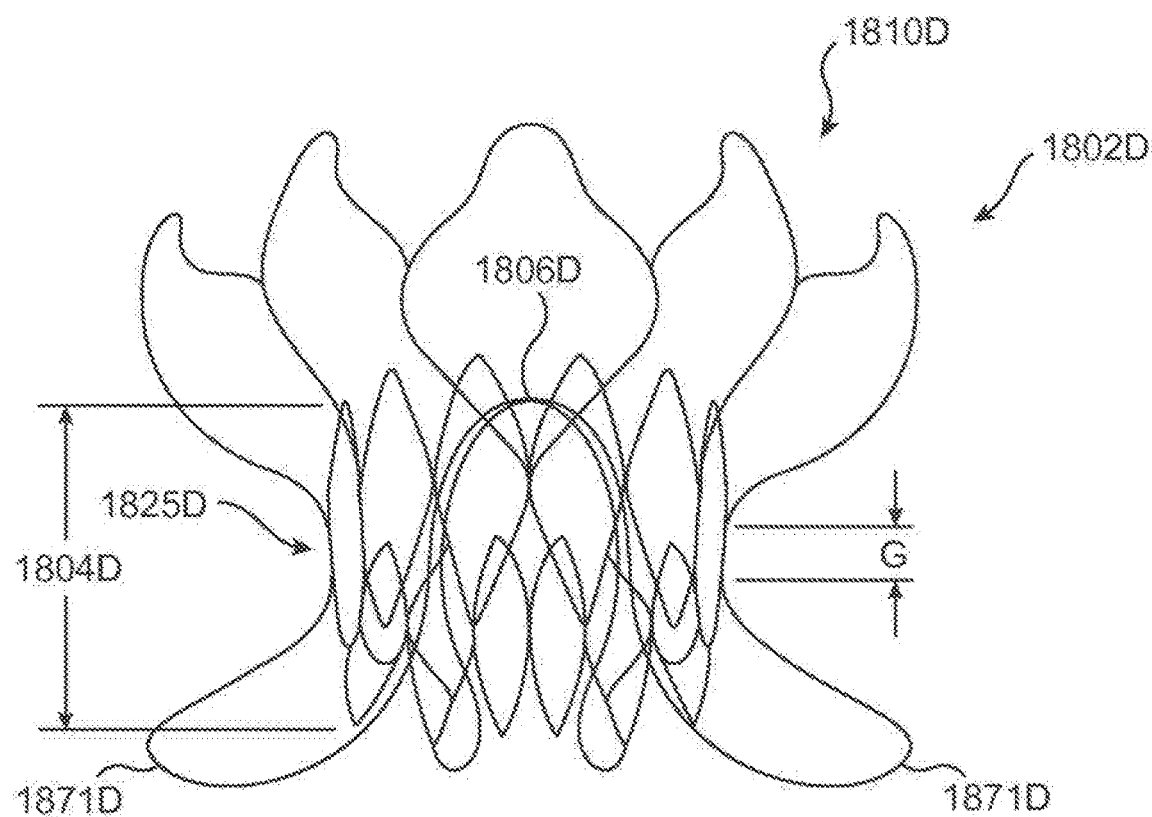
FIGS. 18D and 18E are front or side views of a frame for a valve prosthesis in accordance with other embodiments hereof.
Figure 18E:
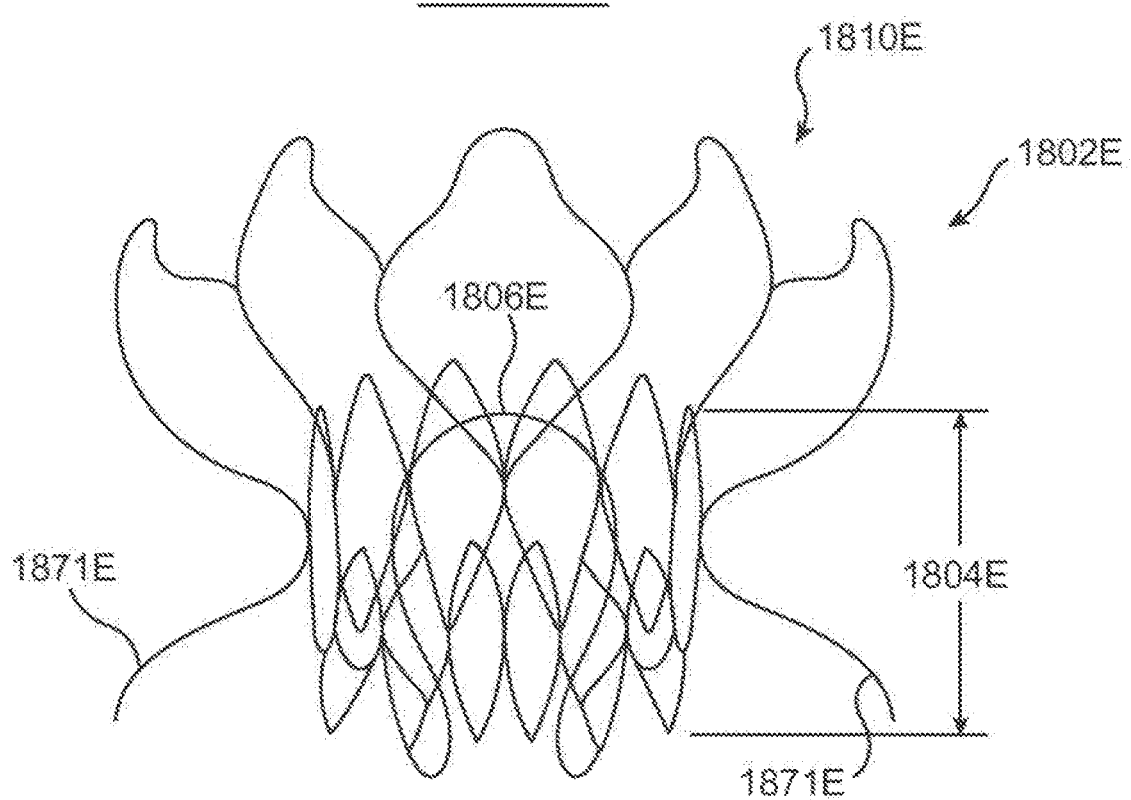

Valve prosthesis 1800 includes a valve body or component 1820 supported by frame 1810. Frame 1810 may include an inlet portion 1802, an hourglass-shape along a central or valve-retaining tubular portion 1804 and support arms 1806. Support arms 1806 may be configured to capture the native valve leaflets during device delivery. Axial fixation of frame 1810 can be achieved through the hourglass-shape of frame 1810 along central portion 1804 that pinches a muscular ridge of the native annulus (MVA). The hourglass shape portion of frame 1810 may be formed by the atrial portion of the frame, i.e., inflow portion 1802, and a ventricular portion of the frame, i.e., second arms 1871A, 1871B that outwardly extend from the reduced-waist region 1825, such that frame 1810 axially engages, fixates, or pinches the annulus from both the atrial and ventricular sides of the annulus. In embodiments hereof, the outwardly-extending second arms 1871A, 1871B along central portion 1804 extend from each support arm 1806 to be disposed along a circumference of the central portion about 90 degrees from each support arm, or stated another way to be formed along the circumference of central portion 1804 approximately half way between the support arms 1806. In the embodiment of FIG. 18, the atrial and ventricular portions of frame 1810 that form the hourglass shape originate from the same node location of central portion 1804. In another embodiment shown in FIG. 18D, support arms 1806D and corresponding second arms 1871D of frame 1810D may originate from a different node location of central portion 1804D than inflow portion 1802D such that a gap G is present therebetween within reduced-waist region 1825D. In another embodiment shown in FIG. 18E, support arms 1806E and second arms 1871E of frame 1810E are separate structures that act independently from one and other. As in the embodiment of FIG. 18, inflow portion 1802E of frame 1810E and second arms 1871E of frame 1810E may originate from the same node location of central portion 1804D. In another embodiment, inflow portion 1802E of frame 1810E and second arms 1871E of frame 1810E may originate from different node locations of central portion 1804E similar to the embodiment of FIG. 18D.

In some embodiments, frame 1810 may geometrically vary along its length. For example, frame 1810 may comprise a geometric cross-sectional shape that matches the shape of a native valve annulus. Frame 1810 may have a portion with an elliptical cross-section such as an outflow or distal end portion 1805 and/or frame 1810 may have a portion having a tubular or D-shaped cross-section, for example, to match the shape of the native valve annulus. The larger diameter of the ellipse or D-shape frame portion may be positioned near the mitral valve commissures of the native valve (MV). The shorter diameter of the ellipse or D-shape frame portion may be positioned near the aorta-mitral fibrous continuity of the native valve. Although outflow end 1805 may be elliptical, valve body 1820 attached to frame 1810 may remain cylindrical or circular. One example of such a configuration is shown in FIGS. 18, 18A, 18B and 18C. Frame 1810 may also provide axial fixation by creating by creating tensioning of the chordae tendinae (CT). Support arms 1806 may transfer tension to the chordae tendinae (CT) and/or the support arms 1806 may apply a force, for example at the distal ends of the support arms, to the ventricular side of the annulus to prevent movement or migration of the prosthesis into the atrium. In some embodiments, valve prosthesis may comprise one or more support arms 1806. In some embodiments, valve prosthesis may comprise one or more support arms for engaging or capturing valve leaflets and one or more support arms for engaging one or more commissures. For example, in one embodiment, valve prosthesis includes one support arm positioned or located in the middle of the posterior leaflet of a native mitral valve and two support arms positioned or located at the left and right trigone, commissures, or with reference to FIG. 1A, the A1 and A3 locations of the anterior leaflet. For example, in one embodiment, the valve prosthesis includes one support arm positioned or located in the middle of the anterior leaflet and two support arms positioned or located, with reference to FIG. 1A, at the P1 and P3 portions of the posterior leaflet. In some embodiments, support arms may engage or interact with leaflets as well as commissures. In some embodiments, support arms may apply one or more forces such as a radial force, a axial force, a lateral force, an inward force, an outward force, an upstream force, and/or a downstream force to one or more heart structures and/or tissues.

Figure 19:
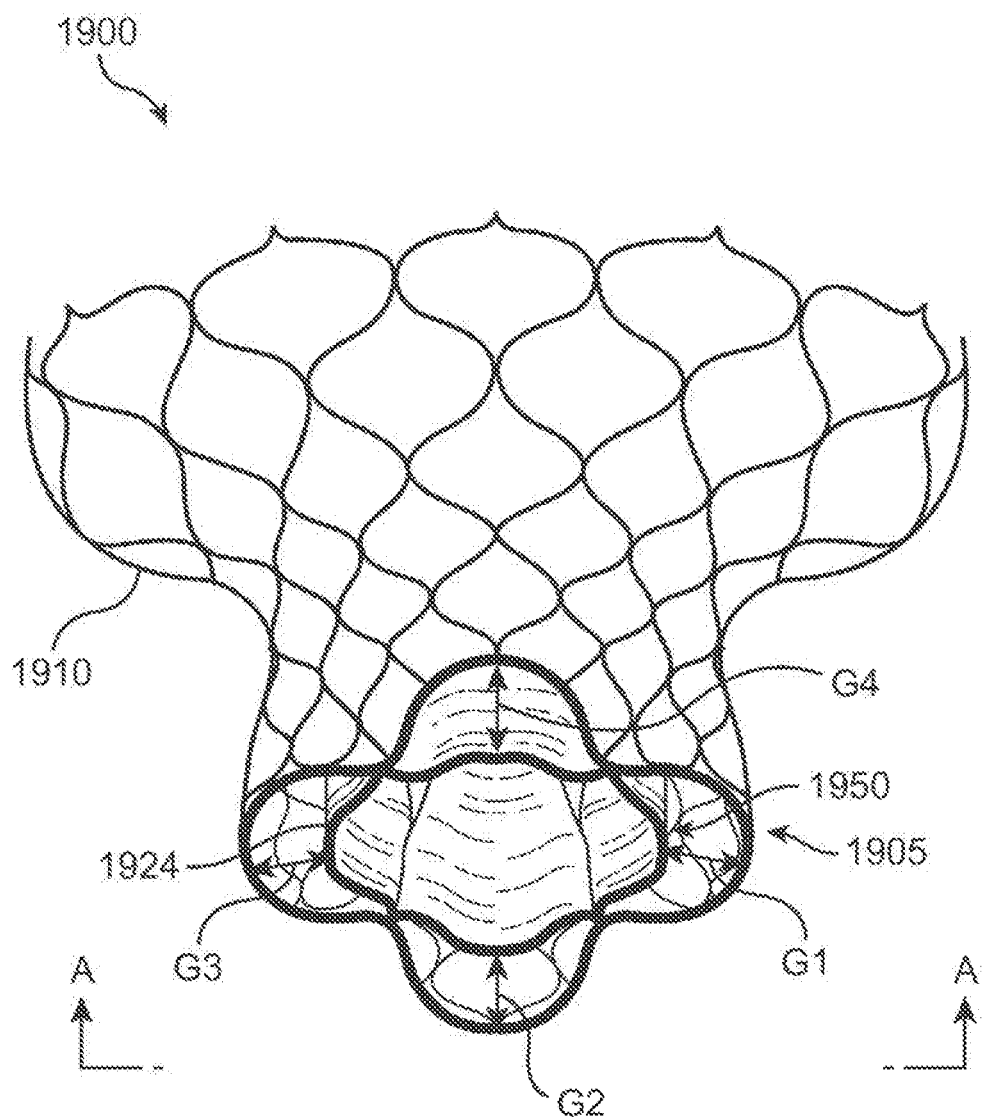
FIG. 19 is an outflow or bottom front perspective view of a valve prosthesis in an open position in accordance with an embodiment hereof.
Figure 19A:
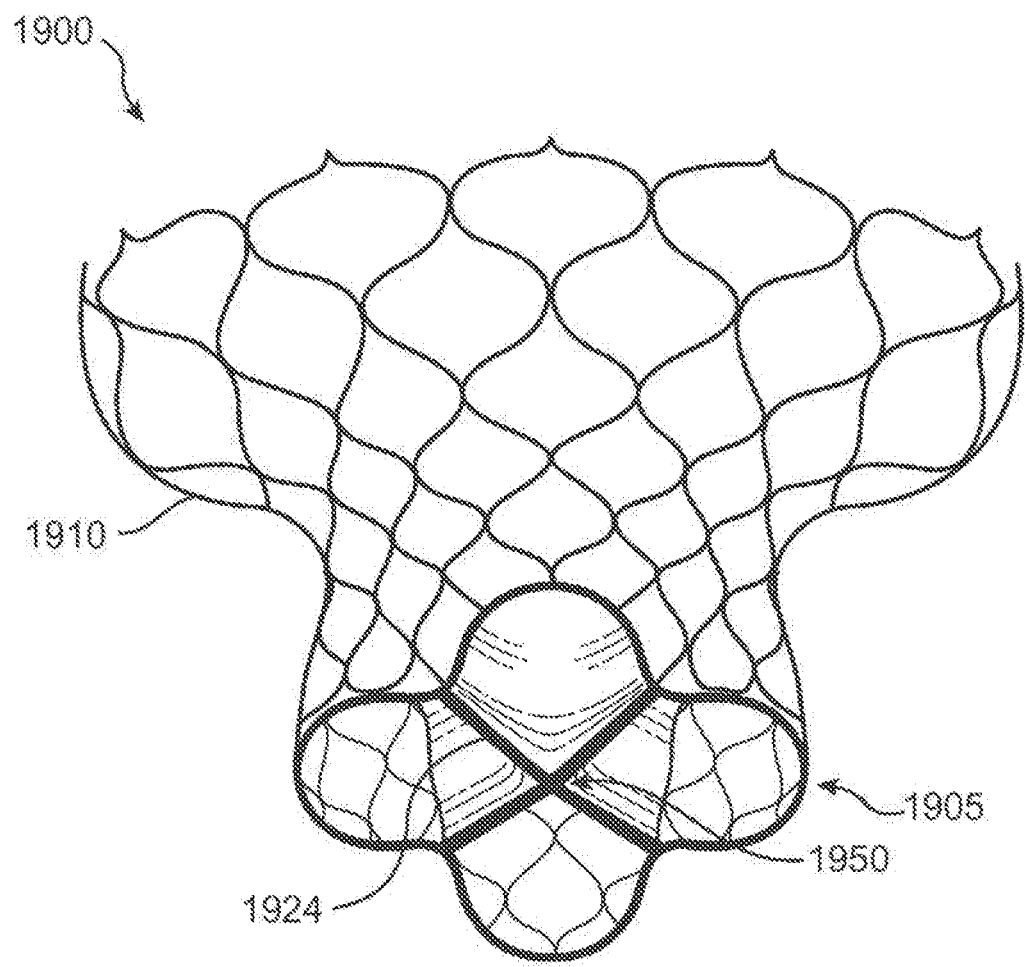
FIG. 19A illustrates an outflow or bottom front perspective view of the valve prosthesis of FIG. 19 in a closed position.

FIGS. 19 and 19A illustrate a valve prosthesis 1900 having a prosthetic valve component with four valve leaflets 1924. FIG. 19 is an outflow or bottom front perspective view of valve prosthesis 1900 in an open position in accordance with an embodiment hereof. FIG. 19A illustrates an outflow or bottom front perspective view of valve prosthesis 1900 of FIG. 19 in a closed position. Valve prosthesis 1900 includes a frame 1910 along with a valve body or component including four prosthetic valve leaflets 1924. An outflow end 1905 of frame 1910 may flare outwardly to allow for gaps G1-G4 between an outflow end 1950 of each valve leaflet 1924 and outflow end 1905 of frame 1910. In accordance with embodiments hereof, frame 1910 may be adapted to include one or more support arms as described herein.

Figure 20:
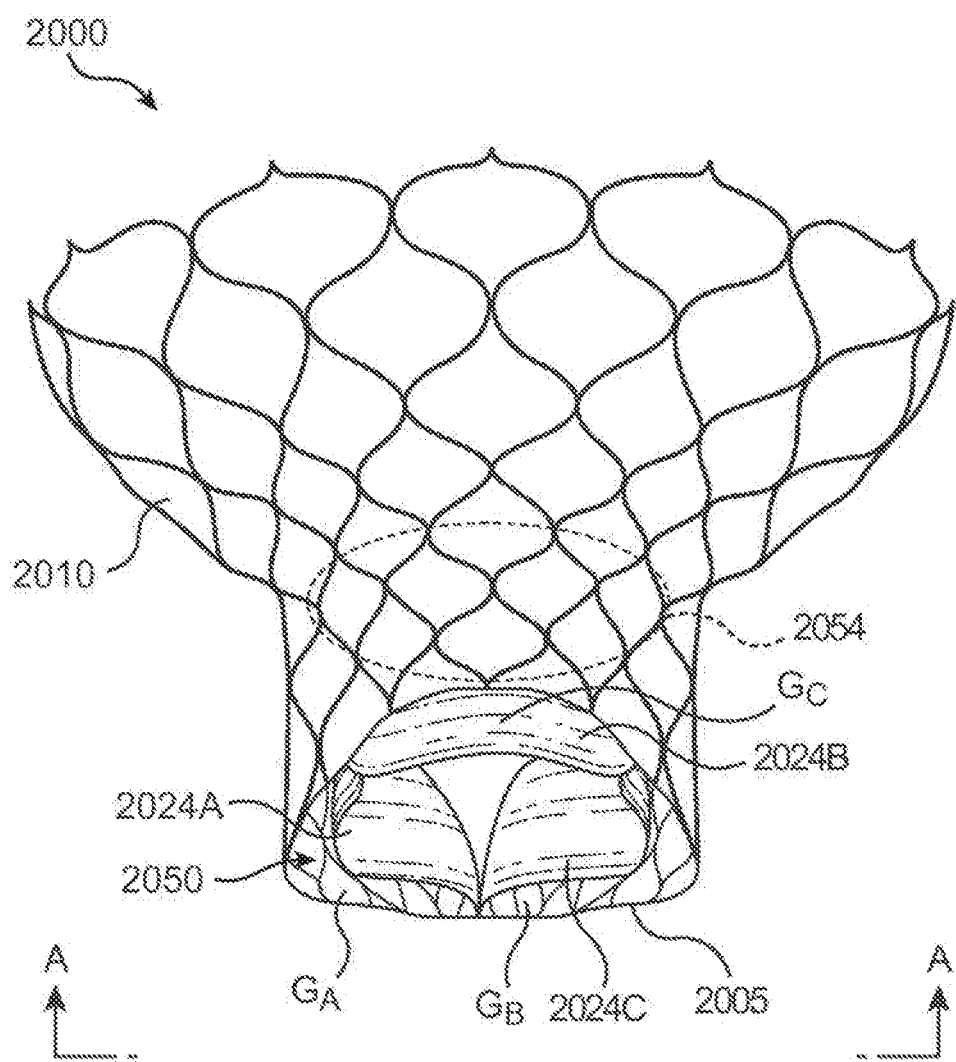
FIG. 20 is an outflow or bottom front perspective view of a valve prosthesis in an open position in accordance with an embodiment hereof.
Figure 20A:
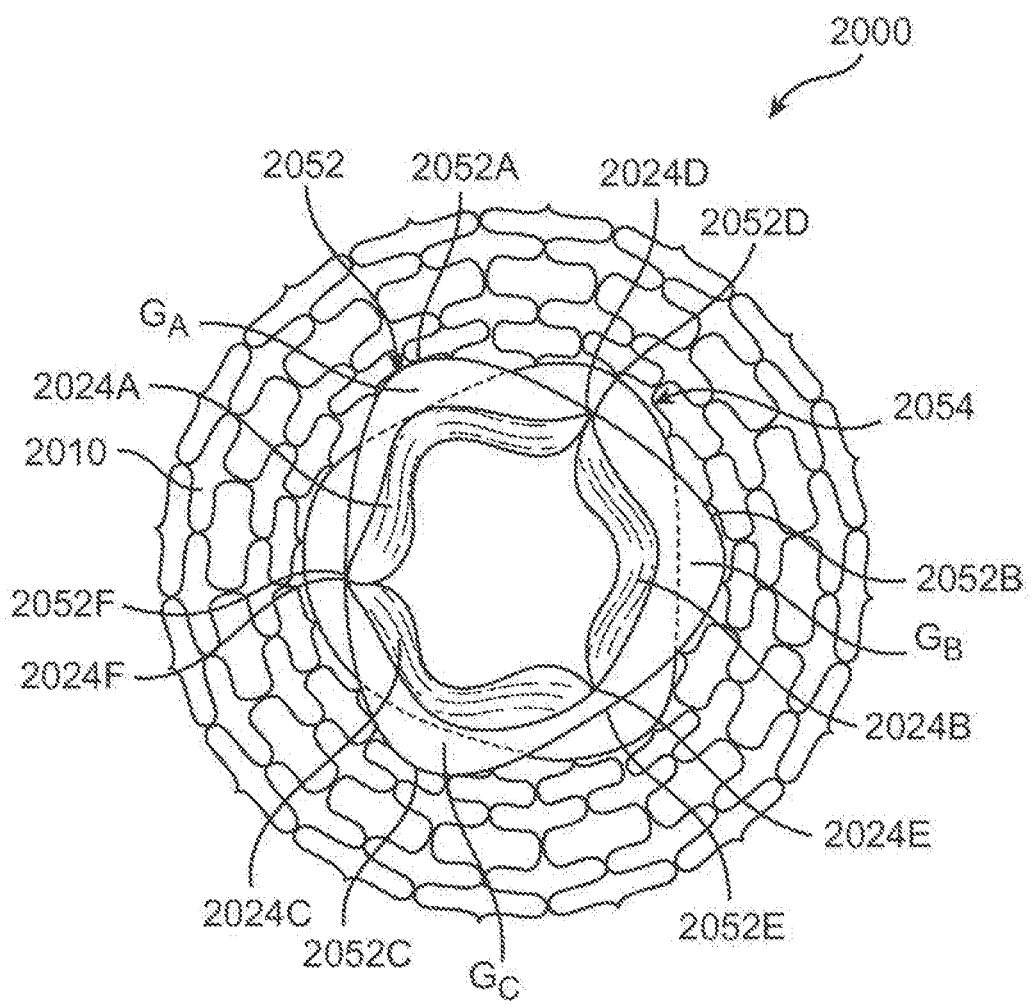
FIG. 20A is an outflow or bottom view of the valve prosthesis of FIG. 20 taken in the direction of line A-A therein.

FIGS. 20 and 20A illustrate a valve prosthesis 2000. FIG. 20 illustrates an outflow or bottom front perspective view of valve prosthesis 2000 in an open position. FIG. 20A illustrates an outflow or bottom view of valve prosthesis 2000 taken in the direction of line A-A in FIG. 20. Valve prosthesis 2000 may include a frame 2010 with a valve body or component including prosthetic valve leaflets 2024A, 2024B, 2024C secured therein. As shown, for example in FIG. 20A, a transverse cross-section of a valve outlet 2052 of frame 2010 may be a rounded triangle with each vertex 2052A, 2052B, 2052C of the triangle aligned with a corresponding leaflet 2024A, 2024B, 2024C of the valve body to provide gaps $G_A$, $G_B$, $G_C$ between an outflow end 2005 of frame 2010 and the outflow end 2050 of valve leaflets 2024A, 2024B, 2024C when the leaflets are fully open. In embodiments hereof, a mid-section or midpoint of sides 2052D, 2052E, 2052F of the rounded triangle defined by valve outlet 2052 of frame 2010 are aligned with corresponding commissures 2024D, 2024E, 2024F of the valve body. A transverse cross-section of a valve base 2054 of frame 2010 can be a rounded triangular and rotated about 60 degrees relative to the transverse cross-section of valve outlet 2052 of frame 2010 so that the valve body forms a roughly cylindrical shape, as shown in FIGS. 20 and 20A. In accordance with embodiments hereof, frame 2010 may be adapted to include one or more support arms as described herein.

Figure 21:
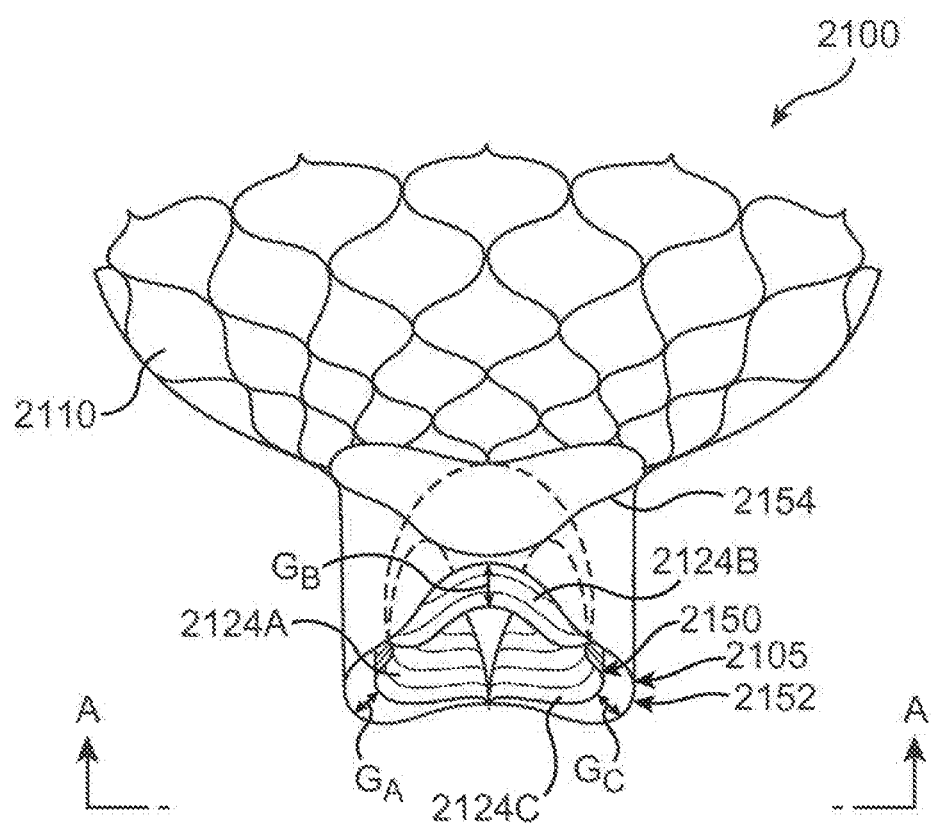
FIG. 21 is an outflow or bottom front perspective view of a valve prosthesis in an open position in accordance with an embodiment hereof.
Figure 21A:
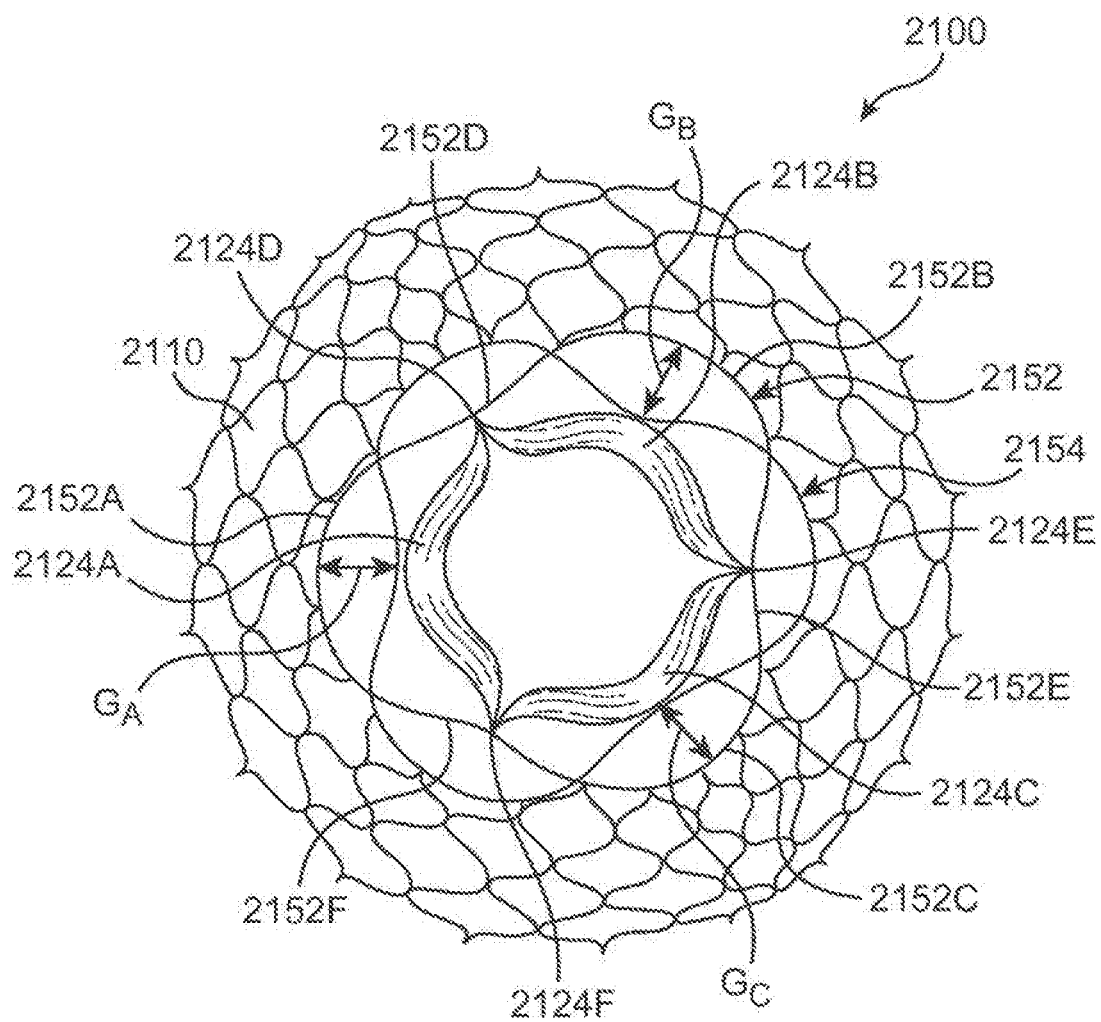
FIG. 21A is an outflow or bottom view of the valve prosthesis of FIG. 21 taken in the direction of line A-A therein.

FIGS. 21 and 21A illustrate a valve prosthesis 2100. FIG. 21 illustrates valve prosthesis 2100 in an open position with FIG. 21A depicting an outflow or bottom view of valve prosthesis 2100 in the open position. Valve prosthesis 2100 includes a frame 2110 having a valve body or component including prosthetic valve leaflets 2124A, 2124B, 2124C secured therein. In accordance with embodiments hereof, frame 2110 may be adapted to include one or more support arms as described herein. Frame 2110 is configured to allow for gaps $G_A$, $G_B$, $G_C$ between an outflow end 2150 of valve leaflets 2124A, 2124B, 2124C and an outflow end 2105 of frame 2110 when valve leaflets 2124A, 2124B, 2124C are fully open. In embodiments hereof, gaps $G_A$, $G_B$, $G_C$ can be sized and shaped to minimize or eliminate contact between valve leaflets 2124A, 2124B, 2124C and frame 2110. In embodiments hereof, gaps $G_A$, $G_B$, $G_C$ can be up to 5 millimeters wide. In other embodiments hereof, gaps $G_A$, $G_B$, $G_C$ can be larger than 5 millimeters.

Valve outlet 2152 of frame 2110 includes three sides 2152D, 2152E, 2152F that curve inward from apexes or vertex 2052A, 2052B, 2052C. In embodiments hereof, a mid-section or midpoint of sides 2152D, 2152E, 2152F are aligned with corresponding commissures 2124D, 2124E, 2124F of the valve body. The overall shape of the transverse cross-section of valve outlet 2152 can be described as clover-leaf shaped. In addition, sides of the rounded triangle of valve base 2154 curve inward and can also be described as clover-leaf shaped. The cross-section of valve base 2154 can be rotated about 60 degrees relative to the cross-section of valve outlet 2152 so that the valve forms a roughly cylindrical shape. In embodiments hereof, valve base 2154 can be substantially cylindrical and valve outlet 2152 can flare out from valve base 2154. In embodiments hereof, valve leaflets 2124A, 2124B, 2124C can be attached at valve base 2154.

FIG. 22A depicts a patterned tube 2210A for forming a frame 2210B in accordance with an embodiment hereof that has been laid flat for illustrative purposes. FIG. 22B depicts a saddle shape of frame 2210B when expanded. In some embodiments, a non-planar or saddle shape of one or more of the various frames or portions thereof as described herein can be achieved by changing the location of nodes formed within the frame. In some embodiments, a non-planar or saddle shape of one or more of the various frames or portions thereof as described herein can be achieved through a shape setting process. In some embodiments, a combination of shape setting and node placement patterns may be used to form non-planar or saddle shapes of one or more of the various frames or portions thereof as described herein. For example, a laser cut pattern of a frame can be modified, along with new fixtures for shape setting to achieve a non-planar configuration. In particular, patterned tube 2210A includes nodes 2260 arranged in a sinusoidal pattern. In some embodiments, such a configuration can have the effect of changing the shape of frame 2210B when frame 2210B is expanded. The sinusoidal pattern of nodes 2260 within patterned tube 2210A can, for example, result in a three dimensional saddle shape 2262 of frame 2210B, shown for example in FIG. 22B, that can mimic the native anatomy at a valve annulus, such as a mitral valve. In some embodiments, patterned tube 2210A can include a saddle-shaped inflow section 2202A and an unmodified center or valve-retaining tubular section 2204A, such as inflow portion 202 of valve prosthesis 200 shown in FIG. 2. In some embodiments, a shape-setting process alone may be used without a sinusoidal pattern of nodes to create a frame having an s-shaped and/or saddle shaped inflow section that matches the saddle shape of a native valve annulus.

Figure 23:
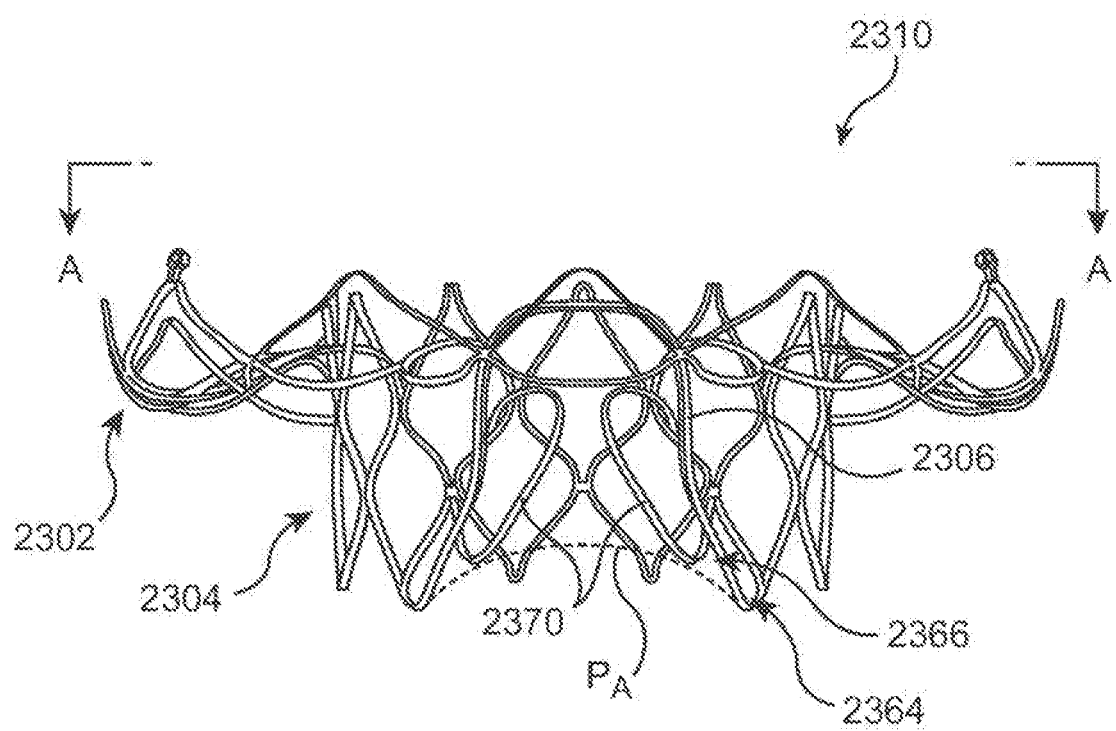
FIG. 23 is a front or side view of a frame in accordance with an embodiment hereof.
Figure 23A:
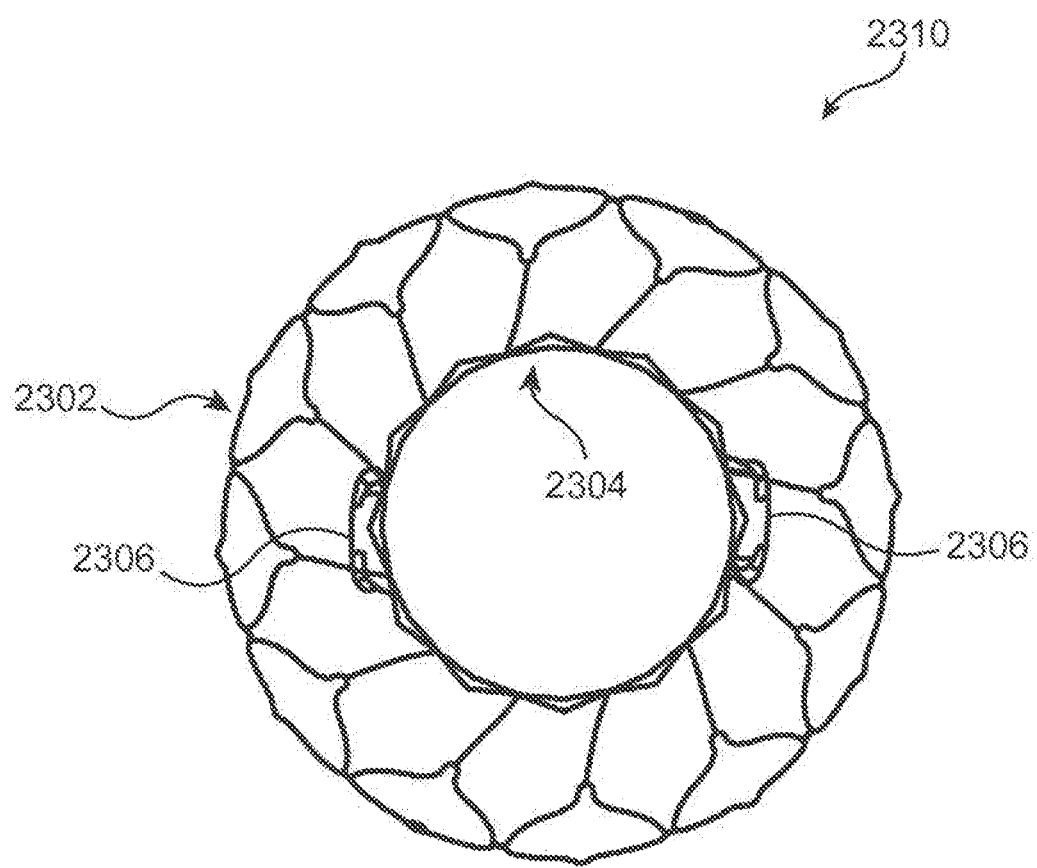
FIG. 23A is a top or inflow view of the frame of FIG. 23 taken in the direction of line A-A therein.

FIGS. 23 and 23A illustrate a frame 2310 for a valve prosthesis in accordance with another embodiment hereof. FIG. 23 is a front or side view of frame 2310 with FIG. 23A being an inflow or top view of frame 2310 taken in the direction of line A-A in FIG. 23. Frame 2310 may include central or valve-retaining tubular portion 2304, inlet or inflow portion 2302, and chordae engagement or guiding element 2370. A chordae guiding element 2370 may extend from each support arm 2306 and may be configured to engage chordae of the native valve site. As described above, chordae tendinae connect to native valve leaflets and act like "tie rods" in an engineering sense. As described above in some embodiments hereof, it may be desirable to impart tension onto the chordae tendinae with the support arms, such as support arms 2306. However, excessive tension can cause the chordae tendinae to rupture which can reduce the effectiveness of a valve prosthesis. In order to address such a concern in embodiments hereof a shape and location of the support arms, such as the shape and location of support arms 2306 on frame 2310 of FIGS. 23 and 23A, can reduce tension imparted onto the chordae tendinae by the support arms.

In embodiments hereof, chordae engagement or guiding element 2370 can be formed by a rigid wire material and can be shaped to avoid hard angles and/or sharp edges. In embodiments hereof, chordae guiding element 2370 may be the same thickness and material as the support arms 2306. In embodiments hereof, chordae guiding element 2370 may be bent in the shape of a semi-circle, oval, lobe, or other suitable shape. In embodiments hereof, one or more chordae engagement or guiding elements may be connected, coupled, attached, and/or extend from one or more locations on one or more support arms, the outflow portion, the inflow portion, and/or the central portion of the valve prosthesis. In embodiments hereof, one or more support arms, the inflow portion, the central portion, and/or the outflow portion of the valve prosthesis may comprise one or more chordae engagement or guiding elements. One or more chordae engagement elements 2370 of frame 2310 may be configured to angle the chordae tendinae so that the chordae are stretched to restrict movement of a valve prosthesis in an upstream direction of blood flow at the valve site. In embodiments hereof, chordae guiding element 2370 may be configured to interact with one or more native valve leaflets instead of the chordae tendinae. In embodiments hereof, one or more of the above configurations can be used in combination with other coatings, coverings, or configurations to reduce chordae abrasion or rupture, as described in more detail below. In embodiments hereof, any corners of one or both of support arms 2306 and chordae guiding elements 2370 may be rounded, which in some embodiments can avoid sharp corners that can cause chordae abrasion or rupture. In embodiments hereof, chordae guiding element 2370 is positioned such that the chordae tendinae are stretched to prevent movement of the valve prosthesis relative to the native valve over the course of the cardiac cycle, without rupturing the chordae tendinae. In embodiments hereof, such a configuration can provide added stability to the valve prosthesis while preventing damage to the chordae. In some embodiments, chordae guiding element 2370 may be directly attached to support arm 2306 and may extend outward from the leaflet securing arm. A first end and a second end of chordae guiding element 2370 may be attached to central portion 2304 of frame 2310. In embodiments hereof, one end of chordae guiding elements 2370 may be directly attached to support arm 2306 and a second end of chordae guiding element 2370 may be directly attached to central portion 2304. In some embodiments, chordae guiding element 2370 and/or support arms 2306 may contain one or more features for holding or restricting motion of the leaflets or chordae. These features may include, but are not limited to, barbs for engaging the leaflets and/or chordae. In some embodiments, leaflets and/or chordae, and/or portions thereof, may be clamped, pinched, or otherwise engaged or fixed by or between the support arms 2306 and/or the chordae guiding elements 2370.

In embodiments hereof, chordae guiding element 2370 may reduce bending of the native chordae by redistributing the force applied by support arm 2306 to the chordae. In embodiments hereof, an outflow end 2364 of support arm 2306 is longitudinally offset from an outflow end 2366 of chordae guiding element 2370 by a distance to reduce the bending of the chordae. The longitudinal offset can be, for example, from about 1 mm to about 5 mm in the longitudinal direction. In embodiments hereof, outflow end 2364 of support arm 2306 is laterally offset from outflow end 2366 of chordae guiding element 2370 by a distance to reduce the bending of the chordae. The lateral offset can be, for example, from about 1 mm to about 5 mm in the lateral direction.

In embodiments hereof, chordae guiding element 2370 may be configured to create a tapered entry for the chordae. In embodiments hereof, a longitudinal and/or lateral offset between support arms 2306 and chordae guiding element 2370 may be configured to guide chordae substantially along a portion of an arc, such as along a portion of parabolic arc PA (shown in broken lines) in FIG. 23. In embodiments hereof, arc PA can be circular rather than parabolic, stepped, or another desired shape. In embodiments hereof, arc PA can guide chordae exiting support arm 2306 and chordae guiding element 2370 to approximate a native anatomical angle. In embodiments hereof, such a configuration can reduce abrasion of the chordae and/or maintain a desired chordal tension. In embodiments hereof, a desired chordal tension is sufficient to prevent frame 2310 from lifting into the atrium. In embodiments hereof, a desired chordal tension is sufficient to substantially prevent frame 2310 from moving and/or rocking during the cardiac cycle. In embodiments hereof, the angle formed by arc PA can serve to decrease an angle of entry of the chordae into support arm 2306, which can reduce chordal abrasion forces acting on the chordae from frame 2310. In embodiments hereof, support arms 2306 and chordae guiding element 2370 are configured to substantially eliminate bending of the chordae. In some embodiments, support arms 2306 and chordae guiding element 2370 are configured to bend the chordae less than approximately 90 degrees. In embodiments hereof, chordae are guided solely by chordae guiding element 2370 and are guided by chordae guiding element so as not to touch support arms 2306.

Figure 24:
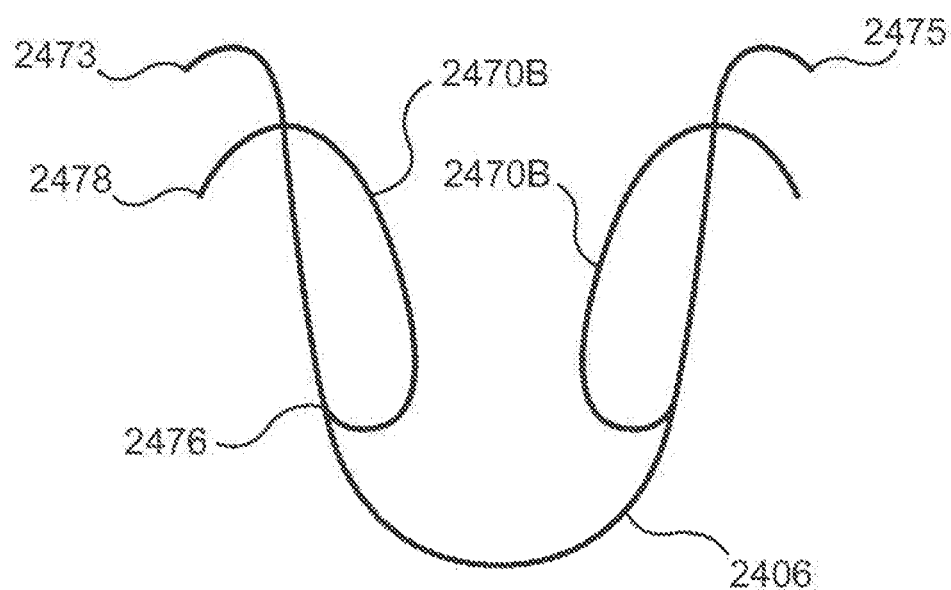
FIG. 24 illustrates a simplified drawing of a portion of a frame in accordance with an embodiment hereof.

FIG. 24 illustrates a simplified drawing of a support arm 2406. Support arm 2406 may include a first end 2473 and a second end 2475. One or both of first end 2473 and second end 2475 may be connected to the same or different portions of the frame (not shown). Support arm 2406 may include a first and second chordae guiding element 2470A, 2470B, which can function similarly to the chordae guiding elements described above. Each chordae guiding element 2470A, 2470B may include a first end 2476 attached to support arm 2406 and a second end 2478 attached to the frame. In embodiments hereof, first end 2476 may also be connected to the frame. In some embodiments hereof, both first end 2476 and second end 2478 of each chordae guiding element 2470A, 2470B may be connected to support arm 2406. In some embodiments hereof, both ends 2476 of elements 2470B may be connected to each other instead of or in addition to connecting to support arm 2406.

With reference to FIGS. 5A-5D the operation of support arms in accordance with some embodiments hereof will be described. Frame 310 is utilized in a valve prosthesis 300 with a valve component 320 attached within the interior portion thereof, and has two support arms or positioning elements 306A, 306B, although more than two and less than two support arms or positioning elements may alternatively be used in embodiments hereof. Valve component 320 is a prosthetic bicuspid valve having two leaflets 324A, 324B, although other configurations, such as a tricuspid leaflet configuration, may alternatively be used in embodiments hereof. Each support arm 306A, 306B may bend or rotate more than ninety degrees with respect to its compressed, delivery configuration during deployment of valve prosthesis 300. In one embodiment, each support arm 306A, 306B rotates between 135 degrees and 180 degrees during deployment of valve prosthesis 300. In a delivery configuration of FIGS. 5A and 5C, each support arm 306A, 306B may distally extend from distal or outflow end 305 of frame 310. When released from a delivery sheath or other delivery device (not shown), each support arm 306A, 306B may gradually bend outwardly and then towards an outer surface of the delivery device or frame 310 until it reaches a deployed configuration of FIGS. 5B and 5D in which each support arm 306A, 306B proximally extends from distal or outflow end 305 of frame 310. Once deployed, support arms 306A, 306B may function to position and anchor valve prosthesis 300 at a native valve target site, such as a mitral valve target site. In one embodiment, when deployed at a native mitral valve target site, the configuration/structure of a valve prosthesis as well as the delivery system and method of use must accommodate the size of the left ventricle and refrain from obstructing the left ventricular outflow tract. By rotating from an initial distally-extending configuration to a final proximally-extending configuration, support arm 306A, 306B as well as those shown and described in other embodiments hereof are particularly configured to be deployed within a native mitral valve target site as will be explained in more detail below.

As discussed above, each positioning element or support arm may be coupled to a distal or outflow end portion of the frame of the valve prosthesis. In embodiments hereof, each support arm may be coupled to the frame at multiple connection points. More specifically referring to FIG. 5A and FIG. 25 that is an enlarged portion of FIG. 5A, each support arm 306A, 306B may be coupled to distal end 305 of frame 310 via two V-shaped connectors 390A, 390AA and 390B, 390BB, respectively, such that four connection points A1, A2, A3, A4 and B1, B2, B3, B4, respectively, are located between each support arm 306A, 306B and frame 310. In one embodiment, the eight connection points A1, A2, A3, A4, B1, B2, B3, B4 are approximately equally spaced around the perimeter of distal end 305 of frame 310 and collectively function to prevent the prosthetic valve leaflets from obstructing the outflow end of valve prosthesis 300 and the left ventricular outflow tract. Stated another way, V-shaped connectors 390A, 390AA, 390B, 390BB increase the number of connection points between each support arm 306A, 306B, respectively, and frame 310, and thereby shorten or minimize the open space or distance between adjacent connection points. V-shaped connectors 390A, 390AA, 390B, 390BB may act as an obstacle in the path that the prosthetic valve leaflets would follow when overlapping onto frame 310 and can thereby keep the flow path clear. Although described as "V-shaped connectors," it will be apparent to those of ordinary skill in the art that two straight components formed generally in the shape of a "V" may be utilized in embodiments hereof rather than one single V-shaped component. In addition, although described with respect to support arms 306A, 306B and frame 310, such connectors may be utilized for forming multiple connection points between any embodiment described herein. In some embodiments, a graft material may be used between connection points B1 and B4 to help create a clear flow path as described above.

In embodiments hereof and as described herein, support arms 306A, 306B and frame 310 may be formed as an integral unitary structure, such as by laser cutting or etching the support arms and frame from a single hollow tube or sheet. In another embodiment, V-shaped connectors 390A, 390AA, 390B, 390BB and/or support arms 306A, 306B may be separate components that are formed separately and mechanically coupled to each other and to frame 310 via any suitable mechanical method, including welding, soldering, or by another mechanical method.

Figure 25A:
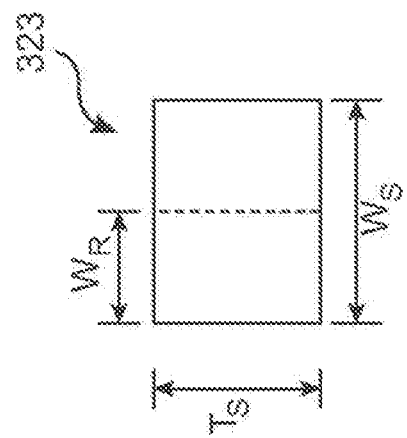
FIG. 25A is a cross-sectional view taken along line A-A of FIG. 25.
Figure 25:
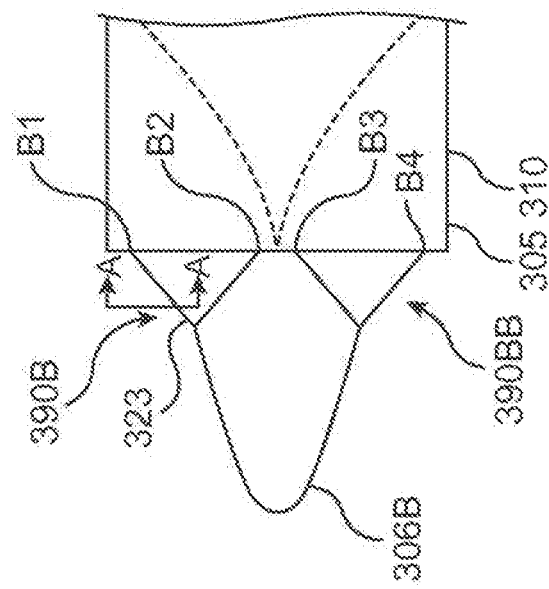
FIG. 25 is a side view of an enlarged portion of the valve prosthesis of FIG. 5A, wherein a support arm is coupled to the frame at four connection points.

In order to lower the amount of stress and/or strain that occurs in V-shaped connectors 390A, 390AA, 390B, 390BB as support arms 306A, 306B transform between the initial distally-extending compressed configuration and the final proximally-extending deployed configuration, the width of the wire(s) or tubular member(s) which form V-shaped connectors 390A, 390AA, 390B, 390BB may be increased as compared to the width or dimension of support arms 306A, 306B as well as compared to the width or dimension of the wire or tubular member which forms frame 310. More particularly, FIG. 25A illustrates a sectional view along line A-A of FIG. 25 showing a strut 323 of V-shaped connector 390B according to an embodiment hereof. A reference width $W_R$ is shown in phantom in FIG. 25A and represents the width of the wire or tubular member which forms frame 310 and/or support arms 306A, 306B. A width $W_S$ of strut 323B is widened or increased relative to width $W_R$, thereby increasing the amount of material of V-shaped connector 390B such that it can handle the deformation that occurs thereto during deployment of valve prosthesis 300. In order to widen or increase the width of strut 323, material may be added or banded to strut 323 around the width direction thereof. In an embodiment, material may be added to include the width of strut 323 up to three times of width $W_R$. Preferably, a thickness $T_S$ of strut 323 is not increased relative to the thickness of the wire or tubular member which forms frame 310 due to size constraints on the compressed outer diameter or profile of valve prosthesis 300 when in a compressed configuration. As utilized herein, thickness $T_S$ of strut 323 refers to the strut material that extends in a radial direction relative to frame 310. Although illustrated as constant or uniform, thickness $T_S$ of strut 323 may vary or increase from an inner surface relative to an outer surface of strut 323.

FIGS. 26A-26F illustrates various configurations of generally U-shaped or V-shaped support arms according to embodiments hereof. Referring also to FIG. 26A, support arm 2606A is generally shown as being a wire or tubular structure formed into a U-shaped or generally U-shaped configuration such that the support arm has two straight side segments 2680A, 2682A with a bottom curved segment 2684A. As will be understood by those of ordinary skill in the art, "side" and "bottom" are relative terms and utilized herein for illustration purposes only. The straight side segments may be parallel to each other as shown in FIG. 26A, or may be slanted or angled away from each other as shown in support arm 2606B of FIG. 26B in which two straight slanted side segments 2680B, 2682B flare apart as they extend from bottom curved segment 2684B. As utilized herein, "generally" U-shaped includes wire or tubular structures formed into: a horseshoe shape support arm 2606C as shown in FIG. 26C in which two curved side segments 2680C, 2682C have ends that converge together as they extend from bottom curved segment 2684C; a semi-circle support arm 2606D as shown in FIG. 26D; and an oblong shape support arm 2606F as shown in FIG. 26F in which two parallel straight side segments 2680F, 2682F have a straight bottom segment 2684F therebetween. In another embodiment hereof, the positioning elements may be generally V-shaped as shown in support arm 2606E of FIG. 26E in which two straight slanted side segments 2680C, 2682C are connected together by a curved apex 2684E. In some embodiments, one or more support arms, as described herein, may be considerably longer, shorter, wider, or narrower than shown. In some embodiments, one or more support arms, as described herein, may be narrower at the base, bottom or proximal end portion where the support arms couple to the inflow portion, central portion and/or the outflow portion of the valve prosthesis and wider at the top or distal end portion of the support arm. In some embodiments, one or more support arms, as described herein, may be wider at the base, bottom, or proximal end portion where the support arms couple to the inflow portion, central portion and/or the outflow portion of the valve prosthesis and narrower at the top or distal end portion of the support arm. In some embodiments, one or more support arms, as described herein, may be configured to be a shape and size that can provide a positioning function, valve leaflet capturing function, a stabilization function, an anti-migration function, and/or an anchoring function for valve prosthesis in accordance herewith when the prosthesis is deployed at a native valve site. In some embodiments, one or more support arms, as described herein, may interact, engage, capture, clamp, push against one or more native tissues or structures such as valve leaflets, chordae, annulus, ventricle, and/or atrium. In some embodiments, one or more support arms, as described herein, may comprise a first portion that extends in a forward direction and a second portion that extends in a backward direction. In some embodiments, one or more support arms, as described herein, may comprise a first portion that extends in a backward direction and a second portion that extends in a forward direction. In some embodiments, one or more support arms, as described herein, may be connected, coupled, attached, and/or extend from one or more locations positioned on the inflow portion, the central portion and/or the outflow portion of the valve prosthesis. For example, if the valve prosthesis is positioned within the native mitral valve annulus, the support arms may extend from the frame of valve prosthesis in accordance herewith on the ventricular or outflow side of the mitral valve and provide interference with the native valve leaflets and/or the walls of the left ventricle, thereby inhibiting motion of the valve prosthesis.

FIGS. 27A, 27B, 27C, 27D illustrate an embodiment of a valve prosthesis 2700 having support arms 2706A, 2706B with double or dual support arms that may be utilized in any embodiment described herein. FIGS. 27A and 27C are schematic side and top views, respectively, of valve prosthesis 2700 having support arms 2706A, 2706B with outer and inner U-shaped support arms according to an embodiment hereof, wherein valve prosthesis 2700 is in a delivery or compressed configuration with the support arms 2706A, 2706B distally extending from a distal end 2705 of the prosthesis. FIGS. 27B and 27D are schematic side and top views, respectively, of valve prosthesis 2700 of FIGS. 27A and 27C, wherein the valve prosthesis is in an expanded or deployed configuration with support arms 2706A, 2706B proximally extending from distal end 2705 of the prosthesis. More particularly, FIGS. 27C and 27D are a side view of the frame 2710 as shown in FIGS. 27A and 27B rotated 90° about a longitudinal axis $L_A$ thereof from the orientation shown in FIGS. 27A and 27B.

Similar to embodiments described above, valve prosthesis 2700 may include a frame, framework or stent 2710, a valve component 2720 attached within the interior portion of frame 2710 that is capable of blocking flow in one direction to regulate flow through valve prosthesis 2700 via leaflets 2724A, 2724B, and two support arms 2706A, 2706B. Frame 2710 of valve prosthesis 2700 may be a generally tubular expandable body having a stepped outer diameter or profile extending between a proximal end 2703 and distal end 2705. Similar to embodiments described above, the stepped outer diameter of frame 2710 may include a distal, outflow, central or ventricular segment 2704 and a proximal, inflow or atrial segment 2702 having an expanded diameter which is greater than the expanded diameter of outflow segment 2704.

Support arms 2706A, 2706B may extend from opposing sides of frame 2710. With reference to support arm 2706A in FIG. 27A, support arm 2706A may include a first or outer U-shaped support arm 2786A and a second or inner U-shaped support arm 2788A that each distally extend from a distal end 2705 of frame 2710. Although not shown in the figures, support arm 2706B may also include a second or inner U-shaped support arm within an outer U-shaped support arm. When released from a delivery sheath (not shown), each of the U-shaped support arms may gradually bend outwardly and then towards an outer surface of the delivery device or frame of the valve prosthesis until they transform from their compressed configuration of FIGS. 27A and 27C to their deployed configuration of FIGS. 27B and 27D in which each of the U-shaped support arms proximally extends from distal end 2705 of frame 2710. As in embodiments described above, each of the U-shaped support arms may bend or rotate more than ninety degrees with respect to a compressed, delivery configuration during deployment of valve prosthesis 2700. In one embodiment, each U-shaped support arm rotates between 135 degrees and 180 degrees during deployment of valve prosthesis 2700. Compared to a single U-shaped support arm, outer and inner U-shaped support arms may provide additional spring force for improved anchoring and/or positioning of the valve prosthesis.

Figure 30B:
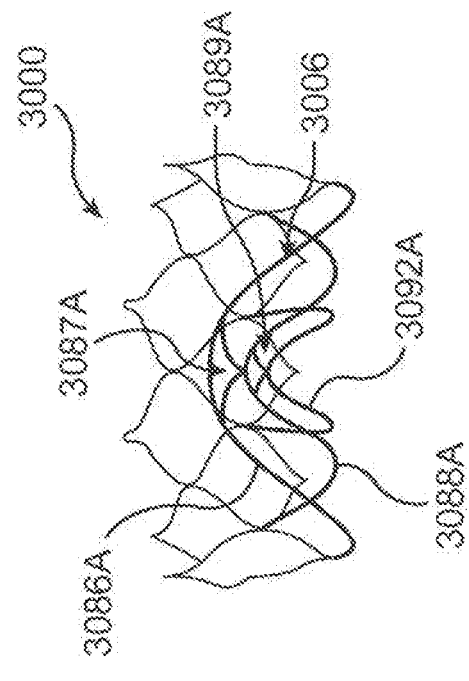
FIG. 30B is an enlarged view of a portion of the valve prosthesis of FIG. 30A.

Adjacent outer and inner U-shaped support arms of each support arm 2706A, 2706B may be coupled together. With reference to support arm 2706A in FIG. 27A, adjacent outer and inner U-shaped support arms 2786A, 2788A of support arm 2706A may be coupled together via a connector 2787A which ensures that both U-shaped support arms of support arm 2706A remain in the same plane during deployment. Connector 2787A may have a flared V-shaped configuration in which an apex 2745 of connector 2787A is coupled to a peak or crest 2743 of inner support arm 2788A. More particularly, connector 2787A may include two curved legs 2746A, 2746B. First ends of legs 2746A, 2746B may be coupled to peak 2743 of inner support arm 2788A, and curved legs 2746A, 2746B of connector 2787A may extend or flare away from each other such that second ends of legs 2746A, 2746B may be coupled adjacent to or on opposing sides of a peak or crest 2741 of outer support arm 2786A. Due to the curved legs 2746A, 2746B of connector 2787A, the distance or space between the crowns of outer and inner U-shaped support arms may be adjustable and allowed to change. Legs 2746A, 2746B may allow distance or space between peak 2743 of inner support arm 2788A and peak 2741 of outer support arm 2786A because the curved legs of connector 2787A may bend, resulting in a shorter distance between peak 2743 and peak 2141, or the legs of connector 2787A may straighten, resulting in a greater distance between peak 2743 and peak 2141. In some embodiments, one or more support arms may include outer and inner support arm members coupled together directly without the use of a connector, for example as shown in FIG. 6. In some embodiments, one or more support arms may include outer and inner support arm members not coupled together, for example as shown in FIG. 17. In some embodiments, one or more support arms may include two or more support arm members coupled together with or without the use of a connector, for example as shown in FIG. 22. In some embodiments, one or more support arms may include two or more support arm members not coupled together and/or two or more support arm members coupled together with or without the use of a connector, for example as shown in FIGS. 30B and 42B.

The distance or space between peak 2743 and peak 2741 may increase during crimping when valve prosthesis 2700 is in a compressed configuration shown in FIG. 27A, 27C, and the distance or space may decrease during expansion when valve prosthesis 2700 is in a deployed configuration. Connector 2787A, as well as the inner and outer U-shaped support arms, may be laser cut from a tube of self-expanding material and thereby integrally formed as part of the frame 2710 of the valve prosthesis, or may be formed separately and subsequently attached to the frame 2710. Although connector 2787A is only visible in FIGS. 27A, 27B between inner support arm 2788A and outer support arm 2786A, it will be understood by one of ordinary skill in the art that such a connector may couple the outer and inner support arms of support arm 2706B that also extend from distal end 2705 of valve prosthesis 2700.

FIGS. 28A, 28B, 28C illustrate an embodiment of a valve prosthesis 2800 including a lattice frame or stent framework 2810 and positioning elements or support arms 2806A, 2806B with dual U-shaped support arms that distally extend from a distal end 2805 of the valve prosthesis. More particularly, support arms 2806A, 2806B may include a first or outer U-shaped support arm 2886A, 2886B, respectfully, and a second or inner U-shaped support arm 2888A, 2888B that may each bend or rotate more than ninety degrees with respect to a compressed, delivery configuration during deployment. Each outer support arm may be connected to a respective inner support arm via a connector, such as connector 2887A shown in FIGS. 28A and 28C, and as described above with respect to connector 2787A. In the embodiment of FIGS. 28A, 28B, 28C, the U-shaped support arms may extend from the distalmost crowns or apexes 2817 of lattice frame 2810. Compared to the embodiment shown in FIGS. 29A-29C, frame 2810 and thus valve prosthesis 2800 may have a smaller crimped profile for delivery.

FIGS. 29A, 29B, 29C illustrate an embodiment of a valve prosthesis 2900 that is similar to valve prosthesis 2800, except that support arms 2906A, 2906B do not extend from distalmost crowns or apexes 2917 of a lattice frame 2910. Rather, support arms 2906A, 2906B may extend from between the distalmost crowns or apexes 2917 of a lattice frame 2910. As best shown in FIG. 29B, in order to shorten or minimize the open space or distance D between adjacent support arms 2906A, 2906B, support arms 2906A, 2906B may extend from opposing sides of a distalmost crown 2917 such that the support arms are separated only by the width of the crown. More particularly, support arms 2906A, 2906B may distally extend from a distal end 2905 of the valve prosthesis and may include a first or outer U-shaped support arm 2986A, 2986B, respectfully, and a second or inner U-shaped support arm 2988A, 2988B, respectively, that may each bend or rotate more than ninety degrees with respect to its compressed, delivery configuration during deployment. Each outer support arm may be connected to a respective inner support arm via a connector, such as connector 2987A shown in FIGS. 29A, 29C and as described above with respect to connector 2787A. Support arms 2906A, 2906B may extend from between the distalmost crowns or apexes 2917 of lattice frame 2910 to minimize open space or distance D and thereby prevent the prosthetic valve leaflets from obstructing the outflow end of valve prosthesis 2900 and the left ventricular outflow tract (LVOT). Outer U-shaped support arms of support arms 2906A, 2906B may be closer together, and act as an obstacle in the path that the prosthetic valve leaflets would follow when overlapping onto frame 2910 and thereby keep the flow path clear. Another benefit of extending support arms 2906A, 2906B from between the distalmost crowns or apexes 2917 of lattice frame 2910 is that the support arms may be located more proximal along the prosthesis compared to the embodiment shown in FIGS. 28A-28C, which minimizes the length or amount of the valve prosthesis that projects or extends in the left ventricle.

Figure 30A:
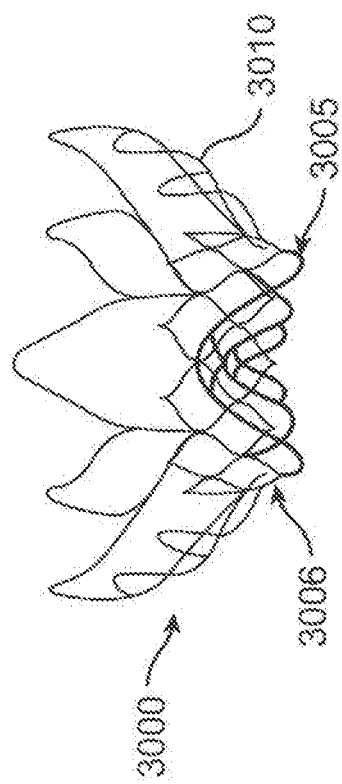
FIG. 30A is a side view of a valve prosthesis having positioning elements with triple U-shaped support arms according to an embodiment hereof, wherein the valve prosthesis is in an expanded or deployed configuration.

FIGS. 30A and 30 illustrate another embodiment of a valve prosthesis 3000 that is similar to valve prosthesis 2900, except that each support arm or positioning element includes triple support arms for additional spring force for improved anchoring and/or positioning of the valve prosthesis. Each support arm 3006 may extend from between the distalmost crowns of a distal end 3005 of a lattice stent or frame 3010 and may include a first or outer U-shaped support arm 3086A, a second or intermediate U-shaped support arm 3088A, and a third or inner U-shaped support arm 3092A. When released from a delivery sheath (not shown in FIG. 30A or FIG. 30B), all of the U-shaped support arms may gradually bend outwardly and then towards an outer surface of the delivery device or frame of the valve prosthesis until they reach a deployed configuration of FIG. 30A and FIG. 30B in which all of the U-shaped support arms may proximally extend from distal end 3005 of frame 3010. As in embodiments described above, all of the U-shaped support arms may bend or rotate more than ninety degrees with respect to a compressed, delivery configuration during deployment of valve prosthesis 3000. In an embodiment, each U-shaped support may arm rotate between 135 degrees and 180 degrees during deployment of valve prosthesis 3000. Although only one support arm or positioning element is shown and described with reference to FIGS. 30A, 30B, it will be understood by those of ordinary skill in the art that valve prosthesis 3000 may include at least two support arms extending from opposing sides of the prosthesis. Each support arm may include triple U-shaped support arms for anchoring and/or positioning the valve prosthesis.

Adjacent support arms of each positioning element may be coupled together via a connector which ensures that each support arm of the positioning element remains in the same plane during deployment. More specifically, outer U-shaped support arm 3086A may be coupled to an intermediate U-shaped support arm 3088A via a connector 3087A and intermediate U-shaped support arm 3088A may be coupled to an inner U-shaped support arm 3092A via a connector 3089A. Connectors 3087A, 3089A may have the same flared V-shaped configuration as connector 2787A described above. Due to the curved or flared legs of connectors 3087A, 3089A, the distance or space between the peaks of adjacent U-shaped support arms may be adjustable and allowed to change as described with respect to connector 2787A.

Figure 31:
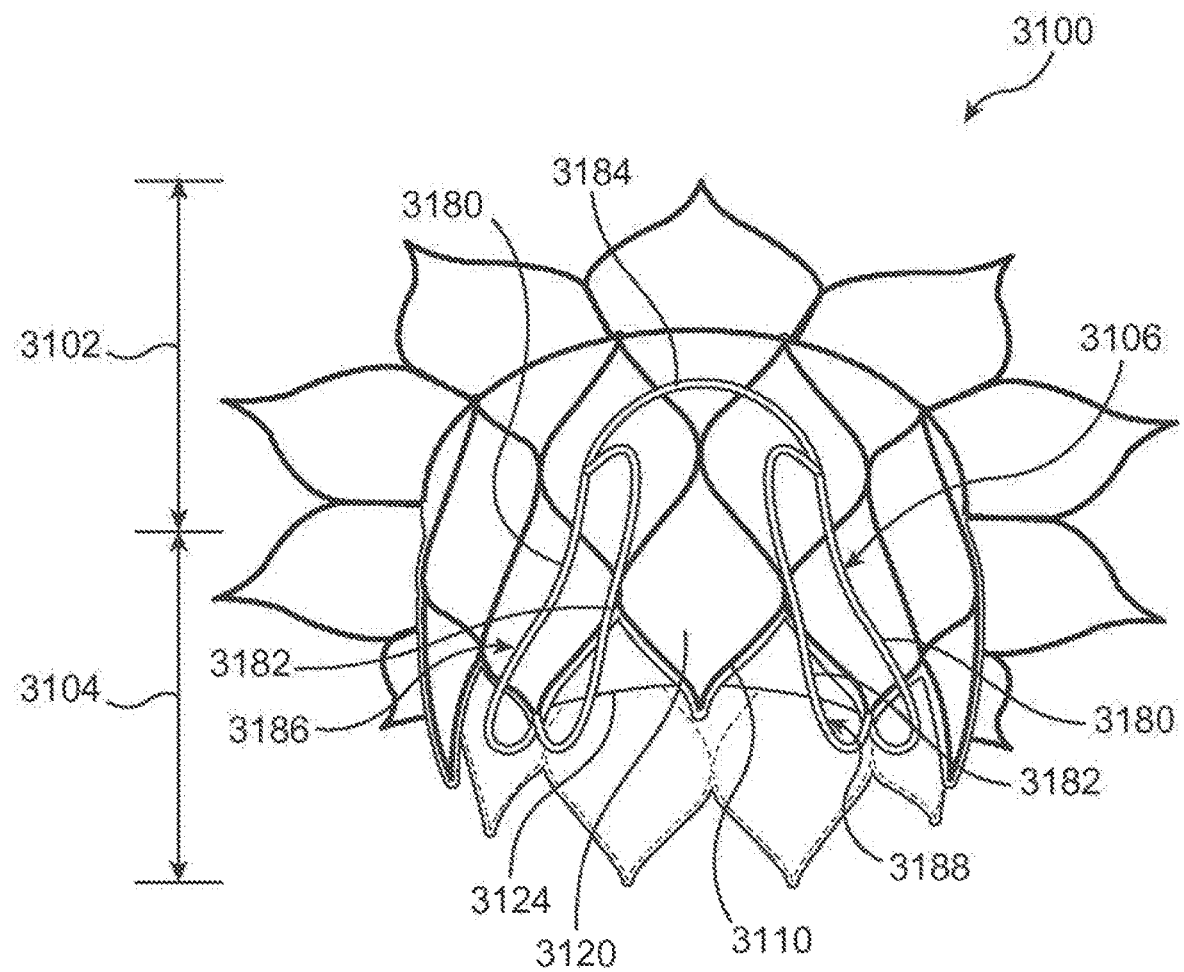
FIG. 31 illustrates a valve prosthesis in accordance with an embodiment hereof.

FIG. 31 illustrates valve prosthesis 3100 in accordance with an embodiment hereof. Valve prosthesis 3100 may include frame 3110 having an inflow portion 3102 and an outflow portion 3104. Outflow portions in some embodiments may also be considered central or valve-retaining tubular portions of frames thereof. Inflow portion 3102 and outflow portion 3104 of valve prosthesis 3100 may have various configurations, for example, those disclosed in U.S. application Ser. No. 13/736,460, which is incorporated by reference herein in its entirety. Valve component 3120 having leaflets 3124 may be secured within an interior of frame 3110. Although not shown in every embodiment, a valve body or component as described herein may be included in each of the following embodiments.

As shown in FIG. 31, valve prosthesis 3100 may include a support arm 3106 having inner support arm 3188 and outer support arm 3186. In certain embodiments, inner support arm 3188 and outer support arm 3186 may be connected to and extend from frame 3110, or may be integrally formed as part of frame 3110. Outer support arm 3186 may include side segments 3180 and curved middle segment 3184 extending between side segments 3180. Inner support arm 3188 may include side segments 3182. In certain embodiments, inner support arm 3188 may also include a middle segment (not shown), which may extend between side segments 3182. Frame 3110, inner support arm 3188, and outer support arm 3186 may each be made of suitable bio-compatible materials, for example, but not limited to, metals such as stainless steel and/or nitinol. It should be noted that certain embodiments disclosed herein illustrate dual support arms, which can improve fatigue performance, such as shown in FIG. 31 by way of inner support arm 3188 and outer support arm 3186. Certain embodiments illustrate only a single support arm. It is understood that one or more support arms can be substituted across various embodiments disclosed herein and the illustrated embodiments are not limited to the number or configuration of support arms illustrated in each figure. In certain embodiments, support arms can be symmetrical or asymmetrical. The support arms can be of any suitable length, and the angle between the support arm and the frame can be any angle up to and including 180 degrees. As shown, for example, in FIG. 31, in certain embodiments, one or more crowns along frame 3110 can be located between the side segments of the support arms.

Figure 32A:
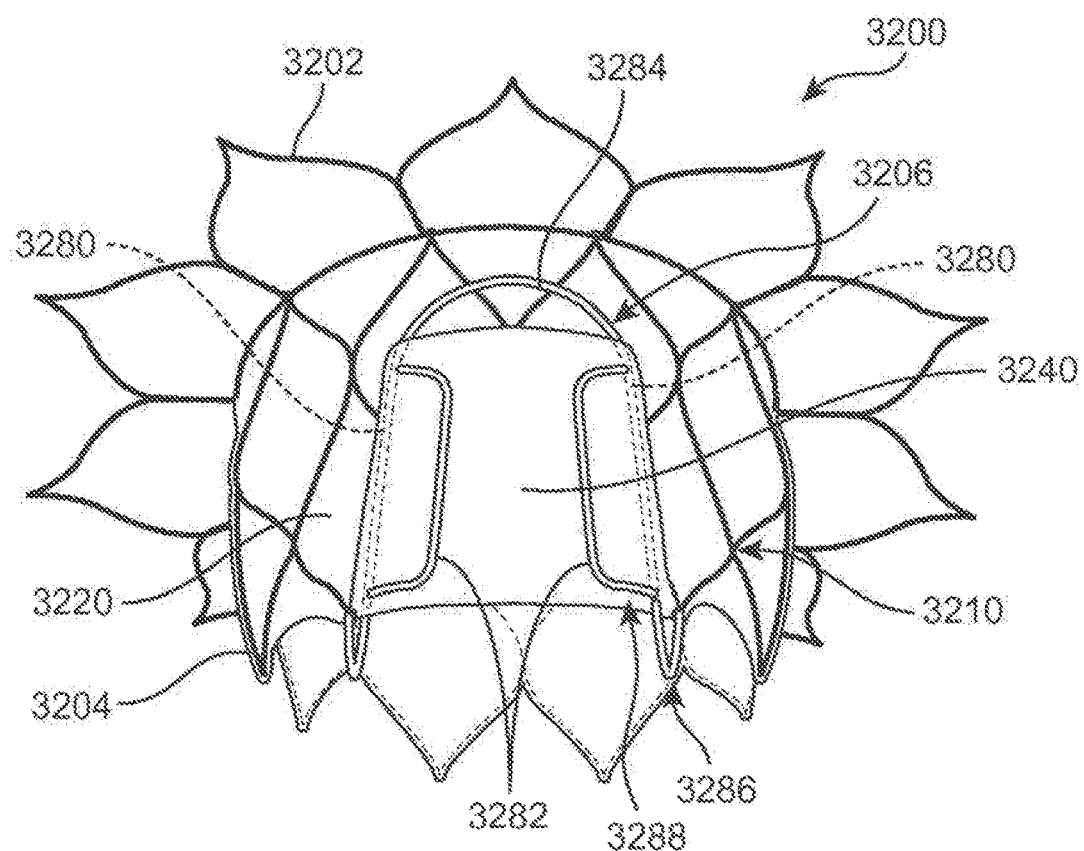
FIGS. 32A and 32B illustrate views of a valve prosthesis in accordance with an embodiment hereof.
Figure 32B:
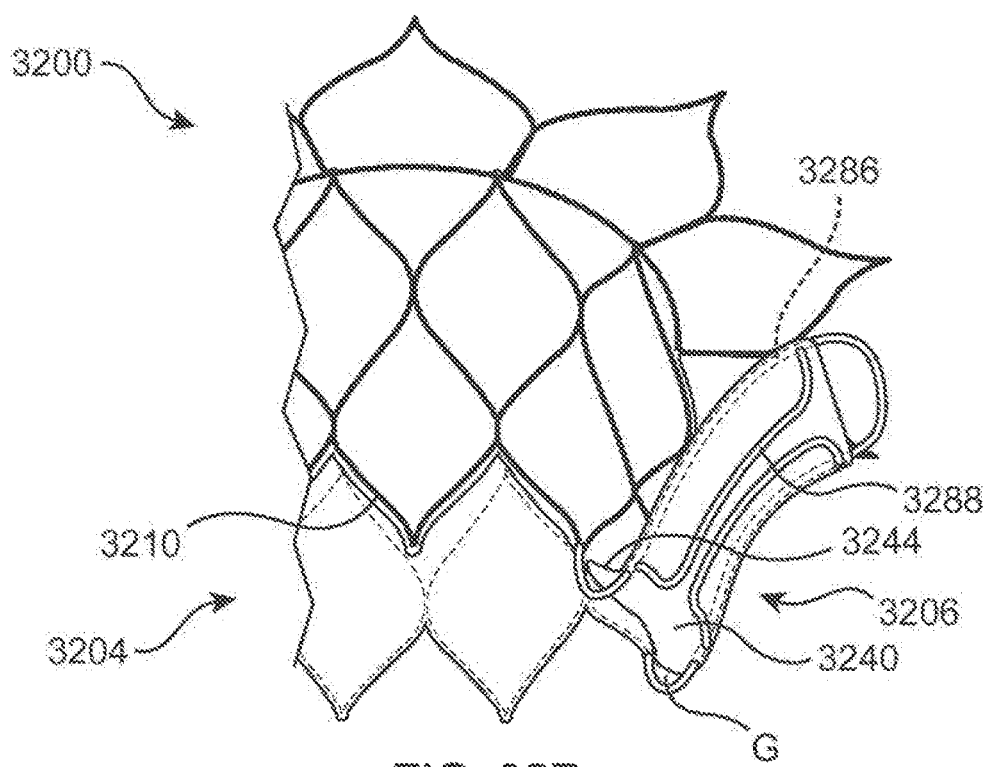

Although not shown in FIG. 31, the embodiments disclosed herein may include a tent portion (e.g., tent portion 3240 in FIGS. 32A and 32B). The tent portion can be made of any suitable material, such as, but not limited to, native or artificial valve tissue, fabric, mesh, and/or elastic materials. In certain embodiments, the tent portion can be a knitted PTFE fabric. In certain embodiments, the tent portion can be connected in various configurations to any or all of frame 3110, inner support arm 3188, outer support arm 3186, or any other part of valve prosthesis 3100. The tent portion can be attached by any suitable means, for example, with sutures. The tent portion can provide cushioning for the native chordae in order to reduce or eliminate direct contact between the support arm and chordae. The tent portion can distribute the tension and load placed on the chordae and reduce or eliminate the relative motion of the chordae and friction imparted to the chordae by providing a forgiving contact surface for the chordae.

FIGS. 32A and 32B illustrate valve prosthesis 3200 in accordance with an embodiment hereof. As shown, valve prosthesis 3200 may include frame 3210 having inflow portion 3202 and outflow portion 3204. Valve component 3220 may have leaflets secured within an interior of frame 3210. Frame 3210 may include dual support arm 3206 having inner support arm 3288 and outer support arm 3286. Inner support arm 3288 may include side segments 3282, which can run generally in a direction of a longitudinal axis of frame 3210. In certain embodiments, inner support arm 3288 may include curved portions along its length. Outer support arm 3286 may include side segments 3280 and middle segment 3284 between side segments 3280. In certain embodiments, outer support arm 3286 can include curved portions along its length.

Valve prosthesis 3200 may also include tent portion 3240, which can be attached at various locations to frame 3210, inner support arm 3288, and/or outer support arm 3286. As shown in FIG. 32A, in certain embodiments, side segment 3282 of inner support arm 3288 can connect to side segment 3280 of outer support arm 3286. In certain embodiments, side segment 3282 of inner support arm 3288 can connect to middle segment 3284 of outer support arm 3286. As shown in FIG. 32B, in certain embodiments, tent portion 3240 can be connected to frame 3210, inner support arm 3288, and outer support arm 3286 in such a way to leave a gap G between tent portion 3240 and a curved portion of outer support arm 3286 near a connection area with outflow portion 3204 of frame 3210. Attaching tent portion 3240 in this manner can create a taut pocket 3244 within which the native chordae may be suspended or cradled.

Figure 33A:
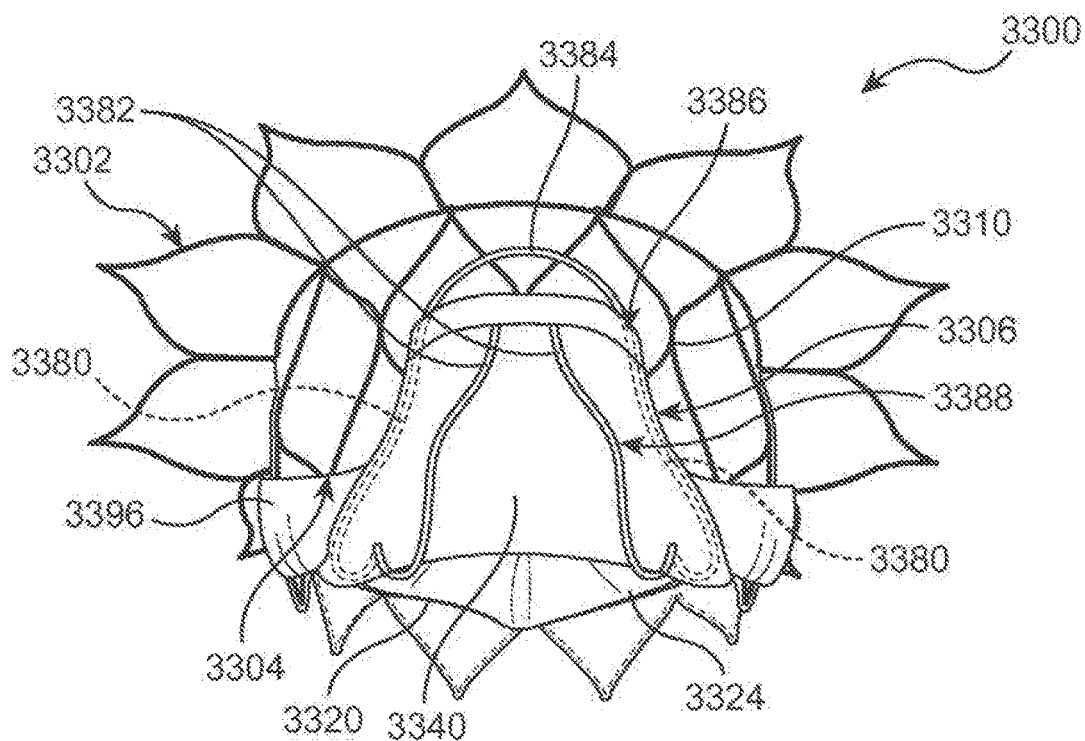
FIGS. 33A and 33B illustrate views of a valve prosthesis in accordance with an embodiment hereof.
Figure 33B:
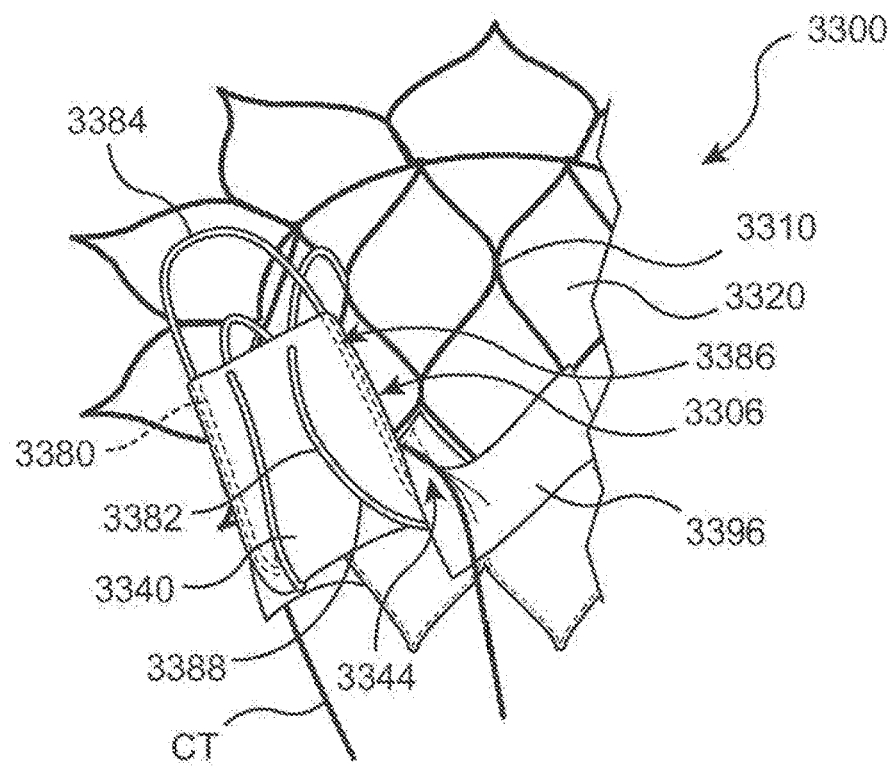

FIGS. 33A and 33B illustrate valve prosthesis 3300 in accordance with an embodiment hereof. Valve prosthesis 3300 may include similar features as described with respect to the embodiment of FIGS. 32A and 32B. Valve prosthesis 3300 may include frame 3310 having inflow portion 3302 and outflow portion 3304. Valve prosthesis 3300 may also include valve component 3320 having leaflets 324. Valve prosthesis 3300 may include a support arm 3306 having inner support arm 3388 having side segments 3382, which can attach to frame 3310 and/or outer support arm 3386. Outer support arm 3386 can include side segments 3380 and middle segment 3384. Valve prosthesis 3300 also can include tent portion 3340, which can be connected to frame 3310, inner support arm 3388, and/or outer support arm 3386.

In certain embodiments, tent portion 3340 can include flap 3396. Flap 3396 can extend to either side of outer support arm 3386. Flap 3396 can be an excess of material of tent portion 3340, and can be free to bend and flex as tension is placed on it from chordae tendinae (CT). As shown, for example, in FIG. 33B, chordae (CT) can rest within pocket 3344 of tent portion 3340. Tension placed upon chordae (CT) can result in flap 3396 bending or flexing to accommodate the tension, which can prevent chordae (CT) from rubbing against frame 3310 and/or inner support arm 3388 and outer support arm 3386 of valve prosthesis 3300. In this manner, flap 3396 can divert chordae (CT) away from inner support arm 3388 and outer support arm 3386. In certain embodiments, an additional strip of material can be attached from a corner of flap 3396 to outer support arm 3386 to provide additional support for chordae (CT).

Figure 34A:
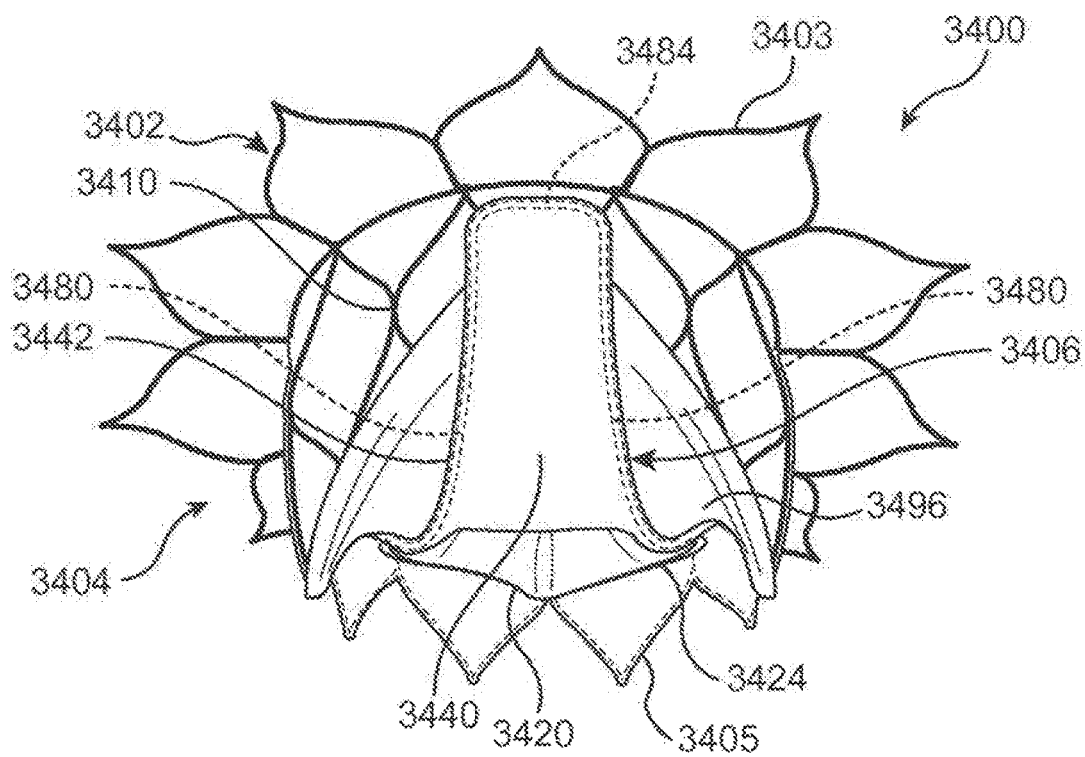
FIGS. 34A and 34B illustrate views of a valve prosthesis in accordance with an embodiment hereof.
Figure 34B:
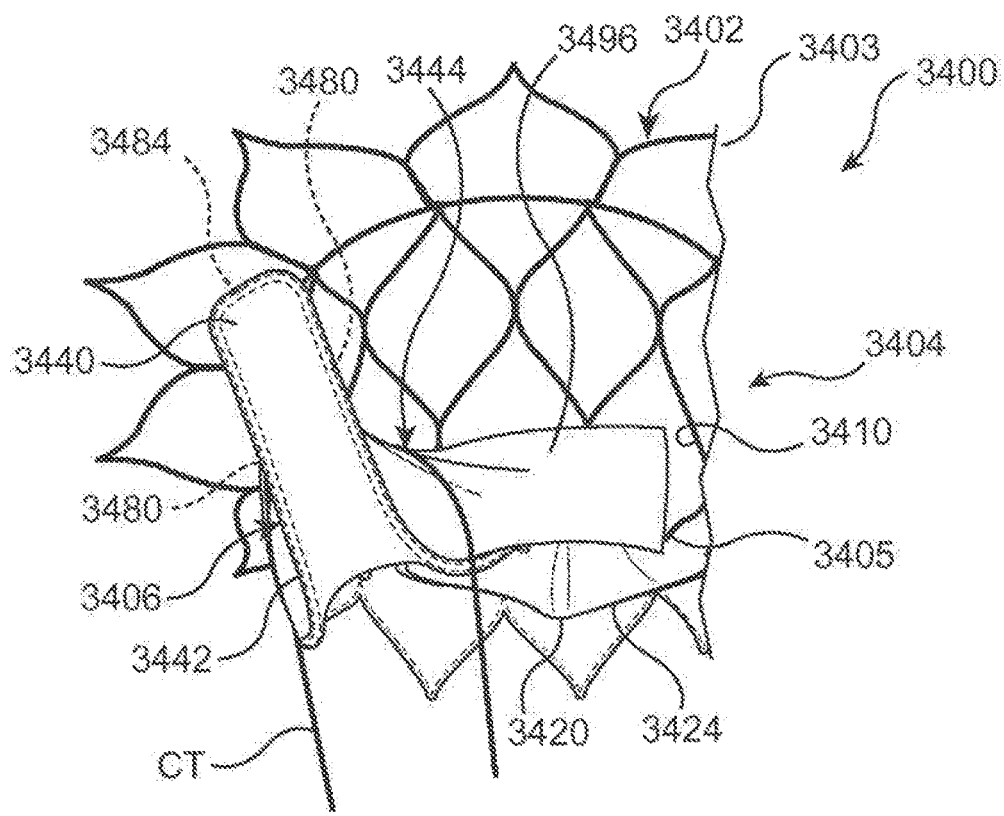

FIGS. 34A and 34B illustrate valve prosthesis 3400 in accordance with an embodiment hereof. As shown, valve prosthesis 3400 may include a U-shaped support arm 3406, as described in previous embodiments hereof and not inner and outer support arms. Valve prosthesis 3400 may include frame 3410 having inflow portion 3402 and outflow portion 3404, along with valve component 3420 having leaflets 3424. As shown in FIGS. 34A and 34B, support arm 3406 may include side segments 3480 and middle segment 3484. In certain embodiments side segments 3480 may be closer together or further apart, creating a narrower or wider support arm 3406. In certain embodiments, middle segment 3484 can run perpendicularly across/between side segments 3480, or middle segment 3484 can have a curved "U" shape. In certain embodiments, side segments can be closer together near outflow end 3405 and further apart near inflow end 3403. Additional shapes and curvatures of support arm 3406 are contemplated.

Tent portion 3440 may be connected to frame 3410 and/or support arm 3406, for example, by sutures 3442. Tent portion 3440 may include flap 3496, which can be attached to frame 4410. This can prevent flap 3496 from bending and flexing as depicted in FIGS. 33A and 33B, which can cause pocket 3444 to be taut between frame 3410 and support arm 3406. Flap 3496 can be various shapes; for example, flap 3496 can be rectangular or diamond-shaped. Chordae (CT) can rest within the taut pocket 3444 between support arm 3406 and frame 3410 of valve prosthesis 3400. As shown, this can cause chordae (CT) to interact only with pocket 3444 of tent portion 3440, without contacting frame 3410 or support arm 3406.

Figure 35:
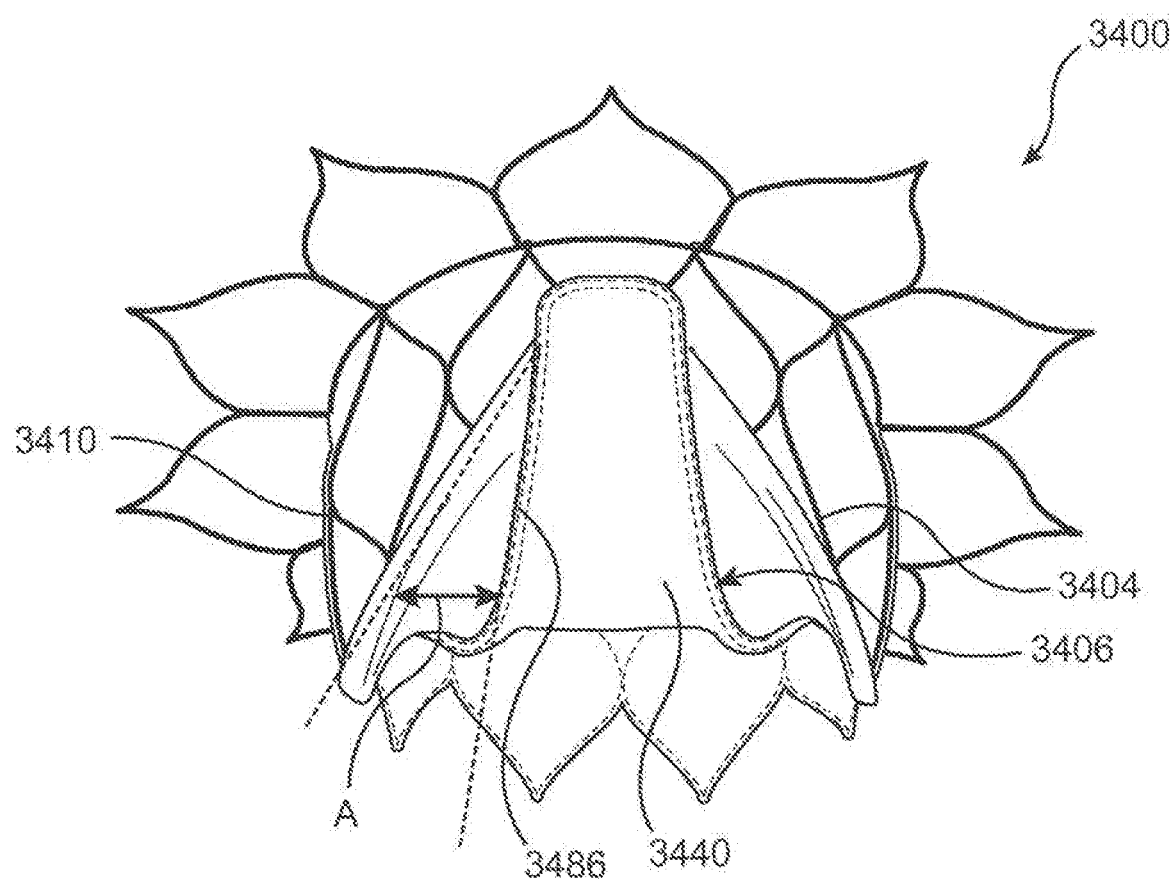
FIG. 35 illustrates a valve prosthesis in accordance with the embodiment of FIGS. 34A and 34B.

FIG. 35 illustrates valve prosthesis 3400, which is the same as the embodiment shown in FIG. 34A. FIG. 35 illustrates angle A created by tent portion 3440 between frame 3410 of outflow portion 3404 and side segment 3486 of support arm 3406. Depending on the size, shape, and configuration of support arm 3406, angle A can be increased or decreased.

Figure 36A:
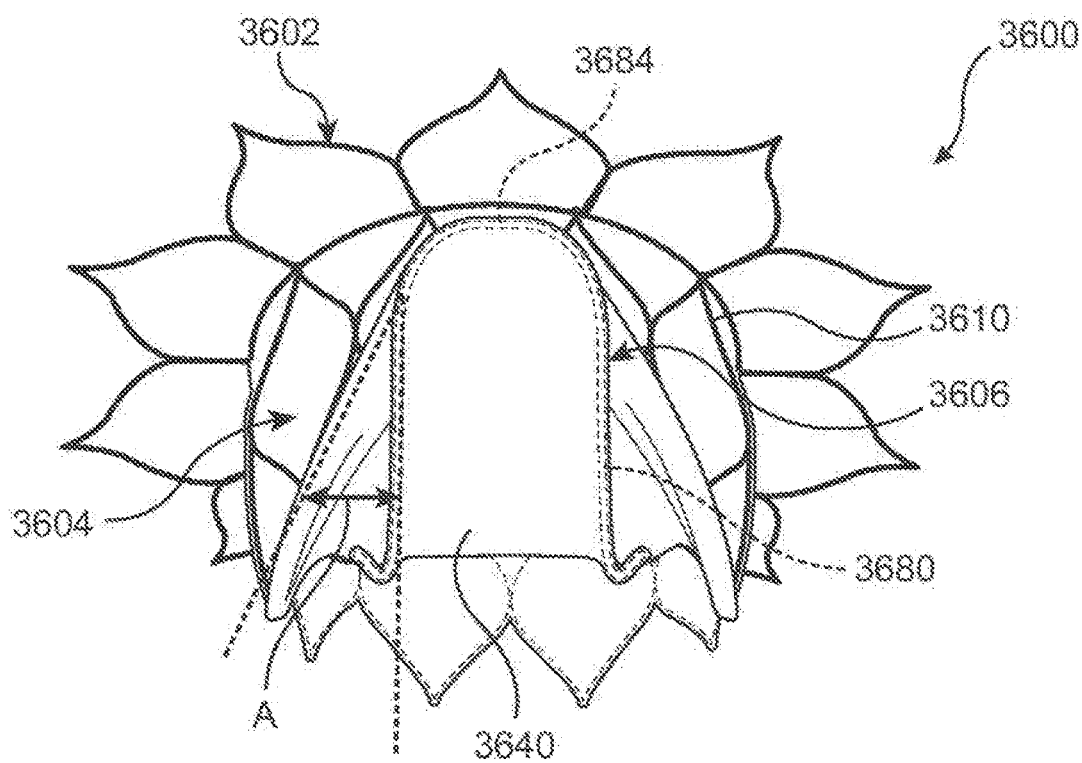
FIGS. 36A and 36B illustrate views of a valve prosthesis in accordance with an embodiment hereof.
Figure 36B:
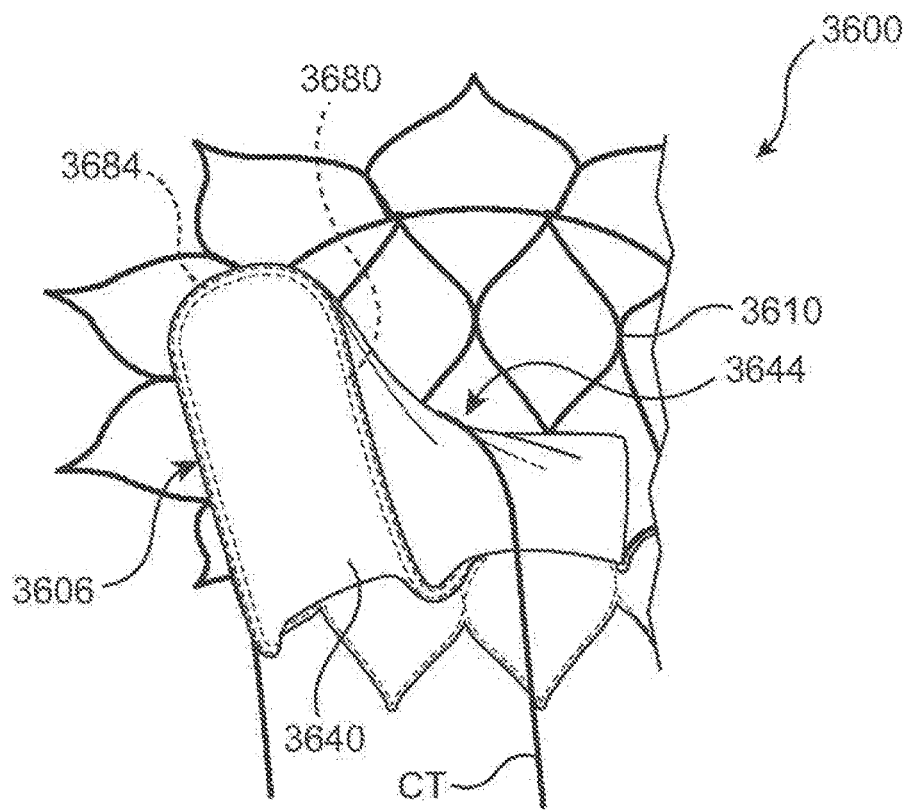

FIGS. 36A and 36B illustrate valve prosthesis 3600 in accordance with an embodiment hereof. Valve prosthesis 3600 may include frame 3610, inflow portion 3602, and outflow portion 3604. As shown, support arm 3606 has a larger, wider, "U"-shaped configuration in comparison to the embodiment shown in FIGS. 34A and 34B. Side segments 3680 can be generally parallel to a longitudinal axis of valve prosthesis 3600 and middle segment 3684 can have a generally curved "U" shape. Tent portion 3640 can be connected between support arm 3606 and frame 3610, creating angle A between frame 3610 and support arm 3606. FIG. 36B shows chordae (CT) within pocket 3644 created by tent portion 3640 extending between support arm 3606 and frame 3610. The wider design of support arm 3606 can facilitate implantation of prosthesis 3600.

Figure 37A:
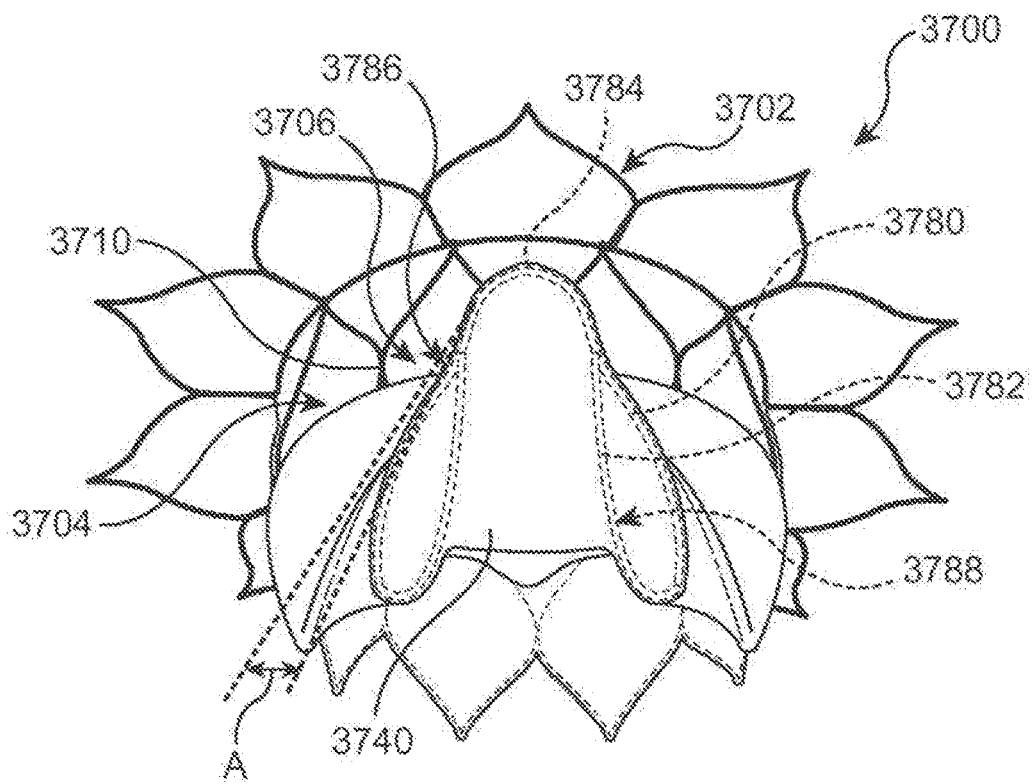
FIGS. 37A and 37B illustrate views of a valve prosthesis in accordance with an embodiment hereof.
Figure 37B:
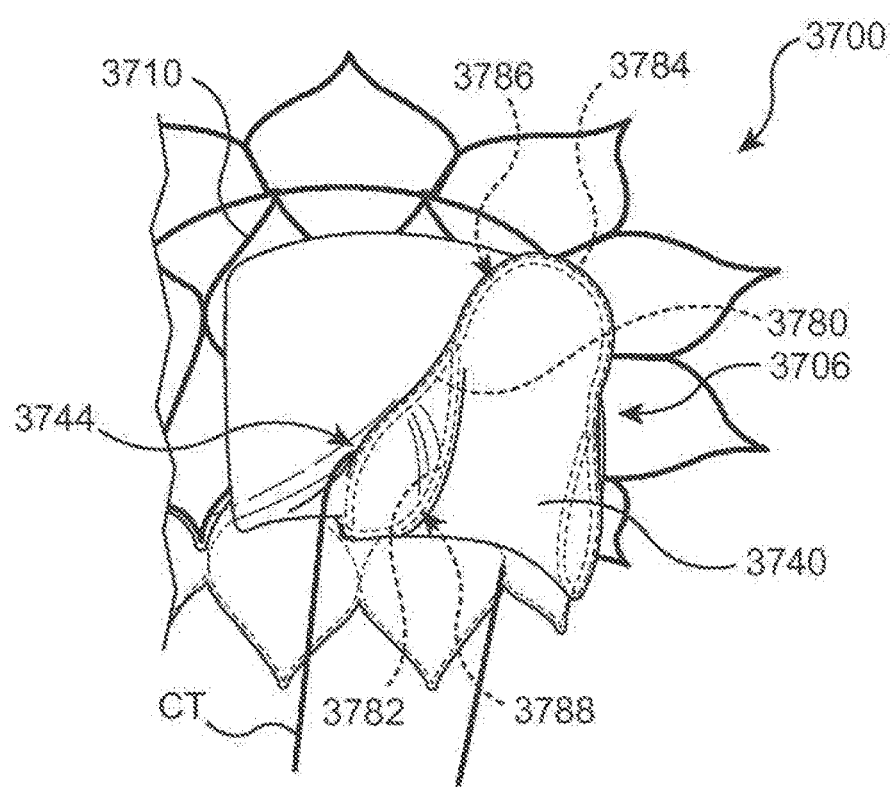

FIGS. 37A and 37B illustrate valve prosthesis 3700 in accordance with an embodiment hereof. Valve prosthesis 3700 may include frame 3710 having inflow portion 3702 and outflow portion 3704. Valve prosthesis 3700 may include a support arm 3706 having inner support arm 3788 and outer support arm 3786. As shown, side segment 3782 of inner support arm 3788 may be connected to side segment 3780 of outer support arm 3786 in a manner to create a space between inner support arm 3788 and outer support arm 3786. Side segments 3780 of outer support arm 3786 may be connected by middle segment 3784 that extends therebetween. Angle A can be created between outflow portion 3704 of frame 3710 and outer support arm 3786. As shown in FIG. 37B, chordae (CT) can rest within pocket 3744 created by tent portion 3740. As also shown in side view of FIG. 37B, in certain embodiments, side segment 3782 of inner support arm 3788 can be curved away from frame 3710 of valve prosthesis 3700.

Figure 38A:
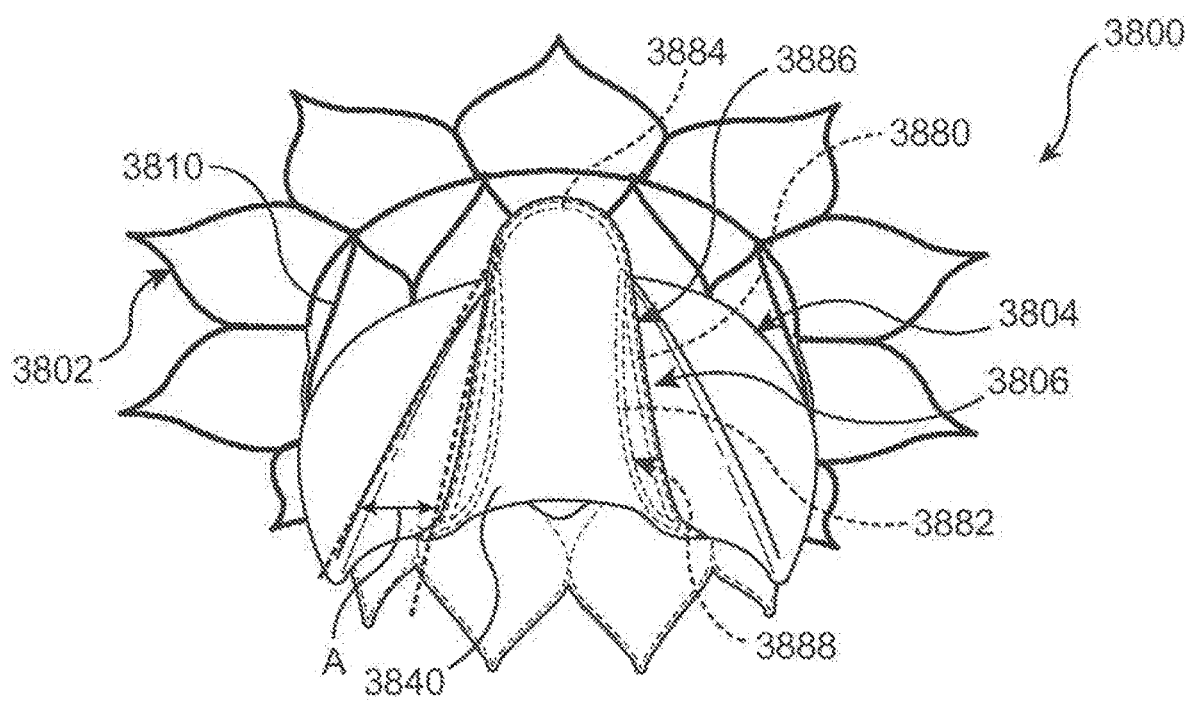
FIGS. 38A and 38B illustrate views of a valve prosthesis in accordance with an embodiment hereof.
Figure 38B:
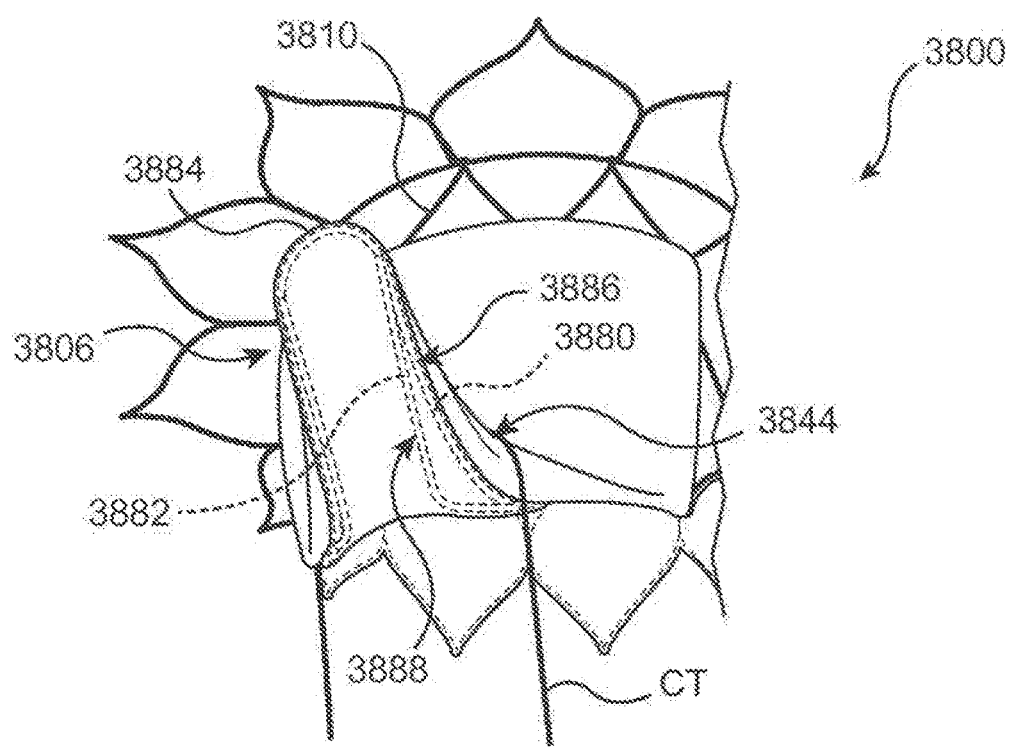

FIGS. 38A and 38B illustrate valve prosthesis 3800 in accordance with an embodiment hereof. Valve prosthesis 3800 may include frame 3810 having inflow portion 3802 and outflow or central portion 3804. Valve prosthesis 3800 may include a support arm 3806 having dual support arms, i.e., inner support arm 3888 and outer support arm 3886. Outer support arm 3886 may include side segments 3880 connected by middle segment 3884 that extends therebetween. As shown, side segment 3882 of inner support arm 3888 can run generally parallel to a longitudinal axis of valve prosthesis 3800 and connect to outer support arm 3886 near an end of middle segment 3884. This can create a narrower space between inner support arm 3888 and outer support arm 3886 in comparison to the embodiment shown in FIGS. 37A and 37B. Angle A can be created between frame 3810 and outer support arm 3886. As shown in FIG. 38B, chordae (CT) can rest within pocket 3844 created by tent portion 3840.

Figure 39A:
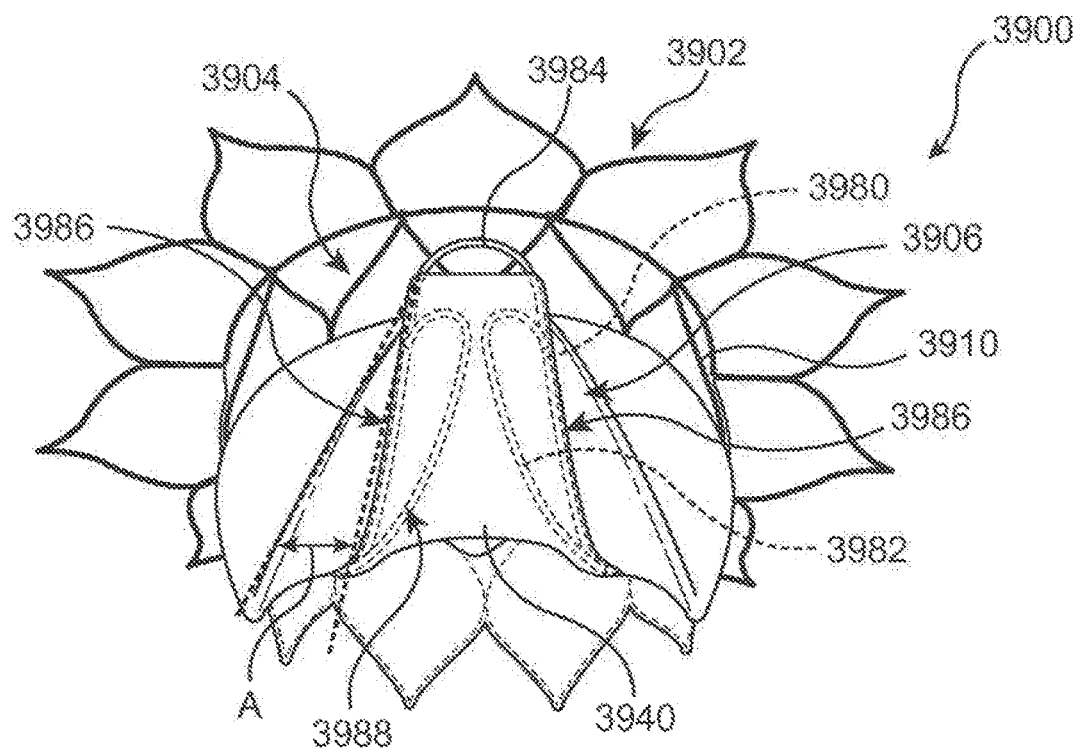
FIGS. 39A and 39B illustrate views of a valve prosthesis in accordance with an embodiment hereof.
Figure 39B:
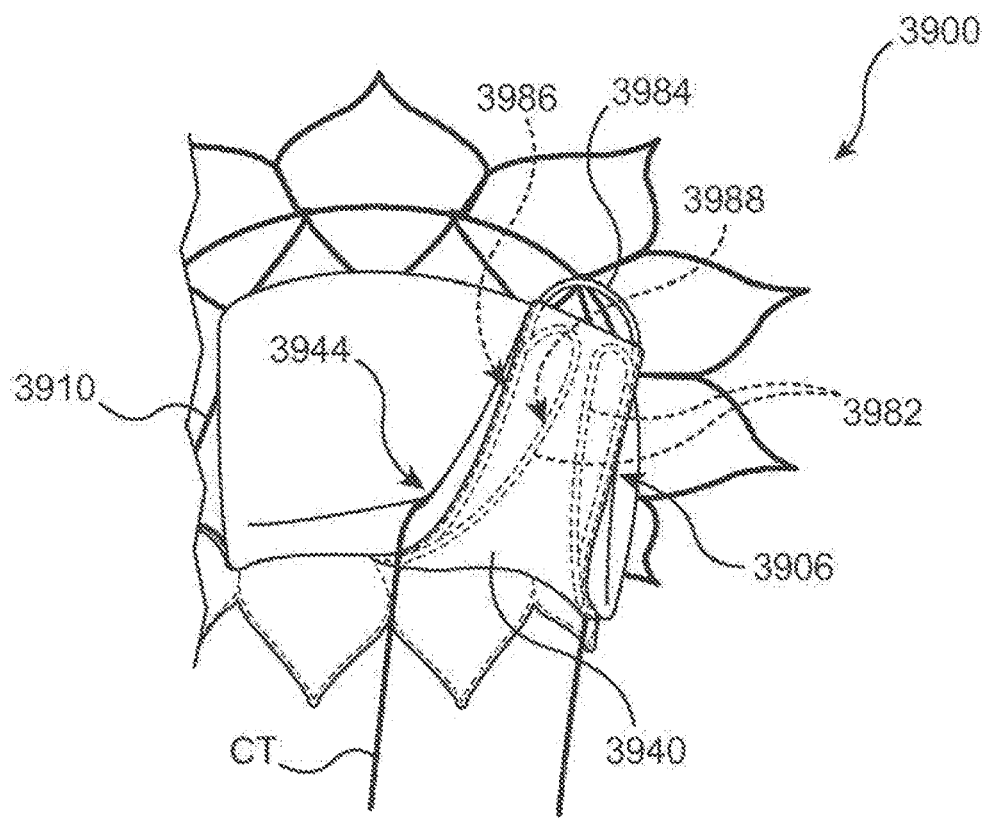

FIGS. 39A and 39B illustrate valve prosthesis 3900 in accordance with an embodiment hereof. Valve prosthesis 3900 may include frame 3910 having inflow portion 3902 and outflow portion 3904. Valve prosthesis 3900 may include support arm 3906 having a dual support arm construction, i.e., inner support arm 3988 and outer support arm 3986. Outer support arm 3986 may include side segments 3980 connected by middle segment 3984 that extends therebetween. As shown, side segments 3982 of inner support arm 3988 may be configured as generally "C" shaped. As shown in FIG. 39A, side segments 3982 of inner support arm 3988 may curve inwardly toward each other as they approach middle segment 3984 of outer support arm 3986. Side segments 3982 can then curve outward and away from middle segment 3984 to connect with side segments 3980 of outer support arm 3986. Angle A can be created between frame 3910 and outer support arm 3986. As shown in FIG. 39B, chordae (CT) can fit within pocket 3944 created by tent portion 3940 extending between frame 3910 and outer support arm 3986.

Figure 40A:
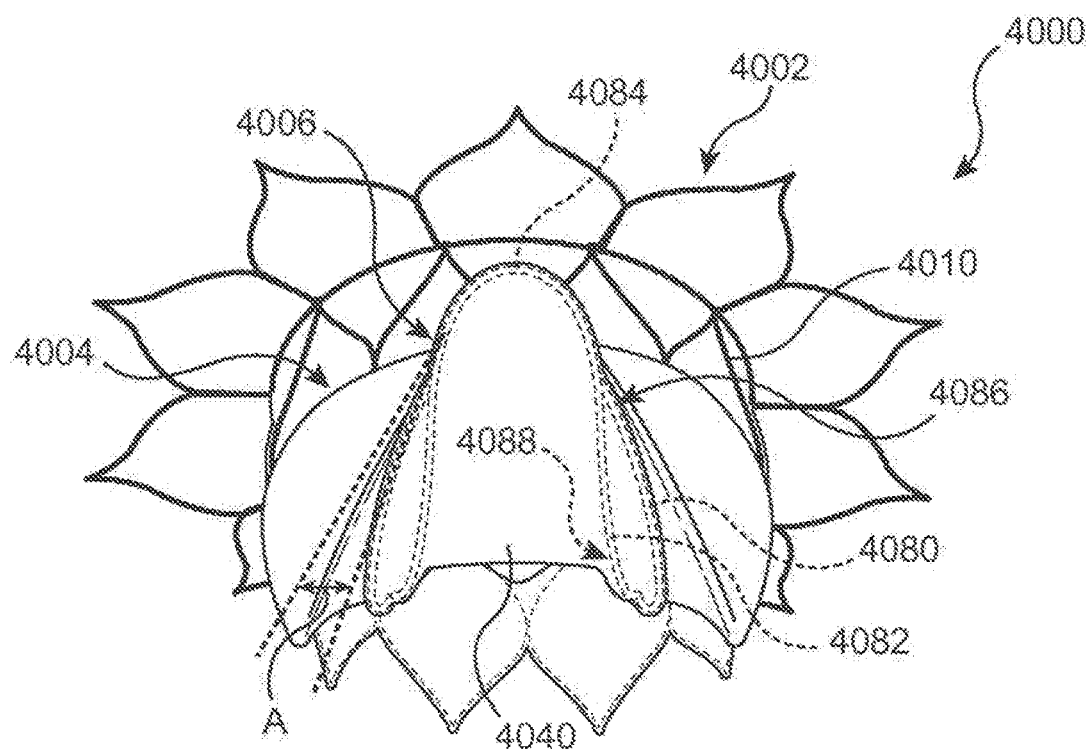
FIGS. 40A and 40B illustrate views of a valve prosthesis in accordance with an embodiment hereof.
Figure 40B:
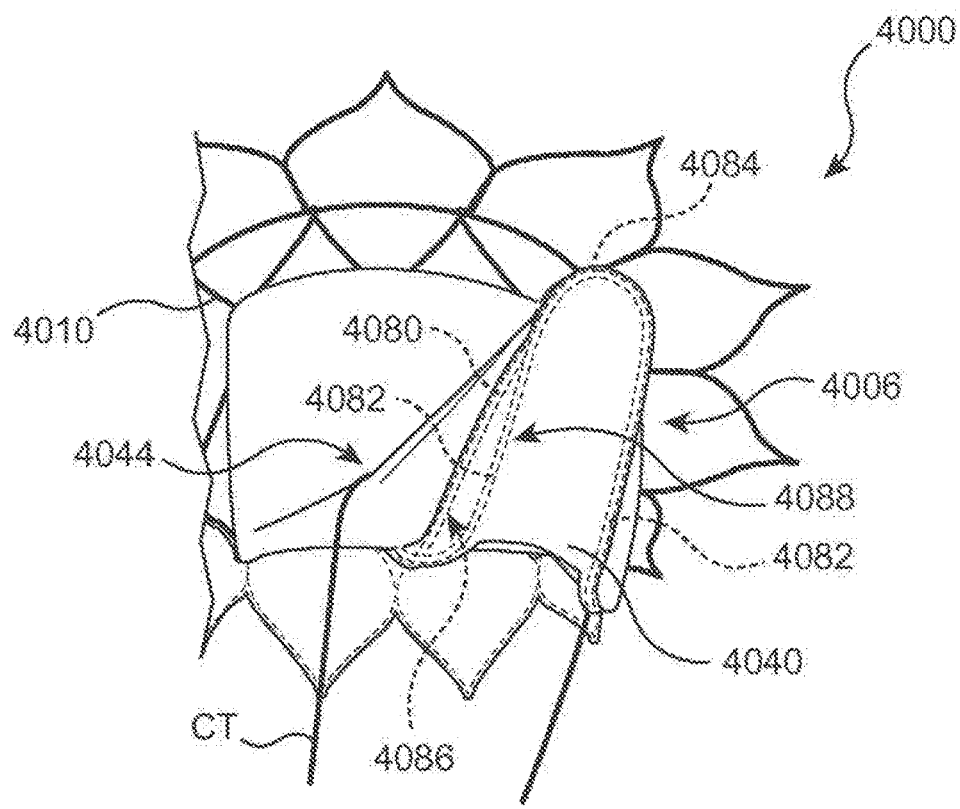

FIGS. 40A and 40B illustrate valve prosthesis 4000 in accordance with an embodiment hereof. Valve prosthesis 4000 may include frame 4010 having inflow portion 40002 and outflow portion 40046. As shown in FIG. 40A, valve prosthesis 4000 may have a support arm 4006 that includes inner support arm 4088 and outer support arm 4086. Outer support arm 4086 includes side segments 4080 connected by middle segment 4084 that extends therebetween. Side segment 4082 of inner support arm 4088 can be generally parallel to a longitudinal axis of valve prosthesis 4000 and connect to outer support arm 4086 near middle segment 4084. Angle A can be created between frame 4010 and outer support arm 4086. As shown in the side view of FIG. 40B, chordae (CT) can rest within pocket 4044 created by tent portion 4040 extending between frame 4010 and outer support arm 4086 of valve prosthesis 4000.

Figure 41:
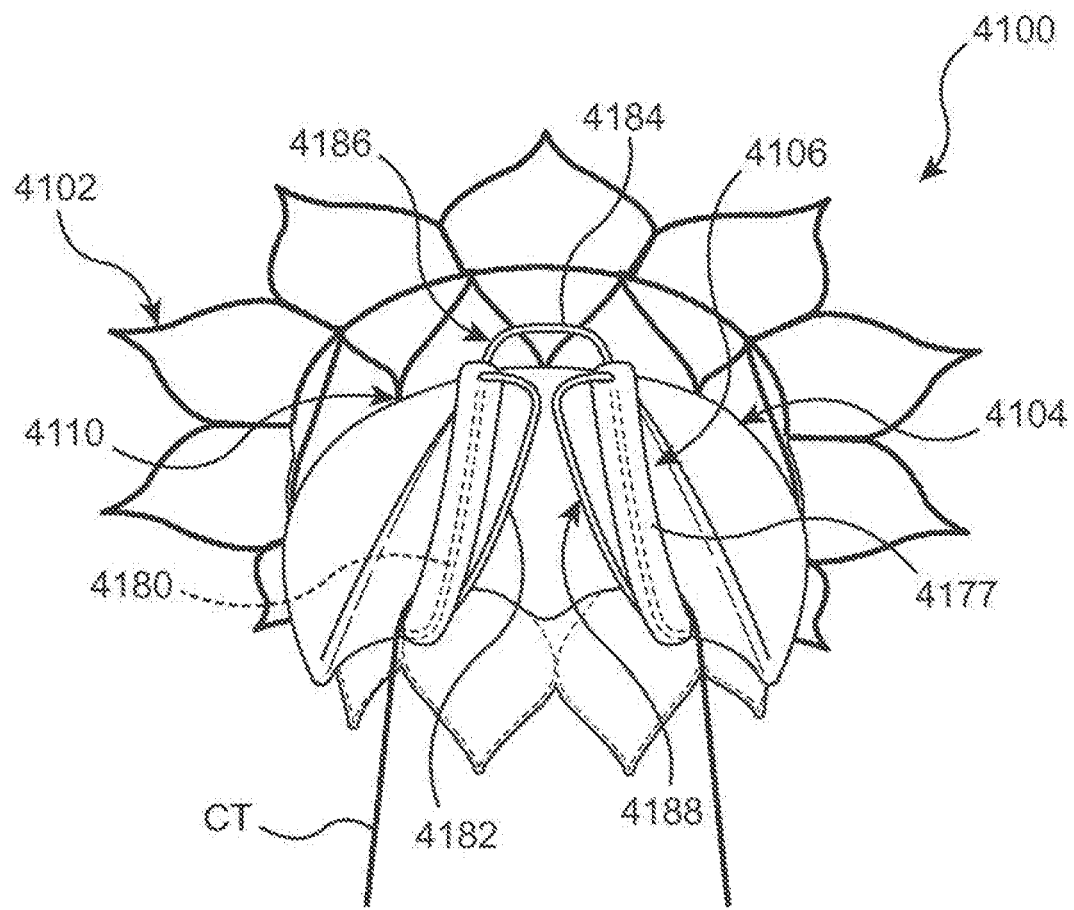
FIG. 41 illustrates a valve prosthesis in accordance with an embodiment hereof.

FIG. 41 illustrates valve prosthesis 4100 in accordance with an embodiment hereof. Valve prosthesis 4100 may include frame 4110, inflow portion 4102, and outflow portion 4104. Valve prosthesis 4100 may have a support arm 4106 that includes inner support arm 4188 having side segment 4182 and outer support arm 4186 having side segment 4180 and middle segment 4184. In certain embodiments, a sleeve 4177 may be wrapped around outer support arm 4186 and/or inner support arm 4188 such that chordae (CT) interacts or engages with sleeve 4177 rather than support arm 4106 or frame 4110 of valve prosthesis 4100. In certain embodiments, sleeve 4177 can be made from the same material as described for tent portions in accordance herewith. In certain embodiments, sleeve 4177 can be a single piece of fabric that can be wrapped around, for example, side segment 4180 of outer support arm 4186 and sutured together. In certain embodiments, sleeve material may be longitudinally and/or spirally wrapped around support arm. Sleeve 4177 can be loosely attached to allow relative motion between sleeve 4177 and outer support arm 4186 to prevent friction with chordae (CT), such that sleeve 4177 can slide on side segment 4180 of outer support arm 4186. In some embodiments, the sleeve 4177 may include one or more materials and/or methods that can reduce friction between the support arm and the sleeve and/or the chordae and the sleeve, including but not limited to, the sleeve being designed to be able to roll over the support arm, or the sleeve being designed to be able to slide across the support arm, or the sleeve comprising a material with a low shear modulus that can deform to absorb any motion, for example caused by the chordae acting on the sleeve. In some embodiments, the sleeve may include a fluid, such as saline, filled balloon or sac that can absorb any motion, for example caused by the chordae acting on the sleeve. In some embodiments, a support arm may comprise a tent-like member. In some embodiments, a support arm may include a covering of graft material.

Figure 42A:
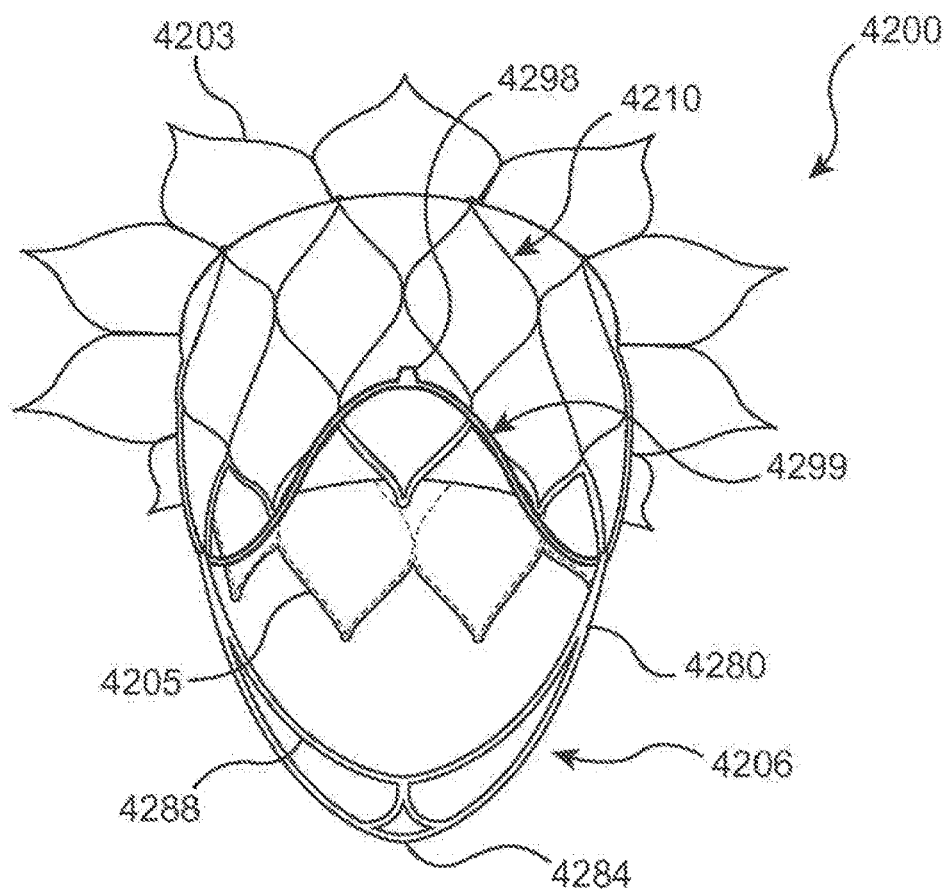
FIGS. 42A and 42B illustrate a valve prosthesis in accordance with an embodiment hereof.
Figure 42B:
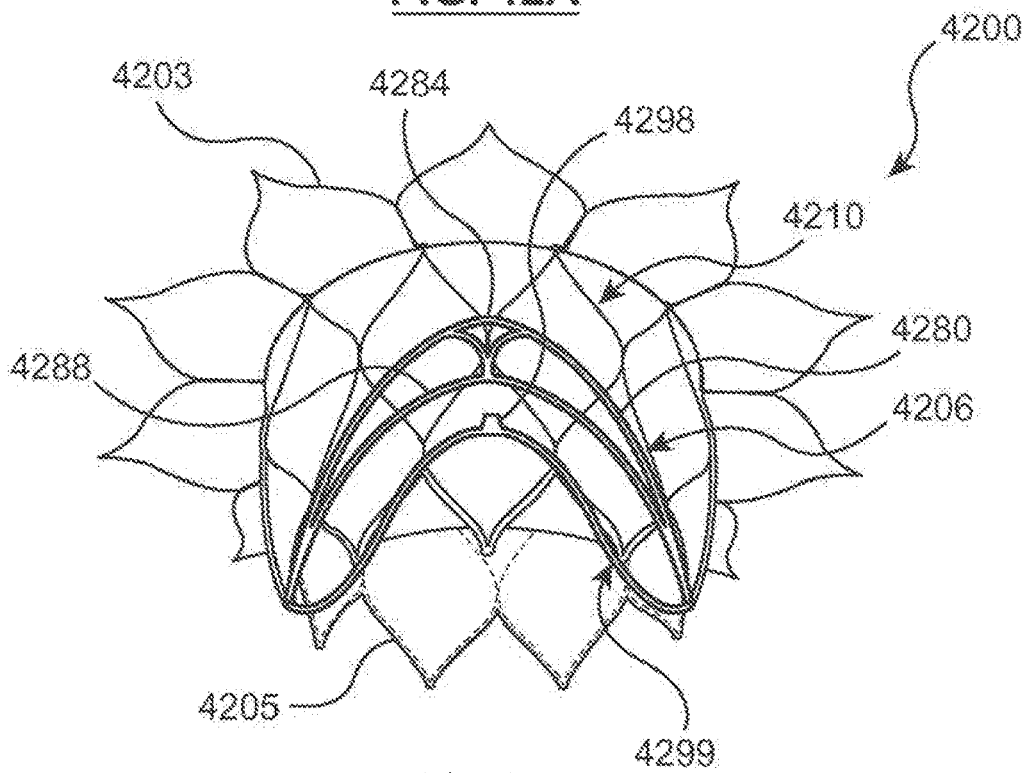
Figure 43:
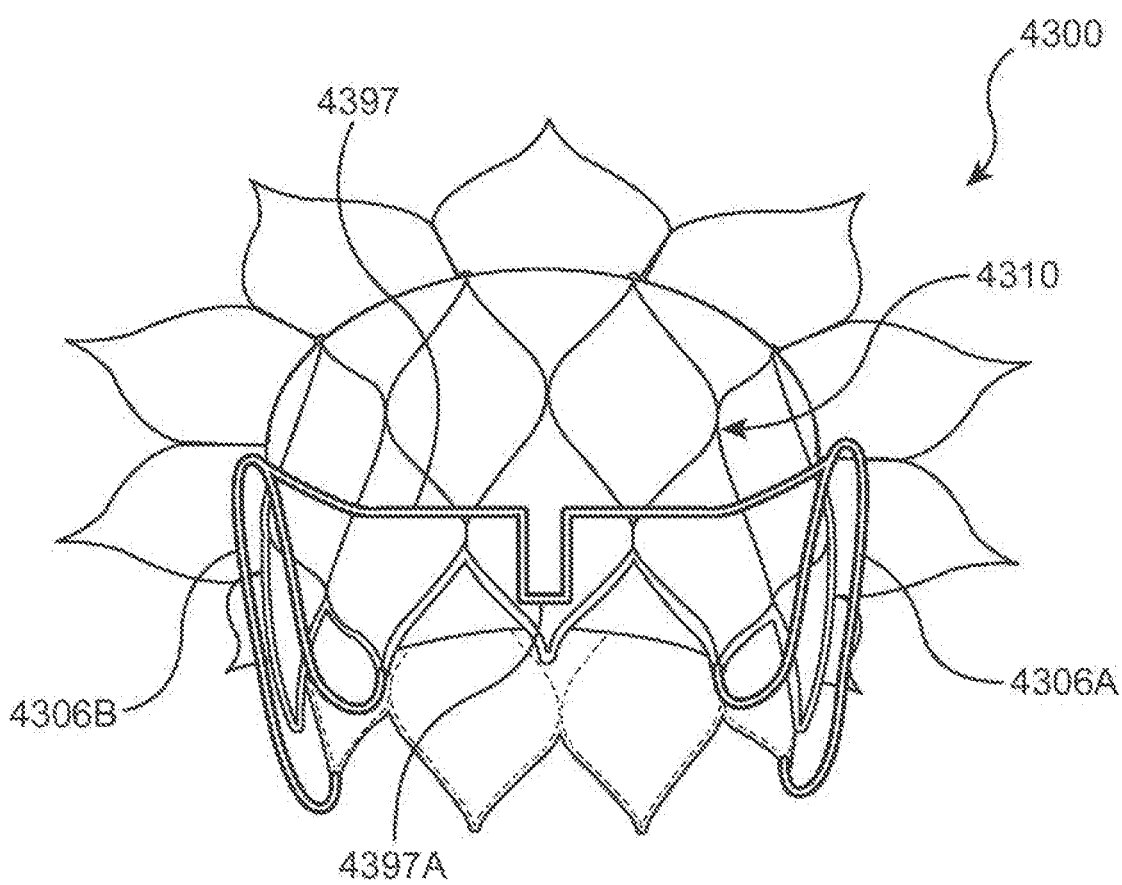
FIG. 43 illustrates a valve prosthesis in accordance with an embodiment hereof.

FIGS. 42A and 42B illustrate valve prosthesis 4200 in accordance with an embodiment hereof. Valve prosthesis 4200 may include frame 4210 and a first support arm 4299, and a second support arm 4206. First support arm 4299 may include barb 4298, which can facilitate anchoring valve prosthesis 4200 in the native valve. Second support arm 4206 may include side portion 4280, middle portion 4284, and inner portion 4288. It is contemplated that side portion 4280, middle portion 4284, and inner portion 4288 may have various curvatures and may connect with each other in various locations. In certain embodiments, valve prosthesis 4200 can include a covering, for example a mesh fabric, similar to the tent portion described above. In some embodiments, during delivery of valve prosthesis 4200 to the native valve and as shown in FIG. 42A, second support arm 4206 may be distally-facing or extending from outflow or distal end 4205 and first support arm 4299 may be proximally-facing. In some embodiments, upon being released from a delivery device as shown in FIG. 42B, second support arm 4206 can fold proximally toward proximal or inflow end 4203, so as to trap a native leaflet between first support arm 4299 and second support arm 4206. In some embodiments, during delivery of valve prosthesis 4200 to the native valve both first support arm 4299 and second support arm 4206 may be distally-facing or extending from outflow or distal end 4205. Depending on the delivery device used, for example a single sheath delivery device vs. a multi-sheath delivery device, and/or the orientation of valve prosthesis 4200 within the delivery device, second support arm 4206 may be released from the delivery device prior to the release of first support arm 4299 or first support arm 4299 may be released prior to the release of second support arm 4206. In some embodiments, following delivery of valve prosthesis first support arm 4299 and second support arm 4206 may be configured to trap, engage, capture, clamp, pin, and/or pinch a native leaflet between the support arms and/or support arm 4299 and support arm 4206 may be configured to trap, engage, capture, clamp, pin, and/or pinch chordae between the support arms and/or support arm 4299 and support arm 4206 may be configured to trap, engage, capture, clamp, pin, and/or pinch one or more leaflets and/or chordae between one or more support arms and the valve prosthesis frame. FIG. 43 illustrates valve prosthesis 4300 in accordance with an embodiment hereof. In certain embodiments, engagement or support arms 4306Aa, 4306B are coupled to one another by ring or bar 4397 that at least partially surrounds valve frame 4310, so as to trap the native leaflets. In certain embodiments, ring or bar 4397 may be shaped to define groove 4397A, so as to hold or contain native chordae within groove 4397A.

FIG. 44 illustrates a side view of a valve prosthesis 4400 in accordance with an embodiment hereof in an expanded or deployed configuration, before being loaded into and after release from its compressed configuration within a delivery system 4430 as shown in FIGS. 44A and 44B. FIGS. 44A and 44B illustrate side and end views, respectively, of valve prosthesis 4400 of FIG. 44 in an unexpanded or compressed delivery configuration loaded into delivery 4430 system in accordance with an embodiment hereof. As described above, each support arm of valve prosthesis in accordance herewith may rotate and transform from a distally-extending compressed configuration to a proximally-extending deployed configuration. With reference to the exemplary valve prosthesis 4400 in FIG. 44, valve prosthesis 4400 may include a tubular frame or stent 4410 that is similar to the frames described above, a valve component (not shown in FIGS. 44, 44A, 44B and 45A-44E for simplicity of illustration) attached within the interior portion of frame 4410, and two positioning elements or support arms 4406. In a compressed or delivery configuration, each support arms 4406 may be approximately parallel with a longitudinal axis $L_a$ of frame 4410 and may distally extend from a distal or outflow end 4405 of frame 4410. Delivery system 4430 may include a catheter 4433 and an outer retractable sheath or tube 4434. Valve prosthesis 4400 may be mounted over an inner shaft 4436 of catheter 4433 at the distal end thereof and sheath 4434 may surround and constrain valve prosthesis 4400 in a compressed configuration. In one embodiment, catheter 4433 may also include a retainer 4438 which temporarily secures proximal or inflow end 4403 of frame 4410 onto catheter 4433. For example, retainer 4438 may include an end stent capture configuration as described in U.S. Patent Pub. No. 2009/0276027 to Glynn, which is incorporated by reference herein in its entirety.

Figure 45D:
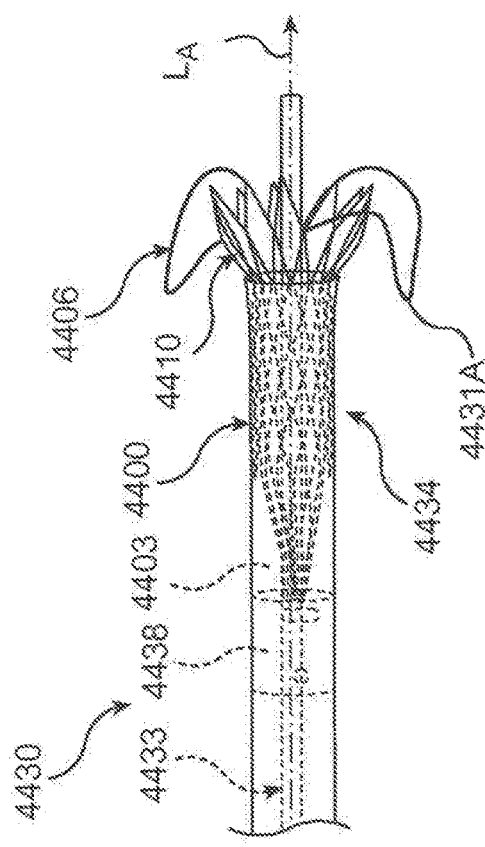

FIGS. 45A-45E illustrate progressive side views of valve prosthesis 4400 loaded within a delivery system 4430, wherein sheath 4434 of delivery system 4430 is progressively proximally retracted to release valve prosthesis 4400 therefrom. In order to begin deployment of valve prosthesis 4400, sheath 4434 may be retracted in a proximal direction to expose and release support arms 4406 as shown in FIG. 45A. Upon initial release from sheath 4434, support arms 4406 flare or spread outwardly from the distal end 4405 of frame 4410 such that support arms 4406 form an acute angle Ø with respect to longitudinal axis $L_A$.

As sheath 4434 is further retracted, support arms 4406 continue to be exposed and continue to bend backwards towards the outer surface of sheath 4434 and frame 4410. Notably, as support arms 4406 are released from sheath 4434, frame 4410 remains constrained within sheath 4434. FIG. 45B illustrates support arms 4406 approaching a transverse reference axis $T_A$ between an initial distally-extending compressed configuration and a final proximally-extending deployed configuration. Transverse reference axis $T_A$ as utilized herein describes an imaginary reference line that extends approximately ninety degrees or perpendicular to the longitudinal axis $L_A$ of frame 4410. FIG. 45C illustrates support arms 4406 after passing over the transverse reference axis $T_A$, with support arms 4406 fully exposed or released from sheath 4434 while frame 4410 is still compressed within sheath 4434. One particular feature of support arms 4406 is apparent when comparing FIGS. 45B and 45C. Support arms 4406 may bend or curve gradually backwards such that distal portions or tips 4431A of support arms 4406 may pass over the transverse reference axis $T_A$ before proximal portions or bases 4431B of support arms 4406. After distal tips 4431A of support arms 4406 pass or cross over the transverse reference axis $T_A$ and are pointing in a proximal direction, proximal bases 4431B of support arms 4406 approach the transverse reference axis $T_A$ as shown in FIG. 10. Stated another way, distal tips 4431A of each support arm 4406 may bend past transverse reference axis $T_A$ prior to proximal bases 4431B of each support arm 4406. Due to the above-described flaring or expanding sequence in which support arms 4406 curve backward, the length of support arms 4406 may be greater than if both the proximal and distal portions of the support arms crossed over the transverse reference axis $T_A$ at the same time, i.e., if the support arms were straight and extended generally parallel to the transverse reference axis $T_A$ during deployment. In addition, since frame 4410 is still compressed within sheath 4434, it can be observed that the length of support arms 4406 may be greater than if frame 4410 was released from sheath 4434 and in a deployed configuration. Accordingly, the length of support arms 4406 is maximized which increases their ability to anchor valve prosthesis 4400 when it is positioned to replace a valve. In an embodiment in which valve prosthesis 4400 is positioned at a mitral valve, the length of each support arm 4406 may be between 10 and 12 mm.

Figure 45E:
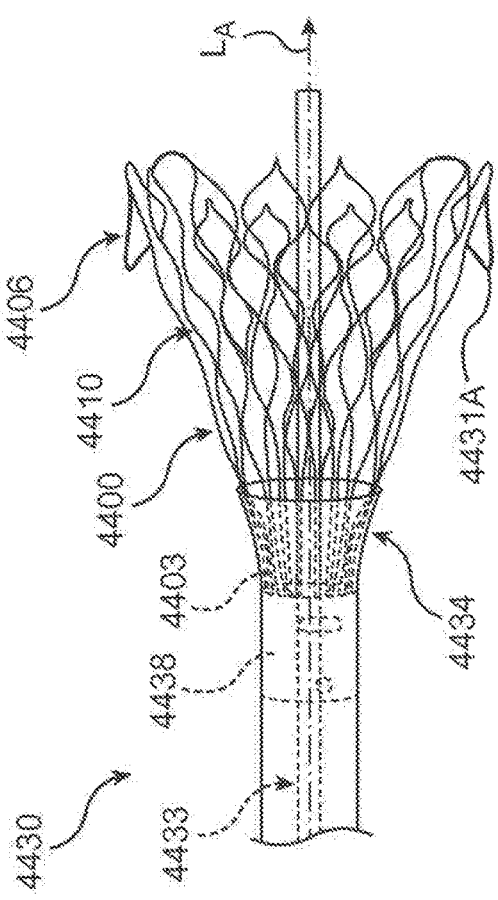

FIGS. 45D and 45E illustrate a continued deployment of valve prosthesis 4400. Sheath 4434 continues to be proximally retracted, exposing self-expanding frame 4410 such that frame 4410 is released to assume a deployed configuration. Sheath 4434 is proximally retracted until proximal or inflow end 4403 of frame 4410 is exposed and allowed to self-expand, thereby uncoupling from retaining tip 4438 of catheter 4433. FIG. 44 illustrates a final deployed configuration of valve prosthesis 4400, in which each support arm 4406 proximally extends from distal or outflow end 4405 of frame 4410. As previously described, the backwards rotation that may occur during deployment may result in each support arm 4406 translating more than ninety degrees from a compressed, delivery configuration. During deployment, each support arm 4406 may essentially deploy or translate in an arc path that may extend between 90 and 180 degrees from an initial compressed configuration and a final deployed configuration. In the embodiment of FIG. 44 shown ex vivo, each support arm 4406 may be bent or rotated approximately 180 degrees between an initial distally-extending compressed configuration shown in FIG. 44A and a final proximally-extending deployed configuration shown therein. However, when positioned in vivo, tissue such as native valve leaflets may be sandwiched between each support arm 4406 and the outer surface of frame 4410 and as a result, the total rotation or bending of support arms 4406 in a final deployed configuration may be less than 180 degrees with respect to an initial distally-extending compressed configuration.

Rotating from an initial distally-extending configuration to a final proximally-extending configuration allows valve prosthesis 4400 to be deployed in the annulus of a native valve, such as a mitral valve, rather than the outflow side of a native valve, thereby minimizing the length which the prosthesis and the delivery system protrudes into a heart chamber, such as the left ventricle.

In some embodiments, the support arms and frame may be deployable via one delivery sheath. In other embodiments, the support arms and frame are deployable via more than one delivery sheath. In one embodiment, a first distal cone or delivery sheath may be distally advanced during deployment to deploy the support arms and then a second proximal delivery sheath may be proximally retracted to deploy the frame. In one embodiment, a first proximal delivery sheath may be proximally advanced during deployment to deploy the support arms and then a second distal delivery cone or sheath may be distally retracted to deploy the frame. For example, the ENGAGER delivery system from Medtronic, Inc. of Minneapolis, Minn. is a valve prosthesis delivery system that deploys a valve prosthesis in this manner and may be adapted for use with embodiments hereof. In accordance with embodiments hereof, valve prosthesis delivery systems and methods disclosed in U.S. Pat. Appl. Pub. No. 2008/0071361 to Tuval et al. and U.S. Pat. Appl. Pub. No. 2010/0100167 to Bortlein et al., each of which is incorporated by reference herein in its entirety, that deploy a valve prosthesis utilizing multiple, split, and/or dual sheaths or delivery catheters may be adapted for use with embodiments hereof.

In order to transform between the initial distally-extending compressed configuration and the final proximally-extending deployed configuration, support arms or positioning elements according to some embodiments described herein are formed from a self-expanding material that has a mechanical memory to return to the proximally-extending deployed configuration as discussed further below.

Figure 46A:
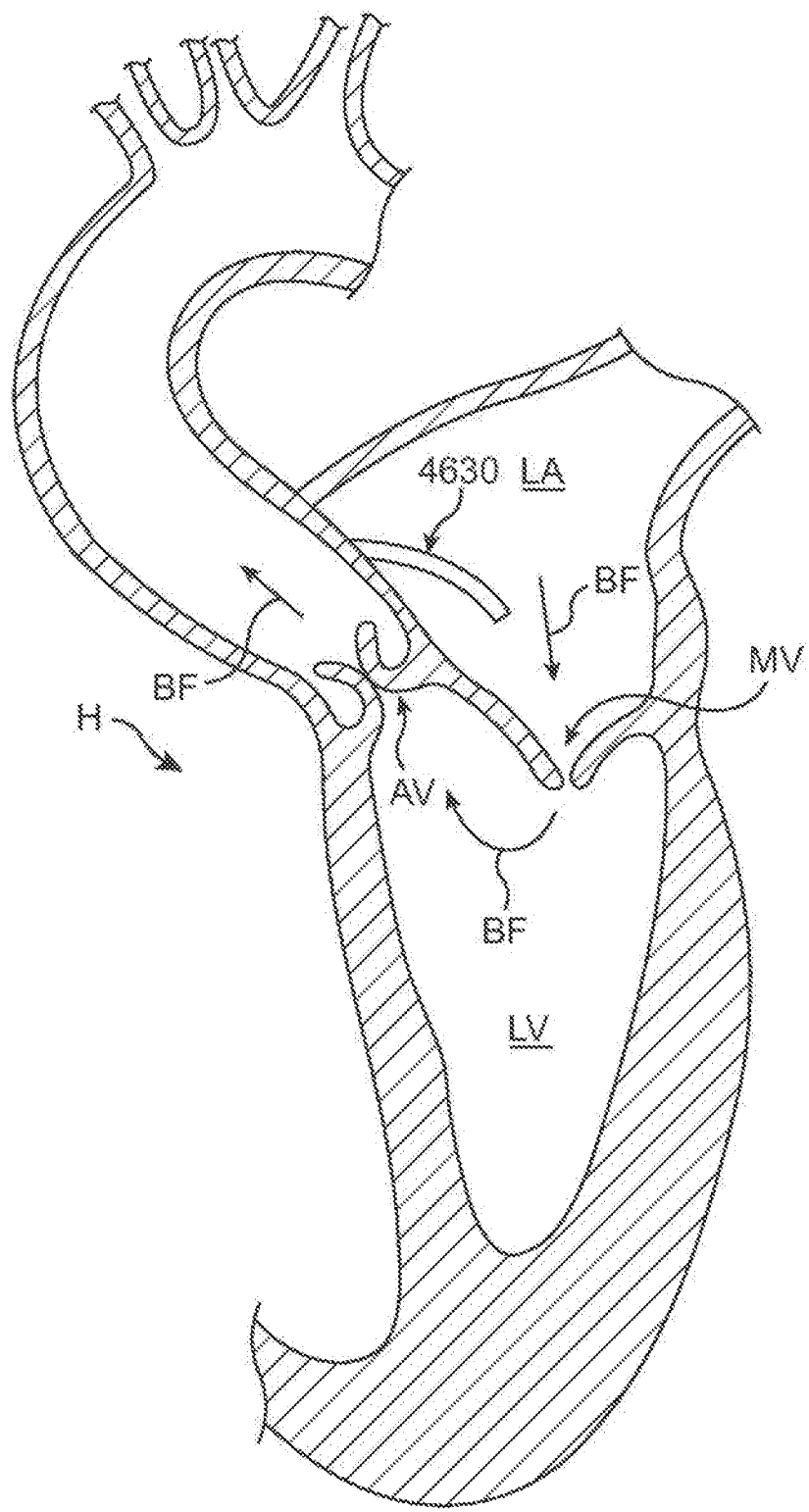
FIGS. 46A-46E illustrate a method of implanting a valve prosthesis at a mitral valve target location within a heart in accordance with an embodiment hereof.

FIGS. 46A-46E illustrate a method of implanting a valve prosthesis 4600 in accordance with an embodiment hereof to perform a heart valve replacement procedure, and more particularly a mitral valve replacement, with minimal blood flow stoppage or interruption. FIG. 46A illustrates a portion of a heart (H) including a left atrium (LA), a left ventricle (LV), a mitral valve (MV) and an aortic valve (AV). Blood flow (BF) is depicted with directional arrows in FIG. 46A in the left atrium (LA), into left ventricle (LV) through mitral valve (MV), and into the aorta through aortic valve (AV). When the native mitral valve is operating properly, the native leaflets will generally function in such a way that blood flows toward the left ventricle (LV) when the leaflets are in an open position, and so that blood is prevented from moving toward or into the left atrium (LA) when the leaflets are in a closed position. A valve prosthesis 4600 in accordance with an embodiment hereof may be positioned in the area of mitral valve (MV) when the native valve is not functioning properly, i.e., to replace the mitral valve, in accordance with the invention, thereby pushing the native leaflets away from the blood flow path.

With reference to FIG. 46A, a prosthetic valve delivery system 4630 is shown after having been introduced into the vasculature via a percutaneous entry point, such as the Seldinger technique, and having been tracked through the vasculature and into the left atrium so that distal tip 4630A is positioned proximate the mitral valve. For example, the percutaneous entry point may be formed in a femoral vein. Thereafter, a guidewire (not shown) is advanced through the circulatory system, eventually arriving at the heart. The guidewire is directed into the right atrium, traverses the right atrium and is made to puncture with the aid of a transeptal needle or pre-existing hole, the atrial septum, thereby entering the left atrium. Once the guidewire is positioned, the endoluminal entry port and the atrial septum are dilated to permit entry of a guide catheter (not shown) and/or prosthetic valve delivery system 4630 into the left atrium. Thereafter, prosthetic valve delivery system 4630 is advanced into the left atrium through the punctured atrial septum and positioned proximate to the mitral valve (MV). Although not shown, it will be understood by those of ordinary skill in the art that prosthetic valve delivery system 4630 may be inserted into a guide catheter in order to be advanced to a position proximate to the mitral valve (MV). In addition, although described as a transfemoral antegrade approach for percutaneously accessing the mitral valve, the valve prosthesis 4600 may be positioned within the desired area of the heart via entry other different methods such as a transseptal antegrade approach via a thoracotomy or a transatrial antegrade approach via a thoracotomy for accessing the mitral valve.

Figure 46B:
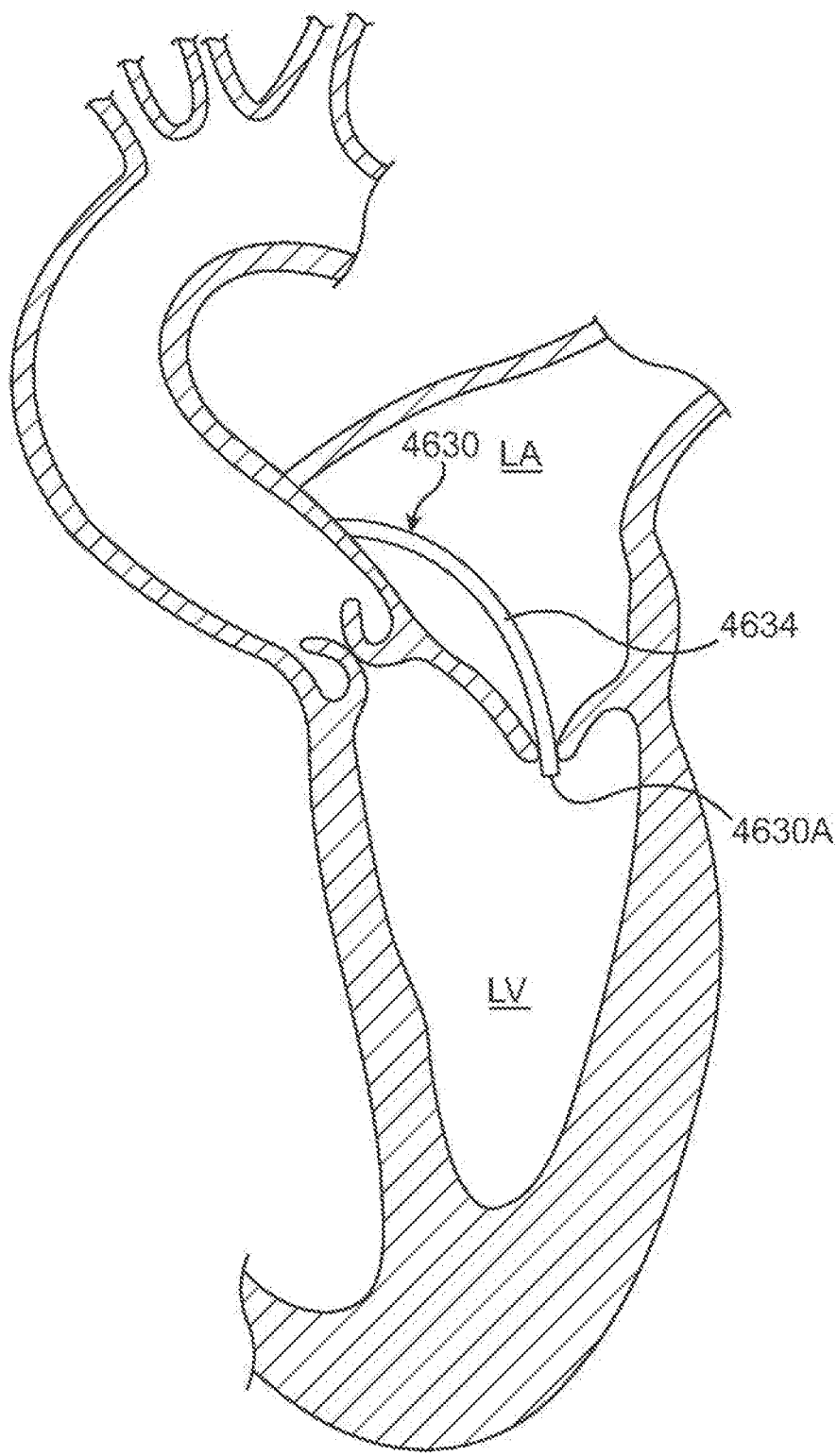

Similar to delivery system 4430 described above with respect to FIGS. 44A, 44B and 45A-45E, prosthetic valve delivery system 4630 includes an outer retractable sheath or tube 4634 positioned over the a catheter (not shown in FIGS. 46A-46E) having compressed valve prosthesis 4600 to keep it from expanding and to minimize interference between the valve prosthesis and the vasculature through which it will be traveling. Valve prosthesis 4600 is mounted over an inner shaft of the catheter at the distal end thereof and sheath 4634 surrounds and constrains valve prosthesis 4600 in the compressed configuration. After being advanced into the left atrium (LA), prosthetic valve delivery system 4630 including sheath 4634 may then be advanced through the mitral valve (MV) and into the left ventricle (LV) as shown in FIG. 46B. Distal tip 4630A of prosthetic valve delivery system 4630 is advanced into the left ventricle (LV) until valve prosthesis 4600 is centered at the native mitral valve, i.e., deployed in the annulus of the native mitral valve, with positioning elements or support arms 4606A, 4606B of valve prosthesis 4600 contained within sheath 4634 and distally extending into the left ventricle (LV). As previously discussed, deploying valve prosthesis 4600 in the middle of the native valve rather than the outflow side of the native mitral valve minimizes the length which the prosthesis and the delivery system protrudes into the left ventricle.

Figure 46C:
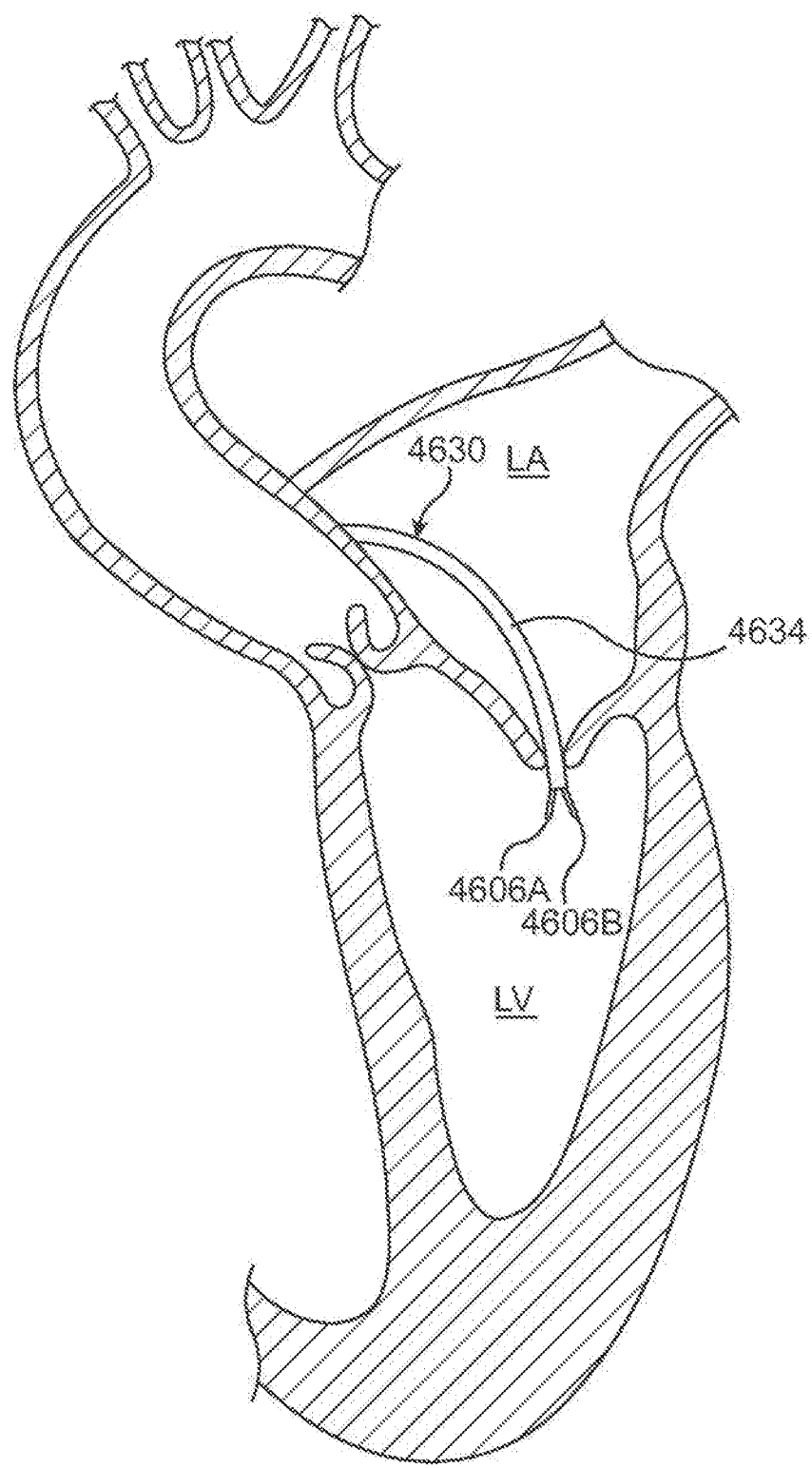

Referring now to FIG. 46C, when valve prosthesis 4600 is in position in the middle of the native mitral valve, support arms 4606A, 4606B of valve prosthesis 4600 are released by retracting sheath 4634 of prosthetic valve delivery system 4630 by a sufficient amount that this portion of the prosthesis is exposed. Due to the self-expanding properties of the support arms, support arms 4606A, 4606B will expand radially outwardly relative to the sheath in which it was enclosed. As shown FIG. 46C, and also referring to FIG. 45A described above, upon initial release from sheath 4634, support arms 4606A, 4606B flare or spread outwardly from the outer surface of the remainder of the prosthesis such that support arms 4606A, 4606B are acutely angled with respect to longitudinal axis $L_A$. During the transformation between the distally-extending compressed configuration and the proximally-extending deployed configuration, support arms 4606A, 4606B are located on outflow side, i.e., the left ventricle (LV) side, of the mitral valve while stent or frame 4610 of prosthesis 4600 is positioned within the mitral valve and still contained within sheath 4634.

Figure 46D:
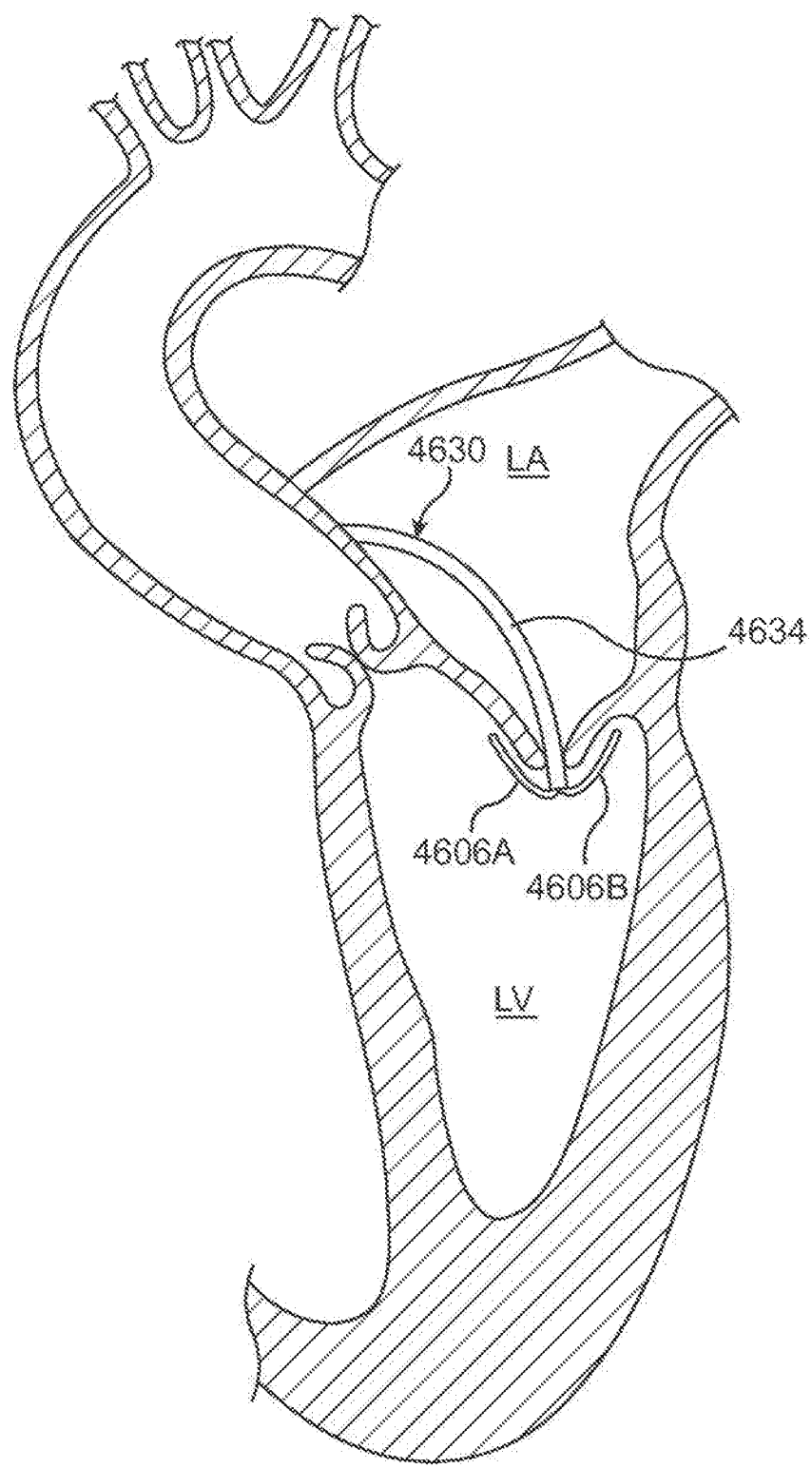

Exposure and rotation of support arms 4606A, 4606B continues as sheath 4634 is retracted. FIG. 46D illustrates support arms 4606A, 4606B fully exposed or released from sheath 4634 while stent 102 is still compressed within sheath 4634. Support arms 4606A, 4606B are now proximally extending, such that they firmly press against the native mitral valve leaflets and/or the left ventricle (LV) in order to position valve prosthesis 4600.

Figure 46E:
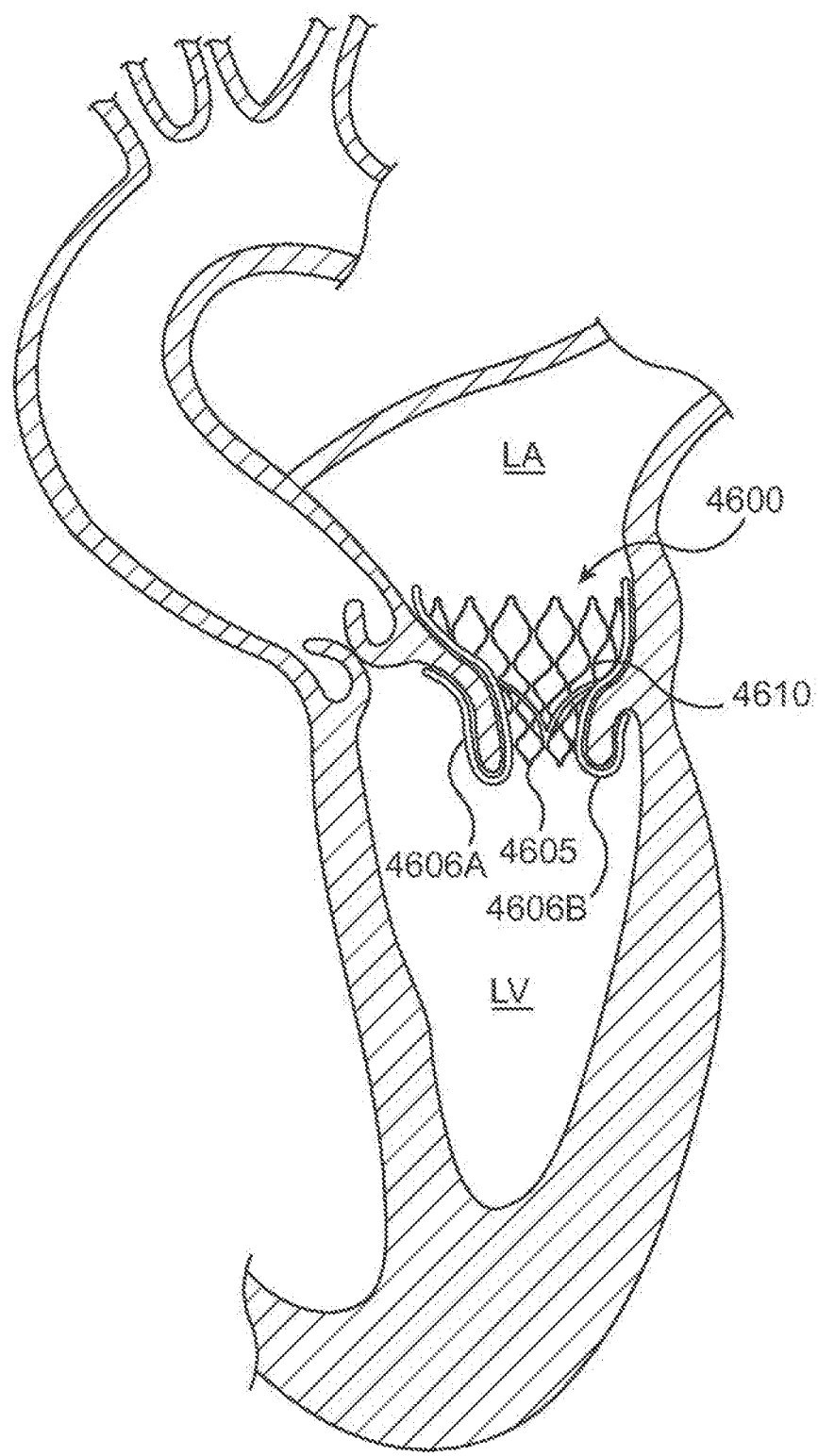

After support arms 4606A, 4606B are deployed to position, anchor and/or hold valve prosthesis 4600 in place as desired, sheath 4634 continues to be proximally retracted, exposing self-expanding frame 4610 such that the frame and the entire valve prosthesis is released from the delivery system to assume its deployed configuration. Due to the self-expanding properties of the stent frame, frame 4610 will expand outwardly relative to the sheath in which it was enclosed. Sheath 4634 is proximally retracted until the proximal end of frame 4610 is exposed and allowed to self-expand, thereby uncoupling mitral valve prosthesis 4600 from delivery system 4630. The delivery system 4630 can then be retracted from the patient, leaving the expanded mitral valve prosthesis 4600 deployed at the mitral valve as shown in FIG. 46E. In the final deployed configuration of valve prosthesis 4600, each support arm 4606A, 4606B proximally extends from a distal or outflow end 4605 of frame 4610. Each support arm 4606A, 4606B rotates in a radial direction between 90 and 180 degrees from the initial distally-extending compressed configuration to the final proximally-extending deployed configuration until the support arms 4606A, 4606B firmly press against the native mitral valve leaflets and/or the left ventricle (LV) in order to properly position mitral valve prosthesis 4600. The amount or degree of rotation may depend upon a patient's individual anatomy and state of the native mitral valve leaflets.

Figure 47:
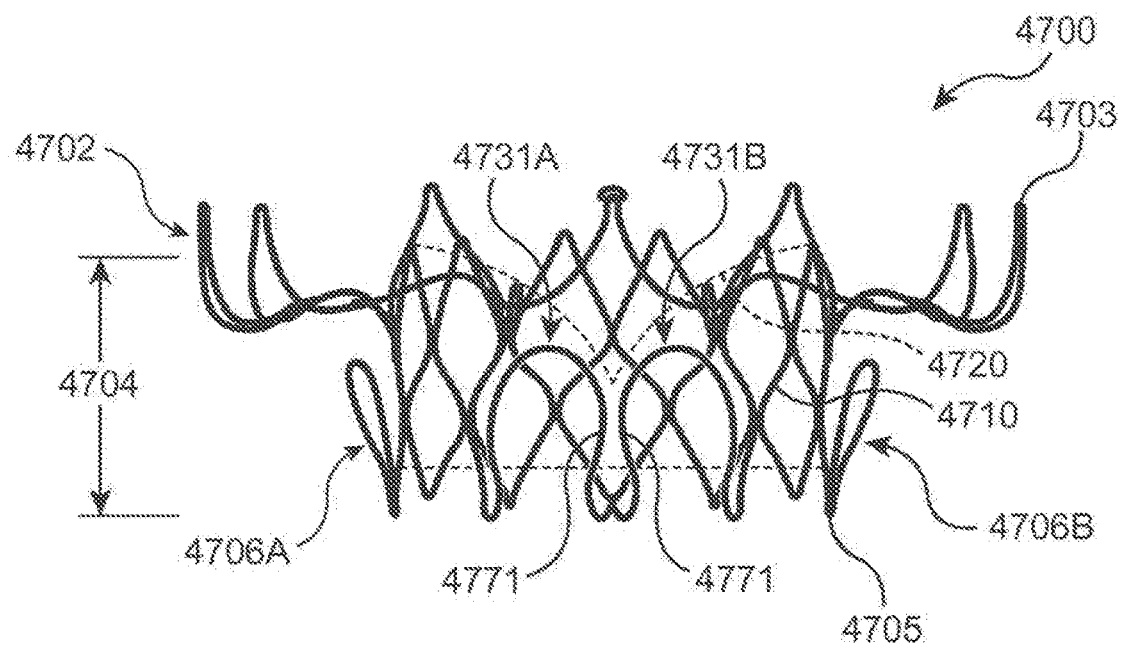
FIG. 47 is a side view of a valve prosthesis having commissural support arms in accordance with an embodiment hereof in an expanded or deployed configuration.

FIG. 47 is a side view of a valve prosthesis 4700 having inflow or commissural support arms 4771 in accordance with an embodiment hereof. Valve prosthesis 4700 is shown in an expanded or deployed configuration in FIG. 47. Valve prosthesis 4700 has an inflow portion 4702 and an outflow or central portion 4704 that holds a prosthetic valve component 4720 that is capable of blocking flow in one direction to regulate flow through valve prosthesis 4700, as similarly described in previous embodiments. Valve prosthesis 4700 includes a self-expanding frame, framework or stent 4710 that defines the inflow and outflow portions 4702, 4704 and includes a pair of support arms 4706A, 4706B that extend from a distal end 4705 thereof. A pair of commissural engagement support arms 4771 also extend from distal end 4705 of frame 4710 and may be an integral part thereof. In the embodiment shown in FIG. 47, the pair of commissural engagement support arms 4771 includes two U-shaped support arms that are side-by-side and positioned along the circumference of central portion 4704 approximately half way between the main support arms 4706A, 4706B. In an embodiment, another pair of commissural engagement support arms is also located at a diametrically opposed location of frame 4710 from the pair of commissural engagement support arms 4771 shown in FIG. 47. Support arms 4706A, 4706B enable native leaflet capture during deployment as described above. However, the additional commissural engagement support arms 4771 are not intended to capture the native leaflets but instead are configured to push against the ventricular side of the mitral valve annulus to aid in securing and sealing of the valve prosthesis within the native valve. In some embodiments, valve prosthesis may comprise one or more leaflet engagement support arms and/or one or more commissural support arms. Commissural or annulus engagement support arms may comprise a variety of shapes, sizes, geometries, and/or configurations as previously described for leaflet engagement support arms and/or chordae engagement support arms. Commissural or annulus engagement support arms are designed or configured to press against the ventricular portion of the native valve annulus with a sufficient force to prevent or minimize valve prosthesis movement and/or migration, for example migration into the left atrium. Commissural or annulus engagement support arms may or may not comprise one or more anchors or barbs.

Figure 47A:
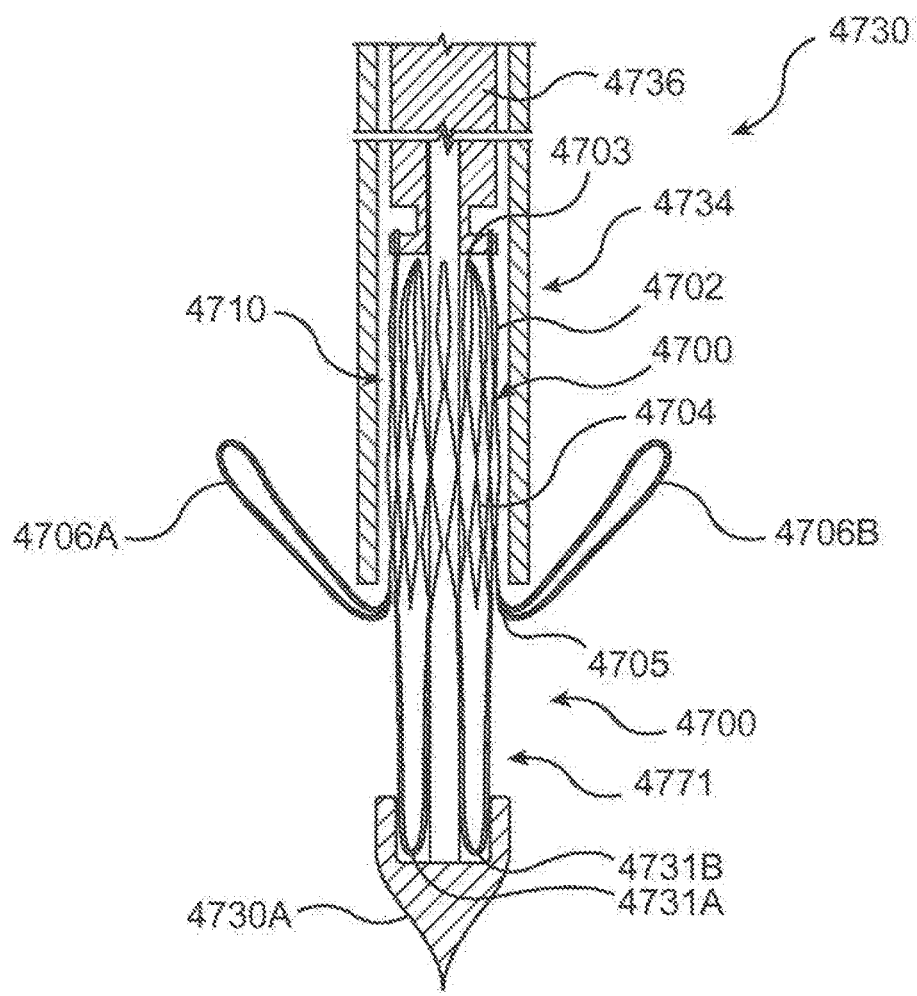
FIG. 47A is a side sectional view of a distal portion of a delivery system with the valve prosthesis of FIG. 47 in a partially deployed configuration, in accordance with an embodiment hereof.

FIG. 47A is a side sectional view of a distal portion of a delivery system 4730 with valve prosthesis 4700 in a partially deployed configuration, in accordance with an embodiment hereof. A proximal or inflow end 4703 of frame 4710 is held by an inner shaft or tubular member 4736 of delivery system 4730 and the inflow and outflow portions 4702, 4704 of frame 4710 are held in a compressed configuration by a sheath or outer tubular member 4734 of delivery system 4730. Support arms 4706A, 4706B and commissural engagement support arms 4771 are loaded in a straightened configuration, as shown in FIG. 47A, such that all extend distally from distal or outflow end 4705 of frame 4710. More particularly, distal ends or tips 4731*a*, 4731B of commissural engagement support arms 4771 are held within a distal cone or tip 4730A of the delivery system 4730. During implantation, sheath 4734 of delivery system 4730 is proximally drawn back, exposing support arms 4706A, 4706B, such that the main support arms 4706A, 4706B may capture the native leaflets as described in detail above. As shown in FIG. 47A, the pair of commissural engagement support arms 4771 is still constrained in the straight, un-deployed configuration at this step. Once leaflet capture is verified, the distal cone 4731A is advanced, or other tip capture mechanism is manipulated, to release the commissural engagement support arms 4771. The embodiment of FIG. 47 is intended to eliminate or minimize complications of chordae entanglement with the commissural support arms and yet still provide additional sealing forces by pushing on the ventricular side of the mitral valve annulus with the commissural engagement support arms 4771 by pinching the annulus between commissural engagement support arms 4771 and the inflow portion 4702 of frame 4710 of valve prosthesis 4700.

FIG. 48 is a side view of a valve prosthesis 4800 having commissural anchors 4861 in accordance with an embodiment hereof. Valve prosthesis 4800 is shown in an expanded or deployed configuration in FIG. 48. Valve prosthesis 4800 has an inflow portion 4802 and an outflow or central portion 4804 that holds a prosthetic valve component 4820 that is capable of blocking flow in one direction to regulate flow through valve prosthesis 4800, as similarly described in previous embodiments. Valve prosthesis 4800 includes a self-expanding frame, framework or stent 4810 that defines the inflow and outflow portions 4802, 4804 and includes a pair of support arms 4806A, 4806B that extend from a distal end 4805 thereof. Support arms 4806A, 4806B enable native leaflet capture during deployment as described above. A plurality of commissural anchors 4861, two of which are shown in FIGS. 48 and 48B, downwardly extend and inwardly curve from inflow portion 4802 of frame 4810 and may be an integral part thereof. In the embodiment shown in FIG. 48, the commissural anchors 4861 may be described as hook-shaped and may be evenly spaced about a circumference of inflow portion 4802. In some embodiments, commissural anchors 4861 may be concentrated in specific locations around the circumference of the inflow portion of the valve prosthesis, such as the commissure regions of the native valve annulus.

FIG. 48A is a side sectional view of a distal portion of a delivery system 4830 with valve prosthesis 4800 in a partially deployed configuration, in accordance with an embodiment hereof. When valve prosthesis 4800 is held in a compressed, loaded configuration within delivery system 4830, sutures 4842 constrain commissural anchors 4861 in a straight configuration. Other methods of constraining anchors 4861 in a straight configuration may include, for example, the use of a rigid sleeve or tube that would pull away from the anchors upon deployment of the valve prosthesis. In some embodiments, the suture or sleeve material may comprise a biodegradable material thereby delaying the release or deployment of the anchors until at a point in time following implantation that corresponding to the degradation rate of the biodegradable material used. With reference to FIG. 48A, a proximal or inflow end 4803 of frame 4810 and commissural anchors 4861 are attached by sutures 4842 to an inner shaft or tubular member 4836 of delivery system 4830 after outflow portion 4804 and support arms 4806A, 4806B of frame 4810 have been deployed from sheath or outer tubular member 4834 of delivery system 4830. Accordingly, valve prosthesis 4800 is implanted using the basic procedure described above, with support arms 4806A, 4806B being deployed to capture the native leaflets and thereafter central portion 4804 with the valve component secured therein and the inflow portion 4802 would be allowed to expand. However, a controlled lengthening of sutures 4842 of delivery system 4830 coincides with the expansion of inflow portion 4802 of frame 4810 as shown in FIG. 48A, such that inflow portion 4802 is expanded but still attached to delivery system 4830 via sutures 4842. At this juncture a clinician can assess the prosthetic valve's function and any complications, such as paravalvular leakage. In the partially deployed configuration of FIG. 48A, the sutures 4842 will keep the commissural anchors 4861 in the straightened configuration. If the clinician approves of the prosthetic valve's performance, the sutures 4842 are released. Without the sutures 4842 constraining the commissural anchors 4861, they will bend into their un-deformed, pre-set positions and pierce the tissue to anchor the frame 4810 in place. FIG. 48B illustrates valve prosthesis 4800 implanted at a mitral valve target location (MV) with commissural anchors 4861 embedded or anchored within the atrial tissue of the heart. If the clinician does not approve of the prosthetic valve's performance upon initial implantation, prosthetic valve 4800 may be removed while the commissural anchors 4861 are still in the straightened configuration of FIG. 48A, prior to any active fixation, i.e., piercing of the heart tissue. In some embodiments, all of the commissural anchors of valve prosthesis may be oriented in the same direction, for example a radially inward direction or a radially outward direction, and/or the commissural anchors may be oriented in a combination of directions, for example some anchors may be oriented in a radially inward direction while some anchors may be oriented in a radially outward direction. In some embodiments, commissural anchors may comprise one or more hooks, tent-stake-like protrusions, and/or barbs to aid in anchoring, for example. In some embodiments, such commissural anchors may be delivered either with the inflow portion or independent of the inflow portion.

Figure 49:
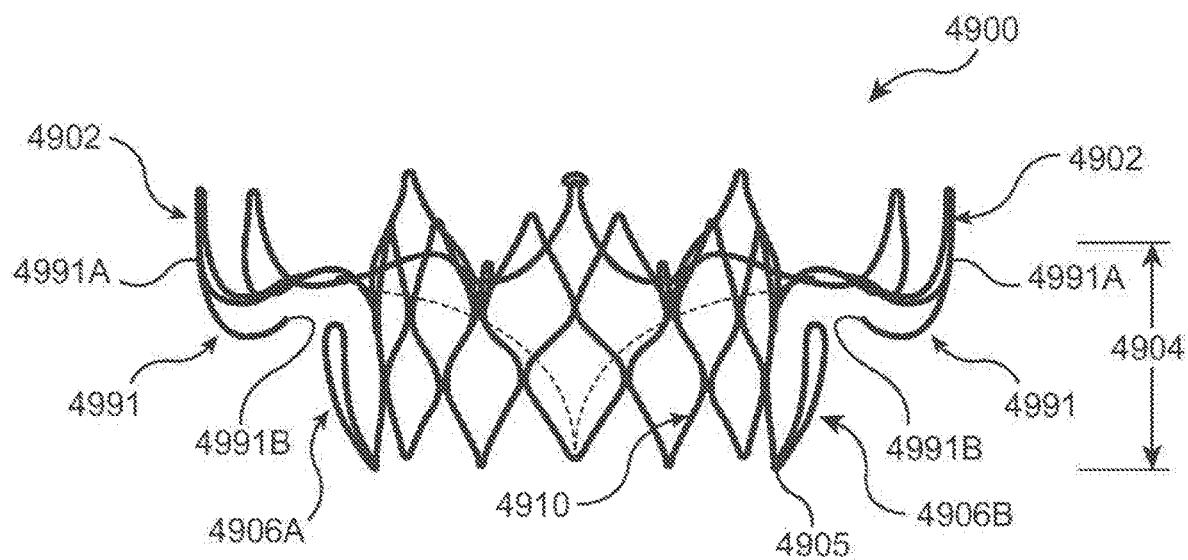
FIG. 49 is a side view of a valve prosthesis having cantilever elements in accordance with an embodiment hereof in an expanded or deployed configuration.

FIG. 49 is a side view of a valve prosthesis 4900 having atrial engagement support arms 4991 in accordance with an embodiment hereof. Valve prosthesis 4900 is shown in an expanded or deployed configuration in FIG. 49. Valve prosthesis 4900 has an inflow portion 4902 having S-shaped struts as described with reference to various embodiments above and an outflow or central portion 4904, which holds a prosthetic valve component (not shown) that is capable of blocking flow in one direction to regulate blood flow through valve prosthesis 4900, as similarly described in previous embodiments. Valve prosthesis 4900 includes a self-expanding frame, framework or stent 4910 that defines the inflow and outflow portions 4902, 4904 and includes a pair of support arms 4906A, 4906B that extend from a distal end 4905 thereof. Support arms 4906A, 4906B enable native leaflet capture during deployment as described above. A plurality of atrial engagement support arms 4991, two of which are shown in FIG. 49, extend and curve inwardly from inflow portion 4902 of frame 4910 and may be an integral part thereof. The atrial engagement support arms may be considered as cantilever elements, wherein each atrial engagement support arm 4991 has a radially outermost end 4991A connected to inflow portion 4902 and an unconnected innermost end 4991B that sits below inflow portion 4902 and radially outward of central portion 4904. In the embodiment shown in FIG. 49, the atrial engagement support arms 4991 may be described as curved beams or struts, and may be evenly spaced about a circumference of inflow portion 4902.

Figure 49A:
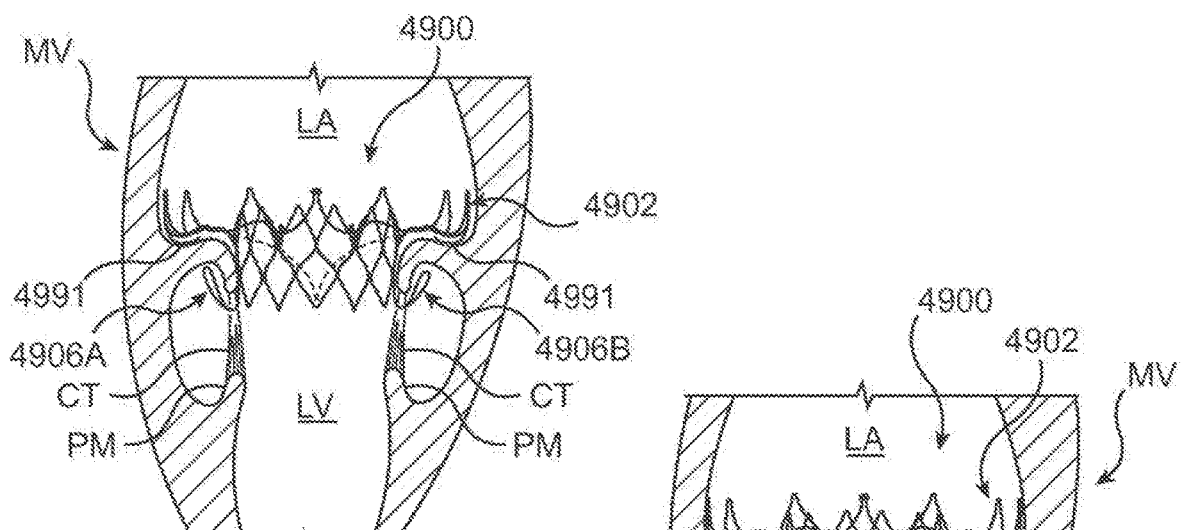
FIGS. 49A and 49B illustrates the valve prosthesis of FIG. 49 implanted at a mitral valve target location within a heart in accordance with an embodiment hereof.
Figure 49B:
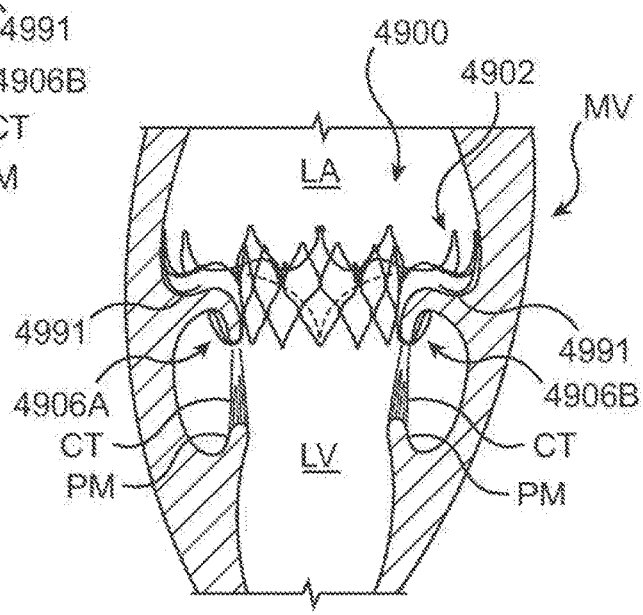

FIGS. 49A and 49B illustrates the valve prosthesis 4900 implanted at a mitral valve (MV) target location within a heart in accordance with an embodiment hereof. Valve prosthesis 4900 is implanted using a method as described above, with support arms 4906A, 4906B being deployed to capture the native leaflets and thereafter central portion 4904 with the valve component secured therein and the inflow portion 4902 being allowed to expand and deploy within the mitral valve (MV). However in the embodiment of FIG. 49 and as shown in FIG. 49A, after initial deployment within the left atrium (LA), atrial engagement support arms 4991 are compressed, or closed between the atrial tissue and the S-shaped struts or primary cantilevers of inflow portion 4902 such that they are not readily visible in FIG. 49A. For example, the cantilever elements may initially have the same shape and/or profile as the inflow portion. In the event that over time chordal damage, elongation, or left ventricle (LV) remodeling causes frame 4910 of valve prosthesis 4900 to move upward or towards the left atrium ($L_A$) as shown in FIG. 49B, decreased loading of inflow portion 4902 of frame 4910 will occur due to the decrease in tension provided by the chordae tendinae (CT). If over time the frame 4910 moves upward enough that the primary cantilever of inflow portion 4902 lifts off of the atrial floor and loses its ability to seal, the secondary cantilever or atrial engagement support arm 4991 will decompress, or open to maintain sealing over a greater amount of frame 4910. Additionally, the secondary cantilever or atrial engagement support arm 4991 may be designed to be much more flexible than the primary cantilever S-shaped struts that form inflow portion 4902. As well in another embodiment, a paravalvular leakage skirt (not shown) may be sewn onto secondary cantilever or atrial engagement support arm 4991, which open towards the radial center of valve prosthesis 4900, to create a pocket around the circumference of inflow portion 4902 such that the atrial engagement support arms 4991 may use the pressure of the blood to help seal against the heart anatomy. In another embodiment, a paravalvular leakage skirt covers the atrial engagement support arms and is attached to frame 4900 in such a manner that the formation of a pocket around the circumference of the frame is prevented but the skirt still allows movement of the atrial engagement support arms as described above.

Figure 50:
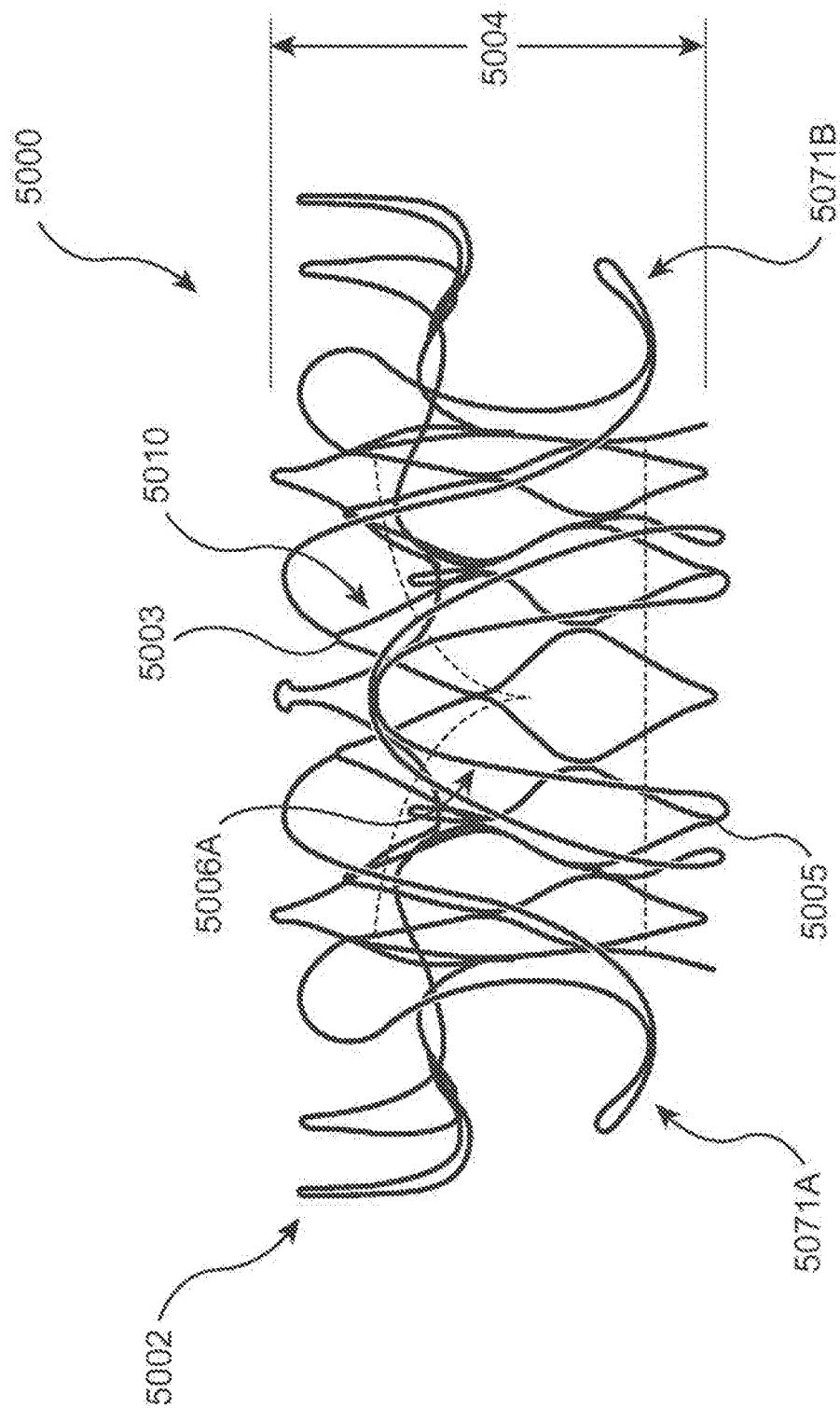
FIG. 50 is a side view of a valve prosthesis having inflow support arms in accordance with an embodiment hereof in an expanded or deployed configuration.

FIG. 50 is a side view of a valve prosthesis 5000 having inflow support arms 5071 in accordance with an embodiment. Valve prosthesis 5000 is shown in an expanded or deployed configuration in FIG. 50. Valve prosthesis 5000 has an inflow portion 5002 and an outflow or central portion 5004, which holds a prosthetic valve component (not shown) for blocking flow in one direction to regulate blood flow through valve prosthesis 5000, as similarly described in previous embodiments. Valve prosthesis 5000 includes a self-expanding frame, framework or stent 5010 that defines the inflow and outflow portions 5002, 5004 and includes a pair of support arms 5006A, 5006B that extend from a distal or outflow end 5005 thereof. A pair of inflow support arms 5071A, 5071B extend from a proximal or inflow end 5003 of frame 5010 and may be an integral part thereof. Inflow support arms 5071A, 5071B may alternatively be described as commissural engagement support arms and/or ventricular engagement support arms. Inflow support arms 5071A, 5071B may be located at diametrically opposed locations of frame 5010 such that each is positioned along the circumference of valve prosthesis 5000 approximately half way between the main support arms 5006A, 5006B. In this manner, each inflow support arm 5071A, 5071B will align with a respective commissure of the native mitral valve upon implantation to engage with tissue on the ventricular-side of the prosthesis. In the embodiment of FIG. 50, each inflow support arm 5071A, 5071B has a dual support arm construction, as seen more clearly in FIGS. 51D and 51E with respect to inflow support arm 5071A includes an outer support arm 5086A and an inner support arm 5088A that is similar to main support arms 206A, 206B of frame 210 in the embodiment of FIG. 4. As in the embodiment of FIG. 47, main support arms 5006A, 5006B enable native leaflet engagement or capture during deployment as described above and the additional inflow support arms 5071A, 5071B are configured to engage or push against the ventricular side of the mitral valve annulus to aid in securing and sealing of valve prosthesis 5000 within the native valve.

Figure 51A:
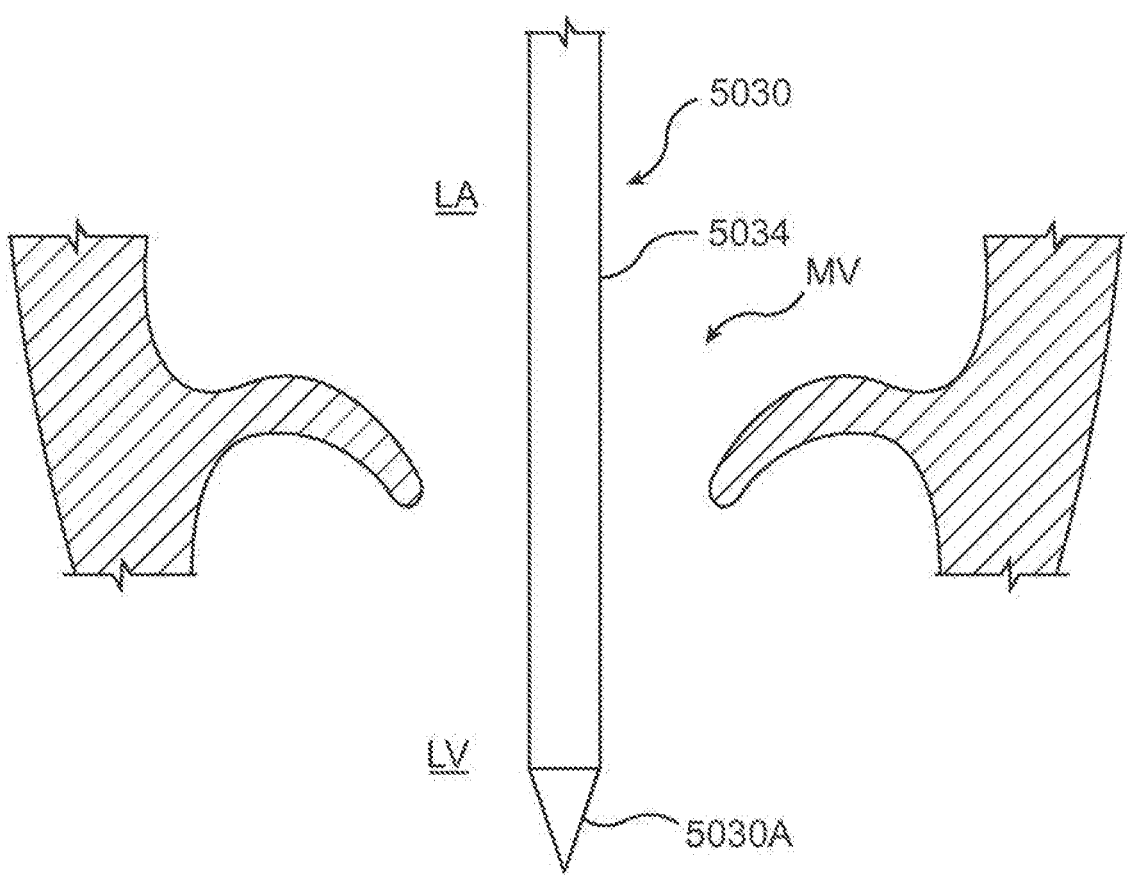
FIGS. 51A, 51AA, 51B, 51BB, 51C, 51CC, 51D, 51DD, 51E, and 51EE illustrate a method of implanting the valve prosthesis of FIG. 50 within a mitral valve of a heart in accordance with an embodiment hereof.

FIGS. 51A, 51AA, 51B, 51BB, 51C, 51CC, 51D, 51DD, 51E, and 51EE illustrate a method of implanting valve prosthesis 5000 within a mitral valve (MV) of a heart in accordance with an embodiment hereof. FIG. 51A is a side view of a distal portion of a prosthetic valve delivery system 5030 with valve prosthesis 5000 loaded therein in a compressed delivery configuration, in accordance with an embodiment hereof. Main support arms 5006A, 5006B and inflow supports arms 5071A, 5071B are held within a sheath 5034 in an unbent or straightened state with the main support arms 5006A, 5006B extending from outflow end 5005 of central portion 5004 and inflow support arms 5071A, 5071B extending from inflow end 5003 of central portion 5004. Delivery system 5030 is shown in FIG. 51A after having been advanced into the left atrium (LA), with sheath 5034 having been advanced through the mitral valve (MV) and into the left ventricle (LV) such that a distal tip 5030A of delivery system 5030 is advanced into the left ventricle (LV) until valve prosthesis 5000 loaded therein is centered at the native mitral valve (MV).

Figure 51B:
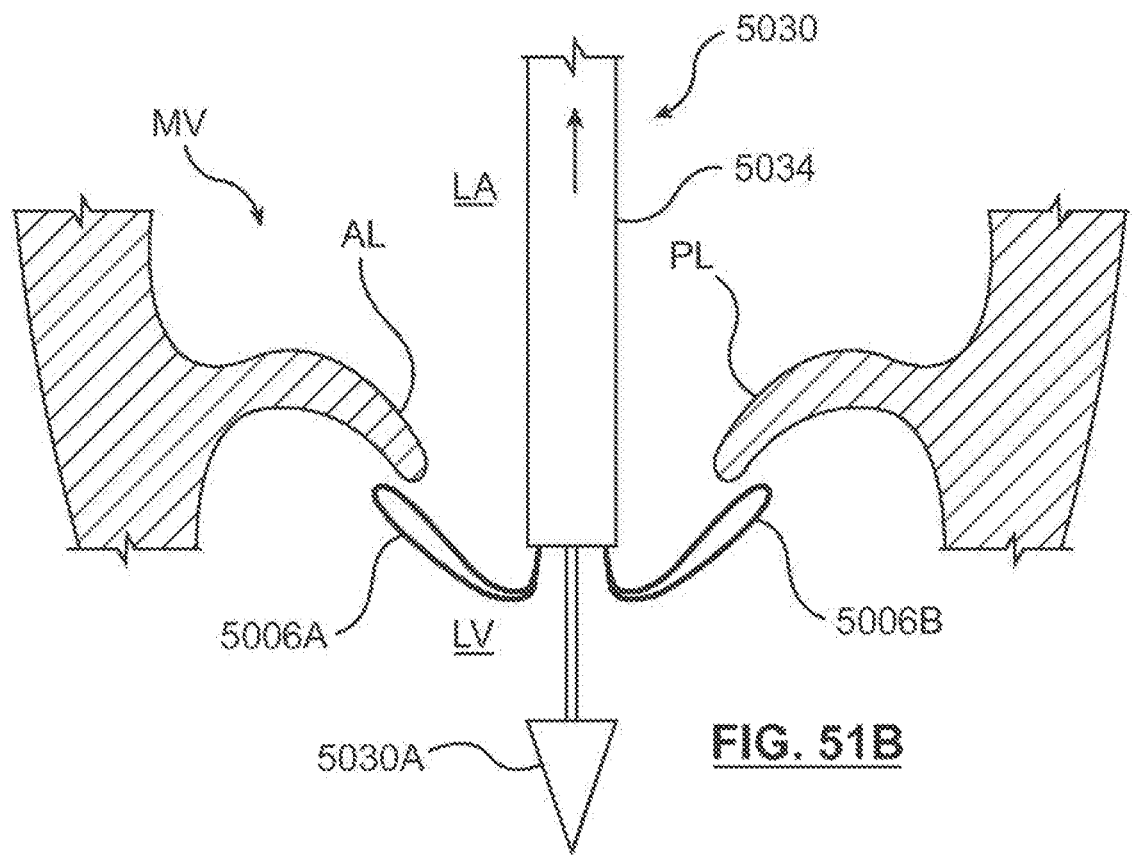
Figure 51B:
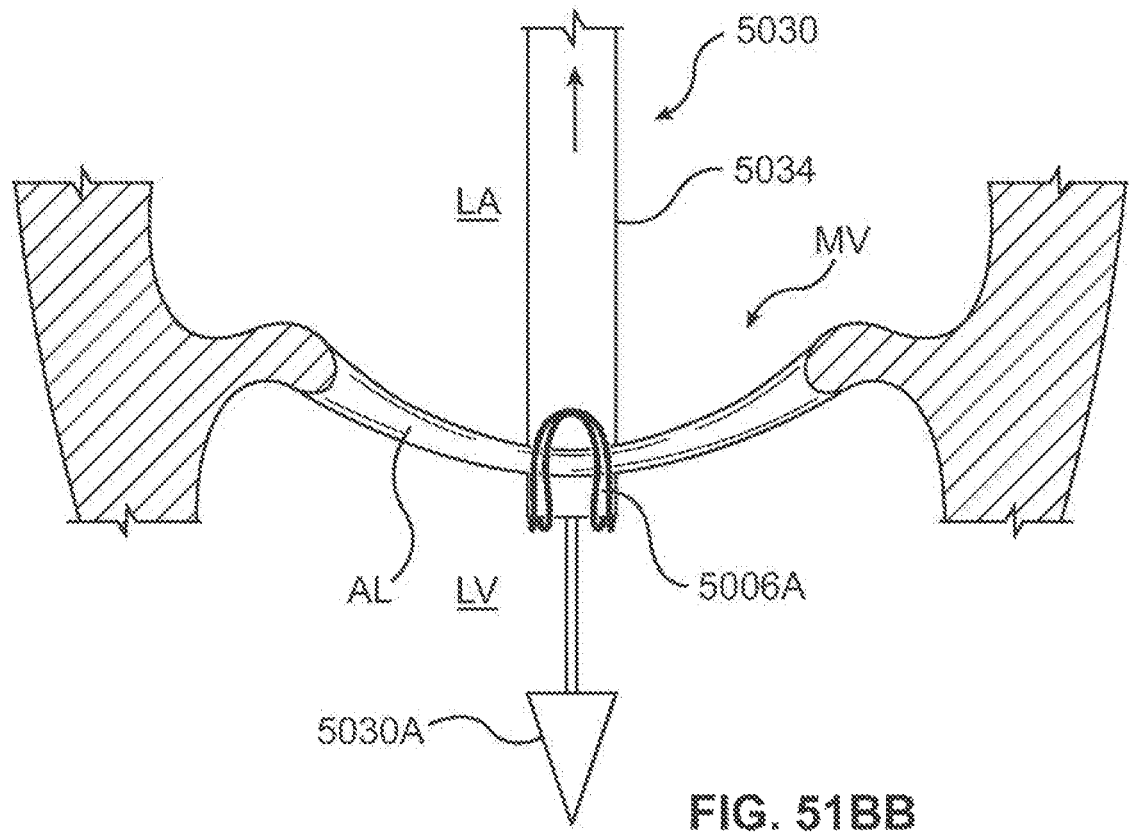

FIGS. 51B and 51BB depict side views of valve prosthesis 5000 positioned in the middle of the native mitral valve (MV) with main support arms 5006A, 5006B of valve prosthesis 5000 released by the proximal retraction sheath 5034. FIG. 51BB is an alternate side view of FIG. 51B rotated 90° clockwise about a longitudinal axis $L_A$ thereof from the orientation shown in FIG. 51B. Due to the self-expanding properties of the support arms, support arms 5006A, 5006B expand radially outwardly relative to the sheath in which they were enclosed and rotate proximally until they each capture their respective native valve leaflet AL, PL. The remainder of frame 5010 and inflow support arms 5071A, 5071B of valve prosthesis 5000 are positioned within the mitral valve (MV) but are still contained within sheath 5034.

Figure 51C:
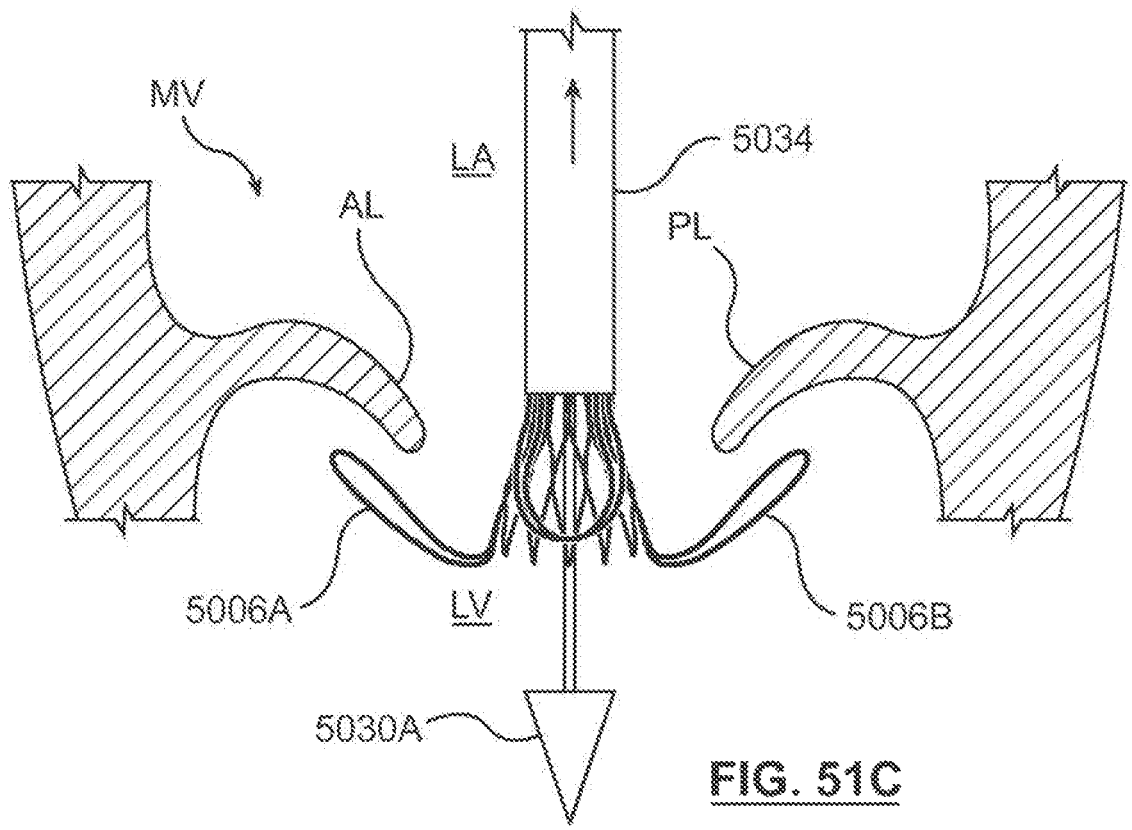
Figure 51C:
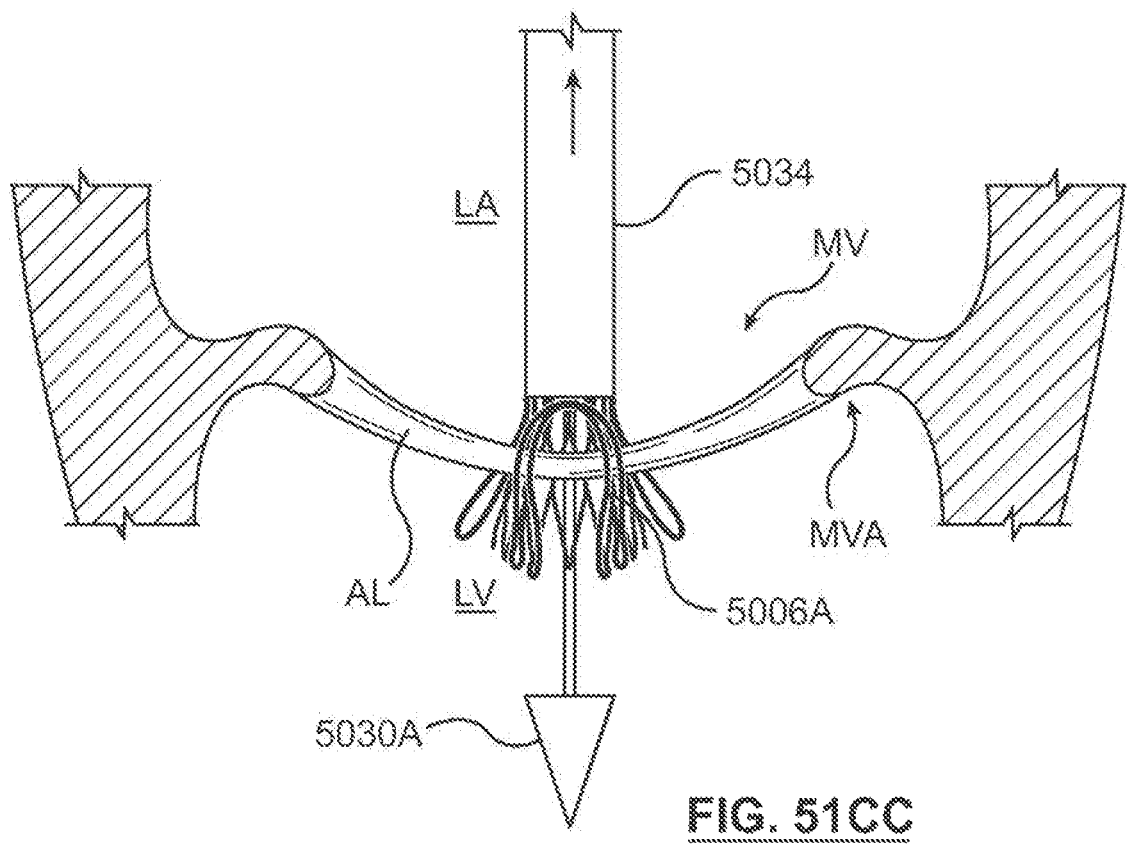

FIGS. 51C and 51CC depict side views of valve prosthesis 5000 with inflow support arms 5071A, 5071B released by further proximal retraction of sheath 5034. FIG. 51CC is an alternate side view of FIG. 51C rotated 90° clockwise about a longitudinal axis $L_A$ thereof from the orientation shown in FIG. 51C. Due to the self-expanding properties of the support arms, inflow support arms 5071A, 5071B expand radially outwardly relative to the sheath in which they were enclosed.

Figure 51D:
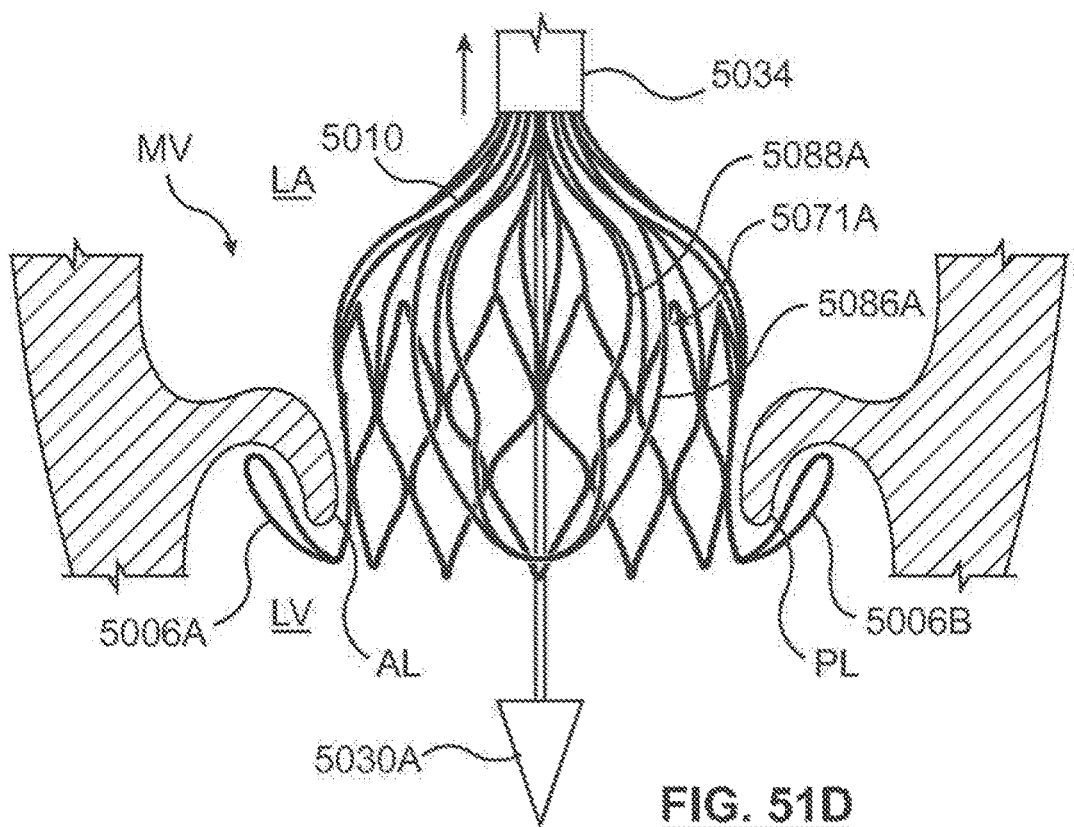
Figure 51D:
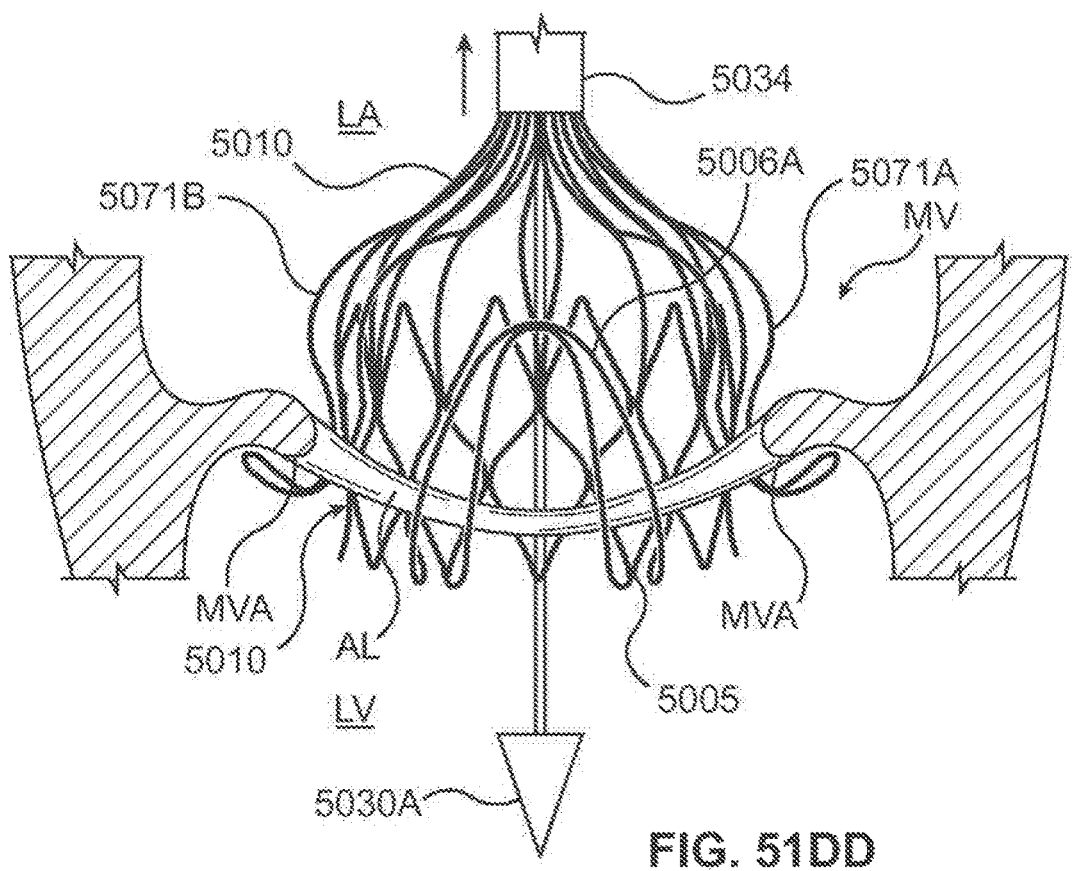

With continued proximal retraction of sheath 5034 as shown in FIGS. 51D and 51DD, inflow support arms 5071A, 5071B continue to rotate proximally through respective commissures of the native mitral valve (MV) until they engage tissue of the left ventricle (LV) on diametrically opposed locations of the mitral valve annulus (MVA). FIG. 51DD is an alternate side view of FIG. 51D rotated 90° clockwise about a longitudinal axis $L_A$ thereof from the orientation shown in FIG. 51D. The remainder of frame 5010 of valve prosthesis 5000 is partially expanded within the mitral valve (MV) and the left atrium ($L_A$).

Figure 51E:
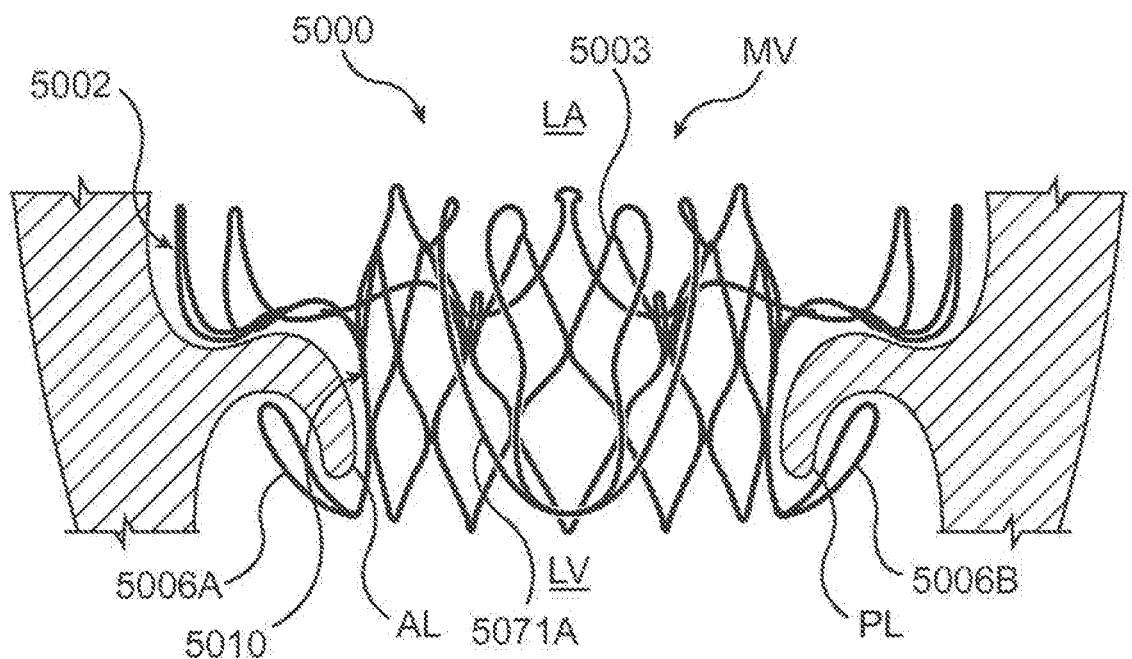
Figure 51E:
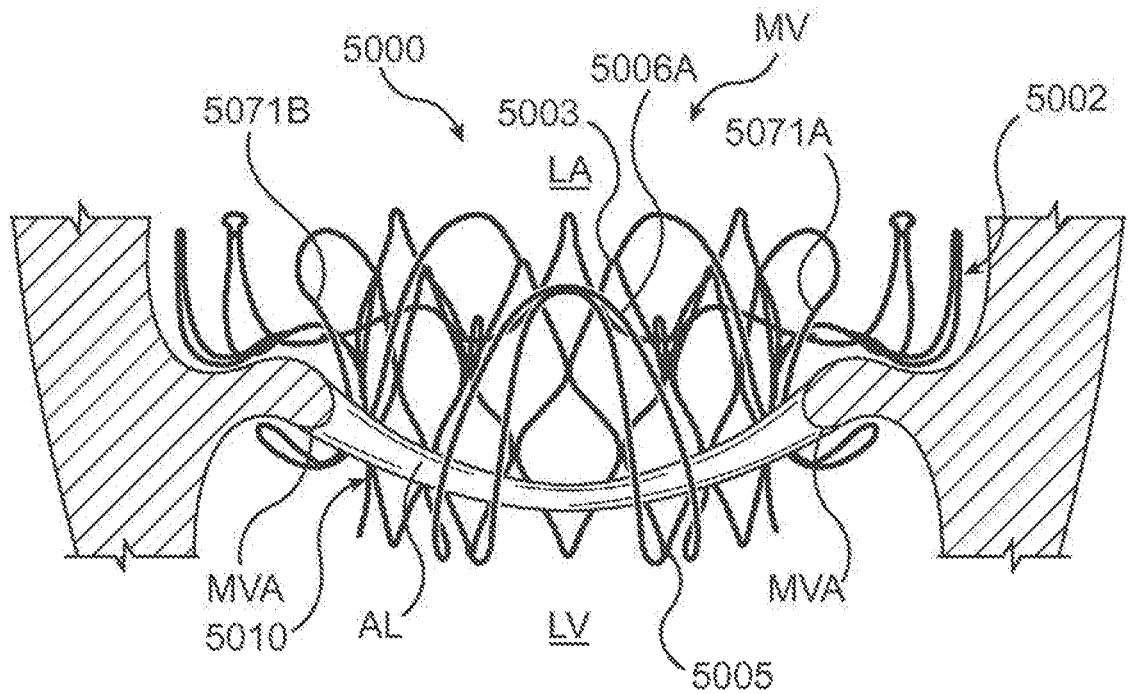

Sheath 5034 is proximally retracted until the proximal or inflow end 5003 of frame 5010 is exposed and allowed to self-expand, thereby uncoupling mitral valve prosthesis 5000 from delivery system 5030. Delivery system 5030 can then be retracted from the patient, leaving the expanded mitral valve prosthesis 5000 deployed at the mitral valve (MV) as shown in FIGS. 51E and 51EE. FIG. 51EE is an alternate side view of FIG. 51E rotated 90° clockwise about a longitudinal axis $L_A$ thereof from the orientation shown in FIG. 51E. In the final deployed configuration of valve prosthesis 5000, each main support arm 5006A, 5006B proximally extends from distal or outflow end 5005 of frame 5010 toward the inflow end thereof and each inflow support arms 5071A, 5071B distally extends from proximal or inflow end 5003 of frame 5010 toward the outflow end thereof. The support arms 5006A, 5006B firmly press against the native mitral valve leaflets (AL, PL) and/or tissue of the left ventricle (LV) in order to properly position mitral valve prosthesis 5000 within the mitral valve annulus (MVA). The inflow support arms 5071A, 5071B provide additional sealing forces by pushing on the ventricular side of the mitral valve annulus (MVA) with the mitral valve annulus (MVA) being pinched or sandwiched between inflow support arms 5071A, 5071B and inflow portion 5002 of frame 5010 of valve prosthesis 5000.

In one or more embodiments, valve prosthesis may comprise an inflow portion, a central portion, and an outflow portion. In one or more embodiments, the valve prosthesis may comprise a single unitary structure or the valve prosthesis may comprise one or more components or portions coupled or connected together. In one or more embodiments, the valve prosthesis may comprise a central portion comprising a valve body, member, or component. In one or more embodiments, the valve body, member, or component may comprise one or more valve leaflets. In one or more embodiments in accordance herewith, the valve leaflets of the valve body, member, or component are attached to an upstream end of the central portion to extend into an atrial or inflow portion of the frame, and into the left atrium when implanted to replace a mitral valve in situ, such that the valve body, member, or component is not solely located on or within the outflow or ventricular portion of the frame, and therefore does not sit only within the left ventricle when implanted to replace a mitral valve in situ. By locating a portion of the valve leaflets in the left atrium, the required length of the central or valve-retaining tubular portion of the frame is minimized and the length of frame that protrudes into the left ventricle may be reduced. In one or more embodiments, valve member and/or one or more of its components may comprise one or more materials, as described herein.

In one or more embodiments, the central portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, an hourglass shape, a polygonal shape, a funnel shape, a nozzle shape, a D-shape, a saddle shape, a planar shape, a non-planar shape, a simple geometric shape, and/or a complex geometric shape. In one or more embodiments, the central portion and/or one or more of its components may comprise one or more fixation elements or members such as anchors, barbs, clips, prongs, grommets, sutures, and/or screws. In one or more embodiments, the central portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the central portion and/or one or more of its components may comprise one or more support arms, components, or members as described herein. In one or more embodiments, one or more support arms may comprise one or more cantilever components or portions. In one or more embodiments, the central portion and/or one or more of its components, such as one or more support arms, may be designed to engage and/or push against the native valve annulus. In one or more embodiments, the central portion and/or one or more of its components, such as one or more support arms, may be designed to engage, capture, clamp, hold, and/or trap one or more native valve leaflets. In one or more embodiments, the central portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the central portion and/or one or more of its components, such as one or more support arms, may be designed to engage and/or push against one or more native valve commissures.

In one or more embodiments, valve prosthesis may comprise an inflow, inlet, upstream, or proximal portion connected, coupled, positioned, and/or located at a proximal end or proximal end portion of the central portion of the valve prosthesis. In one or more embodiments, the inflow portion and/or one or more of its components may contact, engage, fixate, capture, clamp, pierce, hold, position, and/or seal the valve prosthesis to one or more heart structures and/or tissues such as atrial tissue, ventricle tissue, valve tissue, annulus tissue, the floor of an atrium, and/or the floor of a ventricle. For example, the inflow portion and/or one or more of its components may engage atrial tissue if the valve prosthesis is positioned in a native mitral valve whereas the inflow portion and/or one or more of its components may engage ventricle tissue if the valve prosthesis is positioned in a native aortic valve. In one or more embodiments, the inflow portion and/or one or more of its components may exert one or more forces, for example, radial and/or axial forces, to one or more heart structures and/or heart tissues. In one or more embodiments, the inflow portion and/or one or more of its components may comprise one or more fixation elements or members such as anchors, barbs, clips, prongs, grommets, sutures, and/or screws. In one or more embodiments, the inflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the inflow portion and/or one or more of its components may be designed to deform to the shape of the native anatomy when the valve prosthesis is implanted. For example, the inflow portion may deform from a pre-delivery circular shape to a post-delivery D-shape following the delivery of the valve prosthesis to a native mitral valve. In one or more embodiments, the inflow portion and/or one or more of its components may comprise a frame, a framework, or stent-like structure, as described herein. In one or more embodiments, the inflow portion and/or one or more of its components may comprise, be covered with, be coated with, or be attached or coupled to one or more materials, as described herein. In one or more embodiments, the inflow portion and/or one or more of its components may comprise one or more support arms, components, or members as described herein. In one or more embodiments, one or more support arms may comprise one or more cantilever components or portions. In one or more embodiments, the inflow portion and/or one or more of its components, such as one or more support arms, may be designed to engage and/or push against the native valve annulus. In one or more embodiments, the inflow portion and/or one or more of its components, such as one or more support arms, may be designed to engage, capture, clamp, hold, and/or trap one or more native valve leaflets. In one or more embodiments, the inflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the inflow portion and/or one or more of its components, such as one or more support arms, may be designed to engage and/or push against one or more native valve commissures.

In one or more embodiments, valve prosthesis may comprise an outflow, outlet, downstream, or distal portion connected, coupled, positioned, and/or located at a distal end or distal end portion of the central portion of the valve prosthesis. In one or more embodiments, the outflow portion and/or one or more of its components may contact, engage, fixate, capture, clamp, pierce, hold, position, and/or seal the valve prosthesis to one or more heart structures and/or tissues such as atrial tissue, ventricle tissue, valve tissue, valve leaflet tissue, annulus tissue, and/or chordae tissue. For example, the outflow portion and/or one or more of its components may engage leaflet tissue, chordae tissue, and/or ventricle tissue if the valve prosthesis is positioned in a native mitral valve whereas the outflow portion and/or one or more of its components may engage leaflet tissue and/or aortic tissue if the valve prosthesis is positioned in a native aortic valve. In one or more embodiments, the outflow portion and/or one or more of its components may exert one or more forces, for example, radial and/or axial forces, to one or more heart structures and/or heart tissues. In one or more embodiments, the outflow portion and/or one or more of its components may comprise one or more fixation elements or members such as anchors, barbs, prongs, clips, grommets, sutures, and/or screws. In one or more embodiments, the outflow portion and/or one or more of its components may comprise one or more longitudinal or cross-sectional shapes, such as a geometric shape, a non-geometric shape, a tubular shape, a cylindrical shape, a circular shape, an elliptical shape, an oval shape, a triangular shape, a rectangular shape, a hexagonal shape, a square shape, a polygonal shape, a funnel shape, a nozzle shape, a D-shape, an S-shape, a saddle shape, a simple geometric shape, and/or a complex geometric shape. In one or more embodiments, the outflow portion and/or one or more of its components may be designed to deform to the shape of the native anatomy when the valve prosthesis is implanted. For example, the outflow portion may deform from a pre-delivery circular shape to a post-delivery D-shape following the delivery of the valve prosthesis to a native mitral valve. In one or more embodiments, the outflow portion and/or one or more of its components may comprise a frame, a framework, or stent-like structure, as described herein. In one or more embodiments, the outflow portion and/or one or more of its components may comprise, be covered with, be coated with, or be attached or coupled to one or more materials, as described herein. In one or more embodiments, the outflow portion and/or one or more of its components may comprise one or more support arms, components, or members as described herein. In one or more embodiments, the outflow portion and/or one or more of its components, such as one or more support arms, may be designed to engage, capture, clamp, hold, and/or trap one or more native valve leaflets. In one or more embodiments, the outflow portion and/or one or more of its components, such as one or more support arms, may be designed to engage, capture, clamp, hold, and/or trap one or more native chordae. In one or more embodiments, one or more support arms may create or exert a tension force to native chordae. In one or more embodiments, the outflow portion and/or one or more of its components, such as one or more support arms, may be designed to engage and/or push against one or more native valve commissures. In one or more embodiments, the outflow portion and/or one or more of its components, such as one or more support arms, may be designed to engage and/or push against the native valve annulus. In one or more embodiments, one or more support arms may comprise one or more cantilever components or portions.

Valve prosthesis embodiments disclosed herein illustrate support arms having a single arm, support arms with inner and outer support arms and variations of structures thereof, and/or one more pairs of support arms having various structures and attachment points for providing various functions when implanted. It should be understood that the illustrated embodiments hereof are not limited to the number or configuration of support arms illustrated in each figure and that one or more support arms, one or more pairs of support arms and/or the various structures therefore may be substituted across the various embodiments disclosed herein without departing from the scope hereof.

In one or more embodiments, valve prosthesis may comprise one or more support arms for engaging one or more native valve leaflets. In one or more embodiments, valve prosthesis may comprise one or more support arms for engaging one or more native chordae. In one or more embodiments, valve prosthesis may comprise one or more support arms for engaging one or more native valve commissures. In one or more embodiments, valve prosthesis may comprise one or more support arms for engaging a native valve annulus. In one or more embodiments, valve prosthesis may comprise one or more support arms for engaging one or more native valve tissues or structures. For example, one or more support arms may engage or interact with valve leaflets, chordae, commissures and/or annulus. In one or more embodiments, valve prosthesis may comprise one or more support arms for engaging one or more heart tissues or structures. In one or more embodiments, valve prosthesis may comprise one or more support arms for engaging the pulmonary artery. In one or more embodiments, valve prosthesis may comprise one or more support arms for engaging the aorta.

In one or more embodiments, one or more support arms may be coupled or connected to the central portion, the inflow portion and/or the outflow portion of valve prosthesis. In one or more embodiments, valve prosthesis may comprise one or more support arms that may apply one or more forces such as a radial force, an axial force, a lateral force, an inward force, an outward force, an upstream force, and/or a downstream force to one or more valve structures, valve tissues, heart structures and/or heart tissues. In some embodiments, one or more support arms, as described herein, may be considerably longer, shorter, wider, or narrower than shown. In some embodiments, one or more support arms, as described herein, may be narrower at the base, bottom or proximal end portion where the support arms couple to the inflow portion, central portion and/or the outflow portion of the valve prosthesis and wider at the top or distal end portion of the support arm. In some embodiments, one or more support arms, as described herein, may be wider at the base, bottom, or proximal end portion where the support arms couple to the inflow portion, central portion and/or the outflow portion of the valve prosthesis and narrower at the top or distal end portion of the support arm. In some embodiments, one or more support arms, as described herein, may be configured to be a shape and size that can provide a positioning function, valve leaflet capturing function, a stabilization function, an anti-migration function, and/or an anchoring function for valve prosthesis in accordance herewith when the prosthesis is deployed at a native valve site. In some embodiments, one or more support arms, as described herein, may interact, engage, capture, clamp, push against one or more native tissues or structures such as valve leaflets, chordae, annulus, ventricle, and/or atrium. In some embodiments, one or more support arms, as described herein, may comprise a first portion that extends in a forward direction and a second portion that extends in a backward direction. In some embodiments, one or more support arms, as described herein, may comprise a first portion that extends in a backward direction and a second portion that extends in a forward direction. In some embodiments, one or more support arms, as described herein, may comprise one or more portions that may extend horizontally, longitudinally, axially, circumferentially, inward, outward, forward, and/or backward. In some embodiments, one or more support arms, as described herein, may comprise more than one configuration. For example, one or more embodiments of one or more support arms, as described herein, may extend in first direction in a delivery configuration and in a second direction in a deployed configuration. In one example, a first or delivery direction may be a forward direction and a second or deployed direction may be a backward direction. In another example, a first or delivery direction may be a backward direction and a second or deployed direction may be a forward direction. In one or more embodiments, one or more support arms, as described herein, may comprise a first shape in a delivery configuration and a second shape in a deployed configuration. For example, a first or delivery shape may be a straight shape and a second or deployed shape may be a curved shape.

In some embodiments, one or more support arms, as described herein, may comprise one or more portions that comprise one or more spiral shapes, s-shapes, c-shapes, u-shapes, V-shapes, loop shapes, tine shapes, and/or prong shapes. In some embodiments, one or more support arms, as described herein, may comprise a curved, rounded, and/or flared distal end portion. In some embodiments, one or more support arms, as described herein, may be connected, coupled, attached, and/or extend from one or more locations positioned on the inflow portion, the central portion and/or the outflow portion of the valve prosthesis. In some embodiments, one or more support arms, as described herein, may comprise at least a portion that may comprise at least one free end not attached or coupled to the frame of the valve prosthesis. In one or more embodiments, one or more support arms and/or one or more of components of a support arm may comprise one or more fixation elements or members such as anchors, barbs, prongs, clips, grommets, sutures, and/or screws. In one or more embodiments, one or more support arms and/or one or more of components of a support arm may comprise, for example, one or more active and/or passive fixation elements or members.

Figure 52:
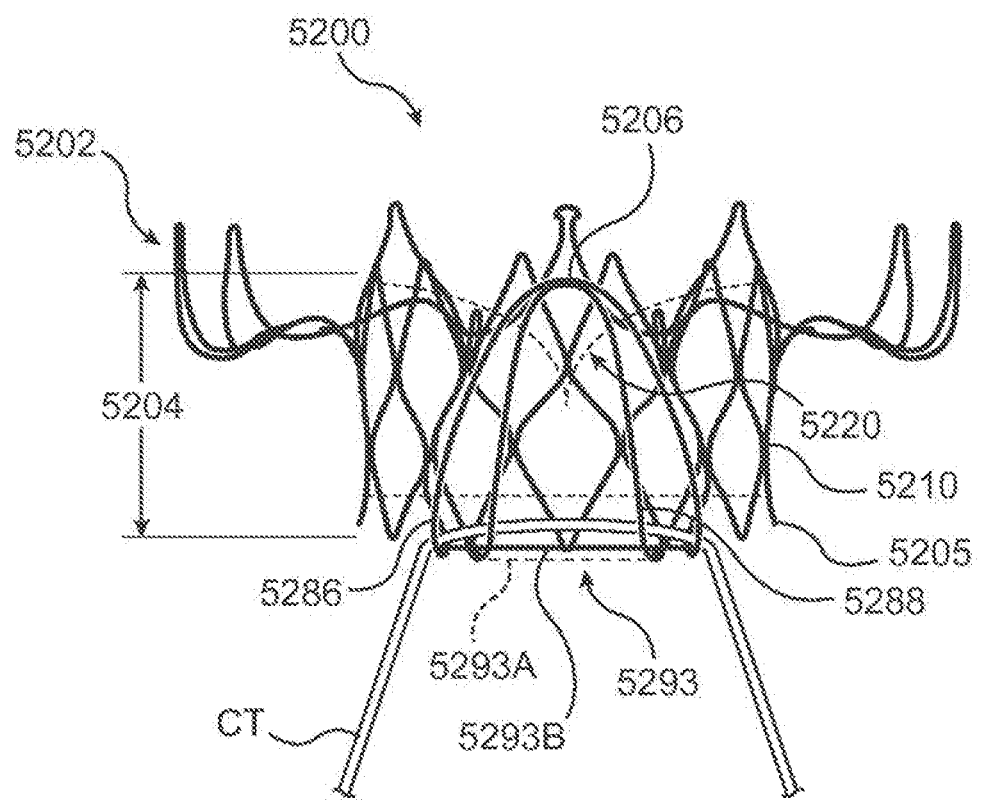
FIG. 52 is a side view of a valve prosthesis in accordance with an embodiment hereof in a first or acute deployed configuration.

In one or more embodiments, a valve prosthesis and/or one or more of its components such as one or more support arms may comprise a first acute configuration and a second chronic configuration. For example, an acute configuration may correspond to an initial and/or early implant configuration and a chronic configuration may correspond to a later-in-time configuration following the implant of the valve prosthesis. In some embodiments, one or more support arms, as described herein, may be narrower at the base, bottom, or proximal end portion in a first acute configuration and then wider at the base, bottom, or proximal end portion in a second chronic configuration. FIG. 52 is a side view of a valve prosthesis 5200 in accordance with an embodiment hereof in a first or acute deployed configuration that after a certain period of time transforms into a second or chronic deployed configuration (not shown). Valve prosthesis 5200 has an inflow portion 5202 and an outflow or central portion 5204, which holds a prosthetic valve component 5220

(depicted by dashed lines) for blocking flow in one direction to regulate blood flow through valve prosthesis 5200. Valve prosthesis 5200 includes a self-expanding frame, framework or stent 5210 that defines the inflow and outflow portions 5202, 5204 and includes a pair of support arms 5206 (only one of which is shown) that extend from a distal end 5205 thereof. In the embodiment shown in FIG. 52, support arms 5206 may include a first or outer U-shaped support arm 5286 and a second or inner U-shaped support arm 5288 that may each bend or rotate more than ninety degrees with respect to a compressed, delivery configuration during deployment, as previously discussed above. The native valve leaflets may be held by support arms 5206, as described above, such that the chordae tendinae (CT) may be held in tension or under load thereby. Any of the tent concepts described above may be used with the embodiment of FIG. 52 in order to prevent the chordae (CT) from rubbing against frame 5210 and more particular from contacting support arms 5206.

Valve prosthesis 5200 provides a means for counteracting stress relaxation or loss of load and/or stretching that occurs over time in biological tissue, and particularly such stretching and/or stress relaxation that may occur in the chordae (CT) when the valve prosthesis is used to replace a mitral valve. Frame 5210 of valve prosthesis 5200 may have two or more unique configurations to counteract stress relaxation and/or stretching in which one configuration is acute or short-term and occurs upon initial deployment or implantation while the other configuration is chronic or long-term and evolves or occurs over time. Stated another way, frame 5210 may be described as a time-released frame having two distinct configurations, one acute configuration and one chronic configuration wherein the acute configuration may be configured to prevent paravalvular leakage (PVL) and damage to the anatomy in the short-term, while the chronic configuration may be configured to provide for optimal long-term performance to include preventing paravalvular leakage (PVL) over a longer period. In an embodiment, the transition from the acute configuration to the chronic configuration may occur within the same time period as the stress relaxation of the chordae.

In order to provide the first, acute or short-term deployed configuration upon initial deployment at a native valve site and for a period of time thereafter, valve prosthesis 5200 may include one or more resorbable or biodegradable sutures 5293 attached at outflow end 5205 of frame 5210 to radially constrain or hold the outflow end of support arms 5206 and/or frame 5210 to a reduced diameter or a narrower dimension than its fully expanded state. As previously described the support arms tension the chordae upon implantation of valve prosthesis 5200; however, in the embodiment of FIG. 52 valve prosthesis 5200 in the acute configuration temporarily constrains support arms 5206 from fully expanding with resorbable or biodegradable sutures 5293, which shortens the papillary muscle-chordae-valve leaflet-chordae-papillary-muscle length to prevent damage to the anatomy upon initial deployment and for a short-term thereafter. In some embodiments valve prosthesis 5200 may include first and second resorbable or biodegradable sutures 5293A, 5293B that radially constrain inner and outer support arms 5288, 5286, respectively, at outflow end 5205 in order to constrain support arms 5206 to a reduced diameter or dimension when the valve prosthesis is in the acute deployed configuration. In some embodiments, first and second resorbable or biodegradable sutures 5293A, 5293B may have different dissolution rates in order to provide a more gradual transition to the chronic configuration, or stated another way to permit a more gradual expansion of support arms 5206 and/or frame 5210. In some embodiments, one of the first and second sutures 5293A, 5293B may degrade in the range of 10 to 14 days to partially release the support arms and/or frame and the other or remaining of the first and second sutures 5293A, 5293B may degrade in the range of 28 to 35 days to fully release the support arms and/or frame and thereby obtain the chronic configuration. It should be understood by the foregoing description that the chronic configuration of valve prosthesis 5200 evolves over time as one or more of the resorbable or biodegradable sutures 5293 are absorbed or degraded. The chronic configuration has a longer papillary muscle-chordae-valve leaflet-chordae-papillary muscle length than the acute configuration due to the wider dimension of the unconstrained, fully expanded support arms 5206, which is intended to tension the chordae back to the initial optimal load to prevent chronic paravalvular leakage (PVL) without acutely damaging the sub-valvular anatomy. In accordance with embodiments hereof, any support arm and/or frame disclosed herein may have an acute configuration and a chronic configuration to include support arms of any of the inflow portions, and central or outflow portions described above.

In one or more embodiments, the valve prosthesis may comprise one or more active and/or passive fixation elements or members such as anchors, barbs, prongs, clips, grommets, sutures, and/or screws. In one or more embodiments, one or more active and/or passive fixation elements or members may be delivered separately from the valve prosthesis. In one or more embodiments, one or more active and/or passive fixation elements or members may be delivered during the valve prosthesis implant procedure. In one or more embodiments, one or more active and/or passive fixation elements or members may be delivered after the valve prosthesis implant procedure. In one or more embodiments, one or more active and/or passive fixation elements or members may be delivered using the valve prosthesis delivery system. In one or more embodiments, one or more active fixation elements or members may be activated by pushing, pulling, twisting, screwing and/or turning motion or movement. In one or more embodiments, one or more fixation elements or members may be released or engaged via an unsheathing, an unsleeving, a dissolving, and/or a degrading action. In one or more embodiments, one or more active and/or passive fixation elements or members may be delivered using a fixation element delivery system. In one or more embodiments, one or more active and/or passive fixation elements or members may be coupled, connected, and/or attached to the valve prosthesis stent or frame. In one or more embodiments, the valve prosthesis stent or frame may comprise a unitary structure that comprises one or more active and/or passive fixation elements. In one or more embodiments, one or more active and/or passive fixation elements may be coupled, connected, and/or attached to the valve prosthesis skirt and/or graft material. In one or more embodiments, one or more fixation elements or members may be designed to increasingly engage one or more heart tissues and/or structures via any movement of the valve prosthesis relative to heart tissue and/or structures during one or more cardiac cycles. For example, a barbed fixation element that further embeds itself into tissue via movement of the valve prosthesis relative to tissue in one direction and then resists movement of the valve prosthesis relative to tissue in the opposite direction.

The choice of materials for the various heart valve prostheses described herein can be informed by the requirements of mechanical properties, temperature sensitivity, biocompatibility, moldability properties, or other factors apparent to a person having ordinary skill in the art. For example, one more of the parts (or a portion of one of the parts), components, and/or portions can be made from suitable plastics, such as a suitable thermoplastic, suitable metals, and/or other suitable materials.

In order to transform between an initial compressed configuration and the deployed configuration shown in the figures hereof, frames and support arms in accordance with embodiments described herein may be formed from a self-expanding material that has a mechanical memory to return to the deployed configuration. Accordingly in accordance with embodiments hereof, frames may be made from stainless steel, a pseudo-elastic metal such as a nickel titanium alloy or nitinol, or a so-called super alloy, which may have a base metal of nickel, cobalt, chromium, or other metal. Mechanical memory may be imparted to the tubular structure that forms the frames by thermal treatment to achieve a spring temper in stainless steel, for example, or to set a shape memory in a susceptible metal alloy, such as nitinol, or a polymer, such as any of the polymers disclosed in U.S. Pat. Appl. Pub. No. 2004/0111111 to Lin, which is incorporated by reference herein in its entirety. In accordance with other embodiments hereof, a frame of a valve prosthesis can be formed entirely or in part by a biocompatible material. In accordance with other embodiments hereof, one or more portions of a frame of a valve prosthesis can be self-expandable and/or balloon expandable.

In accordance with embodiments hereof, the valve body or component and valve leaflets thereof can be formed, for example, from one or more biocompatible synthetic materials, synthetic polymers, autograft tissue, homograft tissue, xenograft tissue, or one or more other suitable materials. In some embodiments, the valve body or component and valve leaflets thereof can be formed, for example, from bovine, porcine, equine, ovine, and/or other suitable animal tissues. In accordance with embodiments hereof, the valve body or component and valve leaflets thereof may be made of or formed from a natural material obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals. In accordance with other embodiments hereof, synthetic materials suitable for use as valve components and valve leaflets thereof include DACRON® polyester commercially available from Invista North America S.A.R.L. of Wilmington, Del., other cloth materials, nylon blends, polymeric materials, and vacuum deposition nitinol fabricated materials. In an embodiment, valve body or component and valve leaflets thereof can be made of an ultra-high molecular weight polyethylene material commercially available under the trade designation DYNEEMA from Royal DSM of the Netherlands. With certain leaflet materials, it may be desirable to coat one or both sides of the leaflet with a material that will prevent or minimize overgrowth. It is further desirable that the leaflet material is durable and not subject to stretching, deforming, or fatigue. In accordance with other embodiments hereof, the valve body or component can comprise one or more valve leaflets. For example, the valve body or component can be in the form of a tri-leaflet bovine pericardium valve, a bi-leaflet valve, or another suitable valve. In accordance with other embodiments hereof, the valve body or component can comprise three leaflets that are fastened together at enlarged lateral end regions to form commissural joints, with the unattached edges forming coaptation edges of the valve body. In accordance with other embodiments hereof, the prosthetic valve leaflets can be fastened to a skirt of a graft material, which in turn can be attached to the frame.

In accordance with embodiments hereof, the graft material or portions thereof may be a low-porosity woven fabric, such as polyester, DACRON® polyester, or polytetrafluoroethylene (PTFE), which creates a one-way fluid passage when attached to the frame of the valve prosthesis. In an embodiment, the graft material or portions thereof may be a looser knit or woven fabric, such as a polyester or PTFE knit, which can be utilized when it is desired to provide a medium for tissue ingrowth and the ability for the fabric to stretch to conform to a curved surface. In another embodiment, polyester velour fabrics may alternatively be used for the graft material or portions thereof, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, the graft material or portions thereof may be a natural material, such as pericardium or another membranous tissue.

In accordance with embodiments hereof, valve-retaining tubular portions and support arms of frames disclosed herein, as well as the graft material and tent-like structures that may be associated therewith, may be modified without departing from the scope of the present invention in view of the disclosures of one or more of U.S. application Ser. No. 13/736,460 filed Jan. 8, 2013 to Igor Kovalsky et al., U.S. Appl. No. 61/822,616 filed May 13, 2013 to Kshitija Garde et al., and U.S. application Ser. No. 13/572,842 filed Aug. 13, 2012 to Igor Kovalsky, each of which is incorporated by reference herein in its entirety.

In one or more embodiments, valve prosthesis and/or one or more of its components or portions may comprise, be covered with, be coated with, or be attached or coupled to one or more biocompatible materials or biomaterials, for example, titanium, titanium alloys, Nitinol, TiNi alloys, shape memory alloys, super elastic alloys, aluminum oxide, platinum, platinum alloys, stainless steels, stainless steel alloys, MP35N, elgiloy, haynes 25, stellite, pyrolytic carbon, silver carbon, glassy carbon, polymers or plastics such as polyamides, polycarbonates, polyethers, polyesters, polyolefins including polyethylenes or polypropylenes, polystyrenes, polyurethanes, polyvinylchlorides, polyvinylpyrrolidones, silicone elastomers, fluoropolymers, polyacrylates, polyisoprenes, polytetrafluoroethylenes, polyethylene terephthalates, fabrics such as woven fabrics, nonwoven fabrics, porous fabrics, semi-porous fabrics, nonporous fabrics, Dacron fabrics, polytetrafluoroethylene (PTFE) fabrics, polyethylene terephthalate (PET) fabrics, materials that promote tissue ingrowth, rubber, minerals, ceramics, hydroxapatite, epoxies, human or animal protein or tissue such as collagen, laminin, elastin or fibrin, organic materials such as cellulose, or compressed carbon, and/or other materials such as glass, and the like. Materials that are not considered biocompatible may be modified to become biocompatible by a number of methods well known in the art. For example, coating a material with a biocompatible coating may enhance the biocompatibility of that material. Biocompatible materials or biomaterials are usually designed and constructed to be placed in or onto tissue of a patient's body or to contact fluid of a patient's body. Ideally, a biocompatible material or biomaterial will not induce undesirable reactions in the body such as blood clotting, tumor formation, allergic reaction, foreign body reaction (rejection) or inflammatory reaction; will have the physical properties such as strength, elasticity, permeability, and flexibility required to function for the intended purpose; may be purified, fabricated and sterilized easily; will substantially maintain its physical properties and function during the time that it remains in contact with tissues or fluids of the body.

In one or more embodiments, one or more surfaces of the valve prosthesis and/or one or more of its components or portions may comprise, be covered with, be coated with, or be attached or coupled to one or more radioactive materials and/or biological agents, for example, an anticoagulant agent, an antithrombotic agent, a clotting agent, a platelet agent, an anti-inflammatory agent, an antibody, an antigen, an immunoglobulin, a defense agent, an enzyme, a hormone, a growth factor, a neurotransmitter, a cytokine, a blood agent, a regulatory agent, a transport agent, a fibrous agent, a protein, a peptide, a proteoglycan, a toxin, an antibiotic agent, an antibacterial agent, an antimicrobial agent, a bacterial agent or component, hyaluronic acid, a polysaccharide, a carbohydrate, a fatty acid, a catalyst, a drug, a vitamin, a DNA segment, a RNA segment, a nucleic acid, a lectin, an antiviral agent, a viral agent or component, a genetic agent, a ligand and/or a dye (which acts as a biological ligand). Biological agents may be found in nature (naturally occurring) or may be chemically synthesized by a variety of methods well known in the art.

In one or more embodiments, valve prosthesis and/or one or more of its components or portions may comprise, be coated with, be covered with, or be attached or coupled to one or more biological cells or tissues, for example, tissue cells, cardiac cells, contractile cells, muscle cells, heart muscle cells, smooth muscle cells, skeletal muscle cells, autologous cells, allogenic cells, xenogenic cells, stem cells, genetically engineered cells, non-engineered cells, mixtures of cells, precursor cells, immunologically neutral cells, differentiated cells, undifferentiated cells, natural tissue, synthetic tissue, animal tissue, human tissue, porcine tissue, equine tissue, porcine tissue, bovine tissue, ovine tissue, autologous tissue, allogenic tissue, xenogenic tissue, autograft tissue, genetically engineered tissue, non-engineered tissue, mixtures of tissues, cardiac tissue, pericardial tissue, cardiac valve tissue, membranous tissue, and/or intestinal submucosa tissue. In one or more embodiments, valve prosthesis and/or one or more of its components or portions may comprise, be covered with, be coated with, or be attached or coupled to one or more materials that promote the growth of cells and/or tissue. In one or more embodiments, the cell and/or tissue promoting materials may comprise, possess or be configured to possess physical characteristics such as size, shape, porosity, matrix structure, fiber structure, and/or chemical characteristics such as growth factors, biological agents, that promote and/or aid, for example, in the adherence, proliferation and/or growth of desired cells and/or tissues in vivo following implantation or ex vivo prior to implantation. In one or more embodiments, the cell and/or tissue promoting materials may accelerate the healing response of the patient following the implantation of the valve prosthesis. In one or more embodiments, the cell and/or tissue promoting materials may comprise pockets, parachutes, voids, and/or openings, for example, that may trap cells and/or tissues and/or promote cells and/or tissues to proliferate, grow and/or heal.

In one or more embodiments, valve prosthesis and/or one or more of its components or portions may comprise, be coated with, be covered with, be constrained by, or be attached or coupled to a shape memory material, a bioresorbable material, and/or a biodegradable material, such as a natural or synthetic biodegradable polymer, non-limiting examples of which include polysaccharides such as alginate, dextran, cellulose, collagen, and chemical derivatives thereof, proteins such as albumin, and copolymer blends thereof, alone or in combination with synthetic polymers, polyhydroxy acids, such as polylactides, polyglycolides and copolymers thereof, poly(ethylene terephthalate), poly(hydroxybutyric acid); poly(hydroxyvaleric acid), poly [lactide-co-(E-caprolactone)]; poly[glycolide-co-(E-caprolactone)], polycarbonates, poly(pseudo amino acids); poly(amino acids); poly(hydroxyalkanoate)s, polyanhydrides; polyortho esters, and blends and copolymers thereof. In one or more embodiments, one or more surfaces of the valve prosthesis and/or one or more of its components or portions may comprise, be covered with, be coated with, or be attached or coupled to one or more glues and/or adhesives, such as a bioglue or bioadhesive used to help anchor and/or seal the valve prosthesis to native tissue.

In one or more embodiments, valve prosthesis and/or one or more of its components or portions may be compressible and/or expandable, for example, self-expandable, balloon expandable, or mechanically expandable.

One or more of the valve prostheses described herein can be implanted into an annulus of a native cardiac valve through a suitable delivery method. For example, the valve prosthesis can be implanted through conventional open-heart surgery techniques. In some embodiments, the valve prosthesis can be delivered percutaneously. For example, in some percutaneous techniques, valve prosthesis can be compacted and loaded onto a delivery device for advancement through a patient's vasculature. The valve prosthesis can be delivered through an artery or vein, a femoral artery, a femoral vein, a jugular vein, a subclavian artery, an axillary artery, an aorta, an atrium, and/or a ventricle. The valve prosthesis may be delivered via a transfemoral, transapical, transseptal, transatrial, transventrical, or transaortic procedure.

In some embodiments, the valve prosthesis can be delivered transfemorally. In such a delivery, the delivery device and the valve prosthesis can be advanced in a retrograde manner through the femoral artery and into the patient's descending aorta. A catheter can then be advanced under fluoroscopic guidance over the aortic arch, through the ascending aorta, into the left ventricle, and mid-way across the defective mitral valve. Once positioning of the catheter is confirmed, the delivery device can deploy the valve prosthesis within the annulus. The valve prosthesis can then expand against and align the prosthesis within the annulus. In some embodiments, as the valve prosthesis is expanded, it can trap leaflets against the annulus, which can retain the native valve in a permanently open state.

In some embodiments, the valve prosthesis can be delivered via a transapical procedure. In a transapical procedure, a trocar or over-tube can be inserted into a patient's left ventricle through an incision created in the apex of the patient's heart. A dilator can be used to aid in the insertion of the trocar. In this approach, the native valve (for example, the mitral valve) can be approached from the downstream relative to the blood flow. The trocar can be retracted sufficiently to release the self-expanding valve prosthesis. The dilator can be presented between the leaflets. The trocar can be rotated and adjusted to align the valve prosthesis in a desired alignment. The dilator can be advanced into the left atrium to begin disengaging the proximal section of the valve prosthesis from the dilator.

In some embodiments, the valve prosthesis can be delivered via a transatrial procedure. In such a procedure, a dilator and trocar can be inserted through an incision made in the wall of the left atrium of the heart. The dilator and trocar can then be advanced through the native valve and into the left ventricle of heart. The dilator can then be withdrawn from the trocar. A guide wire can be advanced through the trocar to the point where the valve prosthesis comes to the end of the trocar. The valve prosthesis can be advanced sufficiently to release the self-expanding frame from the trocar. The trocar can be rotated and adjusted to align the valve prosthesis in a desired alignment. The trocar can be withdrawn completely from the heart such that the valve prosthesis self-expands into position and can assume the function of the native valve.

Mitral valve prosthesis in accordance with embodiments hereof may be delivered via a transapical implantation procedure or via a transatrial implantation procedure. Suitable transapical and/or transatrial implantation procedures that may be adapted for use with mitral valve prosthesis described herein are disclosed in U.S. application Ser. No. 13/572,842 filed Aug. 13, 2012 to Igor Kovalsky, U.S. Appl. Pub. No. 2011/0208297 to Tuval et al., and U.S. Appl. Pub. No. 2012/0035722 to Tuval et al, each of which is incorporated by reference herein in its entirety.

In one or more embodiments of the present invention, valve prosthesis and/or one or more of its components or portions may be delivered, for example, through a thoracotomy, a sternotomy, percutaneously, transvenously, arthroscopically, endoscopically, for example, through a percutaneous port, a stab wound or puncture, through a small incision, for example, in the chest, groin, abdomen, neck, leg, arm, or in combinations thereof. In one or more embodiments of the present invention, valve prosthesis and/or one or more of its components or portions may be delivered, for example, via a transvascular method, a transarterial method, a transvenous method, a transcardiac method, a transatrial method, a transventrical method, transapical method, a transseptal method, a transaortic method, a transcatheter method, a surgical method, a beating heart method, a stopped heart method, a pump-assisted method, and/or a cardiopulmonary bypass method.

In one or more embodiments of the present invention, valve prosthesis and/or one or more of its components or portions may be positioned in, positioned through, and/or positioned adjacent to, for example, a natural valve, a native valve, a synthetic valve, a replacement valve, a tissue valve, a mechanical valve, a mitral valve, an aortic valve, a pulmonary valve, a tricuspid valve, a valve component, a valve annulus, a valve leaflet, chordae, and/or a valve commissure.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A valve prosthesis for implantation into a native valve site, the valve prosthesis comprising:
   a valve body; and
   a frame comprising,
      a central portion supporting the valve body, the central portion configured to fit within an annulus of the native valve site,
      an inflow portion configured to engage an upstream side of the annulus and restrict movement of the valve prosthesis in a downstream direction of blood flow at the native valve site, the inflow portion including an s-shaped extension that protrudes in a substantially radially outward direction from the central portion to an inflow end of the frame, wherein the s-shaped extension includes a first curve forming a valley of the s-shaped extension and a second curve forming a peak of the s-shaped extension, the second curve disposed radially closer to the central portion than the first curve,
      a first leaflet support arm being configured to engage a native valve leaflet and restrict movement of the valve prosthesis in an upstream direction of blood flow at the native valve site,
      a second leaflet support arm being configured to engage a native valve leaflet and restrict movement of the valve prosthesis in an upstream direction of blood flow at the native valve site, the second leaflet support arm being diametrically opposed to the first leaflet support arm, and
      a plurality of atrial engagement support arms extending from the inflow portion adjacent to the first curve to provide axial fixation of the valve prosthesis within the native valve site, wherein each atrial engagement support arm is a curved strut with a radially outermost end connected to the inflow portion and an unconnected innermost end that sits distal to the inflow portion and radially outward of the central portion, and wherein each atrial engagement support arm is configured to have a greater flexibility than the s-shaped extension.

2. The valve prosthesis of claim 1, wherein the plurality of atrial engagement support arms are evenly spaced about a circumference of the inflow portion.

3. The valve prosthesis of claim 1, wherein the inflow portion comprises a substantially saddle shaped portion.

4. The valve prosthesis of claim 1, wherein the plurality of atrial engagement support arms each have a substantially straightened delivery configuration.

5. The valve prosthesis of claim 1, wherein the native valve site is a native mitral valve and each atrial engagement support arm is configured to abut against atrial tissue of the native mitral valve.

6. The valve prosthesis of claim 5, wherein each atrial engagement support arm is configured to decompress in situ and open to maintain sealing over a greater amount of the frame.

7. A valve prosthesis for implantation into a native valve site, the valve prosthesis comprising:
   a valve body; and
   a frame comprising,
      a central portion supporting the valve body, the central portion configured to fit within an annulus of the native valve site,
      an inflow portion configured to engage an upstream side of the annulus and restrict movement of the valve prosthesis in a downstream direction of blood flow at the native valve site, the inflow portion including an s-shaped extension that protrudes in a substantially radially outward direction from the central portion to an inflow end of the frame, wherein the s-shaped extension includes a first curve forming a valley of the s-shaped extension and a second curve forming a peak of the s-shaped extension, the second curve disposed radially closer to the central portion than the first curve, a first leaflet support arm being configured to engage a native valve leaflet and restrict movement of the valve prosthesis in an upstream direction of blood flow at the native valve site, a second leaflet support arm being configured to engage a native valve leaflet and restrict movement of the valve prosthesis in an upstream direction of blood flow at the native valve site, the second leaflet support arm being diametrically opposed to the first leaflet support arm, and a plurality of atrial engagement support arms extending from the inflow portion adjacent to the first curve to provide axial fixation of the valve prosthesis within the native valve site, each atrial engagement support arm being a curved strut with a radially outermost end connected to the inflow portion and an unconnected innermost end that sits distal to the inflow portion and radially outward of the central portion, wherein each atrial engagement support arm is configured to have a greater flexibility than the s-shaped extension, and wherein the native valve site is a native mitral valve and each atrial engagement support arm is configured to abut against atrial tissue of the native mitral valve.

8. The valve prosthesis of claim 7, wherein the plurality of atrial engagement support arms are evenly spaced about a circumference of the inflow portion.

\* \* \* \* \*